(12) United States Patent
Shipps, Jr. et al.

(10) Patent No.: US 9,351,965 B2
(45) Date of Patent: May 31, 2016

(54) INDAZOLE DERIVATIVES USEFUL AS ERK INHIBITORS

(75) Inventors: Gerald W. Shipps, Jr., Stoneham, MA (US); Xiaohua Huang, Brookline, MA (US); Yongqi Deng, Newton, MA (US); Liang Zhu, Waltham, MA (US); Alan B. Cooper, West Caldwell, NJ (US); Binyuan Sun, Chestnut Hill, MA (US); Abdelghani Achab, Melrose, MA (US); Sie-Mun Lo, Springfield, VA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 130 days.

(21) Appl. No.: 13/994,224

(22) PCT Filed: Dec. 16, 2011

(86) PCT No.: PCT/US2011/065318
§ 371 (c)(1),
(2), (4) Date: Jun. 14, 2013

(87) PCT Pub. No.: WO2012/087772
PCT Pub. Date: Jun. 28, 2012

(65) Prior Publication Data
US 2013/0261125 A1 Oct. 3, 2013

Related U.S. Application Data

(60) Provisional application No. 61/425,613, filed on Dec. 21, 2010.

(51) Int. Cl.
| | |
|---|---|
| *C07D 231/56* | (2006.01) |
| *C07D 401/04* | (2006.01) |
| *C07D 471/04* | (2006.01) |
| *C07D 401/14* | (2006.01) |
| *C07D 403/14* | (2006.01) |
| *C07D 417/04* | (2006.01) |
| *A61K 31/416* | (2006.01) |
| *A61K 31/4439* | (2006.01) |
| *A61K 45/06* | (2006.01) |
| *A61K 31/437* | (2006.01) |

(52) U.S. Cl.
CPC ............ *A61K 31/4439* (2013.01); *A61K 31/416* (2013.01); *A61K 31/437* (2013.01); *A61K 45/06* (2013.01); *C07D 231/56* (2013.01); *C07D 401/04* (2013.01); *C07D 401/14* (2013.01); *C07D 403/14* (2013.01); *C07D 417/04* (2013.01); *C07D 471/04* (2013.01)

(58) Field of Classification Search
CPC ............ A61K 31/416; A61K 2300/00; A61K 31/437; A61K 31/4439; A61K 45/06; C07D 231/56; C07D 401/04; C07D 471/04; C07D 401/14; C07D 403/14; C07D 417/04
See application file for complete search history.

(56) References Cited

U.S. PATENT DOCUMENTS

2004/0077877 A1   4/2004   Bhagwat et al.

FOREIGN PATENT DOCUMENTS

| | | |
|---|---|---|
| EP | 1380576 B1 | 1/2004 |
| WO | 2008153858 A1 | 12/2008 |
| WO | 2011019648 A1 | 2/2011 |
| WO | 2012084704 A1 | 6/2012 |

OTHER PUBLICATIONS

Ohori, M. et al., Identification of a selective ERK inhibitor and structural determination of the inhibitor-ERK2 complex, Biochemical and Biophysical Research Communications, 2005, 357-363, 336.

*Primary Examiner* — Kendra D Carter
(74) *Attorney, Agent, or Firm* — Richard S. Parr; Catherine D. Fitch

(57) ABSTRACT

The present invention provides a compound of the Formula I, or a pharmaceutically acceptable salt, solvate or ester thereof, wherein R, $R^1$, $R^2$, $R^3$, m and are as defined herein. The compounds are ERK inhibitors. Also disclosed are pharmaceutical compositions that comprise the above compounds, and methods of treating cancer using the same.

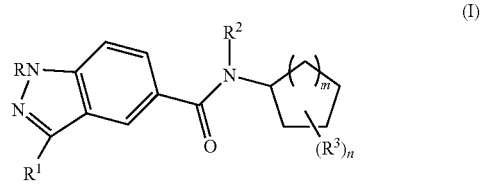

(I)

2 Claims, No Drawings

INDAZOLE DERIVATIVES USEFUL AS ERK INHIBITORS

REFERENCE TO RELATED APPLICATION

This application claims the benefit of U.S. Provisional Application Ser. No. 61/425,613 filed Dec. 21, 2010.

FIELD OF THE INVENTION

This invention related to compounds which can act as inhibitors of kinases, such as ERK, to uses of such compounds and to their preparation.

BACKGROUND OF THE INVENTION

The processes involved in tumor growth, progression, and metastasis are mediated by signaling pathways that are activated in cancer cells. The ERK pathway plays a central role in regulating mammalian cell growth by relaying extracellular signals from ligand-bound cell surface tyrosine kinase receptors such as erbB family, PDGF, FGF, and VEGF receptor tyrosine kinase. Activation of the ERK pathway is via a cascade of phosphorylation events that begins with activation of Ras. Activation of Ras leads to the recruitment and activation of Raf, a serine-threonine kinase. Activated Raf then phosphorylates and activates MEK1/2, which then phosphorylates and activates ERK1/2. When activated, ERK1/2 phosphorylates several downstream targets involved in a multitude of cellular events including cytoskeletal changes and transcriptional activation. The ERK/MAPK pathway is one of the most important for cell proliferation, and it is believed that the ERK/MAPK pathway is frequently activated in many tumors. Ras genes, which are upstream of ERK1/2, are mutated in several cancers including colorectal, melanoma, breast and pancreatic tumors. The high Ras activity is accompanied by elevated ERK activity in many human tumors. In addition, mutations of BRAF, a serine-threonine kinase of the Raf family, are associated with increased kinase activity. Mutations in BRAF have been identified in melanomas (60%), thyroid cancers (greater than 40%) and colorectal cancers. These observations indicate that the ERK1/2 signalling pathway is an attractive pathway for anticancer therapies in a broad spectrum of human tumors.

Therefore, a welcome contribution to the art would be small-molecules (i.e., compounds) that inhibit ERK activity (i.e., ERK1 and ERK2 activity), which small-molecules would be useful for treating a broad spectrum of cancers, such as, for example, melanoma, pancreatic cancer, thyroid cancer, colorectal cancer, lung cancer, breast cancer, and ovarian cancer. Such a contribution is provided by this invention.

PCT publications WO 2007/070398 A1 and WO 2008/153858 A1 disclose polycyclic indazole derivatives useful as ERK inhibitors for the treatment of cancer.

SUMMARY OF THE INVENTION

In its many embodiments, the present invention provides a novel class of compounds, pharmaceutical compositions comprising one or more said compounds, and methods for using said compounds for treating or preventing a disease associated with one or more kinases such as ERK1 and ERK2.

Accordingly, in one aspect, the present invention provides a compound of the Formula

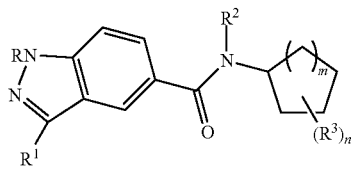

Formula I or a pharmaceutically acceptable salt, solvate or ester thereof, wherein:
R is H or alkyl;
$R^1$ is selected from the group consisting of aryl and heteroaryl, wherein when said aryl or heteroaryl has two substituents on adjacent ring atoms, said substituents together with the ring atoms to which they are attached, optionally form a five- or six-membered heteroaryl or a six-membered aryl;
$R^2$ is H or alkyl;
m is 1 or 2;
n is 1 or 2;
each $R^3$ independently is selected from the group consisting of halo, hydroxyl, alkoxy, alkyl, aryloxy, —$NR^4R^5$, —C(=O)$NR^4R^5$, —N($R^4$)—C(=O)—$R^5$; —C(=O)-aryl, —C(N—OH)-aryl, and —C(=O)OH; and
$R^4$ and $R^5$ independently are hydrogen or alkyl.

In another aspect, the compounds of Formula I, or the pharmaceutically acceptable salts, solvates, or esters thereof can be useful as protein kinase inhibitors.

In another aspect, the compounds of Formula I, or the pharmaceutically acceptable salts, solvates, or esters thereof are useful as protein kinase inhibitors that inhibit the activity of ERK1 and/or the activity of ERK2.

In another aspect, the compounds of Formula I, or the pharmaceutically acceptable salts, solvates, or esters thereof are useful as inhibitors of the phosphorylation of ERK1 and ERK2.

In another aspect, the present invention provides a pharmaceutical composition comprising at least one compound of Formula I, or a pharmaceutically acceptable salt, solvate, or ester thereof and a pharmaceutically acceptable carrier.

In another aspect, the present invention also provides a method of treating cancer in a patient in need of such treatment, said method comprising administering an effective amount of at least one compound of Formula I, or a pharmaceutically acceptable salt, solvate, or ester thereof.

DETAILED DESCRIPTION OF THE INVENTION

As used above, and throughout this disclosure, the following terms, unless otherwise indicated, shall be understood to have the following meanings:

"Patient" includes both human and animals.

"Mammal" means humans and other mammalian animals.

"At least one", as used in reference to the number of compounds of this invention means for example 1-6, generally 1-4, more generally 1, 2 or 3, and usually one or two, and more usually one;

"At least one", as used in reference to the number of chemotherapeutic agents used, means for example 1-6, generally 1-4, more generally 1, 2 or 3, and usually one or two, or one;

"At least one", or "substituted with a (followed by a named substituent)" as used in reference to the number of substituents attached to a particular group, such as an alkyl group, a cycloalkyl group, a heterocyclyl group, an aryl group and an heteroaryl group, means for example 1-6, generally 1-4, more generally 1, 2 or 3, and usually one or two, or one;

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. In one embodiment, the alkyl group contains 1 to 3 carbon atoms, i.e., $C_1$-$C_3$ alkyl. Branched means that one or more lower alkyl groups such as methyl, ethyl or propyl, are attached to a linear alkyl chain. "Lower alkyl" means a group having about 1 to about 6 carbon atoms in the chain which may be straight or branched. "Alkyl" may be unsubstituted or optionally substituted by one or more substituents which may be the same or different, each substituent being independently selected from the group consisting of halo, alkyl, aryl, cycloalkyl, heterocyclyl, heteroaryl, cyano, hydroxy, alkoxy, alkylthio, amino, —NH(alkyl), —NH(cycloalkyl), —N(alkyl)$_2$, —O—C(O)-alkyl, —O—C(O)-aryl, —O—C(O)-cycloalkyl, carboxy and —C(O)O-alkyl. Non-limiting examples of suitable alkyl groups include methyl, ethyl, n-propyl, isopropyl and t-butyl.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. "Alkenyl" may be unsubstituted or optionally substituted by one or more substituents which may be the same or different, each substituent being independently selected from the group consisting of halo, alkyl, heterocyclyl, heteroaryl, aryl, cycloalkyl, cyano, alkoxy and S(alkyl). Non-limiting examples of suitable alkenyl groups include ethenyl, propenyl, n-butenyl, 3-methylbut-2-enyl, n-pentenyl, octenyl and decenyl.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl. "Alkynyl" may be unsubstituted or optionally substituted by one or more substituents which may be the same or different, each substituent being independently selected from the group consisting of alkyl, aryl and cycloalkyl.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. "Heteroaryl" may also include a heteroaryl as defined above fused to an aryl as defined above. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The tetra "heteroaryl" also refers to partially saturated heteroaryl moieties such as, for example, tetrahydroisoquinolyl, tetrahydroquinolyl and the like.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

"Cycloalkenyl" means a non-aromatic mono or multicyclic ring system comprising about 3 to about 10 carbon atoms, preferably about 5 to about 10 carbon atoms which contains at least one carbon-carbon double bond. Preferred cycloalkenyl rings contain about 5 to about 7 ring atoms. The cycloalkenyl can be optionally substituted with one or more "ring system substituents" which may be the same or different, and are as defined above. Non-limiting examples of suitable monocyclic cycloalkenyls include cyclopentenyl, cyclohexenyl, cyclohepta-1,3-dienyl, and the like. Non-limiting example of a suitable multicyclic cycloalkenyl is norbornylenyl.

"Halogen" means fluorine, chlorine, bromine, or iodine. Preferred are fluorine, chlorine and bromine.

"Ring system substituent" means a substituent attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, hydroxy, hydroxyalkyl, alkoxy, aryloxy, acyl, aroyl, halo, nitro, cyano, carboxy, alkoxycarbonyl, aryloxycarbonyl, alkylsulfonyl, arylsulfonyl, heteroarylsulfonyl, alkylthio, arylthio, heteroarylthio, cycloalkyl, heterocyclyl, —C(═N—CN)—NH$_2$, —C(═NH)—NH$_2$, —C(═NH)—NH(alkyl), $Y_1Y_2$N-alkyl-, $Y_1Y_2$NC(O)—, $Y_1Y_2$NSO$_2$— and —SO$_2$NY$_1$Y$_2$, wherein $Y_1$ and $Y_2$ can be the same or different and are independently selected from the group consisting of hydrogen, alkyl, aryl, cycloalkyl, heterocyclyl and heteroaryl. "Ring system substituent" may also mean a single moiety which simultaneously replaces two available hydrogens on two adjacent carbon atoms (one H on each carbon) on a ring system to form a carbocyclic or heterocyclic (aromatic or nonaromatic) ring. Examples of such moiety are methylene dioxy, ethylenedioxy, —C(CH₃)₂— and the like which form moieties such as, for example:

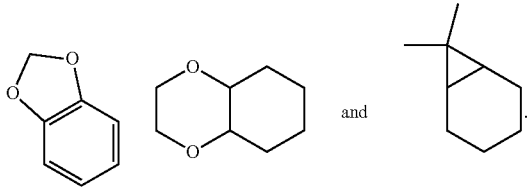
and

"Heterocyclyl" means a non-aromatic saturated monocyclic or multicyclic ring system comprising about 3 to about 10 ring atoms, preferably about 5 to about 10 ring atoms, in which one or more (such as two, three, or four) of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. "Heterocyclyl" may also mean a single moiety (e.g., carbonyl) which simultaneously replaces two available hydrogens on the same carbon atom on a ring system. Example of such moiety is pyrrolidone:

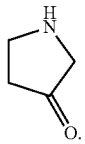

"Heterocyclenyl" means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. The heterocyclenyl can be optionally substituted by one or more ring system substituents, wherein "ring system substituent" is as defined above. The nitrogen or sulfur atom of the heterocyclenyl can be optionally oxidized to the corresponding N-oxide, S-oxide or S,S-dioxide. Non-limiting examples of suitable heterocyclenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluorodihydrofuranyl, 7-oxabicyclo[2.2.1]heptenyl, dihydrothiophenyl, dihydrothiopyranyl, and the like. "Heterocyclenyl" may also mean a single moiety (e.g., carbonyl) which simultaneously replaces two available hydrogens on the same carbon atom on a ring system. Example of such moiety is pyrrolidinone:

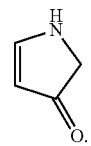

It should be noted that in hetero-atom containing ring systems of this invention, there are no hydroxyl groups on carbon atoms adjacent to a N, O or S, as well as there are no N or S groups on carbon adjacent to another heteroatom. Thus, for example, in the ring:

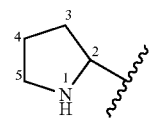

there is no —OH attached directly to carbons marked 2 and 5.

It should also be noted that tautomeric forms such as, for example, the moieties:

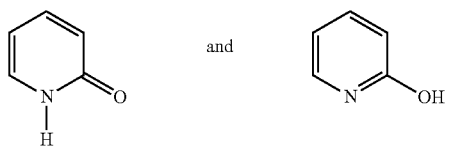 [SMILES: O=c1cccc[nH]1 ; Oc1ccccn1]

are considered equivalent in certain embodiments of this invention.

"Hydroxyalkyl" means a HO-alkyl-group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Alkylsulfonyl" means an alkyl-S($O_2$)— group. Preferred groups are those in which the alkyl group is lower alkyl. The bond to the parent moiety is through the sulfonyl.

"Arylsulfonyl" means an aryl-S($O_2$)— group. The bond to the parent moiety is through the sulfonyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

The term "purified", "in purified form" or "in isolated and purified form" for a compound refers to the physical state of said compound after being isolated from a synthetic process (e.g. from a reaction mixture), or natural source or combination thereof. Thus, the term "purified", "in purified form" or "in isolated and purified form" for a compound refers to the physical state of said compound after being obtained from a purification process or processes described herein or well known to the skilled artisan (e.g., chromatography, recrystallization and the like), in sufficient purity to be characterizable by standard analytical techniques described herein or well known to the skilled artisan.

It should also be noted that any carbon as well as heteroatom with unsatisfied valences in the text, schemes, examples and Tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When any variable (e.g., aryl, heterocycle, $R^3$, etc.) occurs more than one time in any constituent or in Formula (I), its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g., a drug precursor) that is transformed in vivo to yield a compound of Formula (I), or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of Formula I, or a pharmaceutically acceptable salt, hydrate or solvate of the compound contains a carboxylic acid functional group, a prodrug can comprise an ester formed by the replacement of the hydrogen atom of the acid group with a group such as, for example, ($C_1$-$C_8$)alkyl, ($C_2$-$C_{12}$)alkanoyloxymethyl, 1-(alkanoyloxy) ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di($C_1$-$C_2$)alkylcarbamoyl-(C1-C2)alkyl and piperidino-, pyrrolidino- or morpholino($C_2$-$C_3$) alkyl, and the like.

Similarly, if a compound of Formula I contains an alcohol functional group, a prodrug can be formed by the replacement of the hydrogen atom of the alcohol group with a group such as, for example, ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyloxymethyl, N—($C_1$-$C_6$)alkoxycarbonylaminomethyl, succinoyl, ($C_1$-$C_6$)alkanoyl, α-amino ($C_1$-$C_4$)alkanyl, arylacyl and α-aminoacyl, or α-aminoacyl-α-aminoacyl, where each α-aminoacyl group is independently selected from the naturally occurring L-amino acids, P(O)(OH)$_2$, —P(O)(O($C_1$-$C_6$)alkyl)$_2$ or glycosyl (the radical resulting from the removal of a hydroxyl group of the hemiacetal form of a carbohydrate), and the like.

If a compound of any one of Formula I incorporates an amine functional group, a prodrug can be formed by the replacement of a hydrogen atom in the amine group with a group such as, for example, R-carbonyl, RO-carbonyl, NRR'-carbonyl where R and R' are each independently ($C_1$-$C_{10}$) alkyl, ($C_3$-$C_7$)cycloalkyl, benzyl, or R-carbonyl is a natural α-aminoacyl or natural α-aminoacyl, —C(OH)C(O)OY$^1$ wherein Y$^1$ is H, ($C_1$-$C_6$)alkyl or benzyl, C(OY$^2$)Y$^3$ wherein $Y^2$ is $(C_1-C_4)$alkyl and $Y^3$ is $(C_1-C_6)$alkyl, carboxy $(C_1-C_6)$ alkyl, amino$(C_1-C_4)$alkyl or mono-N— or di-N,N—$(C_1-C_6)$ alkylaminoalkyl, $C(Y^4)Y^5$ wherein $Y^4$ is H or methyl and $Y^5$ is mono-N or di-N,N—$(C_1-C_6)$alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

"Effective amount" or "therapeutically effective amount" is meant to describe an amount of compound or a composition of the present invention effective in inhibiting the above-noted diseases and thus producing the desired therapeutic, ameliorative, inhibitory or preventative effect.

The compounds of Formula I can form salts which are also within the scope of this invention. Reference to a compound of Formula I is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein.

Pharmaceutically acceptable (i.e., non-toxic, physiologically acceptable) salts are preferred, although other salts are also useful. Salts of the compounds of Formulae I may be formed, for example, by reacting a compound of Formula I, with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 149; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di($C_{6-24}$)acyl glycerol.

Compounds of Formula I, and salts, solvates, esters and prodrugs thereof, may exist in their tautomeric form (for example, as an amide or imino ether). All such tautomeric forms are contemplated herein as part of the present invention.

The compounds of Formula I as set forth herein may contain asymmetric or chiral centers, and, therefore, exist in different stereoisomeric forms. It is intended that all stereoisomeric forms of the compounds of Formula I as well as mixtures thereof, including racemic mixtures, form part of the present invention. In addition, the present invention embraces all geometric and positional isomers. For example, if a compound of Formula I incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Masher's acid chloride), separating the diastereomers and converting (e.g., hydrolyzing) the individual diastereomers to the corresponding pure enantiomers. Also, some of the compounds of Formula I may be atropisomers (e.g., substituted biaryls) and are considered as part of this invention. Enantiomers can also be separated by use of chiral HPLC column.

It is also possible that the compounds of Formula I may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). (For example, if a compound of Formula I incorporates a double bond or a fused ring, both the cis- and trans-forms, as well as mixtures, are embraced within the scope of the invention. Also, for example, all keto-enol and imine-enamine forms of the compounds are included in the invention.) Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

Certain isotopically-labelled compounds of Formula I (e.g., those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labelled compounds of Formula I can generally be prepared by following procedures analogous to those disclosed in the Schemes and/or in the Examples hereinbelow, by substituting an appropriate isotopically labelled reagent for a non-isotopically labelled reagent.

Polymorphic forms of the compounds of Formula I, and of the salts, solvates, esters and prodrugs of the compounds of Formula I, are intended to be included in the present invention.

The following abbreviations are used below and have the following meanings:

Boc is tert-butoxycarbonyl, dba is dibenzylideneacetone, DMF is N,N-dimethylformamide, DMSO is dimethylsulfoxide, EtOAc is ethyl acetate, LCMS is liquid chromatography mass spectrometry, MeOH is methanol, NMR is nuclear magnetic resonance, PBS is phosphate buffered saline, SPA is scintillation proximity assay, Tf is triflate, TFA is trifluoroacetic acid and Xantphos is 9,9-Dimethyl-4,5-bis(diphenylphosphino)xanthene. Me4Si is tetramethyl silane, DIEA is diisopropyl ethylamine, SGC is silicagel column, TMSCHN2 is trimethylsilyl diazomethane, $BBr_3$ is tribromoborane, m-CPBA is m-chloro perbenzoic acid, CDT is carbodiimidazole, HATU is 2-(1H-azabenzotriazol-1-yl-1,13,3-tetramethyl uranium hexafluorophosphate, NaH is sodium hydride, SiO2 is silica, CBZ is benzyloxy carbonyl, Tos is p-toluene sulfonyl, $CH_3CN$ is acetonitrile.

In another embodiment of the present invention, in Formula I, R is H.

In another embodiment, in Formula I, $R^1$ is heteroaryl, wherein when said heteroaryl has two substituents on adjacent ring atoms, said substituents together with the ring atoms to which they are attached optionally form a five- or six-membered heteroaryl or a phenyl.

In another embodiment, in Formula I, $R^1$ is heteroaryl, which is selected from the group consisting of pyridyl,

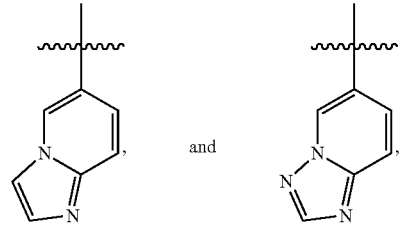 [SMILES: *c1ccc2nccn2c1 ; *c1ccc2ncnn2c1]

each of which independently is unsubstituted or substituted with one to four substitutents independently selected from the group consisting of alkyl, and alkoxy.

In another embodiment, in Formula I, $R^1$ is heteroaryl, which is selected from the group consisting of pyridyl,

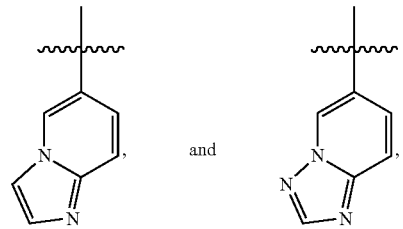 [SMILES: *c1ccc2nccn2c1 ; *c1ccc2ncnn2c1]

each of which independently is unsubstituted or substituted with one to four substitutents independently selected from the group consisting of methyl and isopropyloxy.

In another embodiment, in Formula I, $R^1$ is 4-pyridyl, which is substituted with one substituent selected from the group consisting of alkyl and alkoxy.

In another embodiment, in Formula I, $R^1$ is heteroaryl and is selected from the group consisting of

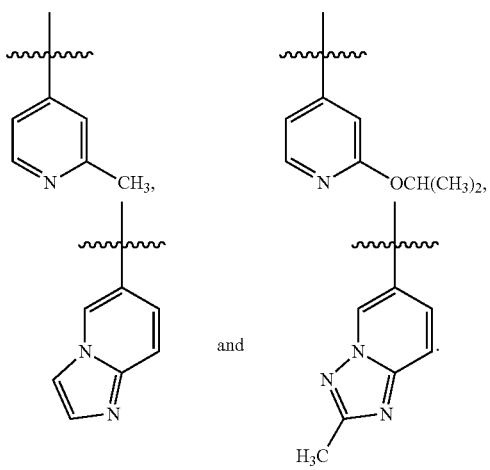

In another embodiment, in Formula I, R¹ is aryl, wherein when said aryl has two substituents on adjacent ring atoms, said substituents together with the ring atoms to which they are attached, optionally form a five- or six-membered heteroaryl.

In another embodiment, in Formula I, R¹ is aryl which is selected from the group consisting of benzopyrazolyl, and benzothiazolyl, each of which is independently unsubstituted or substituted with one to four independently selected alkyl substituents.

In another embodiment, in Formula I, R¹ is aryl which is selected from the group consisting of:

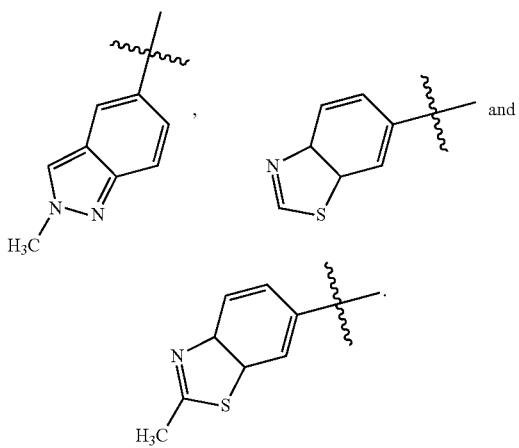

In another embodiment, in Formula I, R² is H.

In another embodiment, in Formula I, R³ is alkyl which is substituted with one to three substituents independently selected from the group consisting of heterocyclyl, aryl, heteroaryl, hydroxyl, and halo, wherein when each of said heterocyclyl, aryl or heteroaryl has two substituents on adjacent ring atoms, said substituents together with the ring atoms to which they are attached, optionally form a five- or six-membered heteroaryl or a six-membered aryl.

In another embodiment, in Formula I, R³ is a substituted $C_1$-$C_3$ alkyl.

In another embodiment, in Formula I, R³ is a substituted methylene, i.e., substituted $C_1$ alkyl (i.e., substituted —CH₂—).

In another embodiment, in Formula I, R³ is alkyl which is substituted with one to three substituents independently selected from the group consisting of heterocyclyl, aryl, heteroaryl, hydroxyl, and halo, wherein when each of said heterocyclyl, aryl or heteroaryl has two substituents on adjacent ring atoms, said substituents together with the ring atoms to which they are attached, optionally form a five- or six-membered heteroaryl or a six-membered aryl; wherein each of said heterocyclyl, aryl and heteroaryl substituents of said R³ alkyl is independently unsubstituted or substituted with one to four substituents independently selected from the group consisting of halo, haloalkyl, cyano, alkyl, and alkoxy.

In another embodiment, in Formula I, R³ is alkyl which is substituted with one to three substituents independently selected from the group consisting of heterocyclyl, aryl, heteroaryl, hydroxyl, and halo, wherein when each of said heterocyclyl, aryl or heteroaryl has two substituents on adjacent ring atoms, said substituents together with the ring atoms to which they are attached, optionally form a five- or six-membered heteroaryl or a six-membered aryl; wherein said heterocyclyl and heteroaryl substituent of said R³ alkyl is selected from the group consisting of: imidazolyl, benzimidazolyl, 1H-benzimidazol-1-yl, pyrazolyl, 1,2,4-triazolyl, 1H-1,2,4-triazol-1-yl, 6-oxo-1(6H)-pyridazinyl, indazolyl, 1H-indazol-1-yl, 2H-indazol-1-yl, 2H-indazol-2-yl, 2-oxo-1(2H)-pyridinyl, pyrazolopyridinyl, 1H-pyrazolo[4,3-b]pyridin-1-yl, 2H-pyrazolo[3,4-b]pyridiN-2-yl, 1H-pyrazolo[3,4-c]pyridin-1-yl, 2H-pyrazolo[3,4-c]pyridin-2-yl, 1H-pyrazolo[3,4-b]pyridin-1-yl, 1H-pyrazolo[4,3-c]pyridin-1-yl, indolyl, 1H-indol-1-yl, imidazopyridinyl, 1H-imidazo[4,5-c]pyridin-1-yl, 3H-imidazo[4,5-b]pyridin-3-yl, 1H-imidazo[4,5-c]pyridin-1-yl, and 2-oxo-1(2H)-quinolinyl, each of which is unsubstituted or substituted with one to four substituents independently selected from the group consisting of halo, haloalkyl, cyano, alkyl, and alkoxy.

In another embodiment, in Formula I, R³ is alkyl which is substituted with one to three substituents independently selected from the group consisting of heterocyclyl, aryl, heteroaryl, hydroxyl, and halo, wherein when each of said heterocyclyl, aryl or heteroaryl has two substituents on adjacent ring atoms, said substituents together with the ring atoms to which they are attached, optionally form a five- or six-membered heteroaryl or a six-membered aryl; wherein said aryl substituent of said R³ alkyl is phenyl which is unsubstituted or substituted with one to four substituents independently selected from the group consisting of halo, haloalkyl, cyano, alkyl, and alkoxy.

In another embodiment, in Formula I, R³ is alkyl which is substituted with one to three substituents independently selected from the group consisting of heterocyclyl, aryl, heteroaryl, hydroxyl, and halo, wherein when each of said heterocyclyl, aryl or heteroaryl has two substituents on adjacent ring atoms, said substituents together with the ring atoms to which they are attached, optionally form a five- or six-membered heteroaryl or a six-membered aryl; wherein said aryl substituent of said R³ alkyl is phenyl which is unsubstituted or substituted with halo and alkoxy.

In another embodiment, in Formula I, the "aryl" portion of each of said R³ aryloxy, —C(=O)-aryl, and —C(=N—OH)-aryl is phenyl which is independently unsubstituted or substituted with one or two substituents independently selected from the group consisting of halo, alkyl, and alkoxy.

In another embodiment, in Formula I, m is 1.

In another embodiment, in Formula I, m is 1, and n is 2.

In another embodiment, the compound of Formula I is represented by a compound of Formula IA Formula IA

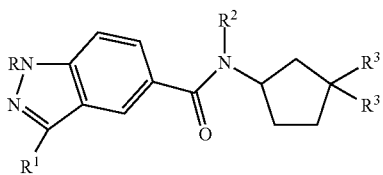

wherein R, $R^1$, $R^2$, and $R^3$ are as defined in Formula I, and each $R^3$ is independently selected.

In another embodiment, in Formula IA, each $R^3$ independently is alkyl.

In another embodiment, in Formula IA, one $R^3$ is alkyl that is substituted with a hydroxyl, and the other $R^3$ is alkyl that is substituted with an aryl, wherein said aryl is substituted with a halo.

In another embodiment, in Formula I, m is 2, i.e., the compound of formula I is represented by a compound of Formula IB:

Formula IB

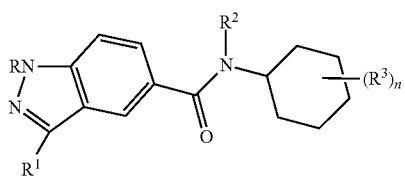

wherein R, $R^1$, $R^2$, $R^3$, and n are as defined in Formula I.

In another embodiment, the compound of Formula IB is represented by a compound of Formula IC or Formula ID:

Formula IC

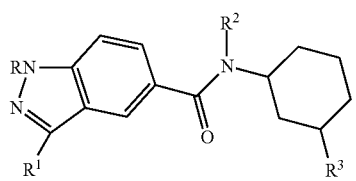

Formula ID

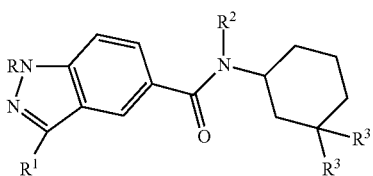

wherein each $R^3$ is independently selected.

In another embodiment, in formula IC, $R^3$ is selected from the group consisting of aryloxy and alkyl, wherein said alkyl is substituted with a heterocyclyl or heteroaryl; wherein when said heterocyclyl or heteroaryl has substitutents on adjacent ring atoms, said substituents together with the ring atoms to which they are attached optionally form a five- or six-membered heteraryl or a phenyl group.

In another embodiment, in formula IC, the "aryl" in said $R^3$ aryloxy is phenyl which is unsubstituted or substituted with one or two substituents selected from the group consisting of halo and alkyl.

In another embodiment, in formula IC, the "aryl" in said $R^3$ aryloxy is phenyl which is unsubstituted or substituted with one or two substituents selected from the group consisting of halo and alkyl; wherein said halo is chloro or fluoro, and said alkyl is methyl.

In another embodiment, in formula IC, $R^3$ is alkyl which is substituted with a heterocyclyl, wherein when said heterocyclyl has substituents on adjacent ring atoms, said substituents together with the ring atoms to which they are attached optionally form a five- or six-membered heteroaryl or a phenyl.

In another embodiment, in formula IC, $R^3$ is alkyl which is substituted with a heterocyclyl, wherein when said heterocyclyl has substituents on adjacent ring atoms, said substituents together with the ring atoms to which they are attached optionally form a five- or six-membered heteroaryl or a phenyl; wherein said heterocyclyl substituent of said $R^3$ alkyl, optionally with said five- or six-membered heteroaryl or phenyl is 2,3-dihydro-2-oxo-1H-indol-1-yl.

In another embodiment, in formula IC, $R^3$ is alkyl which is substituted with a heteroaryl, wherein when said heteroaryl has substituents on adjacent ring atoms, said substituents together with the ring atoms to which they are attached optionally form a five- or six-membered heteroaryl or phenyl.

In another embodiment, in formula IC, $R^3$ is alkyl which is substituted with a heteroaryl, wherein when said heteroaryl has substituents on adjacent ring atoms, said substituents together with the ring atoms to which they are attached optionally form a five- or six-membered heteroaryl or phenyl; wherein said heteroaryl substituent of said $R^3$ alkyl, optionally with said five- or six-membered heteroaryl or phenyl is selected from the group consisting of imidazolyl, benzimidazolyl, pyrazolyl, 1,2,4-triazolyl, indolyl, pyrazolopyridinyl, imidazopyridinyl, 2-oxo-1(2H)-quinolinyl, and indazolyl, each of which independently is unsubstituted or substituted with at least one substituent selected independently from the group consisting of halo, cyano, haloalkyl, and alkyl.

In another embodiment, in formula IC, $R^3$ is alkyl which is substituted with a heteroaryl, wherein when said heteroaryl has substituents on adjacent ring atoms, said substituents together with the ring atoms to which they are attached optionally form a five- or six-membered heteroaryl or phenyl; wherein said heteroaryl substituent of said $R^3$ alkyl, optionally with said five- or six-membered heteroaryl or phenyl is selected from the group consisting of imidazolyl, benzimidazolyl, pyrazolyl, 1,2,4-triazolyl, indolyl, pyrazolopyridinyl, imidazopyridinyl, 2-oxo-1(2H)-quinolinyl, and indazolyl, each of which independently is unsubstituted or substituted with at least one substituent selected independently from the group consisting of halo, cyano, haloalkyl, and alkyl; wherein said imidazolyl is 1H-imidazol-1-yl; said benzimidazolyl is 1H-benzimidazol-1-yl; said pyrazolyl is 1H-pyrazol-1-yl; said 1,2,4-triazolyl is 1H-1,2,4-triazol-1-yl; said indolyl is 1H-indol-1-yl; said pyrazolopyridinyl is selected from the group consisting of 2H-pyrazolo[3,4-b]pyridin-2-yl, 1H-pyrazolo[3,4-b]pyridin-1-yl, 1H-pyrazolo[4,3-c]pyridin-1-yl and 1H-pyrazolo[3,4-c]pyridin-1-yl; said imidazopyridinyl is selected from the group consisting of 1H-imidazo[4,5-]pyridin-1-yl and 3H-imidazo[4,5-b]pyridin-3-yl; and said indazolyl is selected from the group consisting of 1H-indazol-1-yl and 2H-indazol-2-yl.

In another embodiment, in formula IC, said $R^3$ alkyl is $CH_2$-heterocyclyl or $CH_2$-heteroaryl.

In another embodiment, in formula ID, one $R^3$ is selected from the group consisting of halo, hydroxyl, alkoxy, $-NR^4R^5$, $-N(R^4)-C(=O)-R^5$, $-C(=O)NR^4R^5$, $-C(=O)-O$-alkyl, and hydroxyalkyl, and the other $R^3$ is selected from the group consisting of aryloxy, $-C(=O)-O$-aryl, $-C(=N-OH)$-aryl, and alkyl which is substituted with one or two substituents selected from the group consisting of hydroxyl, heterocyclyl, aryl, and heteroaryl; wherein when said heterocyclyl has substituents on adjacent ring atoms, said substituents together with the ring atoms to which they are attached optionally form a five- or six-membered heteroaryl or a phenyl, and wherein when said heteroaryl substituent of said $R^3$ alkyl has substituents on adjacent ring atoms, said substituents together with the ring atoms to which they are attached optionally form a six-membered aryl.

In another embodiment, in formula ID, one $R^3$ is selected from the group consisting of halo, hydroxyl, alkoxy, —$NR^4R^5$, —$N(R^4)$—$C(=O)$—$R^5$, —$C(=O)NR^4R^5$, —$C(=O)$—O-alkyl, and hydroxyalkyl; and the other $R^3$ is selected from the group consisting of aryloxy, —$C(=O)$—O-aryl, —$C(=N$—OH)-aryl, and alkyl which is substituted with one or two substituents selected from the group consisting of hydroxyl, heterocyclyl, aryl, and heteroaryl; wherein said hydroxyalkyl is $CH_2OH$; said —$NR^4R^5$ is $NH_2$; said —$N(R^4)$—$C(=O)$—$R^5$ is selected from the group consisting of N(H)—$C(=O)$—H and N(H)—$C(=O)$-alkyl; and said —$C(=O)NR^4R^5$ is —$C(=O)NH_2$.

In another embodiment, in formula ID, one $R^3$ is selected from the group consisting of halo, hydroxyl, alkoxy, —$NR^4R^5$, —$N(R^4)$—$C(=O)$—$R^5$, —$C(=O)$—O-alkyl, and hydroxyalkyl; and the other $R^3$ is selected from the group consisting of aryloxy, —$C(=O)$—O-aryl, —$C(=N$—OH)-aryl, and alkyl which is substituted with one or two substituents selected from the group consisting of hydroxyl, heterocyclyl, aryl, and heteroaryl; wherein when said heterocyclyl has substituents on adjacent ring atoms, said substituents together with the ring atoms to which they are attached optionally form a five- or six-membered heteroaryl or a phenyl, and wherein when said heteroaryl substituent of said $R^3$ alkyl has substituents on adjacent ring atoms, said substituents together with the ring atoms to which they are attached optionally form a phenyl; wherein said heterocyclyl substituent of said $R^3$ alkyl, optionally with said five- or six-membered heteroaryl is selected from the group consisting of 2,3-dihydro-2-oxo-1H-indol-1-yl.

In another embodiment, in Formula ID, one $R^3$ is selected from the group consisting of halo, hydroxyl, alkoxy, —$NR^4R^5$, —$C(=O)NR^4R^5$, —$C(=O)$—O-alkyl, and hydroxyalkyl; and the other $R^3$ is selected from the group consisting of aryloxy, aryl, —$C(=N$—OH)-aryl, and alkyl which is substituted with one or two substituents selected from the group consisting of hydroxyl, heterocyclyl, aryl, and heteroaryl; wherein when said heterocyclyl has substituents on adjacent ring atoms, said substituents together with the ring atoms to which they are attached optionally form a five- or six-membered heteroaryl or a six-membered aryl, and wherein when said heteroaryl substituent of said $R^3$ alkyl has substituents on adjacent ring atoms, said substituents together with the ring atoms to which they are attached optionally form a six-membered aryl; wherein said aryl substituent of said $R^3$ alkyl and said "aryl" portion of said $R^3$ aryloxy are each phenyl, which is independently unsubstituted or substituted with one or two substituents independently selected from the group consisting of halo, alkyl, and alkoxy.

In another embodiment, in Formula ID, one $R^3$ is selected from the group consisting of halo, hydroxyl, alkoxy, —$NR^4R^5$, —$N(R^4)$—$C(=O)$—$R^5$, —$C(=O)NR^4R^5$, —$C(=O)$—O-alkyl, and hydroxyalkyl; and the other $R^3$ is selected from the group consisting of aryloxy, —$C(=O)$—O-aryl, —$C(=N$—OH)-aryl, and alkyl which is substituted with one or two substituents selected from the group consisting of hydroxyl, heterocyclyl, aryl, and heteroaryl; wherein when said heterocyclyl has substituents on adjacent ring atoms, said substituents together with the ring atoms to which they are attached optionally form a five- or six-membered heteroaryl or a phenyl, and wherein when said heteroaryl substituent of said $R^3$ alkyl has substituents on adjacent ring atoms, said substituents together with the ring atoms to which they are attached optionally form a phenyl; wherein said heteroaryl substituent of said $R^3$ alkyl, optionally with said six-membered aryl, is selected from the group consisting of imadazolyl, pyrazolyl, benzimidazolyl, 1,2,4-triazolyl, 6-oxo-1(6H)-pyridazinyl, indazolyl, 2-oxo-1(2H)-pyridinyl, pyrazolopyridinyl, indolyl, imidazopyridinyl, and 2-oxo-1(2H)-quinolinyl, each of which independently is unsubstituted or substituted with at least one substituent selected independently from the group consisting of halo, cyano, haloalkyl, and alkyl.

In another embodiment, in Formula ID, one $R^3$ is selected from the group consisting of halo, hydroxyl, alkoxy, —$NR^4R^5$, —$N(R^4)$—$C(=O)$—$R^5$, —$C(=O)NR^4R^5$, —$C(=O)$—O-alkyl, and hydroxyalkyl; and the other $R^3$ is selected from the group consisting of aryloxy, aryl, —$C(=N$—OH)-aryl, and alkyl which is substituted with one or two substituents selected from the group consisting of hydroxyl, heterocyclyl, aryl, and heteroaryl; wherein when said heterocyclyl has substituents on adjacent ring atoms, said substituents together with the ring atoms to which they are attached optionally form a five- or six-membered heteroaryl or a phenyl, and wherein when said heteroaryl substituent of said $R^3$ alkyl has substituents on adjacent ring atoms, said substituents together with the ring atoms to which they are attached optionally form a phenyl; wherein said heteroaryl substituent of said $R^3$ alkyl, optionally with said six-membered aryl, is selected from the group consisting of imadazolyl, pyrazolyl, benzimidazolyl, 1,2,4-triazolyl, 6-oxo-1(6H)-pyridazinyl, indazolyl, 2-oxo-1(2H)-pyridinyl, pyrazolopyridinyl, indolyl, imidazopyridinyl, and 2-oxo-1(2H)-quinolinyl, each of which independently is unsubstituted or substituted with at least one substituent selected independently from the group consisting of halo, cyano, haloalkyl, and alkyl; wherein said imidazolyl is 1H-imidazol-1-yl; said benzimidazolyl is 1H-benzimidazol-1-yl; said pyrazolyl is 1H-pyrazol-1-yl; said 1,2,4-triazolyl is 1H-1,2,4-triazol-1-yl; said indolyl is 1H-indol-1-yl; said pyrazolopyridinyl is selected from the group consisting of 2H-pyrazolo[3,4-b]pyridin-2-yl, 1H-pyrazolo[3,4-b]pyridin-1-yl, 1H-pyrazolo[4,3-c]pyridin-1-yl and 1H-pyrazolo[3,4-d]pyridin-1-yl; said imidazopyridinyl is selected from the group consisting of 1H-imidazo[4,5-b]pyridin-1-yl and 3H-imidazo[4,5-b]pyridin-3-yl; and said indazolyl is selected from the group consisting of 1H-indazol-1-yl and 2H-indazol-2-yl.

In another embodiment, in Formula ID, one $R^3$ is OH, and the other $R^3$ is selected from the group consisting of aryloxy, —$C(=O)$—O-aryl, —$C(=N$—OH)-aryl, and alkyl which is substituted with one or two substituents selected from the group consisting of hydroxyl, heterocyclyl, aryl, and heteroaryl; wherein when said heterocyclyl has substituents on adjacent ring atoms, said substituents together with the ring atoms to which they are attached optionally form a five- or six-membered heteroaryl or a six-membered aryl, and wherein when said heteroaryl substituent of said $R^3$ alkyl has substituents on adjacent ring atoms, said substituents together with the ring atoms to which they are attached optionally form a six-membered aryl.

In another embodiment, in Formula ID, one $R^3$ is hydroxyalkyl, and the other $R^3$ is selected from the group consisting of aryloxy, and alkyl which is substituted with an aryl; wherein said aryl and the "aryl" portion of said aryloxy are each phenyl which is independently unsubstituted or substituted with one or two halo substituents.

In another embodiment, in Formula ID, one $R^3$ is selected from the group consisting of halo, —$NR^4R^5$, alkoxy, —$NR^4R^5$, —$N(R^4)$—$C(\!=\!O)$—$R^5$, —$C(\!=\!O)NR^4R^5$, —$C(\!=\!O)$—O-alkyl, and hydroxyalkyl; and the other $R^3$ is alkyl which is substituted with an aryl, wherein said aryl is phenyl which is independently unsubstituted or substituted with one or two halo substituents.

In another embodiment, the compound of formula I is selected from the group consisting of:
N-[3-[(2-fluorophenyl)methyl]-3-hydroxycyclohexyl]-3-(2-methyl-4-pyridinyl)-1H-indazole-5-carboxamide;
N-[3-(hydroxymethyl)-3-phenoxycyclohexyl]-3-(2-methyl-4-pyridinyl)-1H-indazole-5-carboxamide;
N-[3-amino-3-[(2-fluorophenyl)methyl]cyclohexyl]-3-(2-methyl-4-pyridinyl)-1H-indazole-5-carboxamide;
N-[3-[(2-fluorophenyl)methyl]-3-hydroxycyclohexyl]-3-(2-methyl-4-pyridinyl)-1H-indazole-5-carboxamide;
N-[3-(2-fluorophenoxy)cyclohexyl]-3-(2-methyl-4-pyridinyl)-1H-indazole-5-carboxamide;
N-[3-(2-fluorophenoxy)cyclohexyl]-3-(2-methyl-4-pyridinyl)-1H-indazole-5-carboxamide;
N-[3-(1H-imidazol-1-ylmethyl)cyclohexyl]-3-(2-methyl-2H-indazol-5-yl)-1H-indazole-5-carboxamide;
N-[3-(2-chlorophenoxy)cyclohexyl]-3-(2-methyl-4-pyridinyl)-1H-indazole-5-carboxamide;
N-[3-(2,6-dimethylphenoxy)cyclohexyl]-3-(2-methyl-4-pyridinyl)-1H-indazole-5-carboxamide;
N-[3-(2,6-difluorophenoxy)cyclohexyl]-3-(2-methyl-4-pyridinyl)-1H-indazole-5-carboxamide;
N-[3-(aminocarbonyl)-3-(3-fluorophenoxy)cyclohexyl]-3-(2-methyl-4-pyridinyl)-1H-indazole-5-carboxamide;
N-[cis-3-hydroxy-3-(1H-imidazol-1-ylmethyl)cyclohexyl]-3-(2-methyl-2H-indazol-5-yl)-1H-indazole-5-carboxamide;
N-[trans-3-hydroxy-3-(1H-imidazol-1-ylmethyl)cyclohexyl]-3-(2-methyl-2H-indazol-5-yl)-1H-indazole-5-carboxamide;
N-[3-[(2-fluorophenyl)methyl]-3-(formylamino)cyclohexyl]-3-(2-methyl-4-pyridinyl)-1H-indazole-5-carboxamide;
N-[3-[(2-fluorophenyl)methyl]-3-methoxycyclohexyl]-3-(2-methyl-4-pyridinyl)-1H-indazole-5-carboxamide;
N-[3-[(2-fluorophenyl)methyl]-3-methoxycyclohexyl]-3-(2-methyl-4-pyridinyl)-1H-indazole-5-carboxamide;
N-[3-(2-fluorophenoxy)cyclohexyl]-3-(2-methyl-4-pyridinyl)-1H-indazole-5-carboxamide;
N-[3-(3-fluorophenoxy)-3-(hydroxymethyl)cyclohexyl]-3-(2-methyl-4-pyridinyl)-1H-indazole-5-carboxamide;
N-[3-(1H-benzimidazol-1-ylmethyl)cyclohexyl]-3-(2-methyl-2H-indazol-5-yl)-1H-indazole-5-carboxamide;
N-[trans-3-hydroxy-3-(1H-pyrazol-1-ylmethyl)cyclohexyl]-3-(2-methyl-2H-indazol-5-yl)-1H-indazole-5-carboxamide;
N-[cis-3-hydroxy-3-(1H-pyrazol-1-ylmethyl)cyclohexyl]-3-(2-methyl-2H-indazol-5-yl)-1H-indazole-5-carboxamide;
N-[trans-3-(1H-benzimidazol-1-ylmethyl)-3-hydroxycyclohexyl]-3-(2-methyl-2H-indazol-5-yl)-1H-indazole-5-carboxamide;
N-[cis-3-(1H-benzimidazol-1-ylmethyl)-3-hydroxycyclohexyl]-3-(2-methyl-2H-indazol-5-yl)-1H-indazole-5-carboxamide;
N-[3-(difluorophenylmethyl)-3-hydroxycyclohexyl]-3-(2-methyl-4-pyridinyl)-1H-indazole-5-carboxamide;
N-[3-hydroxy-3-(hydroxyphenylmethyl)cyclohexyl]-3-(2-methyl-4-pyridinyl)-1H-indazole-5-carboxamide;
3-imidazo[1,2-a]pyridin-6-yl-N-[3-(1H-pyrazol-1-ylmethyl)cyclohexyl]-1H-indazole-5-carboxamide;
N-(3-benzoyl-3-hydroxycyclohexyl)-3-(2-methyl-4-pyridinyl)-1H-indazole-5-carboxamide;
N-[3-[(2,6-difluorophenyl)methyl]-3-hydroxycyclohexyl]-3-(2-methyl-4-pyridinyl)-1H-indazole-5-carboxamide;
N-[trans-3-hydroxy-3-(1H-1,2,4-triazol-1-ylmethyl)cyclohexyl]-3-(2-methyl-4-pyridinyl)-1H-indazole-5-carboxamide;
N-[cis-3-hydroxy-3-(1H-1,2,4-triazol-1-ylmethyl)cyclohexyl]-3-(2-methyl-4-pyridinyl)-1H-indazole-5-carboxamide;
3-imidazo[1,2-a]pyridiN-6-yl-N-[3-(1H-1,2,4-triazol-1-ylmethyl)cyclohexyl]-1H-indazole-5-carboxamide;
Ethyl-1-[(2-fluorophenyl)methyl]-3-[[[3-(2-methyl-4-pyridinyl)-1H-indazol-5-yl]carbonyl]amino]cyclohexanecarboxylate;
N-[3-[(2-fluorophenyl)methyl]-3-(hydroxymethyl)cyclohexyl]-3-(2-methyl-4-pyridinyl)-1H-indazole-5-carboxamide;
N-[3-(2-chlorophenoxy)cyclohexyl]-3-(2-methyl-4-pyridinyl)-1H-indazole-5-carboxamide;
N-[3(R)-hydroxy-3-(1H-indazol-1-ylmethyl)-1(R)-cyclohexyl]-3-(2-methyl-4-pyridinyl)-1H-indazole-5-carboxamide;
N-[3(S)-hydroxy-3-(1H-indazol-1-ylmethyl)-1(R)-cyclohexyl]-3-(2-methyl-4-pyridinyl)-1H-indazole-5-carboxamide;
N-[trans-3-[(2-fluorophenyl)methyl]-3-hydroxycyclohexyl]-3-imidazo[1,2-a]pyridin-6-yl-1H-indazole-5-carboxamide;
3-(6-benzothiazolyl)-N-[3-[(2-fluorophenyl)methyl]-3-hydroxycyclohexyl]-1H-indazole-5-carboxamide;
1-[(2-fluorophenyl)methyl]-3-[[[3-(2-methyl-4-pyridinyl)-1H-indazol-5-yl]carbonyl]amino]cyclohexanecarboxylic acid;
3-(6-benzothiazolyl)-N-[3-[(2-fluorophenyl)methyl]-3-hydroxycyclohexyl]-1H-indazole-5-carboxamide;
N-[3-[(2-methyl-1H-benzimidazol-1-yl)methyl]cyclohexyl]-3-(2-methyl-6-benzothiazolyl)-1H-indazole-5-carboxamide;
N-[3-[(3-cyano-1H-indol-1-yl)methyl]cyclohexyl]-3-(2-methyl-6-benzothiazolyl)-1H-indazole-5-carboxamide;
N-[trans-3-hydroxy-3-[[2-(trifluoromethyl)-1H-benzimidazol-1-yl]methyl]cyclohexyl]-3-(2-methyl-4-pyridinyl)-1H-indazole-5-carboxamide;
N-[cis-3-hydroxy-3-[[2-(trifluoromethyl)-1H-benzimidazol-1-yl]methyl]cyclohexyl]-3-(2-methyl-4-pyridinyl)-1H-indazole-5-carboxamide;
N-[3-(difluorophenylmethyl)-3-hydroxycyclohexyl]-3-(2-methyl-4-pyridinyl)-1H-indazole-5-carboxamide;
N-[trans-3-hydroxy-3-[(2-methyl-1H-benzimidazol-1-yl)methyl]cyclohexyl]-3-(2-methyl-4-pyridinyl)-H-indazole-5-carboxamide;
N-[cis-3-hydroxy-3-[(2-methyl-1H-benzimidazol-1-yl)methyl]cyclohexyl]-3-(2-methyl-4-pyridinyl)-H-indazole-5-carboxamide;
N-[trans-3-hydroxy-3-(1H-imidazo[4,5-b]pyridin-1-ylmethyl)cyclohexyl]-3-(2-methyl-4-pyridinyl)-1H-indazole-5-carboxamide;
N-[trans-3-hydroxy-3-(3H-imidazo[4,5-b]pyridin-3-ylmethyl)cyclohexyl]-3-(2-methyl-4-pyridinyl)-1H-indazole-5-carboxamide;
N-[3-(2-chlorophenoxy)-1-piperidinyl]-3-(2-methyl-4-pyridinyl)-1H-indazole-5-carboxamide;
N-[3-hydroxy-3-(hydroxyphenylmethyl)cyclohexyl]-3-(2-methyl-4-pyridinyl)-1H-indazole-5-carboxamide;

N-[3-hydroxy-3-(hydroxyphenylmethyl)cyclohexyl]-3-(2-methyl-4-pyridinyl)-1H-indazole-5-carboxamide;

N-[3-(hydroxymethyl)-3-(phenylmethyl)cyclohexyl]-3-(2-methyl-4-pyridinyl)-1H-indazole-5-carboxamide;

N-(3-benzoyl-3-hydroxycyclohexyl)-3-(2-methyl-4-pyridinyl)-1H-indazole-5-carboxamide;

N-[trans-3-hydroxy-3-(2H-pyrazolo[3,4-b]pyridin-2-ylmethyl)cyclohexyl]-3-(2-methyl-4-pyridinyl)-1H-indazole-5-carboxamide;

N-[trans-3-hydroxy-3-(1H-pyrazolo[3,4-c]pyridin-1-ylmethyl)cyclohexyl]-3-(2-methyl-4-pyridinyl)-1H-indazole-5-carboxamide;

N-[trans-3-hydroxy-3-(2H-pyrazolo[3,4-c]pyridin-2-ylmethyl)cyclohexyl]-3-(2-methyl-4-pyridinyl)-1H-indazole-5-carboxamide;

N-[trans-3-hydroxy-3-[(2-methyl-1H-imidazo[4,5-c]pyridin-1-yl)methyl]cyclohexyl]-3-(2-methyl-4-pyridinyl)-1H-indazole-5-carboxamide;

N-[3-[(2-fluorophenyl)methyl]-3-(hydroxymethyl)cyclohexyl]-3-(2-methyl-4-pyridinyl)-1H-indazole-5-carboxamide;

N-[3-(2,4-difluorophenoxy)cyclohexyl]-3-(2-methyl-4-pyridinyl)-1H-indazole-5-carboxamide;

N-[3-(4-fluorophenoxy)-3-(hydroxymethyl)-1-piperidinyl]-3-(2-methyl-4-pyridinyl)-1H-indazole-5-carboxamide;

N-[3-[(2,4-difluorophenyl)methyl]-3-(hydroxymethyl)cyclohexyl]-3-(2-methyl-4-pyridinyl)-1H-indazole-5-carboxamide;

N-[3-[(4-fluorophenyl)methyl]-3-(hydroxymethyl)cyclohexyl]-3-(2-methyl-4-pyridinyl)-1H-indazole-5-carboxamide;

1-[(4-fluorophenyl)methyl]-3-[[[3-(2-methyl-4-pyridinyl)-1H-indazol-5-yl]carbonyl]amino]cyclohexanecarboxylic acid;

N-[3(S)-[(2-fluorophenyl)methyl]-3-hydroxy-1(R)-cyclohexyl]-3-(2-methyl[1,2,4]triazolo[1,5-a]pyridiN-6-yl)-1H-indazole-5-carboxamide;

N-[3(S)-[(2-fluorophenyl)methyl]-3-hydroxy-1(R)-cyclohexyl]-3-(2-methyl-6-benzothiazolyl)-1H-indazole-5-carboxamide;

N-[3(S)-[(2-fluorophenyl)methyl]-3-hydroxy-1(R)-cyclohexyl]-3-imidazo[1,2-a]pyridiN-6-yl-1H-indazole-5-carboxamide;

N-[cis-3-hydroxy-3-(2H-pyrazolo[3,4-b]pyridin-2-ylmethyl)cyclohexyl]-3-(2-methyl-4-pyridinyl)-1H-indazole-5-carboxamide;

N-[cis-3-hydroxy-3-(1H-pyrazolo[3,4-b]pyridin-1-ylmethyl)cyclohexyl]-3-(2-methyl-4-pyridinyl)-1H-indazole-5-carboxamide;

N-[cis-3-hydroxy-3-(1H-pyrazolo[3,4-c]pyridin-1-ylmethyl)cyclohexyl]-3-(2-methyl-4-pyridinyl)-1H-indazole-5-carboxamide;

N-[cis-3-hydroxy-3-(1H-imidazo[4,5-b]pyridin-1-ylmethyl)cyclohexyl]-3-(2-methyl-4-pyridinyl)-1H-indazole-5-carboxamide;

N-[cis-3-hydroxy-3-(3H-imidazo[4,5-b]pyridin-3-ylmethyl)cyclohexyl]-3-(2-methyl-4-pyridinyl)-1H-indazole-5-carboxamide;

3-(2-methyl-4-pyridinyl)-N-[3-(2H-pyrazolo[3,4-b]pyridin-2-ylmethyl)cyclohexyl]-1H-indazole-5-carboxamide;

3-(2-methyl-4-pyridinyl)-N-[3-(1H-pyrazolo[3,4-b]pyridin-1-ylmethyl)cyclohexyl]-1H-indazole-5-carboxamide;

3-(2-methyl-4-pyridinyl)-N-[3-(1H-pyrazolo[3,4-c]pyridin-1-ylmethyl)cyclohexyl]-1H-indazole-5-carboxamide;

N-[3-[(2-methyl-1H-imidazo[4,5-c]pyridin-1-yl)methyl]cyclohexyl]-3-(2-methyl-4-pyridinyl)-1H-indazole-5-carboxamide;

N-[3-(1H-imidazo[4,5-b]pyridin-1-ylmethyl)cyclohexyl]-3-(2-methyl-4-pyridinyl)-1H-indazole-5-carboxamide;

N-[3-(3H-imidazo[4,5-b]pyridin-3-ylmethyl)cyclohexyl]-3-(2-methyl-4-pyridinyl)-1H-indazole-5-carboxamide;

N-[3-[(2,6-difluorophenyl)methyl]-3-(hydroxymethyl)cyclohexyl]-3-(2-methyl-4-pyridinyl)-1H-indazole-5-carboxamide;

N-[3(S)-[(2,6-difluorophenyl)methyl]-3-hydroxy-1(R)-cyclohexyl]-3-(2-methyl-6-benzothiazolyl)-1H-indazole-5-carboxamide;

N-[trans-3-hydroxy-3-(1H-pyrazolo[4,3-c]pyridin-1-ylmethyl)cyclohexyl]-3-(2-methyl-4-pyridinyl)-1H-indazole-5-carboxamide;

N-[trans-3-[(2,3-dihydro-2-oxo-1H-indol-1-yl)methyl]-3-hydroxycyclohexyl]-3-(2-methyl-4-pyridinyl)-1H-indazole-5-carboxamide;

N-[trans-3-hydroxy-3-[(2-oxo-1(2h)-quinolinyl)methyl]cyclohexyl]-3-(2-methyl-4-pyridinyl)-1H-indazole-5-carboxamide;

N-[trans-3-hydroxy-3-(2H-indazol-2-ylmethyl)cyclohexyl]-3-(2-methyl-4-pyridinyl)-1H-indazole-5-carboxamide;

N-[cis-3-hydroxy-3-(1H-pyrazolo[4,3-c]pyridin-1-ylmethyl)cyclohexyl]-3-(2-methyl-4-pyridinyl)-1H-indazole-5-carboxamide;

N-[cis-3-[(2,3-dihydro-2-oxo-1H-indol-1-yl)methyl]-3-hydroxycyclohexyl]-3-(2-methyl-4-pyridinyl)-1H-indazole-5-carboxamide;

N-[cis-3-hydroxy-3-[(2-oxo-1(2h)-quinolinyl)methyl]cyclohexyl]-3-(2-methyl-4-pyridinyl)-1H-indazole-5-carboxamide;

N-[cis-3-hydroxy-3-(2H-indazol-2-ylmethyl)cyclohexyl]-3-(2-methyl-4-pyridinyl)-1H-indazole-5-carboxamide;

3-(2-methyl-4-pyridinyl)-N-[3-(1H-pyrazolo[4,3-c]pyridin-1-ylmethyl)cyclohexyl]-1H-indazole-5-carboxamide;

N-[3-[(2,3-dihydro-2-oxo-1H-indol-1-yl)methyl]cyclohexyl]-3-(2-methyl-4-pyridinyl)-1H-indazole-5-carboxamide;

3-(2-methyl-4-pyridinyl)-N-[3-[(2-oxo-1(2H)-quinolinyl)methyl]cyclohexyl]-1H-indazole-5-carboxamide;

N-[3-(2H-indazol-2-ylmethyl)cyclohexyl]-3-(2-methyl-4-pyridinyl)-1H-indazole-5-carboxamide;

N-[3-(1H-indazol-1-ylmethyl)cyclohexyl]-3-(2-methyl-4-pyridinyl)-1H-indazole-5-carboxamide;

N-[3-[(2-fluorophenyl)methyl]-3-(hydroxymethyl)cyclopentyl]-(2-methyl-4-pyridinyl)-1H-indazole-5-carboxamide;

N-[3-[(2-fluorophenyl)methyl]-3-(hydroxymethyl)cyclopentyl]-3-(2-methyl-4-pyridinyl)-1H-indazole-5-carboxamide;

N-[trans-3-[(4-fluoro-1H-indazol-1-yl)methyl]-3-hydroxycyclohexyl]-3-(2-methyl-4-pyridinyl)-1H-indazole-5-carboxamide;

N-[trans-3-[(6-fluoro-2H-indazol-2-yl)methyl]-3-hydroxycyclohexyl]-3-(2-methyl-4-pyridinyl)-1H-indazole-5-carboxamide;

N-[trans-3-[(7-fluoro-2H-indazol-2-yl)methyl]-3-hydroxycyclohexyl]-3-(2-methyl-4-pyridinyl)-1H-indazole-5-carboxamide;

N-[cis-3-[(4-fluoro-1H-indazol-1-yl)methyl]-3-hydroxycyclohexyl]-3-(2-methyl-4-pyridinyl)-1H-indazole-5-carboxamide;

N-[trans-3-[(7-fluoro-1H-indazol-1-yl)methyl]-3-hydroxycyclohexyl]-3-(2-methyl-4-pyridinyl)-1H-indazole-5-carboxamide;

N-[cis-3-hydroxy-3-[[6-(trifluoromethyl)-1H-indazol-1-yl]methyl]cyclohexyl]-3-(2-methyl-4-pyridinyl)-1H-indazole-5-carboxamide;

N-[3-(2-fluorophenoxy)-1-piperidinyl]-3-(2-methyl-4-pyridinyl)-1H-indazole-5-carboxamide;
N-[-3-[(5-fluoro-2H-indazol-2-yl)methyl]cyclohexyl]-(2-methyl-4-pyridinyl)-1H-indazole-5-carboxamide;
N-[3-[(7-fluoro-1H-indazol-1-yl)methyl]cyclohexyl]-3-(2-methyl-4-pyridinyl)-1H-indazole-5-carboxamide;
N-[cis-3-[(6-fluoro-1H-indazol-1-yl)methyl]-3-hydroxycyclohexyl]-3-(2-methyl-4-pyridinyl)-1H-indazole-5-carboxamide;
N-[3(S)-[(2-fluorophenyl)methyl]-hydroxy-1(R)-cyclohexyl]-3-[2-(1-methylethoxy)-4-pyridinyl]1H-indazole-5-carboxamide;
N-[3(S)-[(2-fluorophenyl)methyl]-3-hydroxy-1(R)-cyclohexyl]-3-[6-(1-methylethoxy)-1-pyridinyl]-1H-indazole-5-carboxamide;
N-[3(S)-[(2,6-difluorophenyl)methyl]-3-hydroxy-1(R)-cyclohexyl]-3-[6-(1-methylethoxy)-3-pyridinyl]-1H-indazole-5-carboxamide;
N-[3(S)-[(2,6-difluorophenyl)methyl]-3-hydroxy-1(R)-cyclohexyl]-3-(2-methyl-2H-indazol-5-yl)-1H-indazole-5-carboxamide;
3-(6-benzothiazolyl)-N-[3(S)-[(2,6-difluorophenyl)methyl]-3-hydroxy-1(R)-cyclohexyl]-1H-indazole-5-carboxamide;
N-[3(S)-[(2,6-difluorophenyl)methyl]-3-hydroxy-1(R)-cyclohexyl]-3-(2-methyl[1,2,4]triazolo[1,5-a]pyridiN-6-yl)-1H-indazole-5-carboxamide;
N-[3(S)-[(2-fluoro-6-methoxyphenyl)methyl]-3-hydroxy-1(R)-cyclohexyl]-3-(2-methyl-4-pyridinyl)-1H-indazole-5-carboxamide;
N-[3(S)-[(2-fluoro-6-methoxyphenyl)methyl]-3-hydroxy-1(R)-cyclohexyl]-3-imidazo[1,2-a]pyridin-6-yl-1H-indazole-5-carboxamide;
N-[3(S)-[(2-fluoro-6-methoxyphenyl)methyl]-3-hydroxy-1(R)-cyclohexyl]-3-(2-methyl-6-benzothiazolyl)-1H-indazole-5-carboxamide;
N-[3(S)-[(2-fluoro-6-methoxyphenyl)methyl]-3-hydroxy-1(R)-cyclohexyl]-3-[2-(1-methylethoxy)-4-pyridinyl]-1H-indazole-5-carboxamide; and
N-[3(S)-[(2-fluoro-6-methoxyphenyl)methyl]-3-hydroxy-1(R)-cyclohexyl]-3-[4-(1-methylethoxy)phenyl]-1H-indazole-5-carboxamide; or a pharmaceutically acceptable salt thereof.

In another embodiment, the compound of formula I is selected from the group consisting of:
N-[3-[(2-fluorophenyl)methyl]-3-hydroxycyclohexyl]-3-(2-methyl-4-pyridinyl)-1H-indazole-5-carboxamide;
N-[3-(hydroxymethyl)-3-phenoxycyclohexyl]-3-(2-methyl-4-pyridinyl)-1H-indazole-5-carboxamide;
N-[3-[(2-fluorophenyl)methyl]-3-hydroxycyclohexyl]-3-(2-methyl-4-pyridinyl)-1H-indazole-5-carboxamide;
N-[3-(2-fluorophenoxy)cyclohexyl]-3-(2-methyl-4-pyridinyl)-1H-indazole-5-carboxamide;
N-[3-(1H-imidazol-1-ylmethyl)cyclohexyl]-3-(2-methyl-2H-indazol-5-yl)-1H-indazole-5-carboxamide;
N-[3-(2-chlorophenoxy)cyclohexyl]-3-(2-methyl-4-pyridinyl)-1H-indazole-5-carboxamide;
N-[3-(aminocarbonyl)-3-(3-fluorophenoxy)cyclohexyl]-3-(2-methyl-4-pyridinyl)-1H-indazole-5-carboxamide;
N-[cis-3-hydroxy-3-(1H-imidazol-1-ylmethyl)cyclohexyl]-3-(2-methyl-2H-indazol-5-yl)-1H-indazole-5-carboxamide;
N-[trans-3-hydroxy-3-(1H-imidazol-1-ylmethyl)cyclohexyl]-3-(2-methyl-2H-indazol-5-yl)-1H-indazole-5-carboxamide;
N-[3-[(2-fluorophenyl)methyl]-3-methoxycyclohexyl]-3-(2-methyl-4-pyridinyl)-1H-indazole-5-carboxamide;
N-[3-(3-fluorophenoxy)-3-(hydroxymethyl)cyclohexyl]-3-(2-methyl-4-pyridinyl)-1H-indazole-5-carboxamide;
N-[3-(1H-benzimidazol-1-ylmethyl)cyclohexyl]-3-(2-methyl-2H-indazol-5-yl)-1H-indazole-5-carboxamide;
N-[trans-3-hydroxy-3-(1H-pyrazol-1-ylmethyl)cyclohexyl]-3-(2-methyl-2H-indazol-5-yl)-1H-indazole-5-carboxamide;
N-[trans-3-(1H-benzimidazol-1-ylmethyl)-3-hydroxycyclohexyl]-3-(2-methyl-2H-indazol-5-yl)-1H-indazole-5-carboxamide;
N-[cis-3-(1H-benzimidazol-1-ylmethyl)-3-hydroxycyclohexyl]-3-(2-methyl-2H-indazol-5-yl)-1H-indazole-5-carboxamide;
N-[3-[(2,6-difluorophenyl)methyl]-3-hydroxycyclohexyl]-3-(2-methyl-4-pyridinyl)-1H-indazole-5-carboxamide;
N-[3(S)-hydroxy-3-(1H-indazol-1-ylmethyl)-1(R)-cyclohexyl]-3-(2-methyl-4-pyridinyl)-1H-indazole-5-carboxamide;
N-[trans-3-[(2-fluorophenyl)methyl]-3-hydroxycyclohexyl]-3-imidazo[1,2-a]pyridiN-6-yl-1H-indazole-5-carboxamide;
N-[trans-3-hydroxy-3-[(2-methyl-1H-benzimidazol-1-yl)methyl]cyclohexyl]-3-(2-methyl-4-pyridinyl)-H-indazole-5-carboxamide;
N-[3-hydroxy-3-(hydroxyphenylmethyl)cyclohexyl]-3-(2-methyl-4-pyridinyl)-1H-indazole-5-carboxamide;
N-[3-hydroxy-3-(hydroxyphenylmethyl)cyclohexyl]-3-(2-methyl-4-pyridinyl)-1H-indazole-5-carboxamide;
N-[3(S)-[(2-fluorophenyl)methyl]-3-hydroxy-1(R)-cyclohexyl]-3-(2-methyl[1,2,4]triazolo[1,5-a]pyridiN-6-yl)-1H-indazole-5-carboxamide;
N-[3(S)-[(2-fluorophenyl)methyl]-3-hydroxy-1(R)-cyclohexyl]-3-(2-methyl-6-benzothiazolyl)-1H-indazole-5-carboxamide;
N-[3(S)-[(2-fluorophenyl)methyl]-3-hydroxy-1(R)-cyclohexyl]-3-imidazo[1,2-a]pyridiN-6-yl-1H-indazole-5-carboxamide;
N-[cis-3-hydroxy-3-(1H-pyrazolo[3,4-b]pyridiN-1-ylmethyl)cyclohexyl]-3-(2-methyl-4-pyridinyl)-1H-indazole-5-carboxamide;
N-[cis-3-hydroxy-3-(1H-pyrazolo[3,4-c]pyridiN-1-ylmethyl)cyclohexyl]-3-(2-methyl-4-pyridinyl)-1H-indazole-5-carboxamide;
3-(2-methyl-4-pyridinyl)-N-[3-(1H-pyrazolo[3,4-b]pyridiN-1-ylmethyl)cyclohexyl]-1H-indazole-5-carboxamide;
3-(2-methyl-4-pyridinyl)-N-[3-(1H-pyrazolo[3,4-c]pyridiN-1-ylmethyl)cyclohexyl]-1H-indazole-5-carboxamide;
N-[3-(3H-imidazo[4,5-b]pyridiN-3-ylmethyl)cyclohexyl]-3-(2-methyl-4-pyridinyl)-1H-indazole-5-carboxamide;
N-[3(S)-[(2,6-difluorophenyl)methyl]-3-hydroxy-1(R)-cyclohexyl]-3-(2-methyl-6-benzothiazolyl)-1H-indazole-5-carboxamide;
N-[trans-3-hydroxy-3-(2H-indazol-2-ylmethyl)cyclohexyl]-3-(2-methyl-4-pyridinyl)-1H-indazole-5-carboxamide;
N-[cis-3-[(2,3-dihydro-2-oxo-1H-indol-1-yl)methyl]-3-hydroxycyclohexyl]-3-(2-methyl-4-pyridinyl)-1H-indazole-5-carboxamide;
N-[cis-3-hydroxy-3-(2H-indazol-2-ylmethyl)cyclohexyl]-3-(2-methyl-4-pyridinyl)-1H-indazole-5-carboxamide;
N-[3-[(2,3-dihydro-2-oxo-1H-indol-1-yl)methyl]cyclohexyl]-3-(2-methyl-4-pyridinyl)-1H-indazole-5-carboxamide;
N-[3-(2H-indazol-2-ylmethyl)cyclohexyl]-3-(2-methyl-4-pyridinyl)-1H-indazole-5-carboxamide;
N-[3-(1H-indazol-1-ylmethyl)cyclohexyl]-3-(2-methyl-4-pyridinyl)-1H-indazole-5-carboxamide;

N-[3-[(2-fluorophenyl)methyl]-3-(hydroxymethyl)cyclopentyl]-3-(2-methyl-4-pyridinyl)-1H-indazole-5-carboxamide;

N-[cis-3-[(4-fluoro-1H-indazol-1-yl)methyl]-3-hydroxycyclohexyl]-3-(2-methyl-4-pyridinyl)-1H-indazole-5-carboxamide;

N-[3-[(7-fluoro-1H-indazol-1-yl)methyl]cyclohexyl]-3-(2-methyl-4-pyridinyl)-1H-indazole-5-carboxamide;

N-[3(S)-[(2-fluorophenyl)methyl]-3-hydroxy-1(R)-cyclohexyl]-3-[6-(1-methylethoxy)-3-pyridinyl]-1H-indazole-5-carboxamide;

N-[3(S)-[(2,6-difluorophenyl)methyl]-3-hydroxy-1(R)-cyclohexyl]-3-(2-methyl-2H-indazol-5-yl)-1H-indazole-5-carboxamide;

3-(6-benzothiazolyl)-N-[3(S)-[(2,6-difluorophenyl)methyl]-3-hydroxy-1(R)-cyclohexyl]-1H-indazole-5-carboxamide;

N-[3(S)-[(2,6-difluorophenyl)methyl]-3-hydroxy-1(R)-cyclohexyl]-3-(2-methyl[1,2,4]triazolo[1,5-]pyridiN-6-yl)-1H-indazole-5-carboxamide;

N-[3(S)-[(2-fluoro-6-methoxyphenyl)methyl]-3-hydroxy-1(R)-cyclohexyl]-3-(2-methyl-4-pyridinyl)-1H-indazole-5-carboxamide;

N-[3(S)-[(2-fluoro-6-methoxyphenyl)methyl]-3-hydroxy-1(R)-cyclohexyl]-3-imidazo[1,2-a]pyridiN-6-yl-1H-indazole-5-carboxamide; and N-[3(S)-[(2-fluoro-6-methoxyphenyl)methyl]-3-hydroxy-1(R)-cyclohexyl]-3-(2-methyl-6-benzothiazolyl)-1H-indazole-5-carboxamide; or a pharmaceutically acceptable salt thereof.

In another embodiment, the compound of formula I is selected from the group consisting of:

N-[3-[(2-fluorophenyl)methyl]-3-hydroxycyclohexyl]-3-(2-methyl-4-pyridinyl)-1H-indazole-5-carboxamide;

N-[3-(aminocarbonyl)-3-(3-fluorophenoxy)cyclohexyl]-3-(2-methyl-4-pyridinyl)-1H-indazole-5-carboxamide;

N-[3-(3-fluorophenoxy)-3-(hydroxymethyl)cyclohexyl]-3-(2-methyl-4-pyridinyl)-1H-indazole-5-carboxamide;

N-[3-(1H-benzimidazol-1-ylmethyl)cyclohexyl]-3-(2-methyl-2H-indazol-5-yl)-1H-indazole-5-carboxamide;

N-[trans-3-(1H-benzimidazol-1-ylmethyl)-3-hydroxycyclohexyl]-3-(2-methyl-2H-indazol-5-yl)-1H-indazole-5-carboxamide;

N-[3-[(2,6-difluorophenyl)methyl]-3-hydroxycyclohexyl]-3-(2-methyl-4-pyridinyl)-1H-indazole-5-carboxamide;

N-[3(S)-hydroxy-3-(1H-indazol-1-ylmethyl)-1(R)-cyclohexyl]-3-(2-methyl-4-pyridinyl)-1H-indazole-5-carboxamide;

N-[3(S)-[(2-fluorophenyl)methyl]-3-hydroxy-1(R)-cyclohexyl]-3-(2-methyl[1,2,4]triazolo[1,5-a]pyridiN-6-yl)-1H-indazole-5-carboxamide;

N-[3(S)-[(2-fluorophenyl)methyl]-3-hydroxy-1(R)-cyclohexyl]-3-(2-methyl-6-benzothiazolyl)-1H-indazole-5-carboxamide;

N-[3(S)-[(2-fluorophenyl)methyl]-3-hydroxy-1(R)-cyclohexyl]-3-imidazo[1,2-a]pyridiN-6-yl-1H-indazole-5-carboxamide;

N-[cis-3-hydroxy-3-(1H-pyrazolo[3,4-b]pyridiN-1-ylmethyl)cyclohexyl]-3-(2-methyl-4-pyridinyl)-1H-indazole-5-carboxamide;

3-(2-methyl-4-pyridinyl)-N-[3-(1H-pyrazolo[3,4-b]pyridiN-1-ylmethyl)cyclohexyl]-1H-indazole-5-carboxamide;

N-[3(S)-[(2,6-difluorophenyl)methyl]-3-hydroxy-1(R)-cyclohexyl]-3-(2-methyl-6-benzothiazolyl)-1H-indazole-5-carboxamide;

N-[cis-3-[(2,3-dihydro-2-oxo-1H-indol-1-yl)methyl]-3-hydroxycyclohexyl]-3-(2-methyl-4-pyridinyl)-1H-indazole-5-carboxamide;

N-[3-(1H-indazol-1-ylmethyl)cyclohexyl]-3-(2-methyl-4-pyridinyl)-1H-indazole-5-carboxamide;

N-[3(S)-[(2,6-difluorophenyl)methyl]-3-hydroxy-1(R)-cyclohexyl]-3-(2-methyl-2H-indazol-5-yl)-1H-indazole-5-carboxamide;

N-[3(S)-[(2-fluoro-6-methoxyphenyl)methyl]-3-hydroxy-1(R)-cyclohexyl]-3-(2-methyl-4-pyridinyl)-1H-indazole-5-carboxamide;

N-[3(S)-[(2-fluoro-6-methoxyphenyl)methyl]-3-hydroxy-1(R)-cyclohexyl]-3-imidazo[1,2-a]pyridiN-6-yl-1H-indazole-5-carboxamide; and N-[3(S)-[(2-fluoro-6-methoxyphenyl)methyl]-3-hydroxy-1(R)-cyclohexyl]-3-(2-methyl-6-benzothiazolyl)-1H-indazole-5-carboxamide; or a pharmaceutically acceptable salt thereof.

The compounds, compositions and methods provided herein are particularly deemed useful for the treatment of cancer. Cancers that may be treated by the compounds, compositions and methods of the invention include, but are not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposirs sarcoma, leiomyoma, hemangioma, lipoma, neurofibroma, fibroma), large bowel (adenocarcinoma, tubular adenoma, villous adenoma, hamartoma, leiomyoma) colorectal; Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast; Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma. Thus, the term "cancerous cell" as provided herein, includes a cell afflicted by any one of the above-identified conditions.

In one embodiment, cancers that may be treated by the compounds, compositions and methods of the invention include, but are not limited to: lung cancer, pancreatic cancer, colon cancer, colorectal cancer, myeloid leukemias, acute myelogenous leukemia, chronic myelogenous leukemia, chronic myelomonocytic leukemia, thyroid cancer, myelodysplastic syndrome, bladder carcinoma, epidermal carcinoma, melanoma, breast cancer, prostate cancer, head and neck cancers, ovarian cancer, brain cancers, cancers of mesenchymal origin, sarcomas, tetracarcinomas, nuroblastomas, kidney carcinomas, hepatomas, non-Hodgkin's lymphoma, multiple myeloma, and anaplastic thyroid carcinoma.

In another embodiment, cancers that may be treated by the compounds, compositions and methods of the invention include, but are not limited to: breast, prostate, colon, colorectal, lung, brain, testicular, stomach, pancrease, skin, small intestine, large intestine, throat, head and neck, oral, bone, liver, bladder, kidney, thyroid and blood.

In another embodiment, cancers that may be treated by the compounds, compositions and methods of the invention include breast, prostate, colon, ovary, endometrium and thyroid.

In another embodiment, cancers that may be treated by the compounds, compositions and methods of the invention include breast and prostate.

The compounds of the invention are also useful in preparing a medicament that is useful in treating cancer.

The instant compounds are also useful in combination with therapeutic, chemotherapeutic and anti-cancer agents. Combinations of the presently disclosed compounds with therapeutic, chemotherapeutic and anti-cancer agents are within the scope of the invention. Examples of such agents can be found in *Cancer Principles and Practice of Oncology* by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Such agents include the following: estrogen receptor modulators, androgen receptor modulators, retinoid receptor modulators, cytotoxic/cytostatic agents, antiproliferative agents, prenyl-protein transferase inhibitors, HMG-CoA reductase inhibitors and other angiogenesis inhibitors, HIV protease inhibitors, reverse transcriptase inhibitors, inhibitors of cell proliferation and survival signaling, bisphosphonates, aromatase inhibitors, siRNA therapeutics, γ-secretase inhibitors, agents that interfere with receptor tyrosine kinases (RTKs) and agents that interfere with cell cycle checkpoints. The instant compounds are particularly useful when co-administered with radiation therapy.

"Estrogen receptor modulators" refers to compounds that interfere with or inhibit the binding of estrogen to the receptor, regardless of mechanism. Examples of estrogen receptor modulators include, but are not limited to, tamoxifen, raloxifene, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenyl-hydrazone, and SH646.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"Retinoid receptor modulators" refers to compounds which interfere or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl) retinamide, and N-4-carboxyphenyl retinamide.

"Cytotoxic/cytostatic agents" refer to compounds which cause cell death or inhibit cell proliferation primarily by interfering directly with the cell's functioning or inhibit or interfere with cell myosis, including alkylating agents, tumor necrosis factors, intercalators, hypoxia activatable compounds, microtubule inhibitors/microtubule-stabilizing agents, inhibitors of mitotic kinesins, histone deacetylase inhibitors, inhibitors of kinases involved in mitotic progression, inhibitors of kinases involved in growth factor and cytokine signal transduction pathways, antimetabolites, biological response modifiers, hormonal/anti-hormonal therapeutic agents, haematopoietic growth factors, monoclonal antibody targeted therapeutic agents, topoisomerase inhibitors, proteosome inhibitors, ubiquitin ligase inhibitors, and aurora kinase inhibitors.

Examples of cytotoxic/cytostatic agents include, but are not limited to, platinum coordinator compounds, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine-platinum(II)]bis[diamine (chloro)platinum (II)]tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxy-10-hydroxycaminomycin, annamycin, galarubicin, elinafide, MEN10755, 4-demethoxy-3-deamino-3-aziridinyl-4-methylsulphonyl-daunorubicin (see WO 00/50032), Raf kinase inhibitors (such as Bay43-9006) and mTOR inhibitors (such as Wyeth's CCI-779).

An example of a hypoxia activatable compound is tirapazamine.

Examples of proteosome inhibitors include but are not limited to lactacystin and MLN-341 (Velcade).

Examples of microtubule inhibitors/microtubule-stabilising agents include taxanes in general. Specific compounds include paclitaxel (Taxol®), vindesine sulfate, 3',4'-didehydro-4'-deoxy-8'-norvincaleukoblastine, docetaxel (Taxotere®), rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl)benzene sulfonamide, anhydrovinblastine, N,N-dimethyl-L-valyl-L-valyl-N-methyl-L-valyl-L-prolyl-L-proline-t-butylamide, TDX258, the epothilones (see for example U.S. Pat. Nos. 6,284,781 and 6,288,237) and BMS188797. In an embodiment the epothilones are not included in the microtubule inhibitors/microtubule-stabilising agents.

Some examples of topoisomerase inhibitors are topotecan, hycaptamine, irinotecan, rubitecan, 6-ethoxypropionyl-3',4'-O-exo-benzylidene-chartreusin, 9-methoxy-N,N-dimethyl-5-nitropyrazolo[3,4,5-kl]acridine-2-(6H) propanamine, 1-amino-9-ethyl-5-fluoro-2,3-dihydro-9-hydroxy-4-methyl-1H,2H-benzo[de]pyrano[3',4':b,7]-indolizino[1,2b]quinoline-10,13(9H,15H)dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, (5a,5aB,8aa,9b)-9-[2-[N-[2-(dimethylamino)ethyl]-N-methylamino]ethyl]-5-[4-hydroxy-3,5-dimethoxyphenyl]-5,5a,6,8,8a,9-hexohydrofuro(3',4':6,7)naphtho(2,3-d)-1,3-dioxol-6-one, 2,3-(methylenedioxy)-5-methyl-7-hydroxy-8-methoxybenzo[c]-phenanthridinium, 6,9-bis[(2-aminoethyl)amino]benzo[g]isoquinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2(diethylamino)ethylamino]-7-methoxy-9-oxo-9H-thioxanthen-4-ylmethyl]formamide, N-(2-(dimethylamino)ethyl)acridine-4-carboxamide, 6-[[2-(dimethylamino)ethyl]amino]-3-hydroxy-7H-indeno[2,1-c]quinolin-7-one, and dimesna.

Examples of inhibitors of mitotic kinesins, and in particular the human mitotic kinesin KSP, are described in Publications WO03/039460, WO03/050064, WO03/050122, WO03/049527, WO03/049679, WO03/049678, WO04/039774, WO03/079973, WO03/099211, WO03/105855, WO03/106417, WO04/037171, WO04/058148, WO04/058700, WO04/126699, WO05/018638, WO05/019206, WO05/019205, WO05/018547, WO05/017190, US2005/0176776. In an embodiment inhibitors of mitotic kinesins include, but are not limited to inhibitors of KSP, inhibitors of MKLP1, inhibitors of CENP-E, inhibitors of MCAK and inhibitors of Rab6-KIFL.

Examples of "histone deacetylase inhibitors" include, but are not limited to, SAHA, TSA, oxamflatin, PXD101, MG98 and scriptaid. Further reference to other histone deacetylase inhibitors may be found in the following manuscript; Miller, T. A. et al. *J. Med. Chem.* 46(24):5097-5116 (2003).

"Inhibitors of kinases involved in mitotic progression" include, but are not limited to, inhibitors of aurora kinase, inhibitors of Polo-like kinases (PLK; in particular inhibitors of PLK-1), inhibitors of bub-1 and inhibitors of bub-R1. An example of an "aurora kinase inhibitor" is VX-680.

"Antiproliferative agents" includes antisense RNA and DNA oligonucleotides such as G3139, ODN698, RVASKRAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydrobenzofuryl)sulfonyl]-N'-(3,4-dichlorophenyl)urea, N6-[4-deoxy-4-[N2-[2(E),4(E)-tetradecadienoyl]glycylamino]-L-glycero-B-L-manno-heptopyranosyl]adenine, aplidine, ecteinascidin, troxacitabine, 4-[2-amino-4-oxo-4,6,7,8-tetrahydro-3H-pyrimidino[5,4-b][1,4]thiazin-6-yl-(S)-ethyl]-2,5-thienoyl-L-glutamic acid, aminopterin, 5-fluorouracil, alanosine, 11-acetyl-8-(carbamoyloxymethyl)-4-formyl-6-methoxy-14-oxa-1,11-diazatetracyclo(7.4.1.0.0)-tetradeca-2,4,6-trien-9-yl acetic acid ester, swainsonine, lometrexol, dexrazoxane, methioninase, 2'-cyano-2'-deoxy-N4-palmitoyl-1-B-D-arabino furanosyl cytosine, 3-aminopyridine-2-carboxaldehyde thiosemicarbazone and trastuzumab.

Examples of monoclonal antibody targeted therapeutic agents include those therapeutic agents which have cytotoxic agents or radioisotopes attached to a cancer cell specific or target cell specific monoclonal antibody. Examples include Bexxar.

"HMG-CoA reductase inhibitors" refers to inhibitors of 3-hydroxy-3-methylglutaryl-CoA reductase. Examples of HMG-CoA reductase inhibitors that may be used include but are not limited to lovastatin (MEVACOR®; see U.S. Pat. Nos. 4,231,938, 4,294,926 and 4,319,039), simvastatin (ZOCOR®; see U.S. Pat. Nos. 4,444,784, 4,820,850 and 4,916,239), pravastatin (PRAVACHOL®; see U.S. Pat. Nos. 4,346,227, 4,537,859, 4,410,629, 5,030,447 and 5,180,589), fluvastatin (LESCOL®; see U.S. Pat. Nos. 5,354,772, 4,911,165, 4,929,437, 5,189,164, 5,118,853, 5,290,946 and 5,356,896), atorvastatin (LIPITOR®; see U.S. Pat. Nos. 5,273,995, 4,681,893, 5,489,691 and 5,342,952) and cerivastatin (also known as rivastatin and BAYCHOL®; see U.S. Pat. No. 5,177,080). The structural formulas of these and additional HMG-CoA reductase inhibitors that may be used in the instant methods are described at page 87 of M. Yalpani, "Cholesterol Lowering Drugs", *Chemistry & Industry*, pp. 85-89 (5 Feb. 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefor the use of such salts, esters, open-acid and lactone forms is included within the scope of this invention.

"Prenyl-protein transferase inhibitor" refers to a compound which inhibits any one or any combination of the prenyl-protein transferase enzymes, including farnesyl-protein transferase (FPTase), geranylgeranyl-protein transferase type T (GGPTase-1), and geranylgeranyl-protein transferase type-11 (GGPTase-II, also called Rab GGPTase).

Examples of prenyl-protein transferase inhibitors can be found in the following publications and patents: WO 96/30343, WO 97/18813, WO 97/21701, WO 97/23478, WO 97/38665, WO 98/28980, WO 98/29119, WO 95/32987, U.S. Pat. No. 5,420,245, U.S. Pat. No. 5,523,430, U.S. Pat. No. 5,532,359, U.S. Pat. No. 5,510,510, U.S. Pat. No. 5,589,485, U.S. Pat. No. 5,602,098, European Patent Publ. 0 618 221, European Patent Publ. 0 675 112, European Patent Publ. 0 604 181, European Patent Publ. 0 696 593, WO 94/19357, WO 95/08542, WO 95/11917, WO 95/12612, WO 95/12572, WO 95/10514, U.S. Pat. No. 5,661,152, WO 95/10515, WO 95/10516, WO 95/24612, WO 95/34535, WO 95/25086, WO 96/05529, WO 96/06138, WO 96/06193, WO 96/16443, WO 96/21701, WO 96/21456, WO 96/22278, WO 96/24611, WO 96/24612, WO 96/05168, WO 96/05169, WO 96/00736, U.S. Pat. No. 5,571,792, WO 96/17861, WO 96/33159, WO 96/34850, WO 96/34851, WO 96/30017, WO 96/30018, WO 96/30362, WO 96/30363, WO 96/31111, WO 96/31477, WO 96/31478, WO 96/31501, WO 97/00252, WO 97/03047, WO 97/03050, WO 97/04785, WO 97/02920, WO 97/17070, WO 97/23478, WO 97/26246, WO 97/30053, WO 97/44350, WO 98/02436, and U.S. Pat. No. 5,532,359. For an example of the role of a prenyl-protein transferase inhibitor on angiogenesis see *European J of Cancer*, Vol. 35, No. 9, pp. 1394-1401 (1999).

"Angiogenesis inhibitors" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-$\alpha$, interleukin-12, pentosan polysulfate, cyclooxygenase inhibitors, including nonsteroidal anti-inflammatories (NSAIDs) like aspirin and ibuprofen as well as selective cyclooxygenase-2 inhibitors like celecoxib and rofecoxib (*PNAS*, Vol. 89, p. 7384 (1992); *JNCI*, Vol. 69, p. 475 (1982); *Arch. Opthalmol.*, Vol. 108, p. 573 (1990); *Anat. Rec.*, Vol. 238, p. 68 (1994); *FEBS Letters*, Vol. 372, p. 83 (1995); *Clin, Orthop.* Vol. 313, p. 76 (1995); *J. Mol. Endocrinol.*, Vol. 16, p. 107 (1996); *Jpn. J. Pharmacol.*, Vol. 75, p. 105 (1997); *Cancer Res.*, Vol. 57, p. 1625 (1997); *Cell*, Vol. 93, p. 705 (1998); *Intl. J. Mol. Med.*, Vol. 2, p. 715 (1998); *J. Biol. Chem.*, Vol. 274, p. 9116 (1999)), steroidal anti-inflammatories (such as corticosteroids, mineralocorticoids, dexamethasone, prednisone, prednisolone, methylpred, betamethasone), carboxyamidotriazole, combretastatin A-4, squalamine, 6-O-chloroacetylcarbonyl)-fumagillol, thalidomide, angiostatin, troponin-1, angiotensin II antagonists (see Fernandez et al., *J. Lab. Clin. Med.* 105:141-145 (1985)), and antibodies to VEGF (see, *Nature Biotechnology*, Vol. 17, pp. 963-968 (October 1999); Kim et al., *Nature*, 362, 841-844 (1993); WO 00/44777; and WO 00/61186).

Other therapeutic agents that modulate or inhibit angiogenesis and may also be used in combination with the compounds of the instant invention include agents that modulate or inhibit the coagulation and fibrinolysis systems (see review in *Clin. Chem. La. Med.* 38:679-692 (2000)). Examples of such agents that modulate or inhibit the coagulation and fibrinolysis pathways include, but are not limited to, heparin (see *Thromb. Haemost.* 80:10-23 (1998)), low molecular weight heparins and carboxypeptidase U inhibitors (also known as inhibitors of active thrombin activatable fibrinolysis inhibitor [TAFIa]) (see *Thrombosis Res.* 101:329-354 (2001)). TAFIa inhibitors have been described in U.S. Ser. Nos. 60/310,927 (filed Aug. 8, 2001) and 60/349,925 (filed Jan. 18, 2002).

"Agents that interfere with cell cycle checkpoints" refer to compounds that inhibit protein kinases that transduce cell cycle checkpoint signals, thereby sensitizing the cancer cell to DNA damaging agents. Such agents include inhibitors of ATR, ATM, the CHK11 and CHK12 kinases and cdk and cdc kinase inhibitors and are specifically exemplified by 7-hydroxystaurosporin, flavopiridol, CYC202 (Cyclacel) and BMS-387032.

"Agents that interfere with receptor tyrosine kinases (RTKs)" refer to compounds that inhibit RTKs and therefore mechanisms involved in oncogenesis and tumor progression. Such agents include inhibitors of c-Kit, Eph, PDGF, Flt3 and c-Met. Further agents include inhibitors of RTKs as described by Bume-Jensen and Hunter, *Nature*, 411:355-365, 2001.

"Inhibitors of cell proliferation and survival signalling pathway" refer to compounds that inhibit signal transduction cascades downstream of cell surface receptors. Such agents include inhibitors of serine/threonine kinases (including but not limited to inhibitors of Akt such as described in WO 02/083064, WO 02/083139, WO 02/083140, US 2004-0116432, WO 02/083138, US 2004-0102360, WO 03/086404, WO 03/086279, WO 03/086394, WO 03/084473, WO 03/086403, WO 2004/041162, WO 2004/096131, WO 2004/096129, WO 2004/096135, WO 2004/096130, WO 2005/100356, WO 2005/100344, US 2005/029941, US 2005/ 44294, US 2005/43361, 60/734,188, 60/652,737, 60/670, 469), inhibitors of Raf kinase (for example BAY-43-9006), inhibitors of MEK (for example CI-1040 and PD-098059), inhibitors of mTOR (for example Wyeth CCI-779), and inhibitors of PI3K (for example LY294002).

As described above, the combinations with NSAID's are directed to the use of NSAID's which are potent COX-2 inhibiting agents. For purposes of this specification an NSAID is potent if it possesses an $IC_{50}$ for the inhibition of COX-2 of 1 μM or less as measured by cell or microsomal assays.

The invention also encompasses combinations with NSAID's which are selective COX-2 inhibitors. For purposes of this specification NSAID's which are selective inhibitors of COX-2 are defined as those which possess a specificity for inhibiting COX-2 over COX-1 of at least 100 fold as measured by the ratio of $IC_{50}$ for COX-2 over 1050 for COX-1 evaluated by cell or microsomal assays. Such compounds include, but are not limited to those disclosed in U.S. Pat. No. 5,474,995, U.S. Pat. No. 5,861,419, U.S. Pat. No. 6,001,843, U.S. Pat. No. 6,020,343, U.S. Pat. No. 5,409,944, U.S. Pat. No. 5,436,265, U.S. Pat. No. 5,536,752, U.S. Pat. No. 5,550, 142, U.S. Pat. No. 5,604,260, U.S. Pat. No. 5,698,584, U.S. Pat. No. 5,710,140, WO 94/15932, U.S. Pat. No. 5,344,991, U.S. Pat. No. 5,134,142, U.S. Pat. No. 5,380,738, U.S. Pat. No. 5,393,790, U.S. Pat. No. 5,466,823, U.S. Pat. No. 5,633, 272 and U.S. Pat. No. 5,932,598, all of which are hereby incorporated by reference.

Inhibitors of COX-2 that are particularly useful in the instant method of treatment are: 3-phenyl-4-(4-(methylsulfonyl)phenyl)-2-(5H)-furanone; and 5-chloro-3-(4-methylsulfonyl)phenyl-2-(2-methyl-5-pyridinyl)pyridine; or a pharmaceutically acceptable salt thereof.

Compounds that have been described as specific inhibitors of COX-2 and are therefore useful in the present invention include, but are not limited to, the following: parecoxib, BEXTRA® and CELEBREX® or a pharmaceutically acceptable salt thereof.

Other examples of angiogenesis inhibitors include, but are not limited to, endostatin, ukrain, ranpirnase, IM862,5-methoxy-4-[2-methyl-3-(3-methyl-2-butenyl)oxiranyl]-1-oxaspiro[2,5]oct-6-yl(chloroacetyl)carbamate, acetyldinanaline, 5-amino-1-[[3,5-dichloro-4-(4-chlorobenzoyl)phenyl]methyl]-1H-1,2,3-triazole-4-carboxamide, CM101, squalamine, combretastatin, RP14610, NX31838, sulfated mannopentaose phosphate, 7,7-(carbonyl-bis[imino-N-methyl-4,2-pyrrolocarbonylimino[N-methyl-4,2-pyrrole]-carbonylimino]-bis-(1,3-naphthalene disulfonate), and 3-[(2,4-dimethylpyrrol-5-yl)methylene]-2-indolinone (SU5416).

As used above, "integrin blockers" refers to compounds which selectively antagonize, inhibit or counteract binding of a physiological ligand to the $\alpha_v\beta_3$ integrin, to compounds which selectively antagonize, inhibit or counteract binding of a physiological ligand to the $\alpha v\beta5$ integrin, to compounds which antagonize, inhibit or counteract binding of a physiological ligand to both the $\alpha_v\beta_3$ integrin and the $\alpha_v\beta_5$ integrin, and to compounds which antagonize, inhibit or counteract the activity of the particular integrin(s) expressed on capillary endothelial cells. The term also refers to antagonists of the $\alpha_v\beta_6$, $\alpha_v\beta_8$, $\alpha_2\beta_1$, $\alpha_5\beta_1$, $\alpha_6\beta_1$ and $\alpha_6\beta_4$ integrins. The term also refers to antagonists of any combination of $\alpha_v\beta_3$, $\alpha_v\beta_5$, $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins.

Some specific examples of tyrosine kinase inhibitors include N-(trifluoromethylphenyl)-5-methylisoxazol-4-carboxamide, 3-[(2,4-dimethylpyrrol-5-yl)methylidenyl)indolin-2-one, 17-(allylamino)-17-demethoxygeldanamycin, 4-(3-chloro-4-fluorophenylamino)-7-methoxy-6-[3-(4-morpholinyl)propoxyl]quinazoline, N-(3-ethynylphenyl)-6,7-bis(2-methoxyethoxy)-4-quinazolinamine, BIBX1382, 2,3,9,10,11,12-hexahydro-10-(hydroxymethyl)-10-hydroxy-9-methyl-9,12-epoxy-1H-diindolo[1,2,3-fg:3',2',1'-kl]pyrrolo[3,4-i][1,6]benzodiazocin-1-one, SH268, genistein, STI571, CEP2563, 4-(3-chlorophenylamino)-5,6-dimethyl-7H-pyrrolo[2,3-d]pyrimidinemethane sulfonate, 4-(3-bromo-4-hydroxyphenyl)amino-6,7-dimethoxyquinazoline, 4-(4'-hydroxyphenyl)amino-6,7-dimethoxyquinazoline, SU6668, STI571A, N-4-chlorophenyl-4-(4-pyridylmethyl)-1-phthalazinamine, and EMD121974.

Combinations with compounds other than anti-cancer compounds are also encompassed in the instant methods. For example, combinations of the instantly claimed compounds with PPAR-γ (i.e., PPAR-gamma) agonists and PPAR-δ (i.e., PPAR-delta) agonists are useful in the treatment of certain malignancies. PPAR-γ and PPAR-δ are the nuclear peroxisome proliferator-activated receptors γ and δ. The expression of PPAR-γ on endothelial cells and its involvement in angiogenesis has been reported in the literature (see *J. Cardiovasc. Pharmacol.* 1998; 31:909-913; *J. Biol. Chem.* 1999; 274: 9116-9121; *Invest. Ophthalmol Vis. Sci.* 2000; 41:2309-2317). More recently, PPAR-γ agonists have been shown to inhibit the angiogenic response to VEGF in vitro; both troglitazone and rosiglitazone maleate inhibit the development of retinal neovascularization in mice. (*Arch. Ophthamol.* 2001; 119:709-717). Examples of PPAR-γ agonists and PPAR-γ/α agonists include, but are not limited to, thiazolidinediones (such as DRF2725, CS-011, troglitazone, rosiglitazone, and pioglitazone), fenofibrate, gemfibrozil, clofibrate, GW2570, SB219994, AR-H039242, JTT-501, MCC-555, GW2331, GW409544, NN2344, KRP297, NP0110, DRF4158, NN622, GI262570, PNU182716, DRF552926, 2-[(5,7-dipropyl-3-trifluoromethyl-1,2-benzisoxazol-6-yl)oxy]-2-methylpropionic acid (disclosed in U.S. Ser. No. 09/782,856), and 2(R)-7-(3-(2-chloro-4-(4-fluorophenoxy) phenoxy)propoxy)-2-ethylchromane-2-carboxylic acid (disclosed in U.S. Ser. No. 60/235,708 and 60/244,697).

Another embodiment of the instant invention is the use of the presently disclosed compounds in combination with gene therapy for the treatment of cancer. For an overview of genetic strategies to treating cancer see Hall et al (*Am. J. Hum. Genet.* 61:785-789, 1997) and Kufe et al (Cancer Medicine, 5th Ed, pp 876-889, BC Decker, Hamilton 2000). Gene therapy can be used to deliver any tumor suppressing gene. Examples of such genes include, but are not limited to, p53, which can be delivered via recombinant virus-mediated gene transfer (see U.S. Pat. No. 6,069,134, for example), a uPA/uPAR antagonist ("Adenovirus-Mediated Delivery of a uPA/uPAR Antagonist Suppresses Angiogenesis-Dependent Tumor Growth and Dissemination in Mice," Gene Therapy, August 1998; 5(8):1105-13), and interferon gamma (*J. Immunol.* 2000; 164:217-222).

The compounds of the instant invention may also be administered in combination with an inhibitor of inherent multidrug resistance (MDR), in particular MDR associated with high levels of expression of transporter proteins. Such MDR inhibitors include inhibitors of p-glycoprotein (P-gp), such as LY335979, XR9576, OC144-093, R101922, VX853 and PSC833 (valspodar).

A compound of the present invention may be employed in conjunction with anti-emetic agents to treat nausea or emesis, including acute, delayed, late-phase, and anticipatory emesis, which may result from the use of a compound of the present invention, alone or with radiation therapy. For the prevention or treatment of emesis, a compound of the present invention may be used in conjunction with other anti-emetic agents, especially neurokinin-1 receptor antagonists, 5HT3 receptor antagonists, such as ondansetron, granisetron, tropisetron, and zatisetron, GABAB receptor agonists, such as baclofen, a corticosteroid such as Decadron (dexamethasone), Kenalog, Aristocort, Nasalide, Preferid, Benecorten or others such as disclosed in U.S. Pat. Nos. 2,789,118, 2,990,401, 3,048,581, 3,126,375, 3,929,768, 3,996,359, 3,928,326 and 3,749,712, an antidopaminergic, such as the phenothiazines (for example prochlorperazine, fluphenazine, thioridazine and mesoridazine), metoclopramide or dronabinol. In another embodiment, conjunctive therapy with an anti-emesis agent selected from a neurokinin-1 receptor antagonist, a 5HT3 receptor antagonist and a corticosteroid is disclosed for the treatment or prevention of emesis that may result upon administration of the instant compounds.

Neurokinin-1 receptor antagonists of use in conjunction with the compounds of the present invention are fully described, for example, in U.S. Pat. Nos. 5,162,339, 5,232,929, 5,242,930, 5,373,003, 5,387,595, 5,459,270, 5,494,926, 5,496,833, 5,637,699, 5,719,147; European Patent Publication Nos. EP 0 360 390, 0 394 989, 0 428 434, 0 429 366, 0 430 771, 0 436 334, 0 443 132, 0 482 539, 0 498 069, 0 499 313, 0 512 901, 0 512 902, 0 514 273, 0 514 274, 0 514 275, 0 514 276, 0 515 681, 0 517 589, 0 520 555, 0 522 808, 0 528 495, 0 532 456, 0 533 280, 0 536 817, 0 545 478, 0 558 156, 0 577 394, 0 585 913, 0 590 152, 0 599 538, 0 610 793, 0 634 402, 0 686 629, 0 693 489, 0 694 535, 0 699 655, 0 699 674, 0 707 006, 0 708 101, 0 709 375, 0 709 376, 0 714 891, 0 723 959, 0 733 632 and 0 776 893; PCT International Patent Publication Nos. WO 90/05525, 90/05729, 91/09844, 91/18899, 92/01688, 92/06079, 92/12151, 92/15585, 92/17449, 92/20661, 92/20676, 92/21677, 92/22569, 93/00330, 93/00331, 93/01159, 93/01165, 93/01169, 93/01170, 93/06099, 93/09116, 93/10073, 93/14084, 93/14113, 93/18023, 93/19064, 93/21155, 93/21181, 93/23380, 93/24465, 94/00440, 94/01402, 94/02461, 94/02595, 94/03429, 94/03445, 94/04494, 94/04496, 94/05625, 94/07843, 94/08997, 94/10165, 94/10167, 94/10168, 94/10170, 94/11368, 94/13639, 94/13663, 94/14767, 94/15903, 94/19320, 94/19323, 94/20500, 94/26735, 94/26740, 94/29309, 95/02595, 95/04040, 95/04042, 95/06645, 95/07886, 95/07908, 95/08549, 95/11880, 95/14017, 95/15311, 95/16679, 95/17382, 95/18124, 95/18129, 95/19344, 95/20575, 95/21819, 95/22525, 95/23798, 95/26338, 95/28418, 95/30674, 95/30687, 95/33744, 96/05181, 96/05193, 96/05203, 96/06094, 96/07649, 96/10562, 96/16939, 96/18643, 96/20197, 96/21661, 96/29304, 96/29317, 96/29326, 96/29328, 96/31214, 96/32385, 96/37489, 97/01553, 97/01554, 97/03066, 97/08144, 97/14671, 97/17362, 97/18206, 97/19084, 97/19942 and 97/21702; and in British Patent Publication Nos. 2 266 529, 2 268 931, 2 269 170, 2 269 590, 2 271 774, 2 292 144, 2 293 168, 2 293 169, and 2 302 689. The preparation of such compounds is fully described in the aforementioned patents and publications, which are incorporated herein by reference.

In an embodiment, the neurokinin-1 receptor antagonist for use in conjunction with the compounds of the present invention is selected from: 2-(R)-(1-(R)-(3,5-bis(trifluoromethyl)phenyl)ethoxy)-3-(S)-(4-fluorophenyl)-4-(3-(5-oxo-1H,4H-1,2,4-triazolo)methyl)morpholine, or a pharmaceutically acceptable salt thereof, which is described in U.S. Pat. No. 5,719,147.

A compound of the instant invention may also be administered with an agent useful in the treatment of anemia. Such an anemia treatment agent is, for example, a continuous eythropoiesis receptor activator (such as epoetin alfa).

A compound of the instant invention may also be administered with an agent useful in the treatment of neutropenia. Such a neutropenia treatment agent is, for example, a hematopoietic growth factor which regulates the production and function of neutrophils such as a human granulocyte colony stimulating factor, (G-CSF). Examples of a G-CSF include filgrastim.

A compound of the instant invention may also be administered with an immunologic-enhancing drug, such as levamisole, isoprinosine and Zadaxin.

A compound of the instant invention may also be useful for treating or preventing cancer in combination with P450 inhibitors including: xenobiotics, quinidine, tyramine, ketoconazole, testosterone, quinine, methyrapone, caffeine, phenelzine, doxorubicin, troleandomycin, cyclobenzaprine, erythromycin, cocaine, furafyline, cimetidine, dextromethorphan, ritonavir, indinavir, amprenavir, diltiazem, terfenadine, verapamil, cortisol, itraconazole, mibefradil, nefazodone and nelfinavir.

A compound of the instant invention may also be useful for treating or preventing cancer in combination with Pgp and/or BCRP inhibitors including: cyclosporin A, PSC833, GF120918, cremophorEL, fumitremorgin C, Ko132, Ko134, Iressa, Imatnib mesylate, EKI-785, C11033, novobiocin, diethylstilbestrol, tamoxifen, resperpine, VX-710, tryprostatin A, flavonoids, ritonavir, saquinavir, nelfinavir, omeprazole, quinidine, verapamil, terfenadine, ketoconazole, nifidepine, FK506, amiodarone, XR9576, indinavir, amprenavir, cortisol, testosterone, LY335979, OC144-093, erythromycin, vincristine, digoxin and talinolol.

A compound of the instant invention may also be useful for treating or preventing cancer, including bone cancer, in combination with bisphosphonates (understood to include bisphosphonates, diphosphonates, bisphosphonic acids and diphosphonic acids). Examples of bisphosphonates include but are not limited to: etidronate (Didronel), pamidronate (Aredia), alendronate (Fosamax), risedronate (Actonel), zoledronate (Zometa), ibandronate (Boniva), incadronate or cimadronate, clodronate, EB-1053, minodronate, neridronate, piridronate and tiludronate including any and all pharmaceutically acceptable salts, derivatives, hydrates and mixtures thereof.

A compound of the instant invention may also be useful for treating or preventing breast cancer in combination with antihormonal agents. Examples of antihormonal agents include, but are not limited to: aromatase inhibitors, antiestrogens, and LHRH analogues.

Examples of aromatase inhibitors include but are not limited to: Anastrozole (e.g., Arimidex), Letrozole (e.g., Femara), Exemestane (Aromasin), Fadrozole and Formestane (e.g., Lentaron).

Examples of antiestrogens include but are not limited to: Tamoxifen (e.g., Nolvadex), Fulvestrant (e.g., Faslodex), Raloxifene (e.g., Evista), and Acolbifene.

Examples of LHRH analogues include but are not limited to: Goserelin (e.g., Zoladex) and Leuprolide (e.g., Leuprolide Acetate, such as Lupron or Lupron Depot)."

Thus, a compound of the instant invention may also be useful for treating or preventing breast cancer in combination with aromatase inhibitors. Examples of aromatase inhibitors include but are not limited to: anastrozole, letrozole and exemestane.

A compound of the instant invention may also be useful for treating or preventing breast cancer in combination with aromatase inhibitors. Examples of aromatase inhibitors include but are not limited to: anastrozole, letrozole and exemestane.

A compound of the instant invention may also be useful for treating or preventing cancer in combination with siRNA therapeutics.

The compounds of the instant invention may also be administered in combination with γ-secretase inhibitors and/or inhibitors of NOTCH signaling. Such inhibitors include compounds described in WO 01/90084, WO 02/30912, WO 01/70677, WO 03/013506, WO 02/36555, WO 03/093252, WO 03/093264, WO 03/093251, WO 03/093253, WO 2004/039800, WO 2004/039370, WO 2005/030731, WO 2005/014553, U.S. Ser. No. 10/957,251, WO 2004/089911, WO 02/081435, WO 02/081433, WO 03/018543, WO 2004/031137, WO 2004/031139, WO 2004/031138, WO 2004/101538, WO 2004/101539 and WO 02/47671 (including LY-450139).

Inhibitors of Akt, as disclosed in the following publications; WO 02/083064, WO 02/083139, WO 02/083140, US 2004-0116432, WO 02/083138, US 2004-0102360, WO 03/086404, WO 03/086279, WO 03/086394, WO 03/084473, WO 03/086403, WO 2004/041162, WO 2004/096131, WO 2004/096129, WO 2004/096135, WO 2004/096130, WO 2005/100356, WO 2005/100344, US 2005/029941, US 2005/44294, US 2005/43361, 60/734,188, 60/652,737, 60/670, 469, and including compounds of the instant invention, are also useful in combination with potassium salts, magnesium salts, beta-blockers (such as atenolol) and endothelin-a (ETa) antagonists with the goal of maintaining cardiovascular homeostasis.

Inhibitors of Akt, as disclosed in the following publications; WO 02/083064, WO 02/083139, WO 02/083140, US 2004-0116432, WO 02/083138, US 2004-0102360, WO 03/086404, WO 03/086279, WO 03/086394, WO 03/084473, WO 03/086403, WO 2004/041162, WO 2004/096131, WO 2004/096129, WO 2004/096135, WO 2004/096130, WO 2005/100356, WO 2005/100344, US 2005/029941, US 2005/44294, US 2005/43361, 60/734,188, 60/652,737, 60/670, 469, and including compounds of the instant invention, are also useful in combination with insulin, insulin secretagogues, PPAR-gamma agonists, metformin, somatostatin receptor agonists such as octreotide, DPP4 inhibitors, sulfonylureas and alpha-glucosidase inhibitors with the goal of maintaining glucose homeostasis.

A compound of the instant invention may also be useful for treating or preventing cancer in combination with PARP inhibitors.

A compound of the instant invention may be used in combination with a chemotherapeutic agent selected from the group consisting of: (1) taxanes, (2) platinum coordinator compounds, (3) epidermal growth factor (EGF) inhibitors that are antibodies, (4) EGF inhibitors that are small molecules, (5) vascular endolithial growth factor (VEGF) inhibitors that are antibodies, (6) VEGF kinase inhibitors that are small molecules, (7) estrogen receptor antagonists or selective estrogen receptor modulators (SERMs), (8) anti-tumor nucleoside derivatives, (9) epothilones, (10) topoisomerase inhibitors, (11) vinca alkaloids, (12) antibodies that are inhibitors of αVβ3 integrins, (13) folate antagonists, (14) ribonucleotide reductase inhibitors, (15) anthracyclines, (16) biologics; (17) inhibitors of angiogenesis and/or suppressors of tumor necrosis factor alpha (TNF-alpha) such as thalidomide (or related imid), (18) Bcr/abl kinase inhibitors, (19) MEK1 and/or MEK 2 inhibitors that are small molecules, (20) IGF-1 and IGF-2 inhibitors that are small molecules, (21) small molecule inhibitors of RAF and BRAF kinases, (22) small molecule inhibitors of cell cycle dependent kinases such as CDK1, CDK2, CDK4 and CDK6, (23) alkylating agents, and (24) farnesyl protein transferase inhibitors (also know as FPT inhibitors or FTI (i.e., farnesyl transfer inhibitors)).

Examples of such chemotherapeutic agents include:

(1) taxanes such as paclitaxel (TAXOL®) and/or docetaxel (Taxotere®);

(2) platinum coordinator compounds, such as, for example, carboplatin, cisplatin and oxaliplatin (e.g. Eloxatin);

(3) EGF inhibitors that are antibodies, such as: HER2 antibodies (such as, for example trastuzumab (Herceptin®., Genentech, Inc.), Cetuximab (Erbitux, IMC-C225, ImClone Systems), EMD 72000 (Merck KGaA), anti-EFGR monoclonal antibody ABX (Abgenix), TheraCIM-h-R3 (Center of Molecular Immunology), monoclonal antibody 425 (Merck KGaA), monoclonal antibody ICR-62 (ICR, Sutton, England); Herzyme (Elan Pharmaceutical Technologies and Ribozyme Pharmaceuticals), PKI 166 (Novartis), EKB 569 (Wyeth-Ayerst), GW 572016 (GlaxoSmithKline), CI-1033 (Pfizer Global Research and Development), trastuzmab-maytansinoid conjugate (Genentech, Inc.), mitumomab (Imclone Systems and Merck KGaA) and Melvax II (Imclone Systems and Merck KgaA);

(4) EGF inhibitors that are small molecules, such as, Tarceva™ (OSI-774, OSI Pharmaceuticals, Inc.), and Iressa (ZD 1839, Astra Zeneca);

(5) VEGF inhibitors that are antibodies such as: bevacizumab (Genentech, Inc.), and IMC-1C11 (ImClone Systems), DC 101 (a KDR VEGF Receptor 2 from ImClone Systems);

(6) VEGF kinase inhibitors that are small molecules such as SU 5416 (from Sugen, Inc), SU 6688 (from Sugen, Inc.), Bay 43-9006 (a dual VEGF and bRAF inhibitor from Bayer Pharmaceuticals and Onyx Pharmaceuticals);

(7) estrogen receptor antagonists or selective estrogen receptor modulators (SERMs), such as tamoxifen, idoxifene, raloxifene, trans-2,3-dihydroraloxifene, levormeloxifene, droloxifene, MDL 103,323, and acolbifene (Schering Corp.);

(8) anti-tumor nucleoside derivatives such as 5-fluorouracil, gemcitabine, capecitabine, cytarabine (Ara-C), fludarabine (F-Ara-A), decitabine, and chlorodeoxyadenosine (Cda, 2-Cda);

(9) epothilones such as BMS-247550 (Bristol-Myers Squibb), and EP0906 (Novartis Pharmaceuticals);

(10) topoisomerase inhibitors such as topotecan (Glaxo SmithKline), and Camptosar (Pharmacia);

(11) vinca alkaloids, such as, navelbine (Anvar and Fabre, France), vincristine and vinblastine;

(12) antibodies that are inhibitors of αVβ3 integrins, such as, LM-609 (see, Clinical Cancer Research, Vol. 6, page 3056-3061, August 2000, the disclosure of which is incorporated herein by reference thereto);

(13) folate antagonists, such as Methotrexate (MIX), and Premetrexed (Alimta);

(14) ribonucleotide reductase inhibitors, such as Hydroxyurea (ITU);

(15) anthracyclines, such as Daunorubicin, Doxorubicin (Adriamycin), and Idarubicin;

(16) biologics, such as interferon (e.g., Intron-A and Roferon), pegylated interferon (e.g., Peg-Intron and Pegasys), and Rituximab (Rittman, antibody used for the treatment of non-Hodgkin's lymphoma);

(17) thalidomide (or related imid);

(18) Bcr/abl kinase inhibitors, such as, for example Gleevec (STI-571), AMN-17, ONO12380, SU11248 (Sunitinib) and BMS-354825;

(19) MEK1 and/or MEK2 inhibitors, such as PD0325901 and Arry-142886 (AZD6244);

(20) IGF-1 and IGF-2 inhibitors that are small molecules, such as, for example, NVP-AEW541;

(21) small molecule inhibitors of RAF and BRAF kinases, such as, for example, BAY 43-9006 (Sorafenib);

(22) small molecule inhibitors of cell cycle dependent kinases such as CDK1, CDK2, CDK4 and CDK6, such as, for example, CYC202, BMS387032, and Flavopiridol;

(23) alkylating agents, such as, for example, Temodar® brand of temozolomide;

(24) farnesyl protein transferase inhibitors, such as, for example:

(a) Sarasar® brand of lonifarnib (i.e., 4-[2-[4-(3,10-dibromo-8-chloro-6,11-dihydro-5H-benzo[5,6]cyclohepta[1,2-b]byridin-11-yl)-1-piperidinyl)-2-oxoethyl]-1-piperidinecarboxamide, see for example, U.S. Pat. No. 5,874,442 issued Feb. 23, 1999, and U.S. Pat. No. 6,632,455 issued Oct. 14, 2003 the disclosures of each being incorporated herein by reference thereto), (b) Zarnestra® brand of tipifarnib (i.e., (R)-6-amino[(4-chlorophenyl)(1-methyl-1H-imidazol-5-yl)methyl]-4-(3-chlorophenyl)-1-methyl-2(1H)-quinolinone, see for example, WO 97/16443 published May 9, 1997 and U.S. Pat. No. 5,968,952 issued Oct. 19, 1999, the disclosures of each being incorporated herein by reference thereto), and (c) Bristol-Myers Squibb 214662:

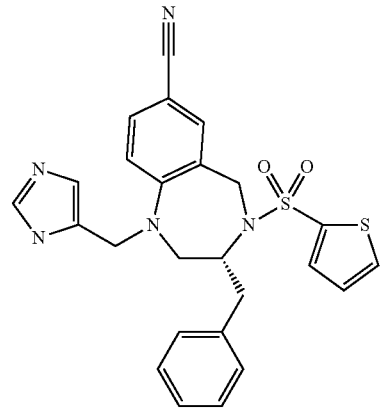 [SMILES: N#Cc1ccc2c(c1)CN(S(=O)(=O)c1cccs1)[C@H](Cc1ccccc1)CN2Cc1cnc[nH]1]

(see WO97/30992 published Aug. 28, 1997, U.S. Pat. No. 6,011,029 issued Jan. 4, 2000, and U.S. Pat. No. 6,455,523, the disclosures of each being incorporated herein by reference thereto).

The Bcr/abl kinase inhibitors, EGF receptor inhibitors, and HER-2 antibodies (EGF receptor inhibitors that are antibodies) described above are also known as signal transduction inhibitors. Therefore, chemotherapeutic agents, as used herein, include signal transduction inhibitors.

Typical signal transduction inhibitors, that are chemotherapeutic agents, include but are not limited to: (i) Bcr/abl kinase inhibitors such as, for example, STI 571 (Gleevec), (ii) Epidermal growth factor (EGF) receptor inhibitor such as, for example, Kinase inhibitors (Iressa, OSI-774) and antibodies (Imclone: C225 [Goldstein et al. (1995), Clin Cancer Res. 1:1311-1318], and Abgenix: ABX-EGF) and (iii) HER-2/neu receptor inhibitors such as, for example, Herceptin® (trastuzumab).

A compound of the instant invention may also be useful for treating cancer in combination with the following chemotherapeutic agents: abarelix (Plenaxis Depot®); aldesleukin (Prokine®); Aldesleukin (Proleukin®); Alemtuzumabb (Campath®); alitretinoin (Panretin®); allopurinol (Zyloprim®); altretamine (Hexylen®); amifostine (Ethyol); anastrozole (Arimidex®); arsenic trioxide (Trisenox®); asparaginase (Elspar®); azacitidine (Vidaza®), bendamustine hydrochloride (Treanda®); bevacuzimab (Avastin®); bexarotene capsules (Targretin®); bexarotene gel (Targretin®); bleomycin (Blenoxane®); bortezomib (Velcade®); brefeldin A; busulfan intravenous (Busulfex®); busulfan oral (Myleran®); calusterone (Methosarb®); capecitabine (Xeloda®); carboplatin (Paraplatin®); carmustine (BCNU®, BiCNU®); carmustine (Gliadel®); carmustine with Polifeprosan 20 Implant (Gliadel Wafer®); celecoxib (Celebrex®); cetuximab (Erbitux®); chlorambucil (Leukeran®); cisplatin (Platinol®); cladribine (Leustatin®, 2-CdA®); clofarabine (Clolar®); cyclophosphamide (Cytoxan®, Neosar®); cyclophosphamide (Cytoxan Injection®); cyclophosphamide (Cytoxan Tablet®); cytarabine (Cytosar-U®); cytarabine liposomal (DepoCyt®); dacarbazine (DTIC-Dome®); dactinomycin, actinomycin D (Cosmegen®); dalteparin sodium injection (Fragmin®); Darbepoetin alfa (Aranesp®); dasatinib (Sprycel®); daunorubicin liposomal (DantioXome®); daunorubicin, daunomycin (Daunorubicin®); daunorubicin, daunomycin (Cerubidine®); degarelix (Firmagon®); Denileukin diftitox (Ontak®); dexrazoxane (Zinecard®); dexrazoxane hydrochloride (Totect®); didemnin B; 17-DMAG; docetaxel (Taxotere®); doxorubicin (Adriamycin PFS®); doxorubicin (Adriamycin®, Rubex®); doxorubicin (Adriamycin PFS Injection®); doxorubicin liposomal (Doxil®); dromostanolone propionate (Dromostanolone®); dromostanolone propionate (Masterone Injection®); eculizumab injection (Soliris); Elliott's B Solution (Elliott's B Solution®); eltrombopag (Promacta®); epirubicin (Ellence®); Epoetin alfa (Epogen®); erlotinib (Tarceva®); estramustine (Emcyt®); ethinyl estradiol; etoposide phosphate (Etopophos®); etoposide, VP-16 (Vepesid®); everolimus tablets (Afinitor®); exemestane (Aromasin®); ferumoxytol (Feraheme Injection®); Filgrastim (Neupogen®); floxuridine (intraarterial) (FUDR®); fludarabine (Fludara®); fluorouracil, 5-FU (Adrucil®); fulvestrant (Faslodex®); gefitinib (Iressa®); geldanamycin; gemcitabine (Gemzar®); gemtuzumab ozogamicin (Mylotarg®); goserelin acetate (Zoladex Implant®); goserelin acetate (Zoladex®); histrelin acetate (Histrelin Implant®); hydroxyurea (Hydrea®); Ibritumomab Tiuxetan (Zevalin®); idarubicin (Idamycin®); ifosfamide (IFEX®); imatinib mesylate (Gleevec®); interferon alfa 2a (Roferon A®); Interferon alfa-2b (Intron A®); iobenguane I 123 injection (AdreView®); irinotecan (Camptosar®); ixabepilone (Ixempra®); lapatinib tablets (Tykerb®); lenalidomide (Revlimid®); letrozole (Femara®); leucovorin (Wellcovorin®, Leucovorin®); Leuprolide Acetate (Eligard®); levamisole (Ergamisol®); lomustine, CCNU (CeeBU®); meclorethamine, nitrogen mustard (Mustargen®); megestrol acetate (Megace®); melphalan, L-PAM (Alkeran®); mercaptopurine, 6-MP (Purinethol®); mesna (Mesnex®); mesna (Mesnex Tabs®); methotrexate (Methotrexate®); methoxsalen (Uvadex®); 8-methoxypsoralen; mitomycin C (Mutamycin®); mitotane (Lysodren®); mitoxantrone (Novantrone®); mitramycin; nandrolone phenpropionate (Durabolin-50®); nelarabine (Arranon®); nilotinib (Tasigna®); Nofetumomab (Verluma); ofatumumab (Arzerra®); Oprelvekin (Neumega®); oxaliplatin (Eloxatin); paclitaxel (Paxene®); paclitaxel (Taxol®); paclitaxel protein-bound particles (Abraxane®); palifermin (Kepivance®); pamidronate (Aredia®); panitumumab (Vectibix®); pazopanib tablets (Votrienttm®); pegademase (Adagen (Pegademase Bovine)®); pegaspargase (Oncaspar®); Pegfilgrastim (Neulasta®); pemetrexed disodium (Alimta®); pentostatin (Nipent®); pipobroman (Vercyte®); plerixafor (Mozobil®); plicamycin, mithramycin (Mithracin®); porfimer sodium (Photofrin®); pralatrexate injection (Folotyn®); procarbazine (Matulane®); quinacrine (Atabrine®); rapamycin; Rasburicase (Elitek®); raloxifene hydrochloride (Evista®); Rituximab (Rituxan®); Ridaforolimus; romidepsin (Istodax®); romiplostim (Nplate®); sargramostim (Leukine®); Sargramostim (Prokine®); sorafenib (Nexavar®); streptozocin (Zanosar®); sunitinib maleate (Sutent®); talc (Sclerosolg); tamoxifen (Nolvadex®); temozolomide (Temodar®); temsirolimus (Torisel®); teniposide, VM-26 (Vumon®); testolactone (Teslac®); thioguanine, 6-TG (Thioguanine®); thiopurine; thiotepa (Thioplex®); topotecan (Hyeamtin); toremifene (Fareston); Tositumomab (Bexxar®); Tositumomab/I-131 tositumomab (Bexxar®); trans-retinoic acid; Trastuzumab (Herceptin®); tretinoin, ATRA (Vesanoid); triethylenemelamine; Uracil Mustard (Uracil Mustard Capsules®); valrubicin (Valstar®); vinblastine (Velban®); vincristine (Oncovin®); vinorelbine (Navelbine®); vorinostat (Zolinza®); wortmannin; and zoledronate (Zometa®).

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR), e.g., 1996 edition (Medical Economics Company, Montvale, N.J. 07645-1742, USA), the Physician's Desk Reference, 56$^{th}$ Edition, 2002 (published by Medical Economics company, Inc. Montvale, N.J. 07645-1742), and the Physician's Desk Reference, 57$^{th}$ Edition, 2003 (published by Thompson PDR, Montvale, N.J. 07645-1742); the disclosures of which is incorporated herein by reference thereto.

For example, the compounds of formula I can be administered orally (e.g., as a capsule), and the chemotherapeutic agents can be administered intravenously, usually as an intravenous (IV) solution. The use of a pharmaceutical composition comprising more than one drug is within the scope of this invention.

The compound of formula I and the chemotherapeutic agents are administered in therapeutically effective dosages to obtain clinically acceptable results, e.g., reduction or elimination of symptoms or of the tumor. Thus, the compound of formula I and chemotherapeutic agents can be administered concurrently or consecutively in a treatment protocol. The administration of the chemotherapeutic agents can be made according to treatment protocols already known in the art.

In general when more than one chemotherapeutic agent is used in the methods of this invention, the chemotherapeutic agents are administered on the same day either concurrently or consecutively in their standard dosage form. For example, the chemotherapeutic agents are usually administered intravenously, preferably by an IV drip using IV solutions well known in the art (e.g., isotonic saline (0.9% NaCl) or dextrose solution (e.g., 5% dextrose)).

When two or more chemotherapeutic agents are used, the chemotherapeutic agents are generally administered on the same day; however, those skilled in the art will appreciate that the chemotherapeutic agents can be administered on different days and in different weeks. The skilled clinician can administer the chemotherapeutic agents according to their recommended dosage schedule from the manufacturer of the agent and can adjust the schedule according to the needs of the patient, e.g., based on the patient's response to the treatment. For example, when gemcitabine is used in combination with a platinum coordinator compound, such as, for example, cisplatin, to treat lung cancer, both the gemcitabine and the cisplatin are given on the same day on day one of the treatment cycle, and then gemcitabine is given alone on day 8 and given alone again on day 15

The compounds of this invention and chemotherapeutic agents can be administered in a treatment protocol that usually lasts one to seven weeks, and is repeated typically from 6 to 12 times. Generally the treatment protocol can last one to four weeks. Treatment protocols of one to three weeks can also be used. A treatment protocol of one to two weeks can also be used. During this treatment protocol or cycle the compounds of this invention can be administered daily while the chemotherapeutic agents can be administered one or more times a week. Generally, a compound of this invention can be administered daily (i.e., once per day), and in one embodiment twice per day, and the chemotherapeutic agent is administered once a week or once every three weeks. For example, the taxanes (e.g., Paclitaxel (e.g., Taxol®) or Docetaxel (e.g., Taxotere®)) can be administered once a week or once every three weeks.

However, those skilled in the art will appreciate that treatment protocols can be varied according to the needs of the patient. Thus, the combination of compounds (drugs) used in the methods of this invention can be administered in variations of the protocols described above. For example, the compounds of this invention can be administered discontinuously rather than continuously during the treatment cycle. Thus, for example, during the treatment cycle the compounds of this invention can be administered daily for a week and then discontinued for a week, with this administration repeating during the treatment cycle. Or the compounds of this invention can be administered daily for two weeks and discontinued for a week, with this administration repeating during the treatment cycle. Thus, the compounds of this invention can be administered daily for one or more weeks during the cycle and discontinued for one or more weeks during the cycle, with this pattern of administration repeating during the treatment cycle. This discontinuous treatment can also be based upon numbers of days rather than a full week. For example, daily dosing for 1 to 6 days, no dosing for 1 to 6 days with this pattern repeating during the treatment protocol. The number of days (or weeks) wherein the compounds of this invention are not dosed do not have to equal the number of days (or weeks) wherein the compounds of this invention are dosed. Usually, if a discontinuous dosing protocol is used, the number of days or weeks that the compounds of this invention are dosed is at least equal or greater than the number of days or weeks that the compounds of this invention are not dosed.

The chemotherapeutic agent could be given by bolus or continuous infusion. The chemotherapeutic agent could be given daily to once every week, or once every two weeks, or once every three weeks, or once every four weeks during the treatment cycle. If administered daily during a treatment cycle, this daily dosing can be discontinuous over the number of weeks of the treatment cycle. For example, dosed for a week (or a number of days), no dosing for a week (or a number of days, with the pattern repeating during the treatment cycle.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences*, 18$^{th}$ Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid faints include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

The compounds of this invention may also be delivered subcutaneously.

Preferably the compound is administered orally or intravenously or intrathecally or some suitable combination(s) thereof.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 0.001 mg to about 500 mg. In one embodiment, the quantity of active compound in a unit dose of preparation is from about 0.01 mg to about 250 mg. In another embodiment, the quantity of active compound in a unit dose of preparation is from about 0.1 mg to about 100 mg. In another embodiment, the quantity of active compound in a unit dose of preparation is from about 1.0 mg to about 100 mg. In another embodiment, the quantity of active compound in a unit dose of preparation is from about 1.0 mg to about 50 mg. In still another embodiment, the quantity of active compound in a unit dose of preparation is from about 1.0 mg to about 25 mg.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 0.01 mg/day to about 2000 mg/day of the compounds of the present invention. In one embodiment, a daily dosage regimen for oral administration is from about 1 mg/day to 1000 mg/day. In another embodiment, a daily dosage regimen for oral administration is from about 1 mg/day to 500 mg/day. In another embodiment, a daily dosage regimen for oral administration is from about 100 mg/day to 500 mg/day. In another embodiment, a daily dosage regimen for oral administration is from about 1 mg/day to 250 mg/day. In another embodiment, a daily dosage regimen for oral administration is from about 100 mg/day to 250 mg/day. In still another embodiment, a daily dosage regimen for oral administration is from about 1 mg/day to 100 mg/day. In still another embodiment, a daily dosage regimen for oral administration is from about 50 mg/day to 100 mg/day. In a further embodiment, a daily dosage regimen for oral administration is from about 1 mg/day to 50 mg/day. In another embodiment, a daily dosage regimen for oral administration is from about 25 mg/day to 50 mg/day. In a further embodiment, a daily dosage regimen for oral administration is from about 1 mg/day to 25 mg/day. The daily dosage may be administered in a single dosage or can be divided into from two to four divided doses.

If the patient is responding, or is stable, after completion of the therapy cycle, the therapy cycle can be repeated according to the judgment of the skilled clinician. Upon completion of the therapy cycles, the patient can be continued on the compounds of this invention at the same dose that was administered in the treatment protocol. This maintenance dose can be continued until the patient progresses or can no longer tolerate the dose (in which case the dose can be reduced and the patient can be continued on the reduced dose).

The chemotherapeutic agents, used with the compounds of this invention, are administered in their normally prescribed dosages during the treatment cycle (i.e., the chemotherapeutic agents are administered according to the standard of practice for the administration of these drugs). For example: (a) about 30 to about 300 mg/m$^2$ for the taxanes; (b) about 30 to about 100 mg/m$^2$ for Cisplatin; (c) AUC of about 2 to about 8 for Carboplatin; (d) about 2 to about 4 mg/m$^2$ for EGF inhibitors that are antibodies; (e) about 50 to about 500 mg/m$^2$ for EGF inhibitors that are small molecules; (f) about 1 to about 10 mg/m$^2$ for VEGF kinase inhibitors that are antibodies; (g) about 50 to about 2400 mg/m$^2$ for VEGF inhibitors that are small molecules; (h) about 1 to about 20 mg for SERMs; (i) about 500 to about 1250 mg/m$^2$ for the anti-tumor nucleosides 5-Fluorouracil, Gemcitabine and Capecitabine; (j) for the anti-tumor nucleoside Cytarabine (Ara-C) 100-200 mg/m$^2$/day for 7 to 10 days every 3 to 4 weeks, and high doses for refractory leukemia and lymphoma, i.e., 1 to 3 gm/m$^2$ for one hour every 12 hours for 4-8 doses every 3 to four weeks; (k) for the anti-tumor nucleoside Fludarabine (F-ara-A) 10-25 mg/m$^2$/day every 3 to 4 weeks; (l) for the anti-tumor nucleoside Decitabine 30 to 75 mg/m$^2$ for three days every 6 weeks for a maximum of 8 cycles; (m) for the anti-tumor nucleoside Chlorodeoxyadenosine (CdA, 2-CdA) 0.05-0.1 mg/kg/day as continuous infusion for up to 7 days every 3 to 4 weeks; (n) about 1 to about 100 mg/m$^2$ for epothilones; (O) about 1 to about 350 mg/m$^2$ for topoisomerase inhibitors; (p) about 1 to about 50 mg/m$^2$ for ulna alkaloids; (q) for the folate antagonist Methotrexate (MTX) 20-60 mg/m$^2$ by oral, IV or 1M every 3 to 4 weeks, the intermediate dose regimen is 80-250 mg/m$^2$ IV over 60 minutes every 3 to 4 weeks, and the high dose regimen is 250-1000 mg/m$^2$ IV given with leucovorin every 3 to 4 weeks; (r) for the folate antagonist Premetrexed (Alimta) 300-600 mg/m$^2$ (10 minutes IV infusion day 1) every 3 weeks; (s) for the ribonucleotide reductase inhibitor Hydroxyurea (HU) 20-50 mg/kg/day (as needed to bring blood cell counts down); (t) the platinum coordinator compound Oxaliplatin (Eloxatin) 50-100 mg/m$^2$ every 3 to 4 weeks (preferably used for solid tumors such as non-small cell lung cancer, colorectal cancer and ovarian cancer); (u) for the anthracycline daunorubicin 10-50 mg/m$^2$/day IV for 3-5 days every 3 to 4 weeks; (v) for the anthracycline Doxorubicin (Adriamycin) 50-100 mg/m$^2$ IV continuous infusion over 1-4 days every 3 to 4 weeks, or 10-40 mg/m$^2$ IV weekly; (w) for the anthracycline Idarubicin 10-30 mg/m$^2$ daily for 1-3 days as a slow IV infusion over 10-20 minutes every 3 to 4 weeks; (x) for the biologic interferon (Intron-A, Roferon) 5 to 20 million IU three times per week; (y) for the biologic pegylated interferon (Peg-intron, Pegasys) 3 to 4 micrograms/kg/day chronic sub cutaneous (until relapse or loss of activity); (z) for the biologic Rittrximab (Rituxan) (antibody used for non-Hodgkin's lymphoma) 200-400 mg/m$^2$ IV weekly over 4-8 weeks for 6 months; (aa) for the alkylating agent temozolomide 75 mg/m$^2$ to 250 mg/m$^2$, for example, 150 mg/m$^2$, or for example, 200 mg/m$^2$, such as 200 mg/m$^2$ for 5 days; and (bb) for the MEK1 and/or MEK2 inhibitor PD0325901, 15 mg to 30 mg, for example, 15 mg daily for 21 days every 4 weeks.

Gleevec can be used orally in an amount of about 200 to about 800 mg/day.

Thalidomide (and related imides) can be used orally in amounts of about 200 to about 800 mg/day, and can be continuously dosed or used until relapse or toxicity. See for example Mitsiades et al., "Apoptotic signaling induced by immunomodulatory thalidomide analogs in human multiple myeloma cells; therapeutic implications", Blood, 99(12):4525-30, Jun. 15, 2002, the disclosure of which is incorporated herein by reference thereto.

The FPT inhibitor Sarasar® (brand of lonifarnib) can be administered orally (e.g., capsule) in amounts of about 50 to about 200 mg given twice a day, or in amounts of about 75 to about 125 mg given twice a day, or in amounts of about 100 to about 200 mg given twice a day, or in an amount of about 100 mg given twice a day.

Paclitaxel (e.g., Taxol®, for example, can be administered once per week in an amount of about 50 to about 100 mg/m$^2$ and in another example about 60 to about 80 mg/m$^2$. In another example Paclitaxel (e.g., Taxol® can be administered once every three weeks in an amount of about 150 to about 250 mg/m$^2$ and in another example about 175 to about 225 mg/m$^2$.

In another example, Docetaxel (e.g., Taxotere®) can be administered once per week in an amount of about 10 to about 45 mg/m$^2$. In another example Docetaxel (e.g., Taxotere®) can be administered once every three weeks in an amount of about 50 to about 100 mg/m$^2$.

In another example Cisplatin can be administered once per week in an amount of about 20 to about 40 mg/m$^2$. In another example Cisplatin can be administered once every three weeks in an amount of about 60 to about 100 mg/m$^2$.

In another example Carboplatin can be administered once per week in an amount to provide an AUC of about 2 to about 3. In another example Carboplatin can be administered once every three weeks in an amount to provide an AUC of about 5 to about 8.

Those skilled in the art will recognize that the actual dosages and protocols for administration employed in the methods of this invention may be varied according to the judgment of the skilled clinician. The actual dosage employed may be varied depending upon the requirements of the patient and the severity of the condition being treated. Determination of the proper dosage for a particular situation is within the skill of the art. A determination to vary the dosages and protocols for administration may be made after the skilled clinician takes into account such factors as the patient's age, condition and size, as well as the severity of the cancer being treated and the response of the patient to the treatment.

The amount and frequency of administration of the compound of formula I and the chemotherapeutic agents will be regulated according to the judgment of the attending clinician (physician) considering such factors as age, condition and size of the patient as well as severity of the cancer being treated.

The chemotherapeutic agent can be administered according to therapeutic protocols well known in the art. It will be apparent to those skilled in the art that the administration of the chemotherapeutic agent can be varied depending on the cancer being treated and the known effects of the chemotherapeutic agent on that disease. Also, in accordance with the knowledge of the skilled clinician, the therapeutic protocols (e.g., dosage amounts and times of administration) can be varied in view of the observed effects of the administered therapeutic agents on the patient, and in view of the observed responses of the cancer to the administered therapeutic agents.

The initial administration can be made according to established protocols known in the art, and then, based upon the observed effects, the dosage, modes of administration and times of administration can be modified by the skilled clinician.

The particular choice of chemotherapeutic agent will depend upon the diagnosis of the attending physicians and their judgement of the condition of the patient and the appropriate treatment protocol.

The determination of the order of administration, and the number of repetitions of administration of the chemotherapeutic agent during a treatment protocol, is well within the knowledge of the skilled physician after evaluation of the cancer being treated and the condition of the patient.

Thus, in accordance with experience and knowledge, the practicing physician can modify each protocol for the administration of an chemotherapeutic agent according to the individual patient's needs, as the treatment proceeds. All such modifications are within the scope of the present invention.

The particular choice of antihormonal agents, optional chemotherapeutic agents and optional radiation will depend upon the diagnosis of the attending physicians and their judgment of the condition of the patient and the appropriate treatment protocol.

The determination of the order of administration, and the number of repetitions of administration of the antihormonal agents, optional chemotherapeutic agents and optional radiation during a treatment protocol, is well within the knowledge of the skilled physician after evaluation of the breast cancer being treated and the condition of the patient.

Thus, in accordance with experience and knowledge, the practicing physician can modify each protocol for the administration of antihormonal agents, optional chemotherapeutic agents and optional radiation according to the individual patient's needs, as the treatment proceeds. All such modifications are within the scope of the present invention.

The attending clinician, in judging whether treatment is effective at the dosage administered, will consider the general well-being of the patient as well as more definite signs such as relief of cancer-related symptoms (e.g., pain, cough (for lung cancer), and shortness of breath (for lung cancer)), inhibition of tumor growth, actual shrinkage of the tumor, or inhibition of metastasis. Size of the tumor can be measured by standard methods such as radiological studies, e.g., CAT or MRI scan, and successive measurements can be used to judge whether or not growth of the tumor has been retarded or even reversed. Relief of disease-related symptoms such as pain, and improvement in overall condition can also be used to help judge effectiveness of treatment.

The compounds of the invention can be made according to the processes described below.

COMMONLY USED ABBREVIATIONS

ACN=Acetonitrile; AcOH=Acetic acid; DAST (diethylamino)sulfur trifluoride; DCC=Dicyclohexylcarbodiimide; DCU=Dicyclohexylurea; DCM=Dichloromethane; DIAD=Diisopropylazodicarboxylate; DIEA=Diisopropylethylamine; DMA=N,N-Dimethylacetamide; DMAP=4-Dimethylaminopyridine; DME=Dimethoxyethane; DMF=Dimethylformamide; DMFDMA N,N-Dimethylformamide dimethylacetal; DMSO=Dimethyl sulfoxide; DTT=Dithiothreitol; EDCI=1-(3-dimethylamino-propyl)-3-ethylcarbodiimide hydrochloride; EtOAc=Ethyl acetate; EtOH=Ethanol; HATU=N,N,N',N'-Tetramethyl-O-(7-Azabenzotriazol-1-yl)Uronium hexafluorophosphate; $H_2O$=water; Hex=hexanes; HOBt=1-Hydroxylbenzotriazole; HPLC=High pressure liquid chromatography; LCMS=Liquid chromatography mass spectrometry; LDA=Lithium diisopropylamide; mCPBA meta-Chloroperoxybenzoic acid; MeOH=Methanol; MIT=(3-[4,5-dimethyl-thiazol-2-yl]-2,5-diphenyltetrazolium bromide, Thiazolyl blue); NaH=Sodium hydride; NMR=Nuclear magnetic resonance; PFP=Pentafluorophenol; PMB p-methoxybenzyl; Pyr=Pyridine; RT=Room temperature; SEMCl=2-(Trimethylsily)ethoxy methyl chloride; TEA=Triethylamine; Tr=Triphenyl methane; TrCl=Triphenyl methane chloride; TFA=Trifluoroacetic acid; THF=Tetrahydrofuran; TLC=Thin layer chromatography; and TMS=Trimethylsilyl.

Analytical Method

The LCMS conditions are: (1) column: C-18 reverse phase, Sum, 4.6×50 mm, (2) MS:PE Sciex API-150EX, and (3) HPLC: Shimadzu LC-10 ADvp, 1 ml/min, linerar gradient 10% acetonitrile in water to 95% acetonitrile in water, both contain 0.05% TF.

Compound Synthesis:

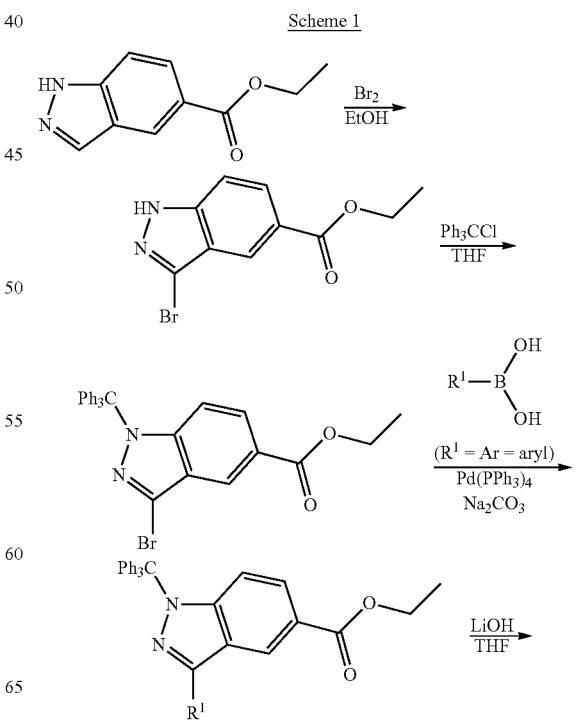

Scheme 1

-continued

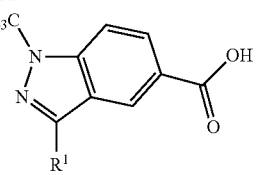

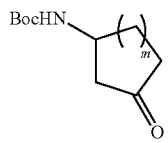 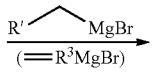

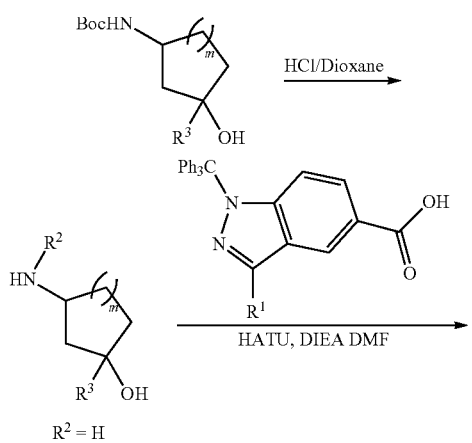

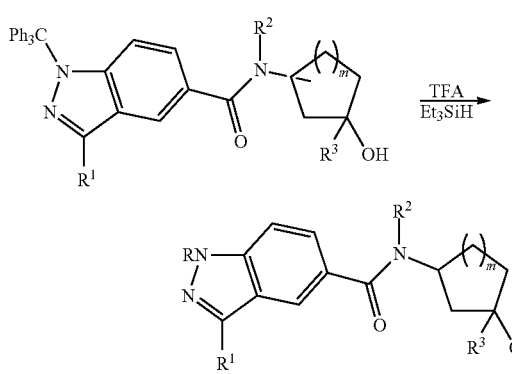

m = 2
R = H;
R$^1$ = Ar
R$^2$ = H;
R$^3$ = R'CH$_2$— ethyl 3-bromo-1H-indazole-5-carboxylate

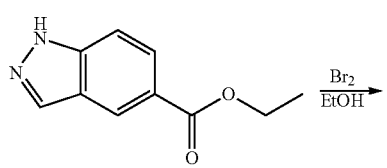

-continued

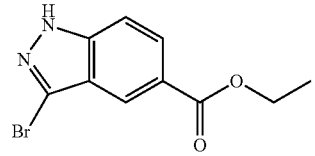

ethyl 1H-indazole-5-carboxylate hydrochloride (146 g, 0.645 mol) was dissolved in ethanol (4 L, anhydrous). Bromine (113.3 g, 0.709 mol) in 200 ethanol was added at room temperature. The reaction mixture was allowed to stir for 17 hours at room temperature. TLC (30% ethyl acetate/hexane) indicated that starting material was left. Bromine (40 g in 100 mL of ethanol) was added at room temperature. After 1 hour, TLC indicated no starting material was left. Ethanol was evaporated (2 L removed) and the mixture was poured into ice-water (8 L). The purple solid was stirred and 750 mL of saturated Na$_2$S$_2$O$_3$ and NaOH solution was added to adjust the pH to 10-11. Total volume was 10 L. The mixture was stirred for 30 minutes and the solid were filtered and washed with 1.5 L of water and dried in a vacuum oven to obtain 170 gram of product as yellow solid.

ethyl 3-bromo-1-trityl-1H-indazole-5-carboxylate

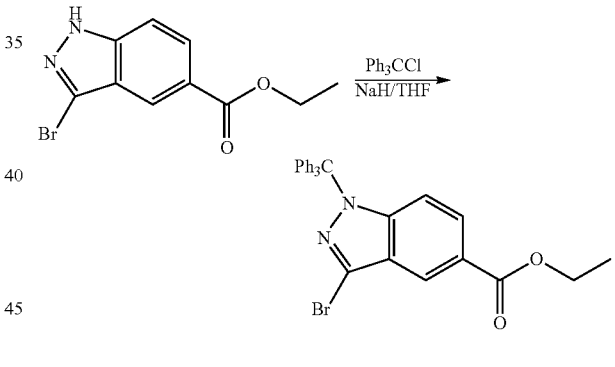

To a suspension of ethyl 3-bromo-1H-indazole-5-carboxylate (10.72 gm, 0.04 mol) in 160 mL of THF was added NaH (2.8 g, 0.068 mol) portionwise at 5-10 C under ice/water bath. The solution was stirred for 15 minutes further until no more bubbling. Tritylchloride (14 g, 0.05 mol) was added in several portions. After the addition, the cooling bath was removed and the orange suspension was stirred at room temperature for overnight. The reaction mixture was poured slowly into 100 mL of saturated NH4Cl with stirring and 100 mL EtOAc. The layers were separated and the aqueous phase extracted with Ethyl acetate (2 L×2). The combined organic layers were washed with water (100 mL), brine (100 mL), dried over Na2SO4, filter and concentrated. The solid was triturated with hexane (100 mL), filtered and washed with hexane and dried under vacuum to give 20 gram product as light yellow solid.

Synthesis of ethyl 3(2-methylpyridin-4-yl)-1-trityl-4H-indazole-5-carboxylate

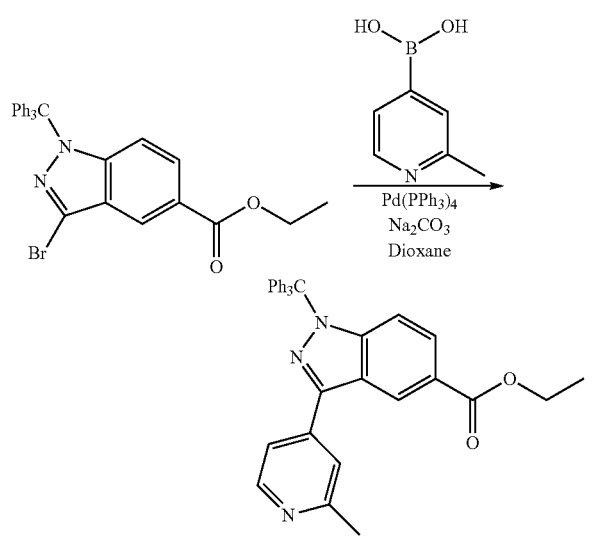

ethyl 3-bromo-1-trityl-1H-indazole-5-carboxylate (510 mg, 1.0 mol) was added to a vial containing 2-methylpyridin-4-ylboronic acid (128 mg, 1.04 mol) and tetrakis(triphenylphosphine)palladium (140 mg, 0.104 mol). After purging the vial with nitrogen gas, dioxane (5 mL) and 2M sodium carbonate (5 mL) was added to the vial respectively. The reaction mixture was stirred and was heated to 80° C. for overnight. Upon completion, the mixture was concentrated under vacuo. The mixture was extracted using ethyl acetate (3×100 mL). The extracts were combined and dried using anhydrous sodium sulfate. The resulting mixture was purified using flash chromatography to give the desired compound in 85% yield.

Preparation of 3-(2-methylpyridin-4-yl)-1-trityl-1H-indazole-5-carboxylic acid

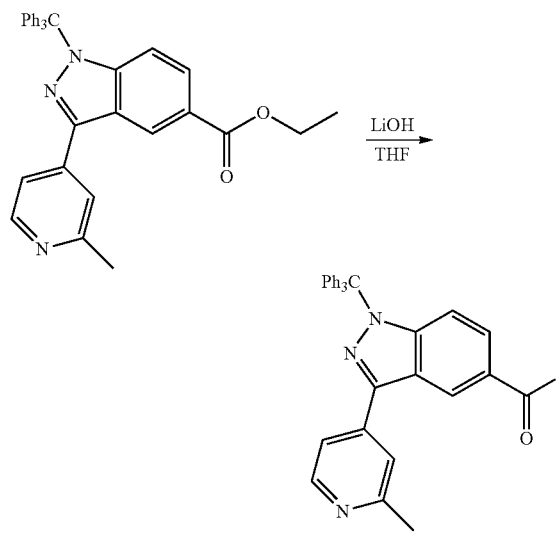

To the solution of ethyl 3-(2-methylpyridin-4-yl)-1-trityl-1H-indazole-5-carboxylate (260 mg, 0.5 mmol) in THF (5 mL) was added LiOH (1M, 2 mL). The reaction mixture was stirred at room temperature for overnight. HCL was added to adjust the pH to 4-5 and ethyl acetated was added. The extract was washed with water (10 mL0 and dry over sodium sulfate and concentrated to give the desired product in 95% yield.

Preparation of tert-butyl 3-(2-fluorobenzyl)-3-hydroxycyclohexylcarbamate

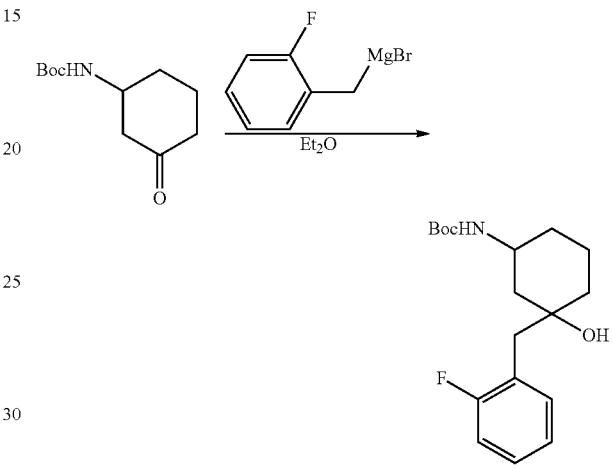

To a solution of tert-butyl 3-oxocyclohexylcarbamate (2 mmol, 426 mg) in ethyl ether (10 mL) was added a solution of (2-fluorobenzyl)magnesium bromide in ether (5 mmol, 0.25 M, 20 mL) at 0° C. The reaction mixture was allowed to warm to room temperature and stirred for overnight. The reaction mixture was added to the $NH_4Cl$ aqueous solution. The organics were extracted with EtOAc. The EtOAc solution was concentrated. The product, tert-butyl 3-(2-fluorobenzyl)-3-hydroxycyclohexylcarbamate was purified by column chromatography on silica gel.

Preparation of 3-amino-1-(2-fluorobenzyl)cyclohexanol

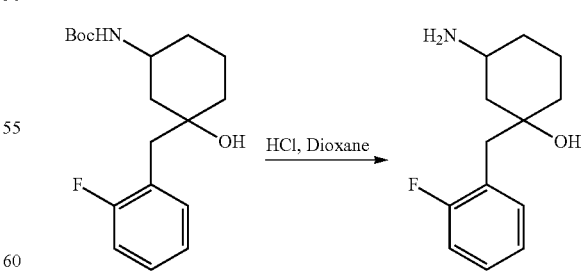

tert-Butyl 3-(2-fluorobenzyl)-3-hydroxycyclohexylcarbamate was stirred in a solution of HCl in dioxane (4 M) at room temperature for one hour. The product, HCl salt of 3-amino-1-(2-fluorobenzyl)cyclohexanol, was obtained after evaporation of solvent.

Preparation of N-(3-(2-fluorobenzyl)-3-hydroxycyclohexyl)-3-(2-methylpyridin-4-yl)-1-trityl-1H-indazole-5-carboxamide N-(3-(2-fluorobenzyl)-3-hydroxycyclohexyl)-3-(2-methylpyridin-4-yl)4H-indazole-5-carboxamide

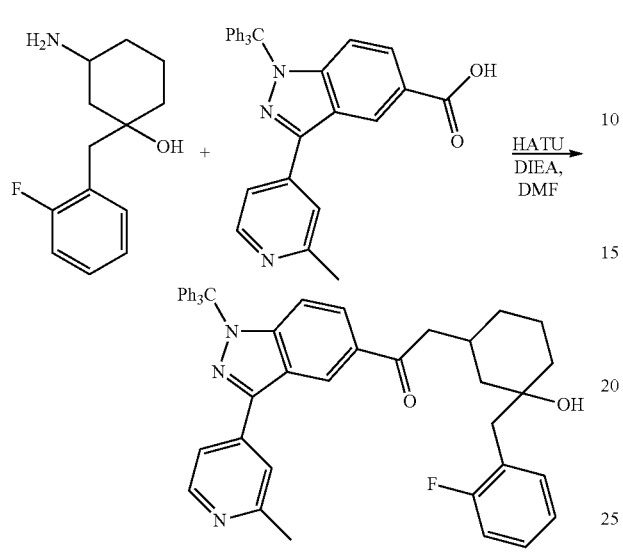

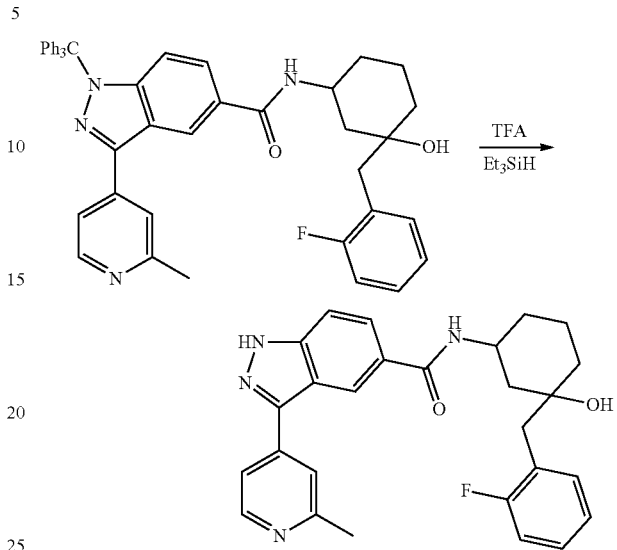

A reaction mixture of 3-(2-methylpyridin-4-yl)-1-trityl-1H-indazole-5-carboxylic acid (0.05 mmol, 24.8 mg), HCl salt of 3-amino-1-(2-fluorobenzyl)cyclohexanol (0.05 mmol, 11 mg), HATU (0.05 mmol, 19 mg) and DIEA (80 µL) in DMA (300 µL) was stirred at room temperature for overnight. The product, N-(3-(2-fluorobenzyl)-3-hydroxycyclohexyl)-3-(2-methylpyridin-4-yl)-1-trityl-1H-indazole-5-carboxamide, was obtained after evaporation of solvent.

N-(3-(2-fluorobenzyl)-3-hydroxycyclohexyl)-3-(2-methylpyridin-4-yl)-1-trityl-1H-indazole-5-carboxamide was stirred in neat TFA at room temperature for 10 minutes, and then Et₃SiH (5 equiv.) was added. The reaction mixture was stirred at room temperature for 5 minutes, and then concentrated. The titled compound was obtained and purified by reverse phase HPLC.

Following compounds were prepared in similar method:

| Compd # | Structure | Chemical Names | aERK IC50 nM | M + 1 Cacld. | M + 1 Obs. | Rf min. |
|---|---|---|---|---|---|---|
| 1 | 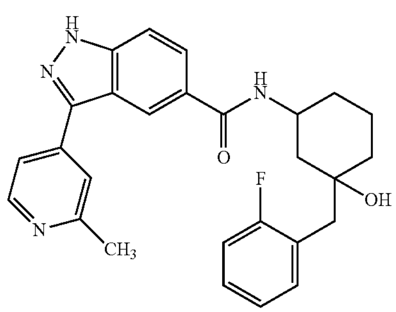 [SMILES: Cc1cc(-c2n[nH]c3ccc(C(=O)NC4CCCC(O)(Cc5ccccc5F)C4)cc23)ccn1] | N-[3-[(2-fluorophenyl)methyl]-3-hydroxycyclohexyl]-3-(2-methyl-4-pyridinyl)-1H-indazole-5-carboxamide (diastereomer 1) | 588.9 | 459.2 | 459.0 | 2.41 |
| 2 | 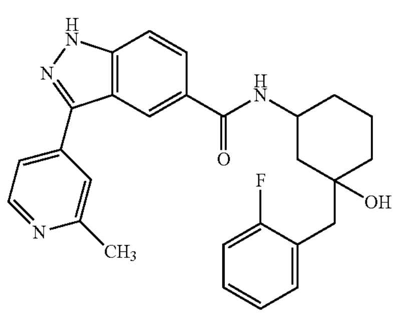 [SMILES: Cc1cc(-c2n[nH]c3ccc(C(=O)NC4CCCC(O)(Cc5ccccc5F)C4)cc23)ccn1] | N-[3-[(2-fluorophenyl)methyl]-3-hydroxycyclohexyl]-3-(2-methyl-4-pyridinyl)-1H-indazole-5-carboxamide (diastereomer 2) | 20.8 | 459.2 | 459.0 | 2.3 |

-continued

| Compd # | Structure | Chemical Names | aERK IC50 nM | M + 1 Cacld. | M + 1 Obs. | Rf min. |
|---|---|---|---|---|---|---|
| 3 | 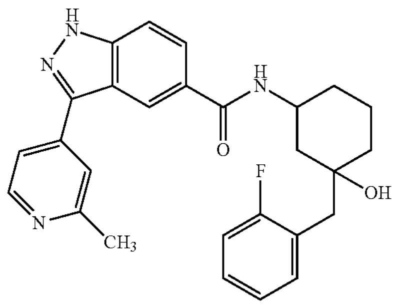 [SMILES: Cc1cc(-c2n[nH]c3ccc(C(=O)NC4CCCC(O)(Cc5ccccc5F)C4)cc23)ccn1] | N-[3-[(2-fluorophenyl)methyl]-3-hydroxycyclohexyl]-3-(2-methyl-4-pyridinyl)-1H-indazole-5-carboxamide (enantiomer a) | 7.6 | 459.2 | 458.9 | 2.29 |
| 4 | 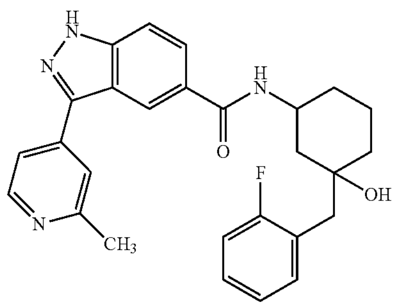 [SMILES: Cc1cc(-c2n[nH]c3ccc(C(=O)NC4CCCC(O)(Cc5ccccc5F)C4)cc23)ccn1] | N-[3-[(2-fluorophenyl)methyl]-3-hydroxycyclohexyl]-3-(2-methyl-4-pyridinyl)-1H-indazole-5-carboxamide (enantiomer b) | 128.2 | 459.2 | 458.9 | 2.29 |
| 5 | 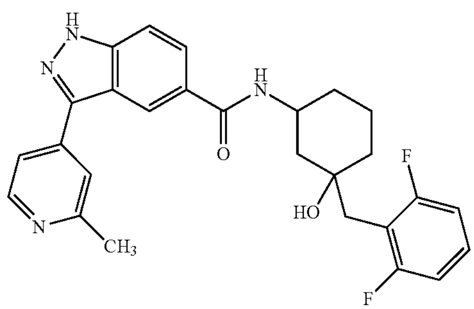 [SMILES: Cc1cc(-c2n[nH]c3ccc(C(=O)NC4CCCC(O)(Cc5c(F)cccc5F)C4)cc23)ccn1] | N-[3-[(2,6-difluorophenyl)methyl]-3-hydroxycyclohexyl]-3-(2-methyl-4-pyridinyl)-1H-indazole-5-carboxamide (isomer 1) | 1000.0 | 477.2 | 477.0 | 2.45 |
| 6 | 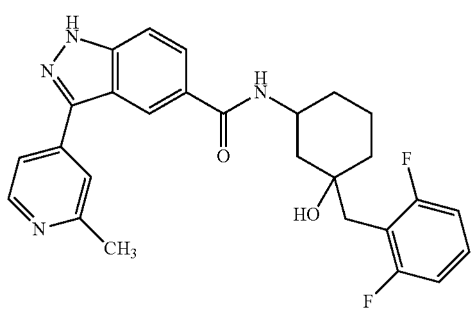 [SMILES: Cc1cc(-c2n[nH]c3ccc(C(=O)NC4CCCC(O)(Cc5c(F)cccc5F)C4)cc23)ccn1] | N-[3-[(2,6-difluorophenyl)methyl]-3-hydroxycyclohexyl]-3-(2-methyl-4-pyridinyl)-1H-indazole-5-carboxamide (isomer 2) | 1000.0 | 477.2 | 477.0 | 2.45 |
| 7 | 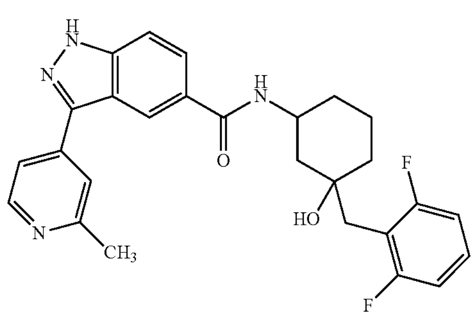 [SMILES: Cc1cc(-c2n[nH]c3ccc(C(=O)NC4CCCC(O)(Cc5c(F)cccc5F)C4)cc23)ccn1] | N-[3-[(2,6-difluorophenyl)methyl]-3-hydroxycyclohexyl]-3-(2-methyl-4-pyridinyl)-1H-indazole-5-carboxamide (isomer 3) | 15.2 | 477.2 | 477.0 | 2.32 |

| Compd # | Structure | Chemical Names | aERK IC50 nM | M + 1 Cacld. | M + 1 Obs. | Rf min. |
|---|---|---|---|---|---|---|
| 8 | 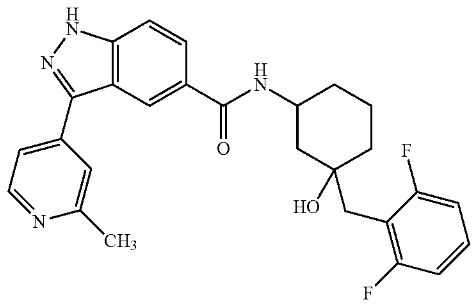 [SMILES: Cc1cc(-c2n[nH]c3ccc(C(=O)NC4CCCC(O)(Cc5c(F)cccc5F)C4)cc23)ccn1] | N-[3-[(2,6-difluorophenyl)methyl]-3-hydroxycyclohexyl]-3-(2-methyl-4-pyridinyl)-1H-indazole-5-carboxamide (isomer 4) | 1000.0 | 477.2 | 477.0 | 2.32 |
| 9 | 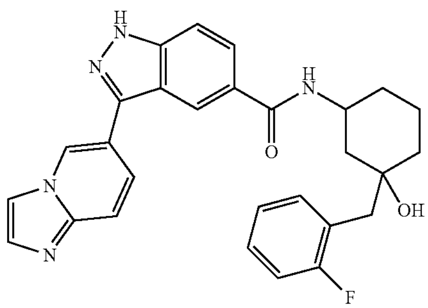 [SMILES: O=C(NC1CCCC(O)(Cc2ccccc2F)C1)c1ccc2[nH]nc(-c3ccc4nccn4c3)c2c1] | N-[trans-3-[(2-fluorophenyl)methyl]-3-hydroxycyclohexyl]-3-imidazo[1,2-a]pyridin-6-yl-1H-indazole-5-carboxamide | 48.7 | 484.2 | 484.0 | 2.34 |
| 10 | 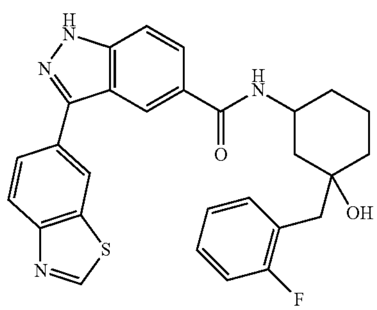 [SMILES: O=C(NC1CCCC(O)(Cc2ccccc2F)C1)c1ccc2[nH]nc(-c3ccc4ncsc4c3)c2c1] | 3-(6-benzothiazolyl)-N-[3-[(2-fluorophenyl)methyl]-3-hydroxycyclohexyl]-1H-indazole-5-carboxamide (isomer 1) | 1000.0 | 501.2 | 501.0 | 3.21 |
| 11 | 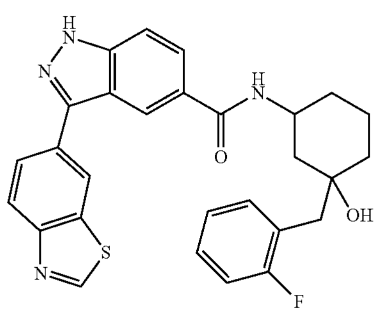 [SMILES: O=C(NC1CCCC(O)(Cc2ccccc2F)C1)c1ccc2[nH]nc(-c3ccc4ncsc4c3)c2c1] | 3-(6-benzothiazolyl)-N-[3-[(2-fluorophenyl)methyl]-3-hydroxycyclohexyl]-1H-indazole-5-carboxamide (isomer 2) | 264.1 | 501.2 | 501.0 | 3.21 |
| 12 | 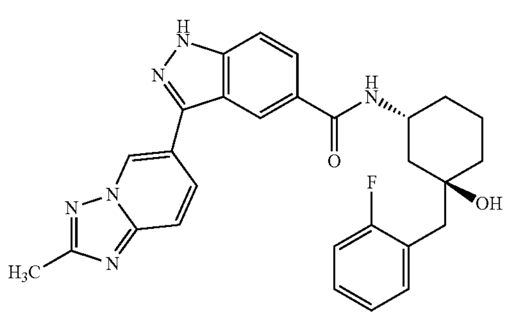 [SMILES: Cc1nc2ccc(-c3n[nH]c4ccc(C(=O)N[C@@H]5CCC[C@](O)(Cc6ccccc6F)C5)cc34)cn2n1] | N-[3(S)-[(2-fluorophenyl)methyl]-3-hydroxy-1(R)-cyclohexyl]-3-(2-methyl[1,2,4]triazolo[1,5-a]pyridin-6-yl)-1H-indazole-5-carboxamide | 14.4 | 499.2 | 499.0 | 2.82 |

| Compd # | Structure | Chemical Names | aERK IC50 nM | M + 1 Cacld. | M + 1 Obs. | Rf min. |
|---|---|---|---|---|---|---|
| 13 | 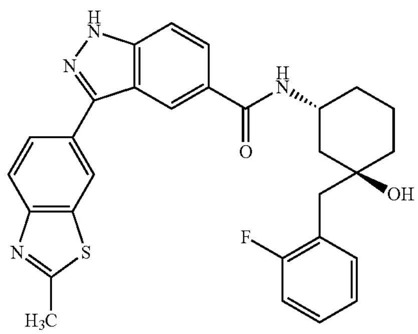 [SMILES: Cc1nc2ccc(-c3n[nH]c4ccc(C(=O)N[C@@H]5CCC[C@](O)(Cc6ccccc6F)C5)cc34)cc2s1] | N-[3(S)-[(2-fluorophenyl)methyl]-3-hydroxy-1(R)-cyclohexyl]-3-(2-methyl-6-benzothiazolyl)-1H-indazole-5-carboxamide | 19.9 | 515.2 | 515.0 | 3.34 |
| 14 | 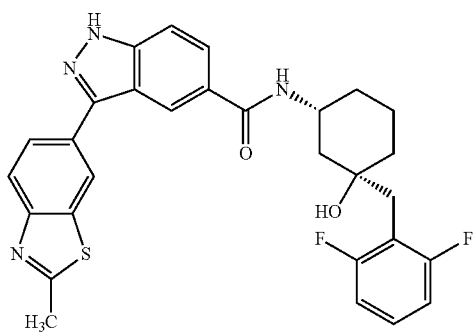 [SMILES: Cc1nc2ccc(-c3n[nH]c4ccc(C(=O)N[C@@H]5CCC[C@](O)(Cc6c(F)cccc6F)C5)cc34)cc2s1] | N-[3(S)-[(2,6-difluorophenyl)methyl]-3-hydroxy-1(R)-cyclohexyl]-3-(2-methyl-6-benzothiazolyl)-1H-indazole-5-carboxamide | 15.4 | 533.2 | 532.9 | 3.22 |
| 15 | 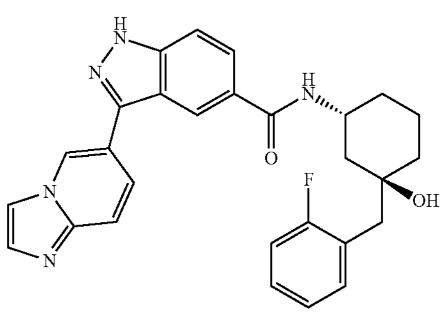 [SMILES: O=C(N[C@@H]1CCC[C@](O)(Cc2ccccc2F)C1)c1ccc2[nH]nc(-c3ccc4nccn4c3)c2c1] | N-[3(S)-[(2-fluorophenyl)methyl]-3-hydroxy-1(R)-cyclohexyl]-3-imidazo[1,2-a]pyridin-6-yl-1H-indazole-5-carboxamide | 8.6 | 484.2 | 484.0 | 2.34 |
| 16 | 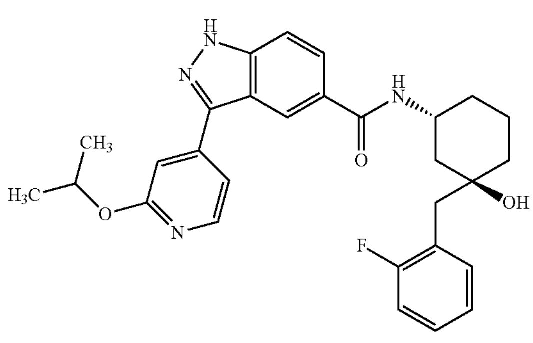 [SMILES: CC(C)Oc1cc(-c2n[nH]c3ccc(C(=O)N[C@@H]4CCC[C@](O)(Cc5ccccc5F)C4)cc23)ccn1] | N-[3(S)-[(2-fluorophenyl)methyl]-3-hydroxy-1(R)-cyclohexyl]-3-[2-(1-methylethoxy)-4-pyridinyl]-1H-indazole-5-carboxamide | 301 | 503.2 | 503.0 | 3.4 |

-continued

| Compd # | Structure | Chemical Names | aERK IC50 nM | M + 1 Cacld. | M + 1 Obs. | Rf min. |
|---|---|---|---|---|---|---|
| 17 | 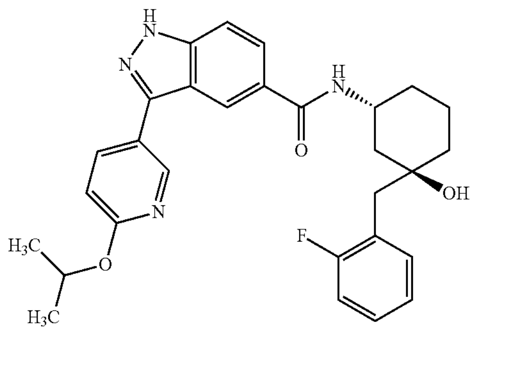 [SMILES: CC(C)Oc1ccc(-c2n[nH]c3ccc(C(=O)N[C@@H]4CCC[C@](O)(Cc5ccccc5F)C4)cc23)cn1] | N-[3-(S)-[(2-fluorophenyl)methyl]-3-hydroxy-1(R)-cyclohexyl]-3-[6-(1-methylethoxy)-3-pyridinyl]-1H-indazole-5-carboxamide | 44.9 | 503.2 | 503.0 | 3.53 |
| 18 | 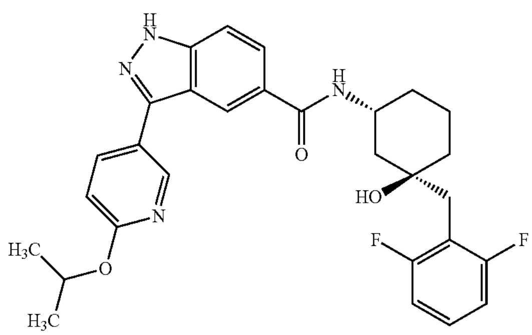 [SMILES: CC(C)Oc1ccc(-c2n[nH]c3ccc(C(=O)N[C@@H]4CCC[C@](O)(Cc5c(F)cccc5F)C4)cc23)cn1] | N-[3(S)-[(2,6-difluorophenyl)methyl]-3-hydroxy-1(R)-cyclohexyl]-3-[6-(1-methylethoxy)-3-pyridinyl]-1H-indazole-5-carboxamide | 139.8 | 521.2 | 520.9 | 3.48 |
| 19 | 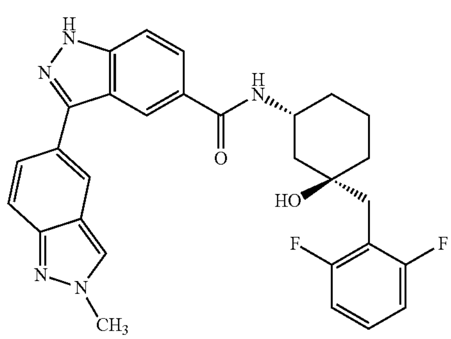 [SMILES: Cn1cc2cc(-c3n[nH]c4ccc(C(=O)N[C@@H]5CCC[C@](O)(Cc6c(F)cccc6F)C5)cc34)ccc2n1] | N-[3(S)-[(2,6-difluorophenyl)methyl]-3-hydroxy-1(R)-cyclohexyl]-3-(2-methyl-2H-indazol-5-yl)-1H-indazole-5-carboxamide | 12.1 | 516.2 | 516.0 | 2.9 |
| 20 | 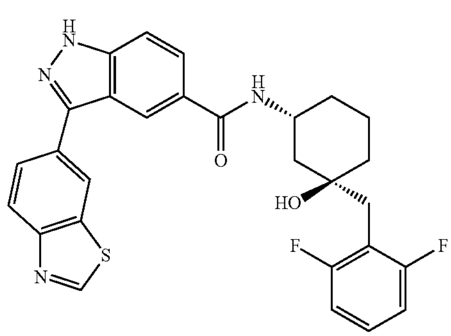 [SMILES: O=C(N[C@@H]1CCC[C@](O)(Cc2c(F)cccc2F)C1)c1ccc2[nH]nc(-c3ccc4ncsc4c3)c2c1] | 3-(6-benzothiazolyl)-N-[3(S)-[(2,6-difluorophenyl)methyl]-3-hydroxy-1(R)-cyclohexyl]-1H-indazole-5-carboxamide | 33.9 | 519.2 | 519.1 | 3.11 |

-continued

| Compd # | Structure | Chemical Names | aERK IC50 nM | M + 1 Cacld. | M + 1 Obs. | Rf min. |
|---|---|---|---|---|---|---|
| 21 | 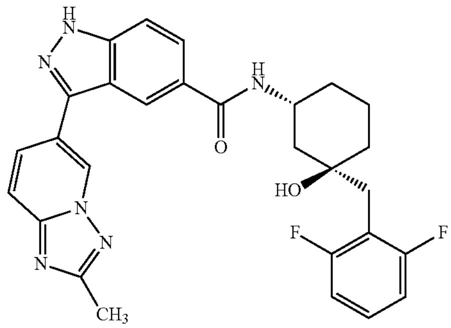 [SMILES: Cc1nc2ccc(-c3n[nH]c4ccc(C(=O)N[C@@H]5CCC[C@](O)(Cc6c(F)cccc6F)C5)cc34)cn2n1] | N-[3-(S)-[(2,6-difluorophenyl)methyl]-3-hydroxy-1(R)-cyclohexyl]-3-(2-methyl[1,2,4]triazolo[1,5-a]pyridin-6-yl)-1H-indazole-5-carboxamide | 20.9 | 517.2 | 517.1 | 2.89 |
| 22 | 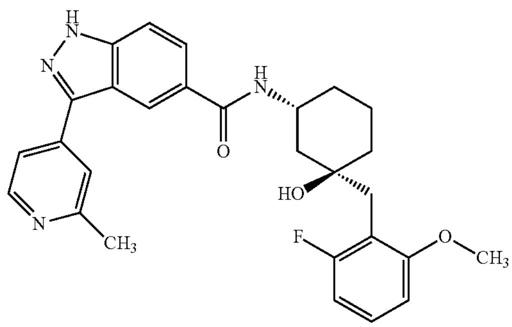 [SMILES: COc1cccc(F)c1C[C@@]1(O)CCC[C@@H](NC(=O)c2ccc3[nH]nc(-c4ccnc(C)c4)c3c2)C1] | N-[3(S)-[(2-fluoro-6-methoxyphenyl)methyl]-3-hydroxy-1(R)-cyclohexyl]-3-(2-methyl-4-pyridinyl)-1H-indazole-5-carboxamide | 2.0 | 489.2 | 489.2 | 2.42 |
| 23 | 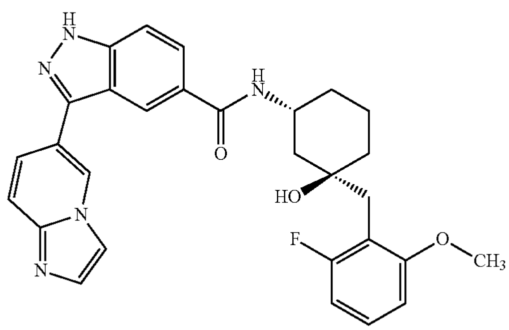 [SMILES: COc1cccc(F)c1C[C@@]1(O)CCC[C@@H](NC(=O)c2ccc3[nH]nc(-c4ccc5nccn5c4)c3c2)C1] | N-[3(S)-[(2-fluoro-6-methoxyphenyl)methyl]-3-hydroxy-1(R)-cyclohexyl]-3-imidazo[1,2-a]pyridin-6-yl-1H-indazole-5-carboxamide | 2.2 | 514.2 | 514.2 | 2.45 |
| 24 | 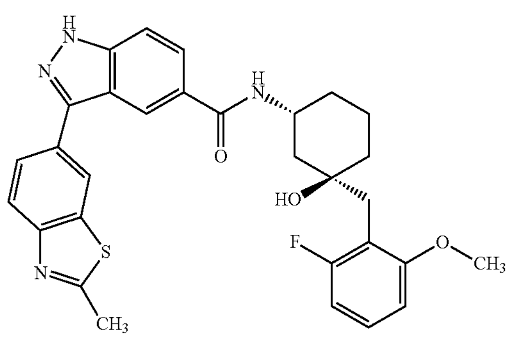 [SMILES: COc1cccc(F)c1C[C@@]1(O)CCC[C@@H](NC(=O)c2ccc3[nH]nc(-c4ccc5nc(C)sc5c4)c3c2)C1] | N-[3(S)-[(2-fluoro-6-methoxyphenyl)methyl]-3-hydroxy-1(R)-cyclohexyl]-3-(2-methyl-6-benzothiazolyl)-1H-indazole-5-carboxamide | 8.9 | 545.2 | 545.2 | 3.44 |

-continued

| Compd # | Structure | Chemical Names | aERK IC50 nM | M + 1 Cacld. | M + 1 Obs. | Rf min. |
|---|---|---|---|---|---|---|
| 25 | 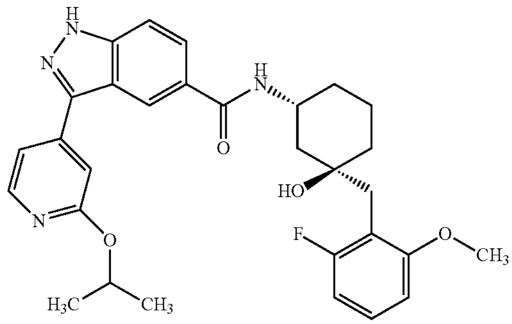 [SMILES: COc1cccc(F)c1C[C@@]1(O)CCC[C@@H](NC(=O)c2ccc3[nH]nc(-c4ccnc(OC(C)C)c4)c3c2)C1] | N-[3(S)-[(2-fluoro-6-methoxyphenyl)methyl]-3-hydroxy-1(R)-cyclohexyl]-3-[2-(1-methylethoxy)-4-pyridinyl]-1H-indazole-5-carboxamide | 332.6 | 533.2 | 533.3 | 3.26 |
| 26 | 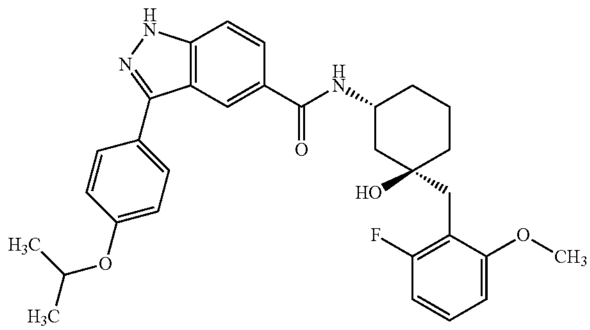 [SMILES: COc1cccc(F)c1C[C@@]1(O)CCC[C@@H](NC(=O)c2ccc3[nH]nc(-c4ccc(OC(C)C)cc4)c3c2)C1] | N-[3(S)-[(2-fluoro-6-methoxyphenyl)methyl]-3-hydroxy-1(R)-cyclohexyl]-3-[4-(1-methylethoxy)phenyl]-1H-indazole-5-carboxamide | 79.0 | 532.3 | 532.3 | 3.83 |

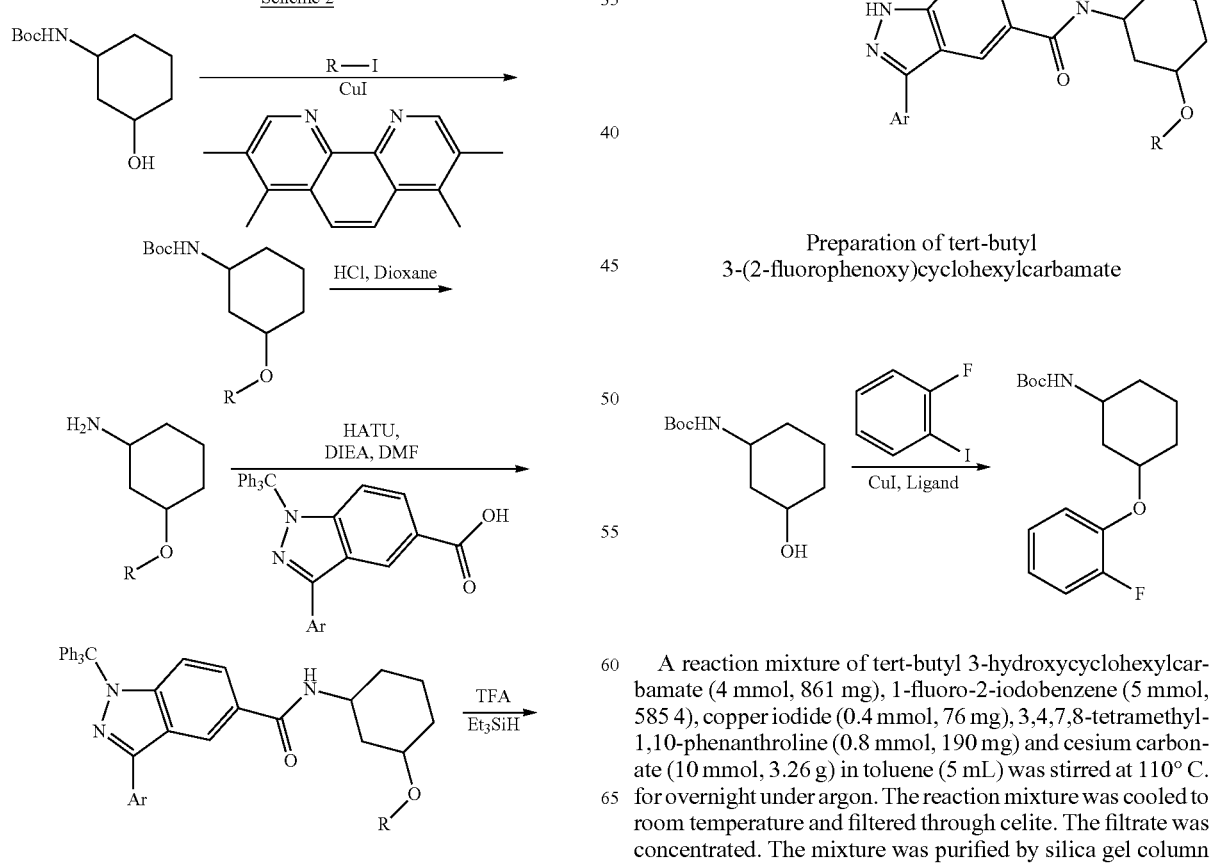

Preparation of tert-butyl 3-(2-fluorophenoxy)cyclohexylcarbamate

A reaction mixture of tert-butyl 3-hydroxycyclohexylcarbamate (4 mmol, 861 mg), 1-fluoro-2-iodobenzene (5 mmol, 585 4), copper iodide (0.4 mmol, 76 mg), 3,4,7,8-tetramethyl-1,10-phenanthroline (0.8 mmol, 190 mg) and cesium carbonate (10 mmol, 3.26 g) in toluene (5 mL) was stirred at 110° C. for overnight under argon. The reaction mixture was cooled to room temperature and filtered through celite. The filtrate was concentrated. The mixture was purified by silica gel column chromatography. The product, tert-butyl 3-(2-fluorophenoxy)cyclohexylcarbamate, was eluted off the column using 15% EtOAc in Hexane.

Preparation of 3-(2-fluorophenoxy)cyclohexanamine

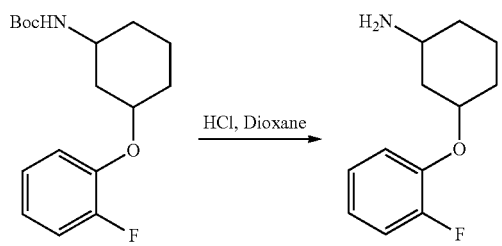 [SMILES: CC(C)(C)OC(=O)NC1CCCC(Oc2ccccc2F)C1 ; NC1CCCC(Oc2ccccc2F)C1]

tert-Butyl 3-(2-fluorophenoxy)cyclohexylcarbamate was stirred in a solution of HCl in dioxane (4 M) at room temperature for overnight. The product, HCl salt of 3-(2-fluorophenoxy)cyclohexanamine, was obtained after removal of solvent.

Preparation of N-(3-(2-fluorophenoxy)cyclohexyl)-3-(2-methylpyridin-4-yl)-1-trityl-4H-indazole-5-carboxamide

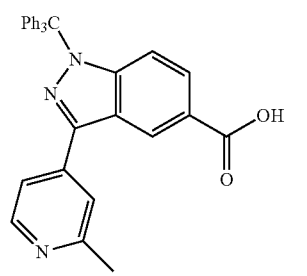

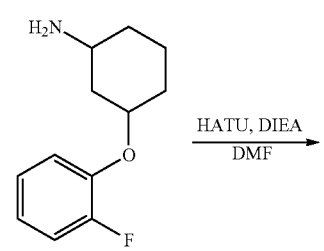

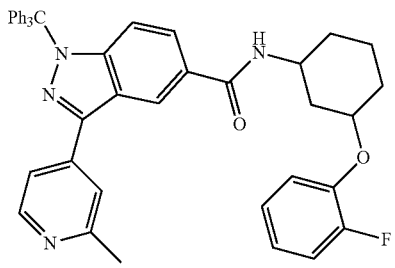

A reaction mixture of 3-(2-methylpyridin-4-yl)-1-trityl-1H-indazole-5-carboxylic acid (0.15 mmol, 74.3 mg), HCl salt of 3-(2-fluorophenoxy)cyclohexanamine (0.15 mmol, 37 mg), HATU (0.15 mmol, 57 mg) and DIEA in DMA was stirred at room temperature for overnight. The product, N-(3-(2-fluorophenoxy)cyclohexyl)-3-(2-methylpyridin-4-yl)-1-trityl-1H-indazole-5-carboxamide, was obtained after evaporation of solvent.

Preparation of N-(3-(2-fluorophenoxy)cyclohexyl)-3-(2-methylpyridin-4-yl)-1H-indazole-5-carboxamide

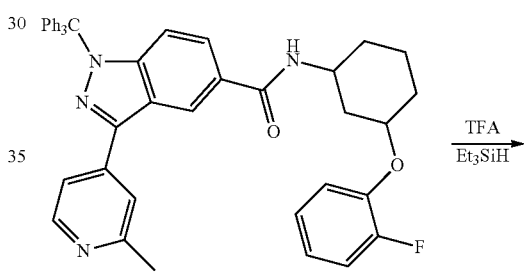

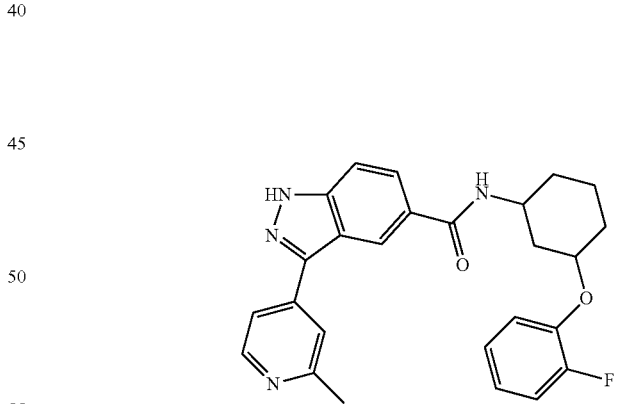

N-(3-(2-fluorophenoxy)cyclohexyl)-3-(2-methylpyridin-4-yl)-1-trityl-1H-indazole-5-carboxamide was stirred in neat TFA at room temperature for 10 minutes, and then Et₃SiH (5 equiv.) was added. The reaction mixture was stirred at room temperature for 30 minutes, and then concentrated. The product N-[3-(2-fluorophenoxy)cyclohexyl]-3-(2-methyl-4-pyridinyl)-1H-indazole-5-carboxamide was obtained and purified by reverse phase HPLC.

The following compounds were prepared with similar method:

| Compd # | Structure | Chemical Names | aERK IC50 nM | M + 1 Cacld. | M + 1 Obs. | Rf min. |
|---|---|---|---|---|---|---|
| 27 | 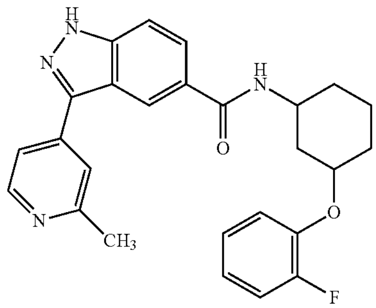 [SMILES: Cc1cc(-c2n[nH]c3ccc(C(=O)NC4CCCC(Oc5ccccc5F)C4)cc23)ccn1] | N-[3-(2-fluorophenoxy)cyclohexyl]-3-(2-methyl-4-pyridinyl)-1H-indazole-5-carboxamidem (isomer 1) | 61.0 | 445.2 | 445.0 | 2.53 |
| 28 | 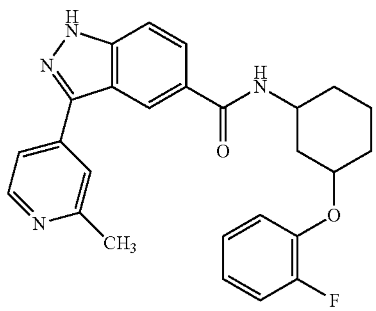 [SMILES: Cc1cc(-c2n[nH]c3ccc(C(=O)NC4CCCC(Oc5ccccc5F)C4)cc23)ccn1] | N-[3-(2-fluorophenoxy)cyclohexyl]-3-(2-methyl-4-pyridinyl)-1H-indazole-5-carboxamide (isomer 2) | 112.9 | 445.2 | 445.0 | 2.58 |
| 29 | 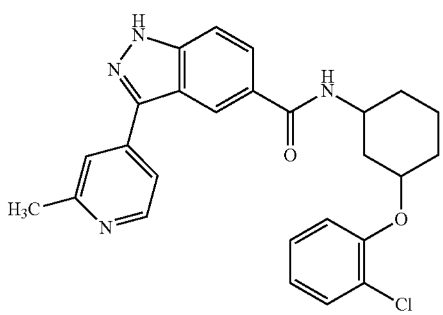 [SMILES: Cc1cc(-c2n[nH]c3ccc(C(=O)NC4CCCC(Oc5ccccc5Cl)C4)cc23)ccn1] | N-[3-(2-chlorophenoxy)cyclohexyl]-3-(2-methyl-4-pyridinyl)-1H-indazole-5-carboxamide (isomer 1) | 1000.0 | 461.2 | 461.0 | 2.7 |
| 30 | 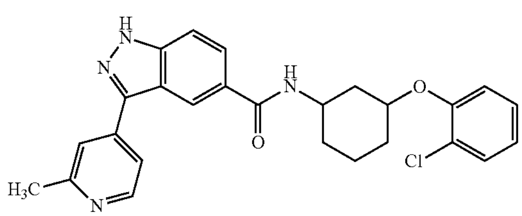 [SMILES: Cc1cc(-c2n[nH]c3ccc(C(=O)NC4CCCC(Oc5ccccc5Cl)C4)cc23)ccn1] | N-[3-(2-chlorophenoxy)cyclohexyl]-3-(2-methyl-4-pyridinyl)-1H-indazole-5-carboxamide (isomer 2) | 38.6 | 461.2 | 461.0 | 2.73 |
| 31 | 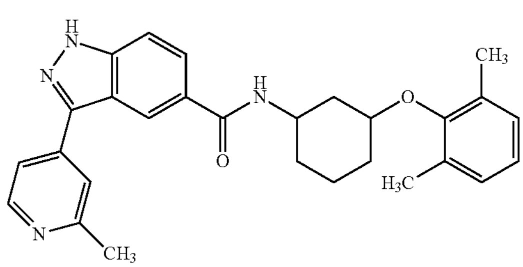 [SMILES: Cc1cc(-c2n[nH]c3ccc(C(=O)NC4CCCC(Oc5c(C)cccc5C)C4)cc23)ccn1] | N-[3-(2,6-dimethylphenoxy)cyclohexyl]-3-(2-methyl-4-pyridinyl)-1H-indazole-5-carboxamide | 469.1 | 455.2 | 455.0 | 2.79 |

| Compd # | Structure | Chemical Names | aERK IC50 nM | M + 1 Cacld. | M + 1 Obs. | Rf min. |
|---|---|---|---|---|---|---|
| 32 | 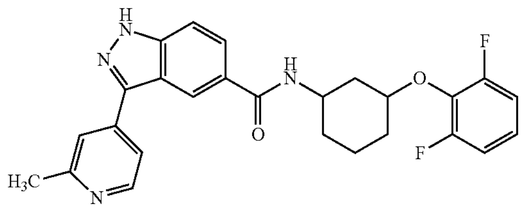 [SMILES: Cc1cc(-c2n[nH]c3ccc(C(=O)NC4CCCC(Oc5c(F)cccc5F)C4)cc23)ccn1] | N-[3-(2,6-difluorophenoxy)cyclohexyl]-3-(2-methyl-4-pyridinyl)-1H-indazole-5-carboxamide | 572.7 | 463.2 | 463.0 | 2.63 |
| 33 | 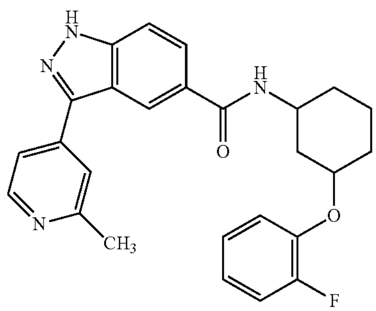 [SMILES: Cc1cc(-c2n[nH]c3ccc(C(=O)NC4CCCC(Oc5ccccc5F)C4)cc23)ccn1] | N-[3-(2-fluorophenoxy)cyclohexyl]-3-(2-methyl-4-pyridinyl)-1H-indazole-5-carboxamide | 114.0 | 445.2 | 445.0 | 2.56 |
| 34 | 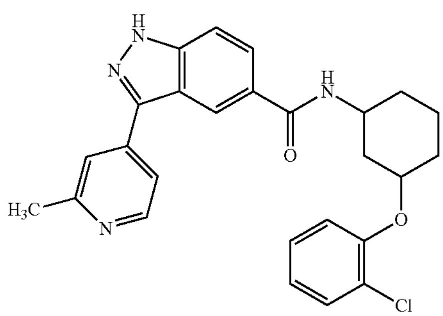 [SMILES: Cc1cc(-c2n[nH]c3ccc(C(=O)NC4CCCC(Oc5ccccc5Cl)C4)cc23)ccn1] | N-[3-(2-chlorophenoxy)cyclohexyl]-3-(2-methyl-4-pyridinyl)-1H-indazole-5-carboxamide (isomer 1) | 197.9 | 461.2 | 461.0 | 2.7 |
| 35 | 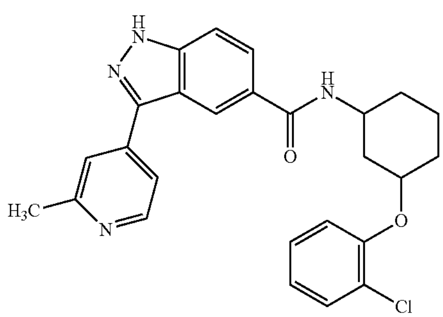 [SMILES: Cc1cc(-c2n[nH]c3ccc(C(=O)NC4CCCC(Oc5ccccc5Cl)C4)cc23)ccn1] | N-[3-(2-chlorophenoxy)cyclohexyl]-3-(2-methyl-4-pyridinyl)-1H-indazole-5-carboxamide (isomer 2) | 191.7 | 461.2 | 460.9 | 2.75 |
| 36 | 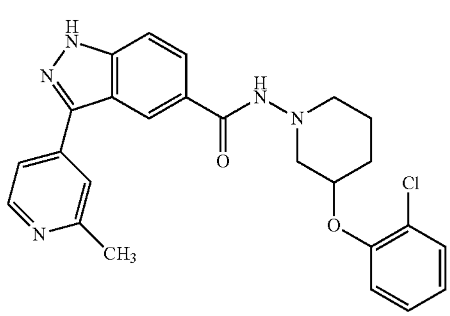 [SMILES: Cc1cc(-c2n[nH]c3ccc(C(=O)NN4CCCC(Oc5ccccc5Cl)C4)cc23)ccn1] | N-[3-(2-chlorophenoxy)-1-piperidinyl]-3-(2-methyl-4-pyridinyl)-1H-indazole-5-carboxamide | 40.4 | 462.2 | 462.0 | 2.38 |

-continued
| Compd # | Structure | Chemical Names | aERK IC50 nM | M + 1 Cacld. | M + 1 Obs. | Rf min. |
|---|---|---|---|---|---|---|
| 37 | 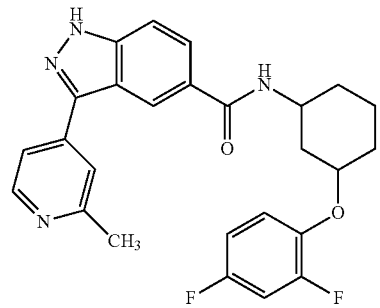 [SMILES: Cc1cc(-c2n[nH]c3ccc(C(=O)NC4CCCC(Oc5ccc(F)cc5F)C4)cc23)ccn1] | N-[3-(2,4-difluorophenoxy)cyclohexyl]-3-(2-methyl-4-pyridinyl)-1H-indazole-5-carboxamide (isomer 1) | 128.2 | 463.2 | 463.0 | 2.62 |
| 38 | 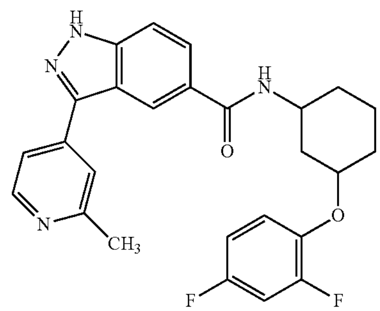 [SMILES: Cc1cc(-c2n[nH]c3ccc(C(=O)NC4CCCC(Oc5ccc(F)cc5F)C4)cc23)ccn1] | N-[3-(2,4-difluorophenoxy)cyclohexyl]-3-(2-methyl-4-pyridinyl)-1H-indazole-5-carboxamide (isomer 2) | 476.0 | 463.2 | 463.0 | 2.66 |
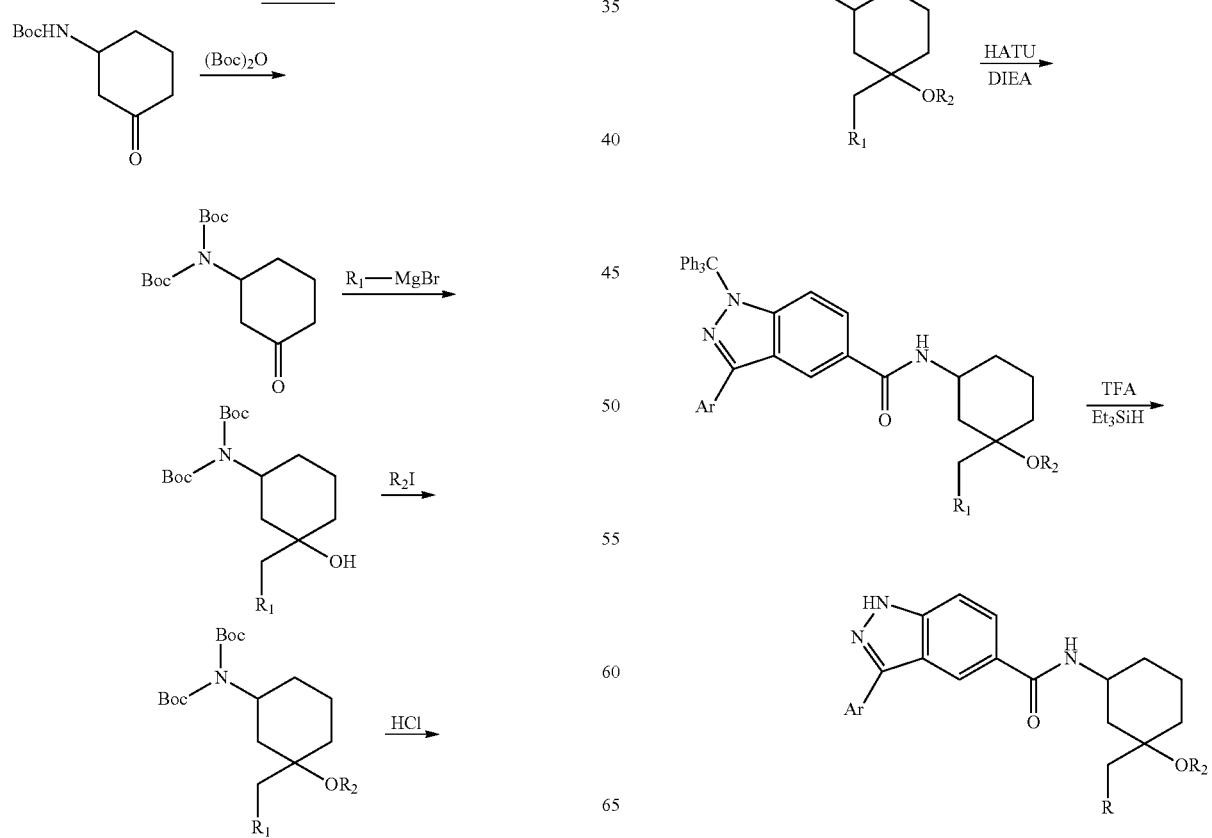
Scheme 3

Preparation of Compound A

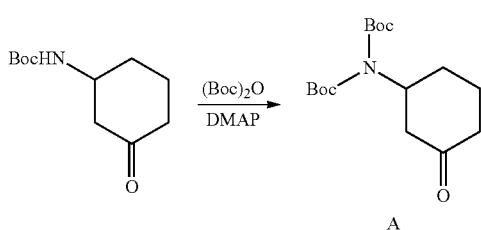

A reaction mixture of tert-butyl 3-oxocyclohexylcarbamate (5 mmol, 1.07 g), di-tert-butyl dicarbonate (12.5 mmol, 2.73 g) and DMAP (0.5 mmol, 61 mg) in refluxing THF (20 mL) was stirred for overnight. The reaction mixture was cooled to room temperature and concentrated. The product A was obtained in a colorless oil (1.28 g, 82% yield) after purification by silica gel column chromatography.

Preparation of Compound B

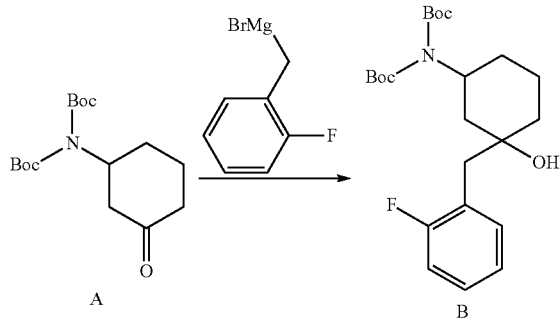

To the solution of A (2 mmol, 626 mg) in THF (5 mL) at room temperature was added a solution of (2-fluorobenzyl) magnesium chloride in ether (2.2 mmol, 0.25 M, 8.8 mL) under argon. The reaction mixture was stirred at room temperature for overnight. Water was added dropwise. The organics were extracted with EtOAc. The product B was purified by silica gel column chromatography.

Preparation of Compound C

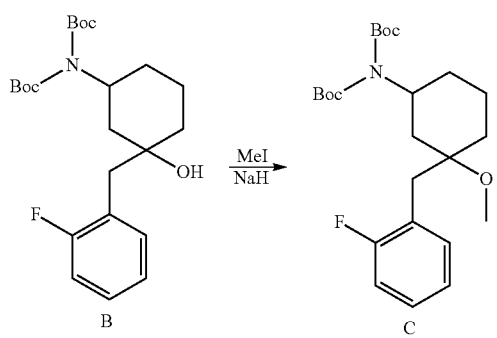

To the solution of B (0.16 mmol, 71 mg) in DMF was added sodium hydride (0.2 mmol, 8 mg) at 0° C. The reaction mixture was stirred at 0° C. for 15 minutes. Methyl iodide (0.8 mmol, 50 μL) was added. The reaction mixture was allowed to warm up to room temperature and stirred for overnight. Water was added. The organics were extracted with EtOAc. The product C was purified by silica gel column chromatography.

Preparation of 3-(2-fluorobenzyl)-3-methoxycyclohexanamine

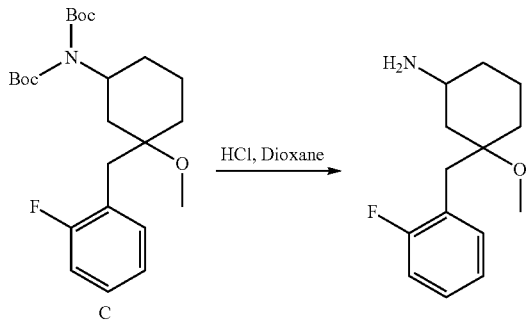

A mixture of product C in a solution of HCl in dioxane (4 M) was stirred at room temperature for overnight. The product, HCl salt of 3-(2-fluorobenzyl)-3-methoxycyclohexanamine, was obtained after evaporation of solvent.

Preparation of N-(3-(2-fluorobenzyl)-3-methoxycyclohexyl)-3-(2-methylpyridin-4-yl)-1-trityl-1H-indazole-5-carboxamide

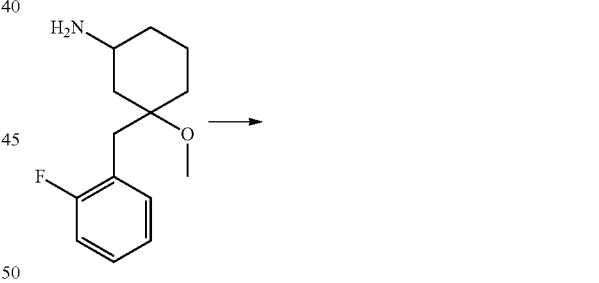

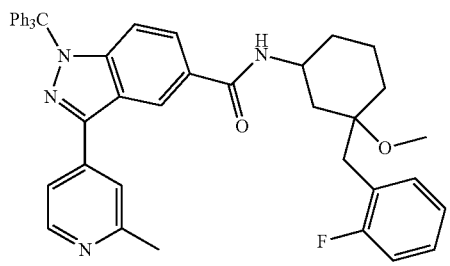

A reaction mixture of 3-(2-methylpyridin-4-yl)-1-trityl-1H-indazole-5-carboxylic acid (0.025 mmol, 12.4 mg), HCl salt of 3-(2-fluorobenzyl)-3-methoxycyclohexanamine (0.025 mmol, 6.8 mg), HATU (0.025 mmol, 9.5 mg) and DIEA (0.1 mL) in DMA (0.5 mL) was stirred at room temperature for overnight. The product, N-(3-(2-fluorobenzyl)-3-methoxycyclohexyl)-3-(2-methylpyridin-4-yl)-1-trityl-1H-indazole-5-carboxamide, was obtained after evaporation of solvent.

Preparation of N-(3-(2-fluorobenzyl)-3-methoxycyclohexyl)-3-(2-methylpyridin-4-yl)-1H-indazole-5-carboxamide

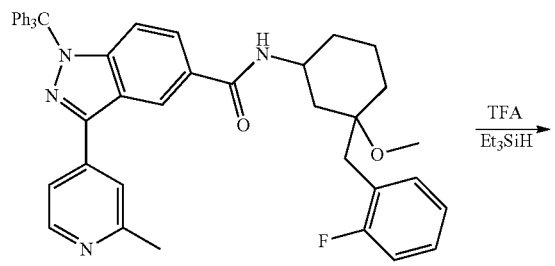

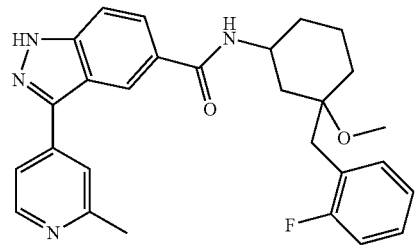

N-(3-(2-fluorobenzyl)-3-methoxycyclohexyl)-3-(2-methylpyridin-4-yl)-1-trityl-1H-indazole-5-carboxamide was stirred in neat TFA at room temperature for 10 minutes, and then $Et_3SiH$ (5 equiv.) was added. The reaction mixture was stirred at room temperature for 5 minutes, and then concentrated. The product was obtained and purified by reverse phase HPLC. Two diastereomers obtained.

| Compd # | Structure | Chemical Names | aERK IC50 nM | M + 1 Cacld. | M + 1 Obs. | Rf min. |
|---|---|---|---|---|---|---|
| 39 | 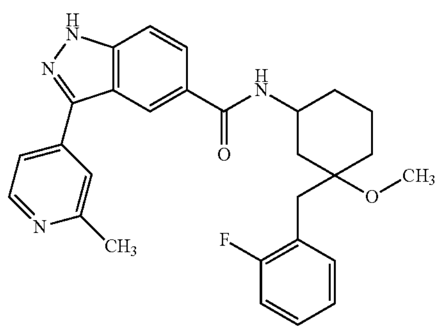 [SMILES: COC1(Cc2ccccc2F)CCCC(NC(=O)c2ccc3[nH]nc(-c4ccnc(C)c4)c3c2)C1] | N-[3-[(2-fluorophenyl)methyl]-3-methoxycyclohexyl]-3-(2-methyl-4-pyridinyl)-1H-indazole-5-carboxamide (diasterimer 1) | 28.5 | 473.2 | 473.0 | 2.57 |
| 40 | 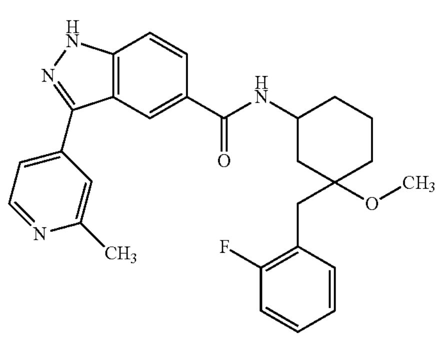 [SMILES: COC1(Cc2ccccc2F)CCCC(NC(=O)c2ccc3[nH]nc(-c4ccnc(C)c4)c3c2)C1] | N-[3-[(2-fluorophenyl)methyl]-3-methoxycyclohexyl]-3-(2-methyl-4-pyridinyl)-1H-indazole-5-carboxamide (diasterimer 2) | 204.6 | 473.2 | 473.0 | 2.64 |

77

Scheme 4

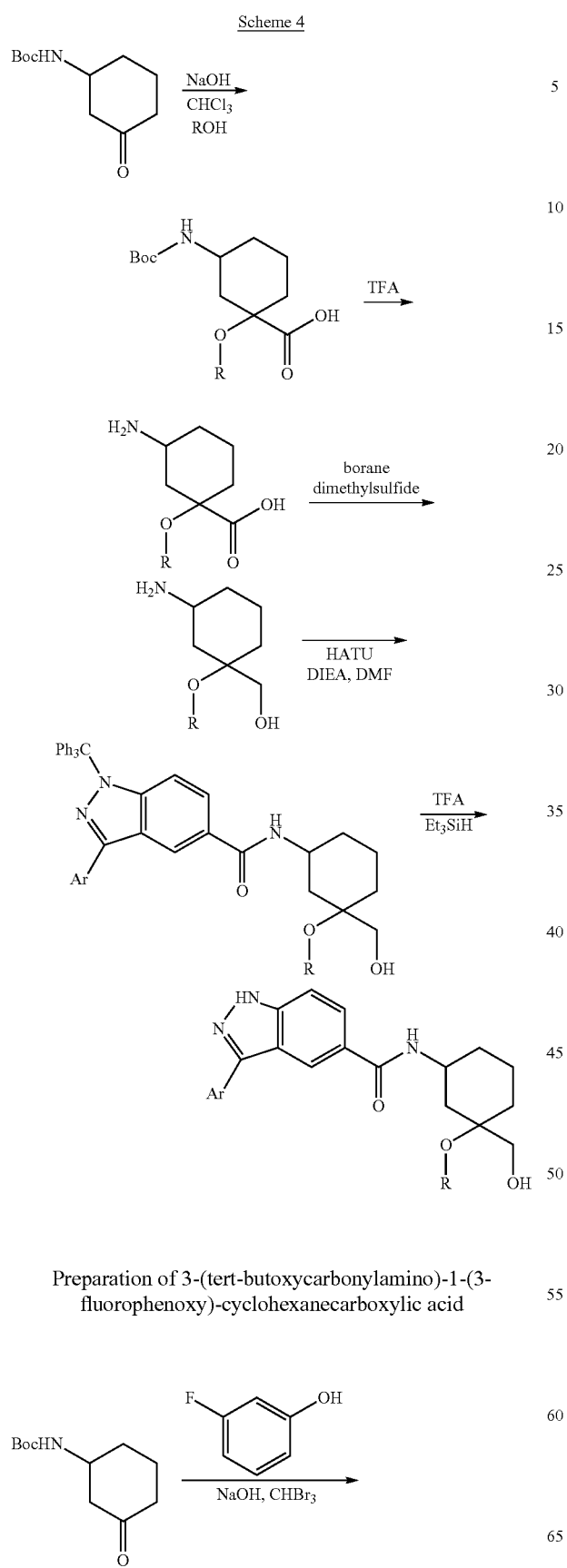

Preparation of 3-(tert-butoxycarbonylamino)-1-(3-fluorophenoxy)-cyclohexanecarboxylic acid

78

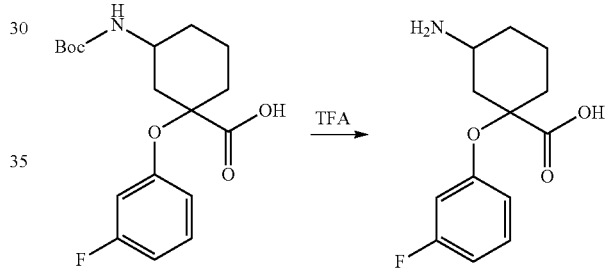

To the mixture of tert-butyl 3-oxocyclohexylcarbamate (5 mmol, 1.065 g), 3-fluorophenol (5 mmol, 560 mg) and NaOH (25 mmol, 1 g) in THF at 0° C. was added bromoform (25 mmol, 2.2 mL) dropwise. The reaction mixture was allowed to warm to room temperature and stirred for overnight. The reaction mixture was concentrated. The product, 3-(tert-butoxycarbonylamino)-1-(3-fluorophenoxy)cyclohexanecarboxylic acid, was obtained (60 mg, 3% yield) after purification by reverse phase HPLC.

Preparation of 3-amino-1-(3-fluorophenoxy)cyclohexanecarboxylic acid

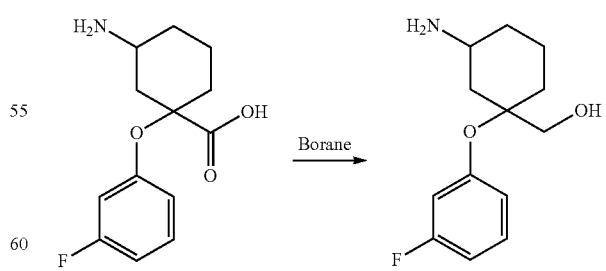

A reaction mixture of 3-(tert-butoxycarbonylamino)-1-(3-fluorophenoxy)cyclohexanecarboxylic acid in TFA (neat) was stirred at room temperature for 10 minutes. The product, 3-amino-1-(3-fluorophenoxy)cyclohexanecarboxylic acid, was obtained after purification by reverse phase HPLC.

Preparation of (3-amino-1-(3-fluorophenoxy)cyclohexyl)methanol

To the solution of 3-amino-1-(3-fluorophenoxy)cyclohexanecarboxylic acid (0.2 mmol, 50.6 mg) in THF was added a solution of borane dimethylsulfide complex in THF (1 mmol, 2 M, 0.5 mL). The reaction mixture was stirred at room temperature for overnight. A solution of HCl in dioxane was added dropwise. The product, HCl salt of (3-amino-1-(3-fluorophenoxy)cyclohexyl)methanol, was obtained after removal of solvent.

Preparation of N-(3-(3-fluorophenoxy)-3-(hydroxymethyl)cyclohexyl)-3-(2-methylpyridin-4-yl)-1-trityl-1H-indazole-5-carboxamide

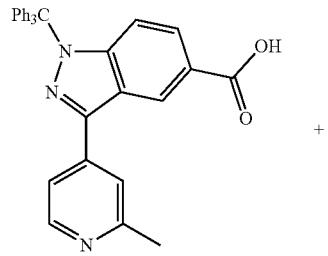

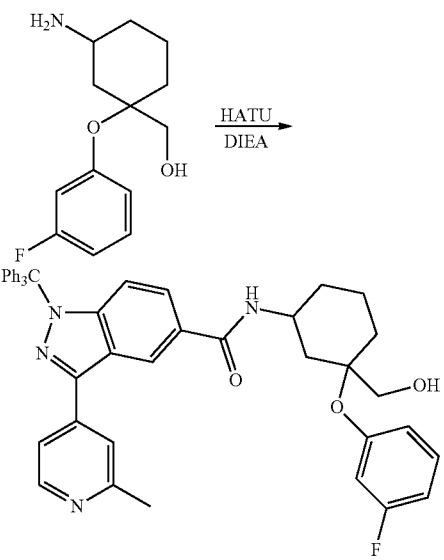

A reaction mixture of 3-(2-methylpyridin-4-yl)-1-trityl-1H-indazole-5-carboxylic acid (0.2 mmol, 100 mg), HCl salt of (3-amino-1-(3-fluorophenoxy)cyclohexyl)methanol (0.2 mmol, 55 mg), HATU (0.2 mmol, 76 mg) and DIEA in DMA was stirred at room temperature for overnight. The product, N-(3-(3-fluorophenoxy)-3-(hydroxymethyl)cyclohexyl)-3-(2-methylpyridin-4-yl)-1-trityl-1H-indazole-5-carboxamide, was obtained after evaporation of solvent.

Preparation of N-(3-(3-fluorophenoxy)-3-(hydroxymethyl)cyclohexyl)-3-(2-methylpyridin-4-yl)-1H-indazole-5-carboxamide

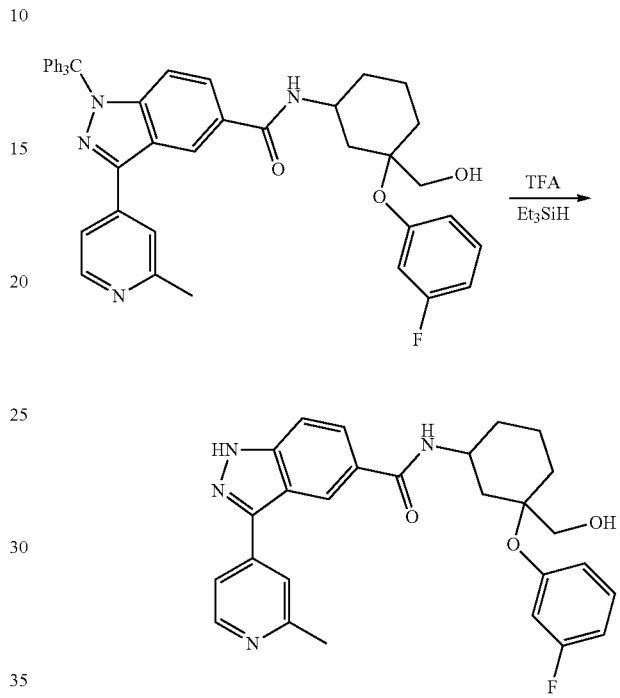

N-(3-(3-fluorophenoxy)-3-(hydroxymethyl)cyclohexyl)-3-(2-methylpyridin-4-yl)-1-trityl-1H-indazole-5-carboxamide was stirred in neat TFA at room temperature for 10 minutes, and then Et$_3$SiH (5 equiv.) was added. The reaction mixture was stirred at room temperature for 5 minutes, and then concentrated. The product was obtained after purification by reverse phase HPLC. The diastereomers were separated and enantiomers were separated on chiral column (AD) on a HPLC.

The following compounds were prepared in a similar method:

| Compd # | Structure | Chemical Names | aERK IC50 nM | M + 1 Cacld. | M + 1 Obs. | Rf min. |
|---|---|---|---|---|---|---|
| 41 | 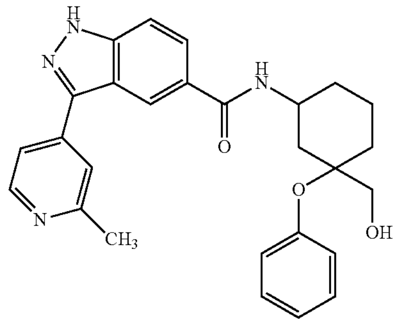 [SMILES: Cc1cc(-c2n[nH]c3ccc(C(=O)NC4CCCC(CO)(Oc5ccccc5)C4)cc23)ccn1] | N-[3-(hydroxymethyl)-3-phenoxycyclohexyl]-3-(2-methyl-4-pyridinyl)-1H-indazole-5-carboxamide | 98.9 | 457.2 | 456.9 | 2.16 |

-continued

| Compd # | Structure | Chemical Names | aERK IC50 nM | M + 1 Cacld. | M + 1 Obs. | Rf min. |
|---|---|---|---|---|---|---|
| 42 | 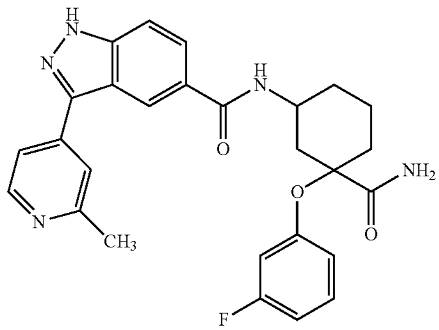 [SMILES: Cc1cc(-c2n[nH]c3ccc(C(=O)NC4CCCC(Oc5cccc(F)c5)(C(N)=O)C4)cc23)ccn1] | N-[3-(aminocarbonyl)-3-(3-fluorophenoxy)cyclohexyl]-3-(2-methyl-4-pyridinyl)-1H-indazole-5-carboxamide | 11.2 | 488.2 | 488.0 | 2.16 |
| 43 | 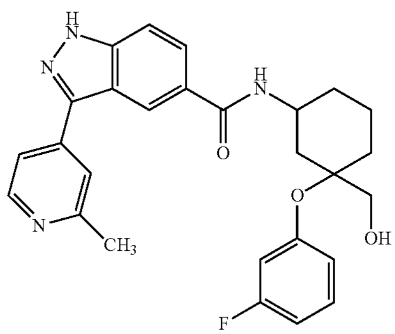 [SMILES: Cc1cc(-c2n[nH]c3ccc(C(=O)NC4CCCC(CO)(Oc5cccc(F)c5)C4)cc23)ccn1] | N-[3-(3-fluorophenoxy)-3-(hydroxymethyl)cyclohexyl]-3-(2-methyl-4-pyridinyl)-1H-indazole-5-carboxamide (isomer 1) | 13.4 | 475.2 | 475.0 | 2.24 |
| 44 | 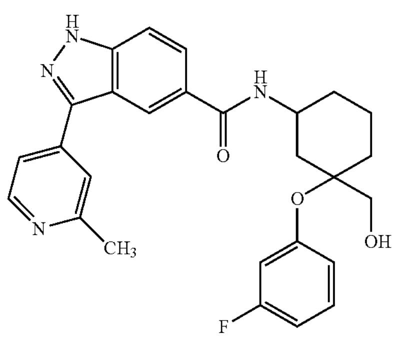 [SMILES: Cc1cc(-c2n[nH]c3ccc(C(=O)NC4CCCC(CO)(Oc5cccc(F)c5)C4)cc23)ccn1] | N-[3-(3-fluorophenoxy)-3-(hydroxymethyl)cyclohexyl]-3-(2-methyl-4-pyridinyl)-1H-indazole-5-carboxamide (isomer 2) | 213.7 | 475.2 | 475.0 | 2.24 |
| 45 | 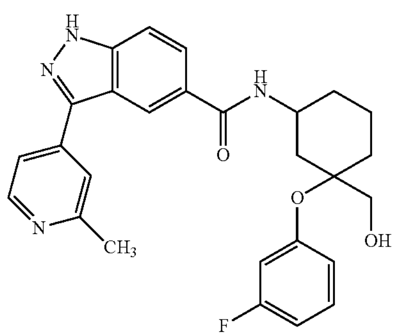 [SMILES: Cc1cc(-c2n[nH]c3ccc(C(=O)NC4CCCC(CO)(Oc5cccc(F)c5)C4)cc23)ccn1] | N-[3-(3-fluorophenoxy)-3-(hydroxymethyl)cyclohexyl]-3-(2-methyl-4-pyridinyl)-1H-indazole-5-carboxamide (isomer 3) | 186.5 | 475.2 | 475.2 | 2.26 |

Preparation of 3-fluoro-3(2-fluorobenzyl)cyclohexanamine

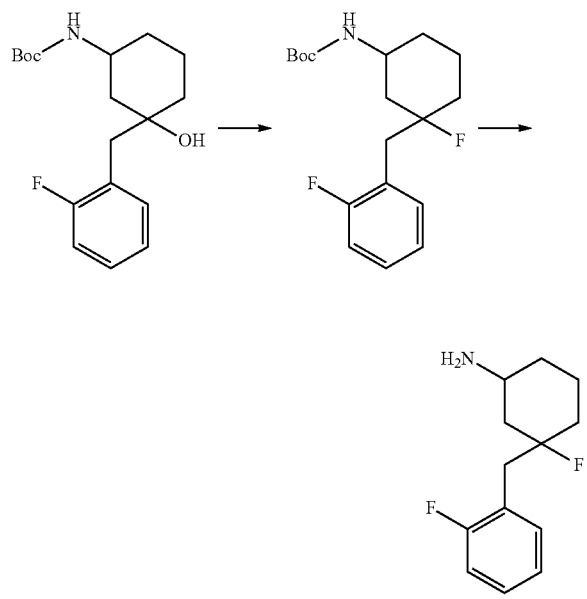

To a solution of tert-butyl-3-(2-fluorobenzyl)-3-hydroxy-cyclohexylcarbamate (1 mmol, 323 mg) in DCM was added Deoxo-Fluor® (2 mmol, 370 μL) at room temperature. The reaction mixture was stirred for overnight. Methanol was added dropwise. The desired product was obtained after the removal of solvent by rotary evaporation.

tert-Butyl-3-fluoro-3-(2-fluorobenzyl)cyclohexylcarbamate was reacted with HCl in dioxane (4 M) at room temperature. After stirring for overnight, 3-fluoro-3-(2-fluorobenzyl)cyclohexanamine was obtained after the removal of solvent by rotary evaporation.

Preparation of 3-amino-1-(difluoro(phenyl)methyl)cyclohexanol

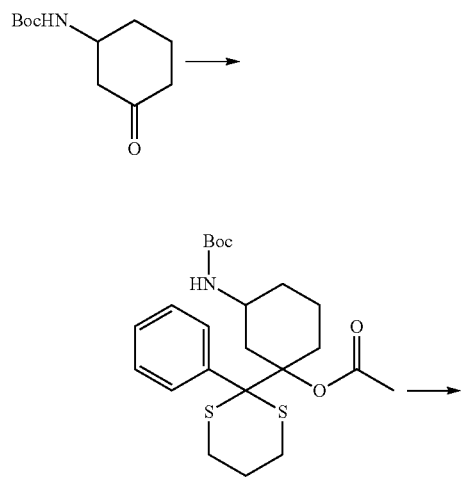

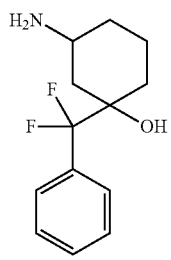

To a solution of 2-phenyl-1,3-dithiane (12 mmol, 2.35 g) in THF (15 mL) at 78° C. was added a solution of lithium diisopropylamide in THF/heptane/ethylbenzene (12 mmol, 1.8 M, 6.7 mL) under argon. The reaction mixture was warmed up to −20° C. and stirred for 30 minutes at −20° C. The reaction mixture was cooled down to −78° C. tert-Butyl 3-oxocyclohexylcarbamate (5 mmol, 1.065 g) in THF was added. The reaction mixture was allowed to warm up to room temperature and stirred for overnight. Acetic anhydride (20 mmol, 1.9 mL) was added. The reaction mixture was stirred at room temperature for 4 hours. Water was added. The organics were extracted with EtOAc. 3-(tert-Butoxycarbonylamino)-1-(2-phenyl-1,3-dithiaN-2-yl)cyclohexyl acetate was obtained after purification by silica gel column chromatography.

To a solution of nitrosonium tetrafluoroborate (1.1 mmol, 128.5 mg) and hydrogen fluoride pyridine (0.5 mL) in DCM (2 mL) at 0° C. under argon was added a solution of 3-(tert-butoxycarbonylamino)-1-(2-phenyl-1,3-dithiaN-2-yl)cyclohexyl acetate (0.5 mmol, 226 mg) in DCM dropwise. The reaction mixture was stirred at 0° C. for 1 hour. Sodium carbonate (solid) was added until no further gas bubbling. The mixture and the methanol washings were filtered. The filtrate was concentrated. 3-Amino-1-(difluoro(phenyl)methyl)cyclohexanol was obtained after purification by reverse phase HPLC.

Preparation of (3-amino-1-hydroxycyclohexyl)(phenyl)methanone

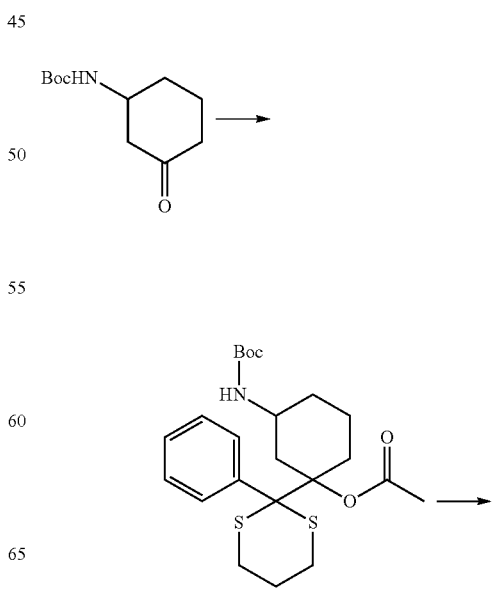

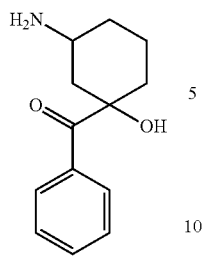
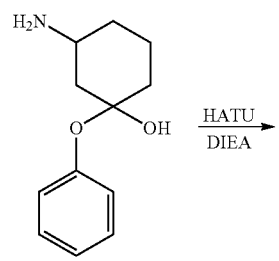

To a solution of 2-phenyl-1,3-dithiane (12 mmol, 2.35 g) in THF (15 mL) at −78° C. was added a solution of lithium diisopropylamide in THF/heptane/ethylbenzene (12 mmol, 1.8 M, 6.7 mL) under argon. The reaction mixture was warmed up to −20° C. and stirred for 30 minutes at −20° C. The reaction mixture was cooled down to −78° C. tert-Butyl 3-oxocyclohexylcarbamate (5 mmol, 1.065 g) in THF was added. The reaction mixture was allowed to warm up to room temperature and stirred for overnight. Acetic anhydride (20 mmol, 1.9 mL) was added. The reaction mixture was stirred at room temperature for 4 hours. Water was added. The organics were extracted with EtOAc. 3-(tert-Butoxycarbonylamino)-1-(2-phenyl-1,3-dithiaN-2-yl)cyclohexyl acetate was obtained after purification by silica gel column chromatography.

To a solution of nitrosonium tetrafluoroborate (1.1 mmol, 128.5 mg) and hydrogen fluoride pyridine (0.5 mL) in DCM (2 mL) at 0° C. under argon was added a solution of 3-(tert-butoxycarbonylamino)-1-(2-phenyl-1,3-dithiaN-2-yl)cyclohexyl acetate (0.5 mmol, 226 mg) in DCM dropwise. The reaction mixture was stirred at 0° C. for 1 hour. Sodium carbonate (solid) was added until no further gas bubbling. The mixture and the methanol washings were filtered.

The filtrate was concentrated. (3-Amino-1-hydroxycyclohexyl)(phenyl)methanone was obtained after purification by reverse phase HPLC.

Preparation of N-(3-benzoyl-3-hydroxycyclohexyl)-3-(2-methylpyridin-4-yl)-1-trityl-1H-indazole-5-carboxamide

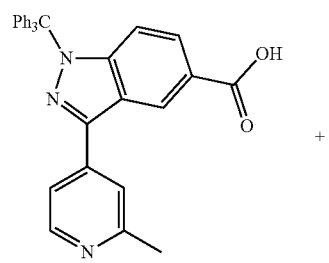

+

A reaction mixture of 3-(2-methylpyridin-4-yl)-1-trityl-1H-indazole-5-carboxylic acid (0.1 mmol, 49.5 mg), HCl salt of (3-amino-1-hydroxycyclohexyl)(phenyl)methanone (0.1 mmol, 25.5 mg), HATU (0.1 mmol, 38 mg) and DIEA (0.15 mL) in DMA (0.65 mL) was stirred at room temperature for overnight. The product, N-(3-benzoyl-3-hydroxycyclohexyl)-3-(2-methylpyridin-4-yl)-1-trityl-1H-indazole-5-carboxamide, was obtained after rotary evaporation of solvent.

Preparation of N-(3-benzoyl-3-hydroxycyclohexyl)-3-(2-methylpyridin-4-yl)-1H-indazole-5-carboxamide

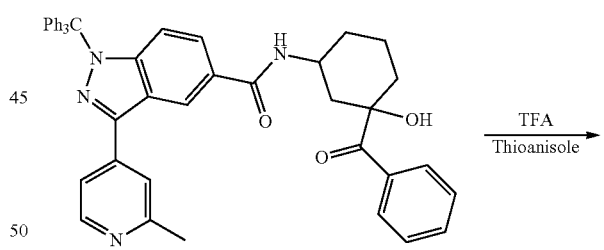

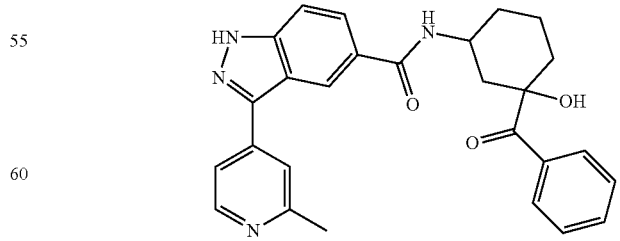

A solution of N-(3-benzoyl-3-hydroxycyclohexyl)-3-(2-methylpyridin-4-yl)-1-trityl-1H-indazole-5-carboxamide in a mixture of TFA (1 mL) and thioanisole (0.5 mL) was stirred at room temperature for 20 minutes, and then concentrated. The product was obtained after purification by reverse phase HPLC.

Preparation of N-(3-hydroxy-3-(hydroxy(phenyl)methyl)cyclohexyl)-3-(2-methylpyridin-4-yl)-1H-indazole-5-carboxamide

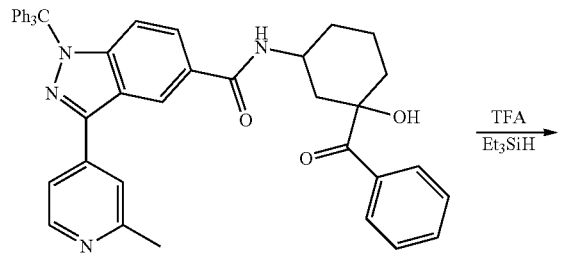

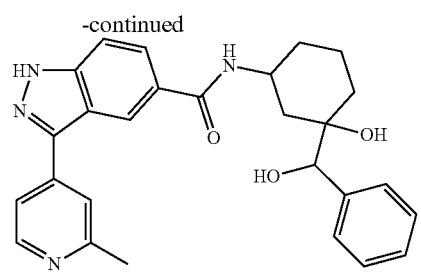

N-(3-Benzoyl-3-hydroxycyclohexyl)-3-(2-methylpyridin-4-yl)-1-trityl-1H-indazole-5-carboxamide was stirred in neat TPA at room temperature for 10 minutes, and then Et$_3$SiH (5 equiv.) was added. The reaction mixture was stirred at room temperature for 5 minutes, and then concentrated. The product was obtained after purification by reverse phase HPLC.

Following compounds were prepared in similar method:

| Compd # | Structure | Chemical Names | aERK IC50 nM | M + 1 Cacld. | M + 1 Obs. | Rf min. |
|---|---|---|---|---|---|---|
| 46 | 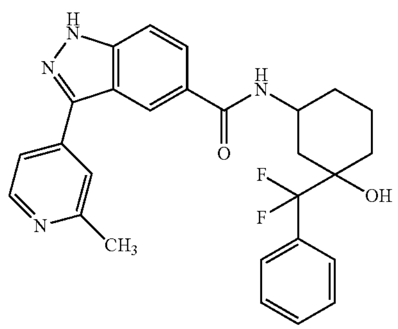 [SMILES: Cc1cc(-c2n[nH]c3ccc(C(=O)NC4CCCC(O)(C(F)(F)c5ccccc5)C4)cc23)ccn1] | N-[3-(difluorophenylmethyl)-3-hydroxycyclohexyl]-3-(2-methyl-4-pyridinyl)-1H-indazole-5-carboxamide | 629.6 | 477.2 | 477.0 | 2.52 |
| 47 | 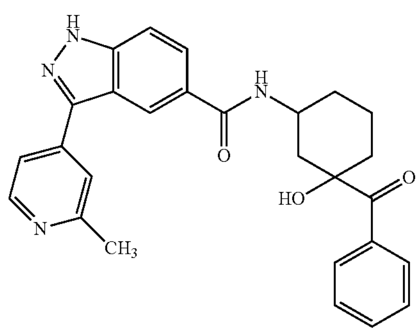 [SMILES: Cc1cc(-c2n[nH]c3ccc(C(=O)NC4CCCC(O)(C(=O)c5ccccc5)C4)cc23)ccn1] | N-(3-benzoyl-3-hydroxycyclohexyl)-3-(2-methyl-4-pyridinyl)-1H-indazole-5-carboxamide | 576.7 | 455.2 | 455.0 | 2.28 |
| 48 | 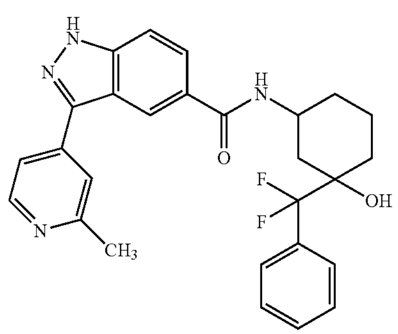 [SMILES: Cc1cc(-c2n[nH]c3ccc(C(=O)NC4CCCC(O)(C(F)(F)c5ccccc5)C4)cc23)ccn1] | N-[3-(difluorophenylmethyl)-3-hydroxycyclohexyl]-3-(2-methyl-4-pyridinyl)-1H-indazole-5-carboxamide | 105.7 | 477.2 | 477.0 | 2.37 |

-continued

| Compd # | Structure | Chemical Names | aERK IC50 nM | M + 1 Cacld. | M + 1 Obs. | Rf min. |
|---|---|---|---|---|---|---|
| 49 | 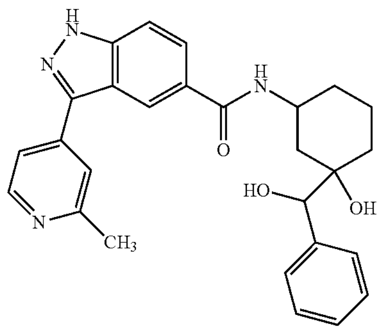 [SMILES: Cc1cc(-c2n[nH]c3ccc(C(=O)NC4CCCC(O)(C(O)c5ccccc5)C4)cc23)ccn1] | N-[3-hydroxy-3-(hydroxyphenylmethyl)cyclohex-yl]-3-(2-methyl-4-pyridinyl)-1H-indazole-5-carboxamide (diasterimer 1) | 25.0 | 457.2 | 457.1 | 1.94 |
| 50 | 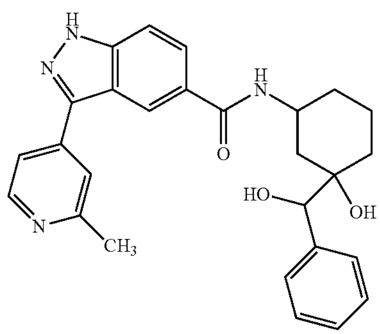 [SMILES: Cc1cc(-c2n[nH]c3ccc(C(=O)NC4CCCC(O)(C(O)c5ccccc5)C4)cc23)ccn1] | N-[3-hydroxy-3-(hydroxyphenylmethyl)cyclohex-yl]-3-(2-methyl-4-pyridinyl)-1H-indazole-5-carboxamide (diasterimer 2) | 47.5 | 457.2 | 457.1 | 1.96 |
| 51 | 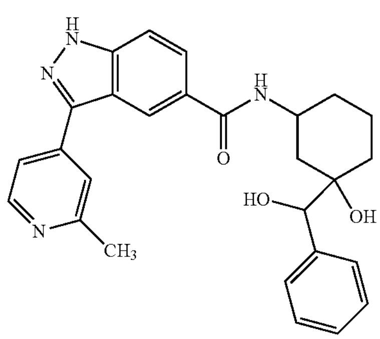 [SMILES: Cc1cc(-c2n[nH]c3ccc(C(=O)NC4CCCC(O)(C(O)c5ccccc5)C4)cc23)ccn1] | N-[3-hydroxy-3-(hydroxyphenylmethyl)cyclohex-yl]-3-(2-methyl-4-pyridinyl)-1H-indazole-5-carboxamide (diasterimer 3) | 204.1 | 457.2 | 457.0 | 2.03 |
| 52 | 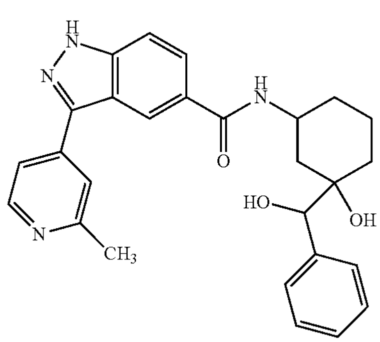 [SMILES: Cc1cc(-c2n[nH]c3ccc(C(=O)NC4CCCC(O)(C(O)c5ccccc5)C4)cc23)ccn1] | N-[3-hydroxy-3-(hydroxyphenylmethyl)cyclohex-yl]-3-(2-methyl-4-pyridinyl)-1H-indazole-5-carboxamide (diasterimer 4) | 293.8 | 457.2 | 457.0 | 2.11 |

| Compd # | Structure | Chemical Names | aERK IC50 nM | M + 1 Cacld. | M + 1 Obs. | Rf min. |
|---|---|---|---|---|---|---|
| 53 | 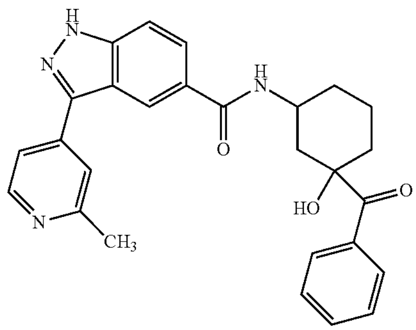 [SMILES: Cc1cc(-c2n[nH]c3ccc(C(=O)NC4CCCC(O)(C(=O)c5ccccc5)C4)cc23)ccn1] | N-(3-benzoyl-3-hydroxycyclohexyl)-3-(2-methyl-4-pyridinyl)-1H-indazole-5-carboxamide | 257.6 | 455.2 | 455.0 | 2.23 |
| 54 | 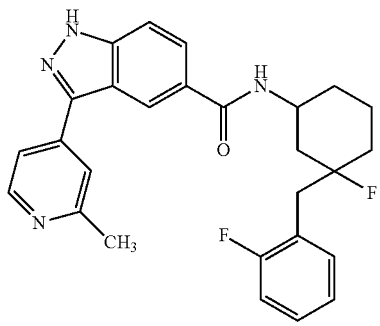 [SMILES: Cc1cc(-c2n[nH]c3ccc(C(=O)NC4CCCC(F)(Cc5ccccc5F)C4)cc23)ccn1] | N-[3-fluoro-3-[(2-fluorophenyl)methyl]cyclohexyl]-3-(2-methyl-4-pyridinyl)-1H-indazole-5-carboxamide (racemic) | 1000.0 | 461.2 | 461.0 | 2.64 |
| 55 | 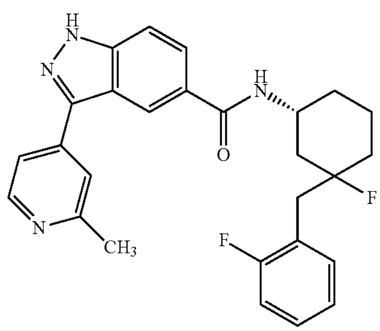 [SMILES: Cc1cc(-c2n[nH]c3ccc(C(=O)N[C@@H]4CCCC(F)(Cc5ccccc5F)C4)cc23)ccn1] | N-[3-fluoro-3-[(2-fluorophenyl)methyl]-1(R)-cyclohexyl]-3-(2-methyl-4-pyridinyl)-1H-indazole-5-carboxamide (isomer 1) | 1000.0 | 461.2 | 460.9 | 2.69 |
| 56 | 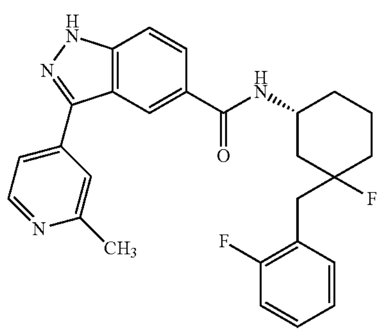 [SMILES: Cc1cc(-c2n[nH]c3ccc(C(=O)N[C@@H]4CCCC(F)(Cc5ccccc5F)C4)cc23)ccn1] | N-[3-fluoro-3-[(2-fluorophenyl)methyl]-1(R)-cyclohexyl]-3-(2-methyl-4-pyridinyl)-1H-indazole-5-carboxamide (isomer 2) | | 461.2 | 460.9 | 2.71 |

Scheme 5

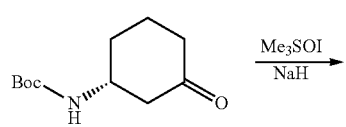

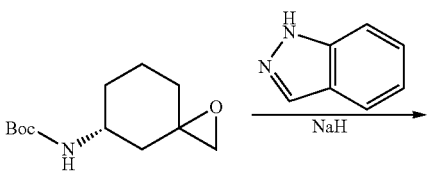

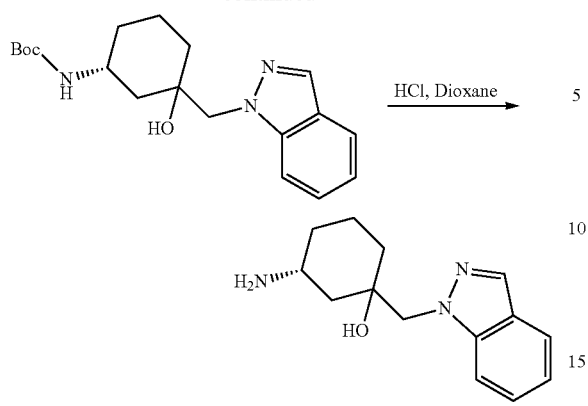

Preparation of
tert-butyl(5R)-1-oxaspiro[2.5]octan-5-ylcarbamate

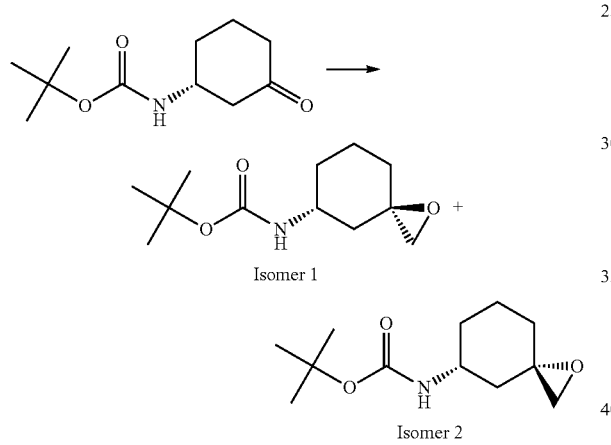

To a solution of Me3SOI (56.2 mmol) in DMSO (80 ml) was added NaH (51.5 mmol) and stirred at room temperature for 2 h until the solution become clear. The resulting solution was added tert-butyl 3-oxocyclohexylcarbamate (23.4 mmol) and stirred at rt overnight. The reaction was quenched with water and extracted with hexane. The extracts were combined and dried using anhydrous sodium sulfate. The product was purified using Biotage. The final products, isomer 1 and isomer 2, were well separated on silicon column with 15%-20% ethyl acetate in hexane. Each single diastereomer was used for the next step.

Preparation of tert-butyl(1R)-3-((1H-indazol-1-yl)methyl)-3-hydroxycyclohexylcarbamate

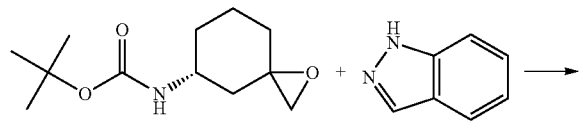

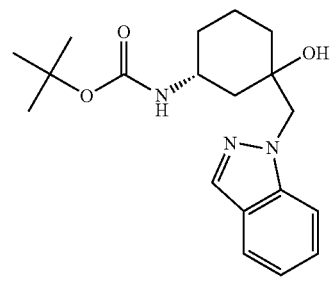

NaH (1.1 mmol) was added to a vial containing indazole (2.2 mmol) in DMF (1 ml). The mixture was stirred at rt for 15 mins, then added tert-butyl-1-oxaspiro[2.5]octaN-5-ylcarbamate (0.22 mmol). The reaction was stirred at 60° C. overnight. Upon completion, the mixture was quenched by water (3 mL). The mixture was extracted using dichloromethane (3×5 mL). The extracts were combined and dried using anhydrous sodium sulfate. The product was purified using HPLC.

Preparation of (3R)-1-((1H-indazol-1-yl)methyl)-3-aminocyclohexanol

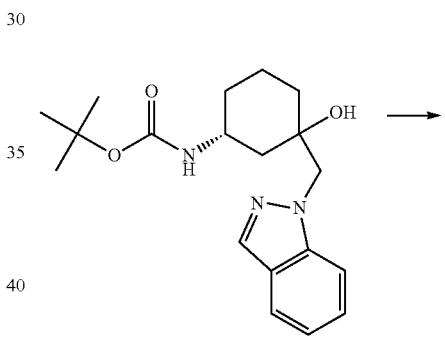

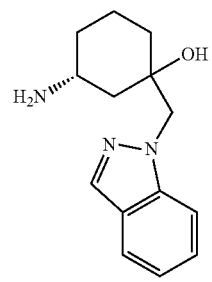

In a flask, hydrochloric acid in dioxane (4M, 2 mL) was added to tert-butyl-3-((1H-indazol-1-yl)methyl)-3-hydroxycyclohexylcarbamate (50 mg), and the reaction was stirred for 30 minutes. The resulting solution was concentrated in vacuo. The crude product was progressed to the next step without further purification.

Preparation of N-((1R)-3-(((1H-indazol-1-yl)methyl)-3-hydroxycyclohexyl)-3-(2-methylpyridin-4-yl)-1-trityl-1H-indazole-5-carboxamide

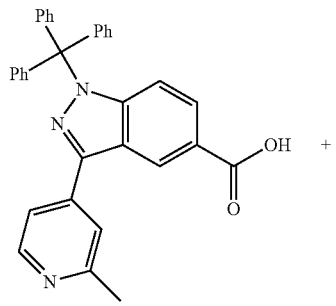

2-(7-Aza-1H-benzotriazole-1-yl)-1,1,3,3-tetramethyluronium hexafluorophosphate (HATU) (0.11 mmol) was added to a suspension of 3-(2-methylpyridin-4-yl)-1-trityl-1H-indazole-5-carboxylic acid (0.1 mmol) in DMF (0.5 mL) and was stirred at room temperature for 15 minutes. A solution of 1((1H-indazol-1-yl)methyl)-3-aminocyclohexanol (0.1 mmol) in DMF (0.5 mL) was added to the reaction and followed by diisopropyl ethyl amine (DIEA) (0.1 mL). The mixture was stirred at room temperature for an additional 30 minutes. The reaction was quenched with water (5 mL) and extracted with ethyl acetate (3×10 mL). The extracts were combined, dried using anhydrous sodium sulfate, filtered, and concentrated in vacuo. The crude product was progressed to the next step without purification.

Preparation of N-((1R,3R)-3-(((1H-indazol-1-yl)methyl)-3-hydroxycyclohexyl)-3-(2-methylpyridin-4-yl)-1H-indazole-5-carboxamide

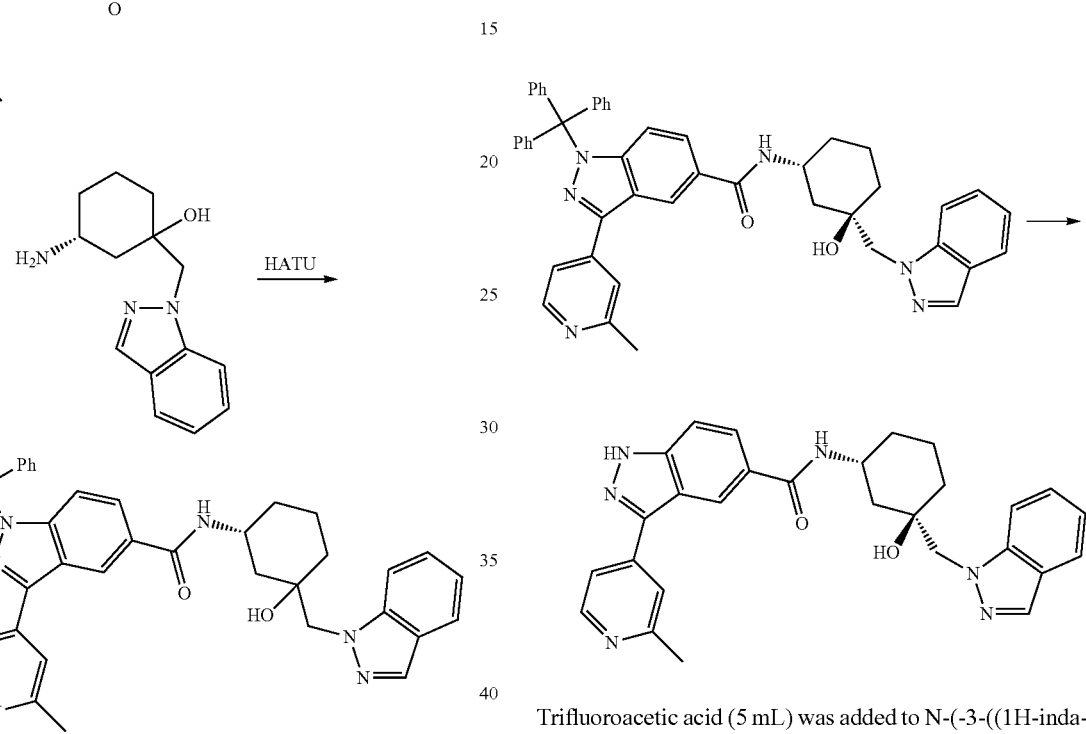

Trifluoroacetic acid (5 mL) was added to N-(-3-((1H-indazol-1-yl)methyl)-3-hydroxycyclohexyl)-3-(2-methylpyridin-4-yl)-1-trityl-1H-indazole-5-carboxamide (0.1 mmol). The reaction was stirred at room temperature for 30 minutes. Triethylsilane (1 drop) was added to the reaction and stirred for an additional 5 minutes. The crude product purified using prep HPLC.

| Compd # | Structure | Chemical Names | aERK IC50 nM | M + 1 Cacld. | M + 1 Obs. | Rf min. |
|---|---|---|---|---|---|---|
| 57 | 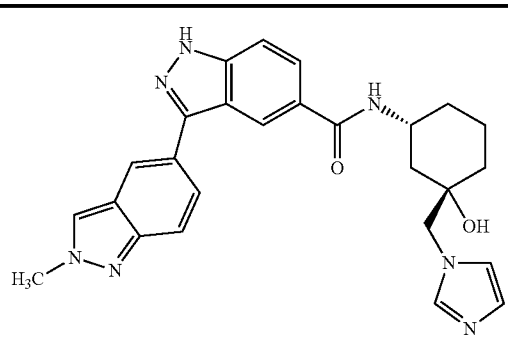 | N-[cis-3-hydroxy-3-(1H-imidazol-1-ylmethyl)cyclohexyl]-3-(2-methyl-2H-indazol-5-yl)-1H-indazole-5-carboxamide | 37.8 | 470.2 | 470.1 | 1.91 |

-continued

| Compd # | Structure | Chemical Names | aERK IC50 nM | M + 1 Cacld. | M + 1 Obs. | Rf min. |
|---|---|---|---|---|---|---|
| 58 | 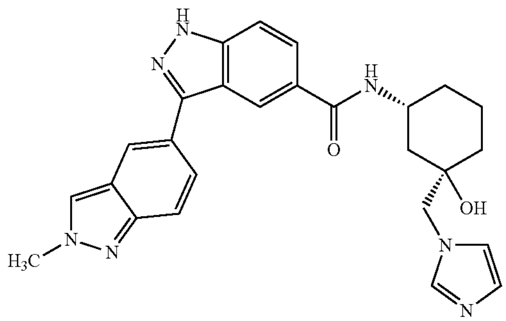 [SMILES: Cn1cc2cc(-c3n[nH]c4ccc(C(=O)N[C@@H]5CCC[C@](O)(Cn6ccnc6)C5)cc34)ccc2n1] | N-[trans-3-hydroxy-3-(1H-imidazol-1-ylmethyl)cyclohexyl]-3-(2-methyl-2H-indazol-5-yl)-1H-indazole-5-carboxamide | 62.0 | 470.2 | 470.2 | 1.92 |
| 59 | 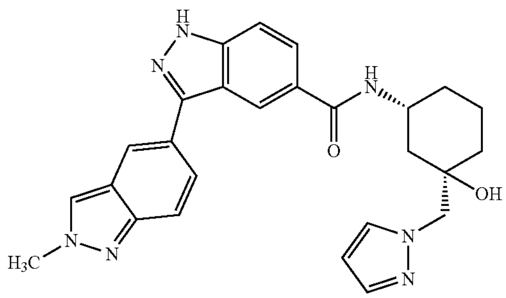 [SMILES: Cn1cc2cc(-c3n[nH]c4ccc(C(=O)N[C@@H]5CCC[C@](O)(Cn6cccn6)C5)cc34)ccc2n1] | N-[trans-3-hydroxy-3-(1H-pyrazol-1-ylmethyl)cyclohexyl]-3-(2-methyl-2H-indazol-5-yl)-1H-indazole-5-carboxamide | 67.4 | 470.2 | 470.0 | 2.34 |
| 60 | 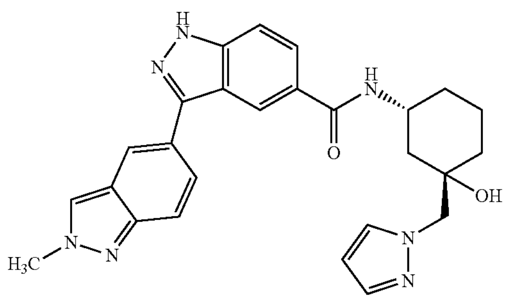 [SMILES: Cn1cc2cc(-c3n[nH]c4ccc(C(=O)N[C@@H]5CCC[C@@](O)(Cn6cccn6)C5)cc34)ccc2n1] | N-[cis-3-hydroxy-3-(1H-pyrazol-1-ylmethyl)cyclohexyl]-3-(2-methyl-2H-indazol-5-yl)-1H-indazole-5-carboxamide | 151.4 | 470.2 | 470.0 | 2.34 |
| 61 | 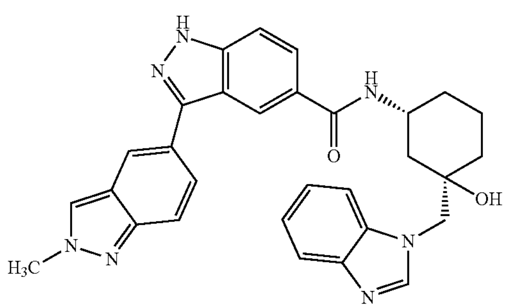 [SMILES: Cn1cc2cc(-c3n[nH]c4ccc(C(=O)N[C@@H]5CCC[C@](O)(Cn6cnc7ccccc76)C5)cc34)ccc2n1] | N-[trans-3-(1H-benzimidazol-1-ylmethyl)-3-hydroxycyclohexyl]-3-(2-methyl-2H-indazol-5-yl)-1H-indazole-5-carboxamide | 19.3 | 520.2 | 520.0 | 1.98 |
| 62 | 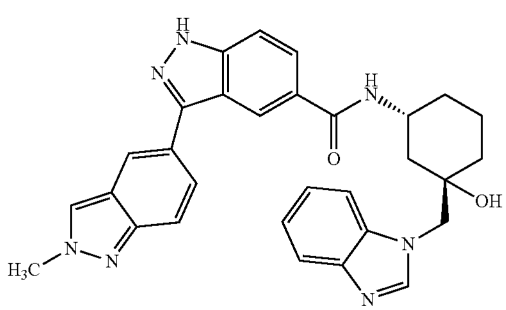 [SMILES: Cn1cc2cc(-c3n[nH]c4ccc(C(=O)N[C@@H]5CCC[C@@](O)(Cn6cnc7ccccc76)C5)cc34)ccc2n1] | N-[cis-3-(1H-benzimidazol-1-ylmethyl)-3-hydroxycyclohexyl]-3-(2-methyl-2H-indazol-5-yl)-1H-indazole-5-carboxamide | 19.9 | 520.2 | 520.0 | 1.98 |

| Compd # | Structure | Chemical Names | aERK IC50 nM | M + 1 Cacld. | M + 1 Obs. | Rf min. |
|---|---|---|---|---|---|---|
| 63 | 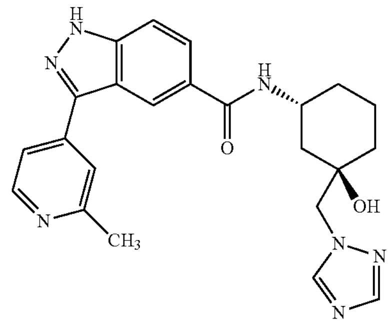 [SMILES: Cc1cc(-c2n[nH]c3ccc(C(=O)N[C@@H]4CCC[C@](O)(Cn5cncn5)C4)cc23)ccn1] | N-[trans-3-hydroxy-3-(1H-1,2,4-triazol-1-ylmethyl)cyclohexyl]-3-(2-methyl-4-pyridinyl)-1H-indazole-5-carboxamide | 197.0 | 432.2 | 432.0 | 1.51 |
| 64 | 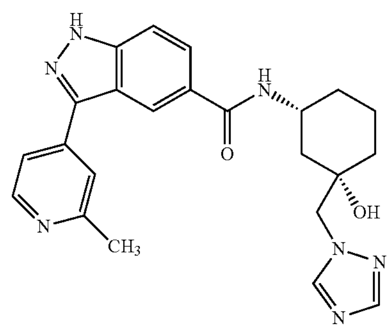 [SMILES: Cc1cc(-c2n[nH]c3ccc(C(=O)N[C@@H]4CCC[C@@](O)(Cn5cncn5)C4)cc23)ccn1] | N-[cis-3-hydroxy-3-(1H-1,2,4-triazol-1-ylmethyl)cyclohexyl]-3-(2-methyl-4-pyridinyl)-1H-indazole-5-carboxamide | 99.9 | 432.2 | 432.1 | 1.65 |
| 65 | 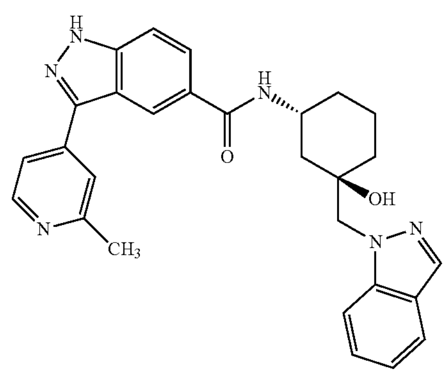 [SMILES: Cc1cc(-c2n[nH]c3ccc(C(=O)N[C@@H]4CCC[C@](O)(Cn5ncc6ccccc65)C4)cc23)ccn1] | N-[3(R)-hydroxy-3-(1H-indazol-1-ylmethyl)-1(R)-cyclohexyl]-3-(2-methyl-4-pyridinyl)-1H-indazole-5-carboxamide | 988.3 | 481.2 | 481.0 | 2.27 |
| 66 | 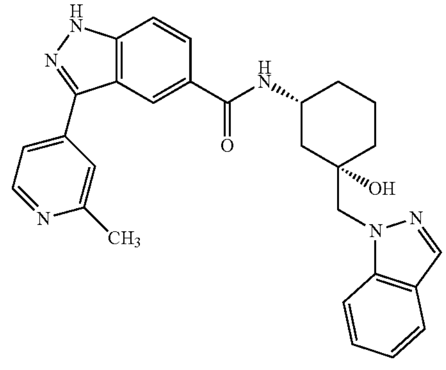 [SMILES: Cc1cc(-c2n[nH]c3ccc(C(=O)N[C@@H]4CCC[C@@](O)(Cn5ncc6ccccc65)C4)cc23)ccn1] | N-[3(S)-hydroxy-3-(1H-indazol-1-ylmethyl)-1(R)-cyclohexyl]-3-(2-methyl-4-pyridinyl)-1H-indazole-5-carboxamide | 7.0 | 481.2 | 481.0 | 2.13 |

-continued

| Compd # | Structure | Chemical Names | aERK IC50 nM | M + 1 Cacld. | M + 1 Obs. | Rf min. |
|---|---|---|---|---|---|---|
| 67 | 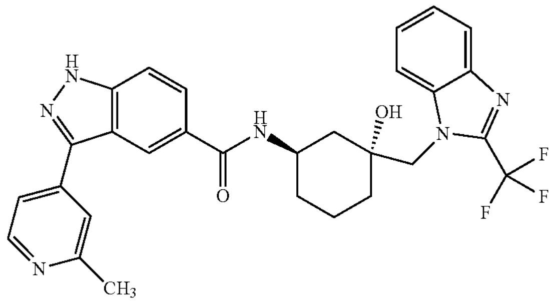 [SMILES: Cc1cc(-c2n[nH]c3ccc(C(=O)N[C@@H]4CCC[C@](O)(Cn5c(C(F)(F)F)nc6ccccc65)C4)cc23)ccn1] | N-[trans-3-hydroxy-3-[[2-(trifluoromethyl)-1H-benzimidazol-1-yl]methyl]cyclohexyl]-3-(2-methyl-4-pyridinyl)-1H-indazole-5-carboxamide | 436.2 | 549.2 | 549.0 | 2.31 |
| 68 | 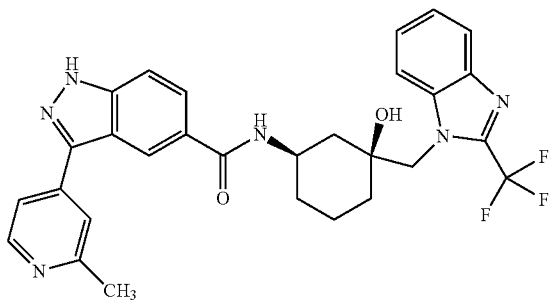 [SMILES: Cc1cc(-c2n[nH]c3ccc(C(=O)N[C@@H]4CCC[C@@](O)(Cn5c(C(F)(F)F)nc6ccccc65)C4)cc23)ccn1] | N-[cis-3-hydroxy-3-[[2-(trifluoromethyl)-1H-benzimidazol-1-y)]methyl]cyclohexyl]-3-(2-methyl-4-pyridinyl)-1H-indazole-5-carboxamide | 820.7 | 549.2 | 549.1 | 2.37 |
| 69 | 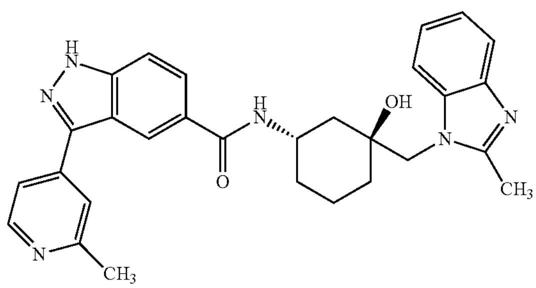 [SMILES: Cc1cc(-c2n[nH]c3ccc(C(=O)N[C@H]4CCC[C@@](O)(Cn5c(C)nc6ccccc65)C4)cc23)ccn1] | N-[trans-3-hydroxy-3-[(2-methyl-1H-benzimidazol-1-yl)methyl]cyclohexyl]-3-(2-methyl-4-pyridinyl)-H-indazole-5-carboxamide | 53.0 | 495.2 | 495.2 | 1.72 |
| 70 | 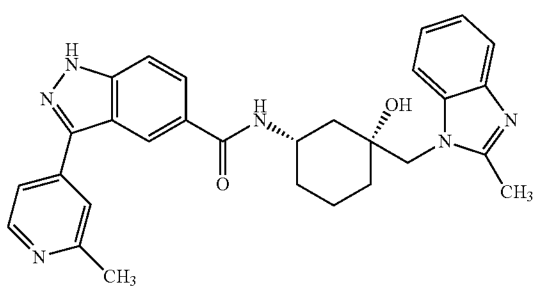 [SMILES: Cc1cc(-c2n[nH]c3ccc(C(=O)N[C@H]4CCC[C@](O)(Cn5c(C)nc6ccccc65)C4)cc23)ccn1] | N-[cis-3-hydroxy-3-[(2-methyl-1H-benzimidazol-1-ylmethyl]cyclohexyl]-3-(2-methyl-4-pyridinyl)-H-indazole-5-carboxamide | 331.8 | 495.2 | 495.2 | 1.52 |
| 71 | 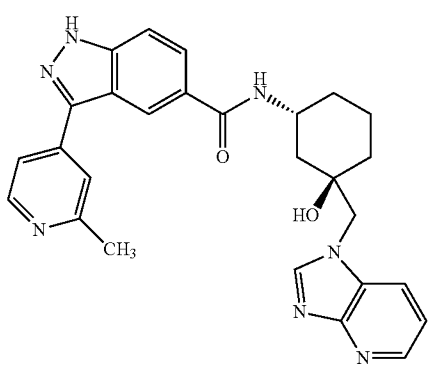 [SMILES: Cc1cc(-c2n[nH]c3ccc(C(=O)N[C@@H]4CCC[C@](O)(Cn5cnc6ncccc65)C4)cc23)ccn1] | N-[trans-3-hydroxy-3-(1H-imidazo[4,5-b]pyridin-1-ylmethyl)cyclohexyl]-3-(2-methyl-4-pyridinyl)-1H-indazole-5-carboxamide | 464.0 | 482.2 | 482.0 | 1.43 |

-continued

| Compd # | Structure | Chemical Names | aERK IC50 nM | M + 1 Cacld. | M + 1 Obs. | Rf min. |
|---|---|---|---|---|---|---|
| 72 | 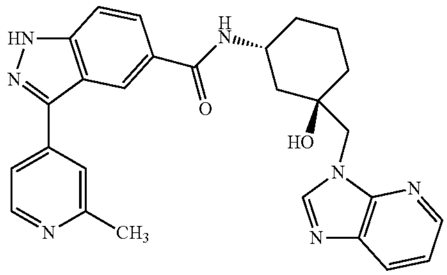 [SMILES: Cc1cc(-c2n[nH]c3ccc(C(=O)N[C@@H]4CCC[C@](O)(Cn5cnc6cccnc65)C4)cc23)ccn1] | N-[trans-3-hydroxy-3-(3H-imidazo[4,5-b]pyridin-3-ylmethyl)cyclohexyl]-3-(2-methyl-4-pyridinyl)-1H-indazole-5-carboxamide | 536.8 | 482.2 | 481.9 | 1.52 |
| 73 | 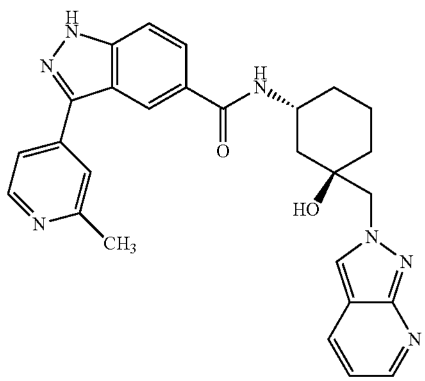 [SMILES: Cc1cc(-c2n[nH]c3ccc(C(=O)N[C@@H]4CCC[C@](O)(Cn5cc6cccnc6n5)C4)cc23)ccn1] | N-[trans-3-hydroxy-3-(2H-pyrazolo[3,4-b]pyridin-2-ylmethyl)cyclohexyl]-3-(2-methyl-4-pyridinyl)-1H-indazole-5-carboxamide | 616.2 | 482.2 | 481.9 | 1.518 |
| 74 | 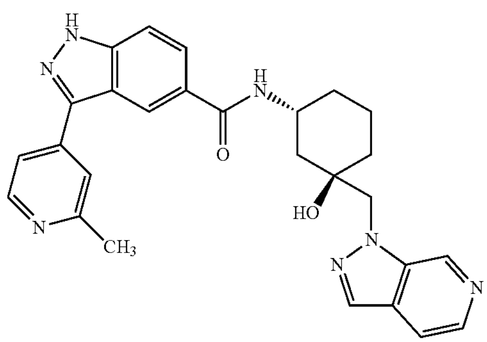 [SMILES: Cc1cc(-c2n[nH]c3ccc(C(=O)N[C@@H]4CCC[C@](O)(Cn5ncc6ccncc65)C4)cc23)ccn1] | N-[trans-3-hydroxy-3-(1H-pyrazolo[3,4-c]pyridin-1-ylmethyl)cyclohexyl]-3-(2-methyl-4-pyridinyl)-1H-indazole-5-carboxamide | 792.1 | 482.2 | 481.9 | 1.078 |
| 75 | 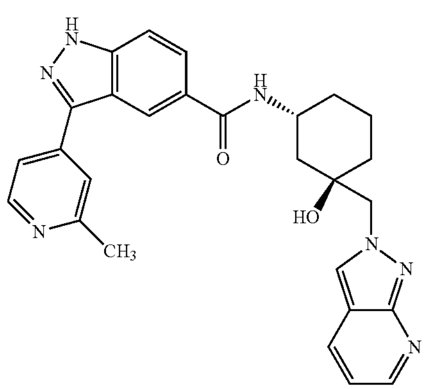 [SMILES: Cc1cc(-c2n[nH]c3ccc(C(=O)N[C@@H]4CCC[C@](O)(Cn5cc6cccnc6n5)C4)cc23)ccn1] | N-[trans-3-hydroxy-3-(2H-pyrazolo[3,4-c]pyridin-2-ylmethyl)cyclohexyl]-3-(2-methyl-4-pyridinyl)-1H-indazole-5-carboxamide | 404.0 | 482.2 | 481.9 | 1.144 |

| Compd # | Structure | Chemical Names | aERK IC50 nM | M + 1 Cacld. | M + 1 Obs. | Rf min. |
|---|---|---|---|---|---|---|
| 76 | 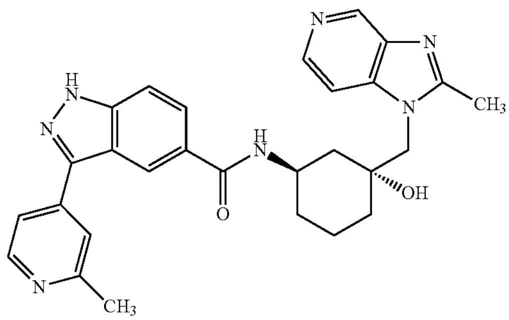 [SMILES: Cc1cc(-c2n[nH]c3ccc(C(=O)N[C@@H]4CCC[C@](O)(Cn5c(C)nc6cnccc65)C4)cc23)ccn1] | N-[trans-3-hydroxy-3-[(2-methyl-1H-imidazo[4,5-c]pyridin-1-yl)methyl]cyclohexyl]-3-(2-methyl-4-pyridinyl)-1H-indazole-5-carboxamide | 135.5 | 496.2 | 496.0 | 1.078 |
| 77 | 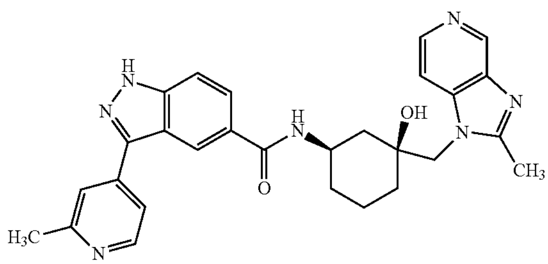 | N-[cis-3-hydroxy-3-[(2-methyl-1H-imidazo[4,5-c]pyridiN-1-yl)methyl]cyclohexyl]-3-(2-methyl-4-pyridinyl)-1H-indazole-5-carboxamide | 1000.0 | 496.2 | 496.2 | 1.342 |
| 78 | 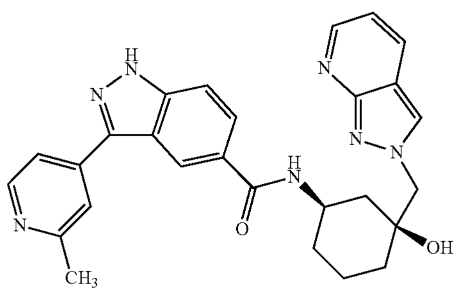 [SMILES: Cc1cc(-c2n[nH]c3ccc(C(=O)N[C@@H]4CCC[C@@](O)(Cn5cc6cccnc6n5)C4)cc23)ccn1] | N-[cis-3-hydroxy-3-(2H-pyrazolo[3,4-b]pyridin-2-ylmethyl)cyclohexyl]-3-(2-methyl-4-pyridinyl)-1H-indazole-5-carboxamide | 591.0 | 482.2 | 482.2 | 1.386 |
| 79 | 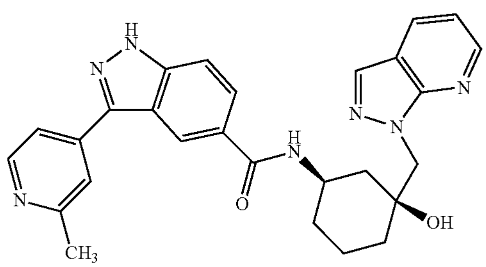 [SMILES: Cc1cc(-c2n[nH]c3ccc(C(=O)N[C@@H]4CCC[C@@](O)(Cn5ncc6cccnc65)C4)cc23)ccn1] | N-[cis-3-hydroxy-3-(1H-pyrazolo[3,4-b]pyridin-1-ylmethyl)cyclohexyl]-3-(2-methyl-4-pyridinyl)-1H-indazole-5-carboxamide | 8.6 | 482.2 | 482.2 | 1.672 |
| 80 | 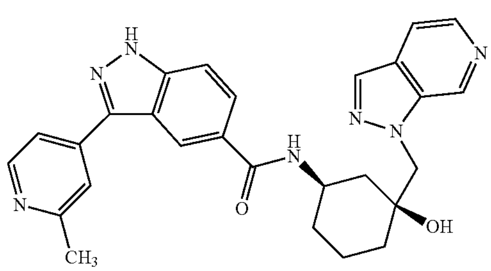 [SMILES: Cc1cc(-c2n[nH]c3ccc(C(=O)N[C@@H]4CCC[C@@](O)(Cn5ncc6ccncc65)C4)cc23)ccn1] | N-[cis-3-hydroxy-3-(1H-pyrazolo[3,4-c]pyridin-1-ylmethyl)cyclohexyl]-3-(2-methyl-4-pyridinyl)-1H-indazole-5-carboxamide | 35.1 | 482.2 | 482.2 | 1.364 |

-continued

| Compd # | Structure | Chemical Names | aERK IC50 nM | M + 1 Cacld. | M + 1 Obs. | Rf min. |
|---|---|---|---|---|---|---|
| 81 | 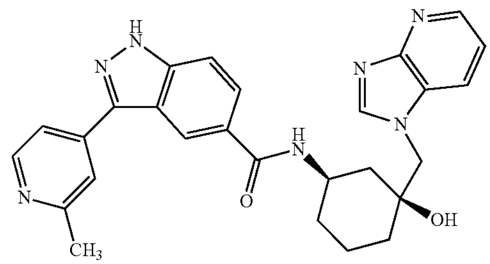 [SMILES: Cc1cc(-c2n[nH]c3ccc(C(=O)N[C@@H]4CCC[C@@](O)(Cn5cnc6ncccc65)C4)cc23)ccn1] | N-[cis-3-hydroxy-3-(1H-imidazo[4,5-b]pyridin-1-ylmethyl)cyclohexyl]-3-(2-methyl-4-pyridinyl)-1H-indazole-5-carboxamide | 824.7 | 482.2 | 482.2 | 1.364 |
| 82 | 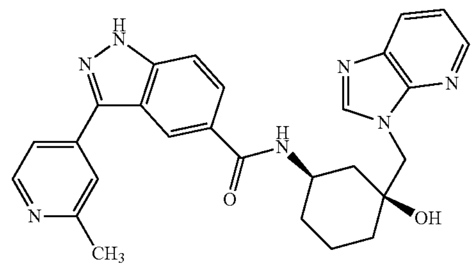 [SMILES: Cc1cc(-c2n[nH]c3ccc(C(=O)N[C@@H]4CCC[C@@](O)(Cn5cnc6cccnc65)C4)cc23)ccn1] | N-[cis-3-hydroxy-3-(3H-imidazo[4,5-b]pyridin-3-ylmethyl)cyclohexyl]-3-(2-methyl-4-pyridinyl)-1H-indazole-5-carboxamide | 97.6 | 482.2 | 482.2 | 1.43 |
| 83 | 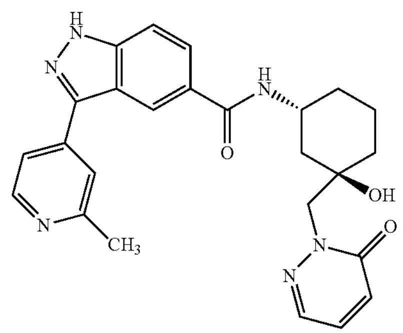 [SMILES: Cc1cc(-c2n[nH]c3ccc(C(=O)N[C@@H]4CCC[C@](O)(Cn5ncccc5=O)C4)cc23)ccn1] | N-[trans-3-hydroxy-3-[(6-oxo-1(6h)-pyridazinyl)methyl]cyclohexyl]-3-(2-methyl-4-pyridinyl)-1H-indazole-5-carboxamide | 1000.0 | 459.2 | 459.0 | 1.37 |
| 84 | 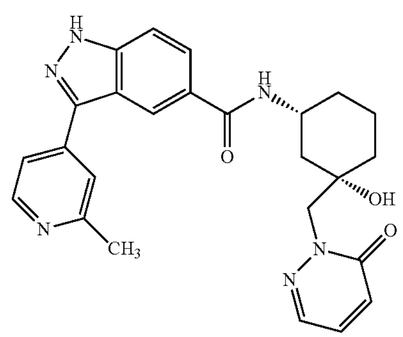 [SMILES: Cc1cc(-c2n[nH]c3ccc(C(=O)N[C@@H]4CCC[C@@](O)(Cn5ncccc5=O)C4)cc23)ccn1] | N-[cis-3-hydroxy-3-[(6-oxo-1(6h)-pyridazinyl)methyl]cyclohexyl]-3-(2-methyl-4-pyridinyl)-1H-indazole-5-carboxamide | 1000.0 | 459.2 | 459.0 | 1.38 |
| 85 | 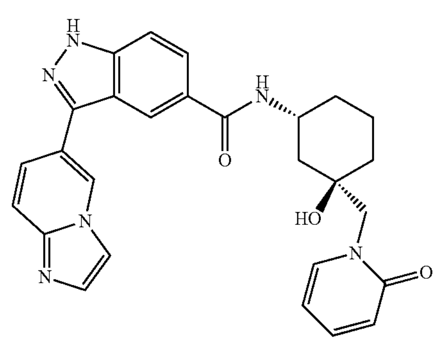 [SMILES: O=C(N[C@@H]1CCC[C@](O)(Cn2ccccc2=O)C1)c1ccc2[nH]nc(-c3ccc4nccn4c3)c2c1] | N-[trans-3-hydroxy-3-[(2-oxo-1(2h)-pyridinyl)methyl]cyclohexyl]-3-imidazo[1,2-a]pyridiN-6-yl-1H-indazole-5-carboxamide | 1000.0 | 483.2 | 483.2 | 1.74 |

-continued

| Compd # | Structure | Chemical Names | aERK IC50 nM | M + 1 Cacld. | M + 1 Obs. | Rf min. |
|---|---|---|---|---|---|---|
| 86 | 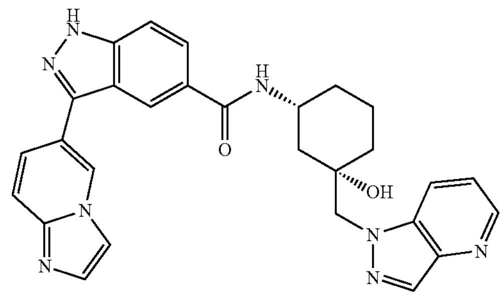 [SMILES: O=C(N[C@@H]1CCC[C@@](O)(Cn2ncc3ncccc32)C1)c1ccc2[nH]nc(-c3ccc4nccn4c3)c2c1] | N-[cis-3-hydroxy-3-(1H-pyrazolo[4,3-b]pyridN-1-ylmethyl)cyclohexyl]-3-imidazo[1,2-a]pyridiN-6-yl-1H-indazole-5-carboxamide | 1000.0 | 507.2 | 508.2 | 1.54 |
| 87 | 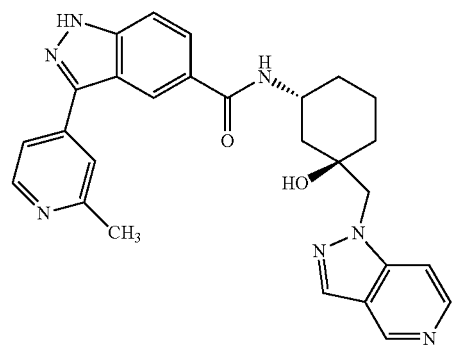 [SMILES: Cc1cc(-c2n[nH]c3ccc(C(=O)N[C@@H]4CCC[C@](O)(Cn5ncc6cnccc65)C4)cc23)ccn1] | N-[trans-3-hydroxy-3-(1H-pyrazolo[4,3-c]pyridin-1-ylmethyl)cyclohexyl]-3-(2-methyl-4-pyridinyl)-1H-indazole-5-carboxamide | 410.2 | 482.2 | 482.0 | 1.078 |
| 88 | 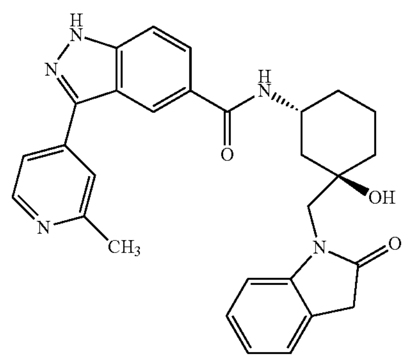 [SMILES: Cc1cc(-c2n[nH]c3ccc(C(=O)N[C@@H]4CCC[C@](O)(CN5C(=O)Cc6ccccc65)C4)cc23)ccn1] | N-[trans-3-[(2,3-dihydro-2-oxo-1H-indol-1-yl)methyl]-3-hydroxycyclohexyl]-3-(2-methyl-4-pyridinyl)-1H-indazole-5-carboxamide | 497.4 | 496.2 | 496.2 | 2.16 |
| 89 | 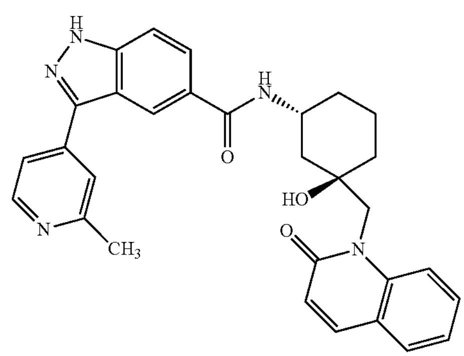 [SMILES: Cc1cc(-c2n[nH]c3ccc(C(=O)N[C@@H]4CCC[C@](O)(Cn5c(=O)ccc6ccccc65)C4)cc23)ccn1] | N-[trans-3-hydroxy-3-[(2-oxo-1(2h)-quinolinyl)methyl]cyclohexyl]-3-(2-methyl-4-pyridinyl)-1H-indazole-5-carboxamide | 714.2 | 508.2 | 508.2 | 2.27 |

-continued

| Compd # | Structure | Chemical Names | aERK IC50 nM | M + 1 Cacld. | M + 1 Obs. | Rf min. |
|---|---|---|---|---|---|---|
| 90 | 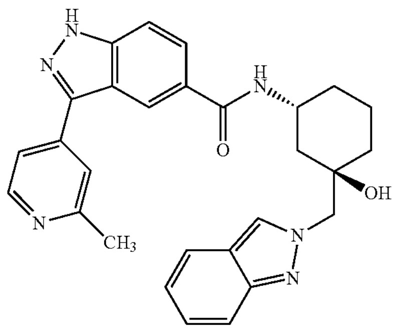 [SMILES: Cc1cc(-c2n[nH]c3ccc(C(=O)N[C@@H]4CCC[C@](O)(Cn5cc6ccccc6n5)C4)cc23)ccn1] | N-[trans-3-hydroxy-3-(2H-indazol-2-ylmethyl)cyclohexyl]-3-(2-methyl-4-pyridinyl)-1H-indazole-5-carboxamide | 27.4 | 481.2 | 481.0 | 1.562 |
| 91 | 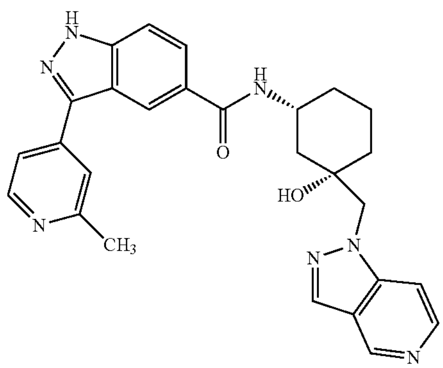 [SMILES: Cc1cc(-c2n[nH]c3ccc(C(=O)N[C@@H]4CCC[C@@](O)(Cn5ncc6cnccc65)C4)cc23)ccn1] | N-[cis-3-hydroxy-3-(1H-pyrazolo[4,3-c]pyridin-1-ylmethyl)cyclohexyl]-3-(2-methyl-4-pyridinyl)-1H-indazole-5-carboxamide | 563.3 | 482.2 | 482.2 | 1.41 |
| 92 | 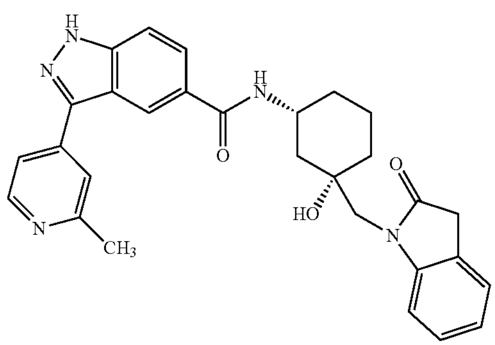 [SMILES: Cc1cc(-c2n[nH]c3ccc(C(=O)N[C@@H]4CCC[C@@](O)(CN5C(=O)Cc6ccccc65)C4)cc23)ccn1] | N-[cis-3-[(2,3-dihydro-2-oxo-1H-indol-1-yl)methyl]-3-hydroxycyclohexyl]-3-(2-methyl-4-pyridinyl)-1H-indazole-5-carboxamide | 10.8 | 496.2 | 497.3 | 2.1 |
| 93 | 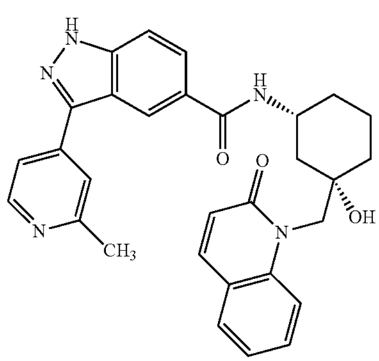 [SMILES: Cc1cc(-c2n[nH]c3ccc(C(=O)N[C@@H]4CCC[C@@](O)(Cn5c(=O)ccc6ccccc65)C4)cc23)ccn1] | N-[cis-3-hydroxy-3-[(2-oxo-1(2h)-quinolinyl)methyl]cyclohexyl]-3-(2-methyl-4-pyridinyl)-1H-indazole-5-carboxamide | 164.6 | 508.2 | 508.2 | 2.32 |

-continued

| Compd # | Structure | Chemical Names | aERK IC50 nM | M + 1 Cacld. | M + 1 Obs. | Rf min. |
|---|---|---|---|---|---|---|
| 94 | 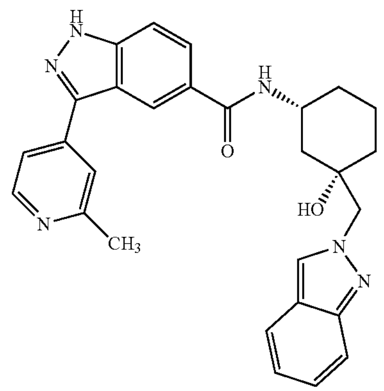 [SMILES: Cc1cc(-c2n[nH]c3ccc(C(=O)N[C@@H]4CCC[C@@](O)(Cn5cc6ccccc6n5)C4)cc23)ccn1] | N-[cis-3-hydroxy-3-(2H-indazol-2-ylmethyl)cyclohexyl]-3-(2-methyl-4-pyridinyl)-1H-indazole-5-carboxamide | 35.0 | 481.2 | 481.4 | 1.4 |
| 95 | 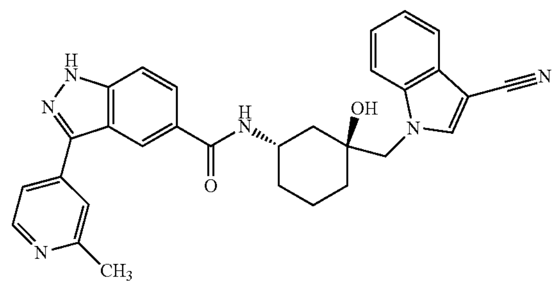 [SMILES: Cc1cc(-c2n[nH]c3ccc(C(=O)N[C@H]4CCC[C@@](O)(Cn5cc(C#N)c6ccccc65)C4)cc23)ccn1] | N-[trans-3-[(3-cyano-1H-indol-1-yl)methyl]-3-hydroxycyclohexyl]-3-(2-methyl-4-pyridinyl)-1H-indazole-5-carboxamide | 1000.0 | 505.2 | 505.2 | 2.35 |
| 96 | 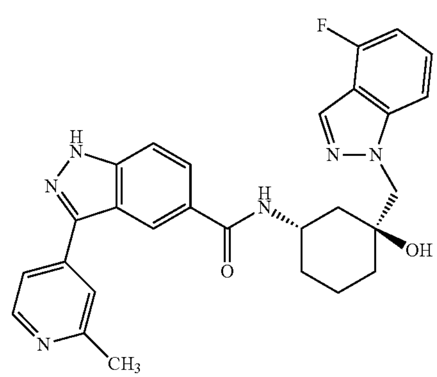 [SMILES: Cc1cc(-c2n[nH]c3ccc(C(=O)N[C@H]4CCC[C@@](O)(Cn5ncc6c(F)cccc65)C4)cc23)ccn1] | N-[trans-3-[(4-fluoro-1H-indazol-1-yl)methyl]-3-hydroxycyclohexyl]-3-(2-methyl-4-pyridinyl)-1H-indazole-5-carboxamide | 576.7 | 499.2 | 499.0 | 2.29 |
| 97 | 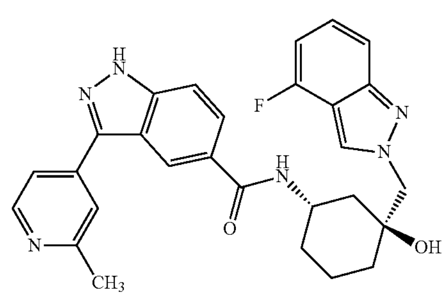 [SMILES: Cc1cc(-c2n[nH]c3ccc(C(=O)N[C@H]4CCC[C@@](O)(Cn5cc6c(F)cccc6n5)C4)cc23)ccn1] | N-[trans-3-[(4-fluoro-2H-indazol-2-yl)methyl]-3-hydroxycyclohexyl]-3-(2-methyl-4-pyridinyl)-1H-indazole-5-carboxamide | 1000.0 | 499.2 | 499.0 | 2.39 |

| Compd # | Structure | Chemical Names | aERK IC50 nM | M + 1 Cacld. | M + 1 Obs. | Rf min. |
|---|---|---|---|---|---|---|
| 98 | 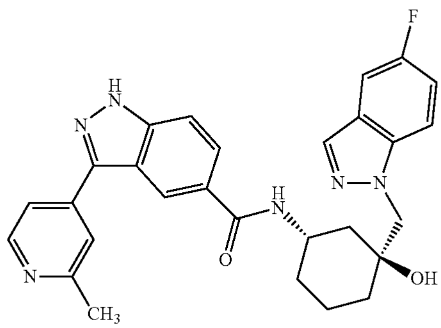 [SMILES: Cc1cc(-c2n[nH]c3ccc(C(=O)N[C@H]4CCC[C@@](O)(Cn5ncc6cc(F)ccc65)C4)cc23)ccn1] | N-[trans-3-[(5-fluoro-1H-indazol-1-yl)methyl]-3-hydroxycyclohexyl]-3-(2-methyl-4-pyridinyl)-1H-indazole-5-carboxamide | 1000.0 | 499.2 | 499.0 | 2.25 |
| 99 | 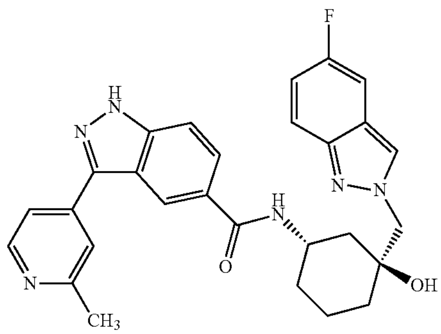 [SMILES: Cc1cc(-c2n[nH]c3ccc(C(=O)N[C@H]4CCC[C@@](O)(Cn5cc6cc(F)ccc6n5)C4)cc23)ccn1] | N-[trans-3-[(5-fluoro-2H-indazol-2-yl)methyl]-3-hydroxycyclohexyl]-3-(2-methyl-4-pyridinyl)-1H-indazole-5-carboxamide | 1000.0 | 499.2 | 499.0 | 2.34 |
| 100 | 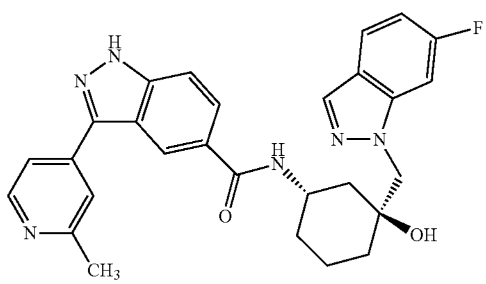 [SMILES: Cc1cc(-c2n[nH]c3ccc(C(=O)N[C@H]4CCC[C@@](O)(Cn5ncc6ccc(F)cc65)C4)cc23)ccn1] | N-[trans-3-[(6-fluoro-1H-indazol-1-yl)methyl]-3-hydroxycyclohexyl]-3-(2-methyl-4-pyridinyl)-1H-indazole-5-carboxamide | 1000.0 | 499.2 | 499.1 | 2.4 |
| 101 | 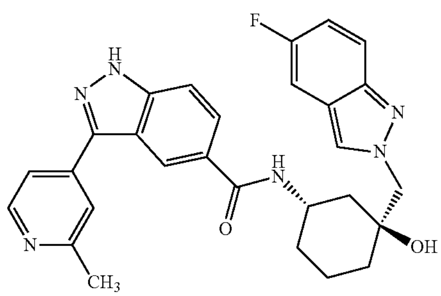 [SMILES: Cc1cc(-c2n[nH]c3ccc(C(=O)N[C@H]4CCC[C@@](O)(Cn5cc6cc(F)ccc6n5)C4)cc23)ccn1] | N-[trans-3-[(6-fluoro-2H-indazol-2-yl)methyl]-3-hydroxycyclohexyl]-3-(2-methyl-4-pyridinyl)-1H-indazole-5-carboxamide | 772.5 | 499.2 | 499.1 | 2.52 |

-continued

| Compd # | Structure | Chemical Names | aERK IC50 nM | M + 1 Cacld. | M + 1 Obs. | Rf min. |
|---|---|---|---|---|---|---|
| 102 | 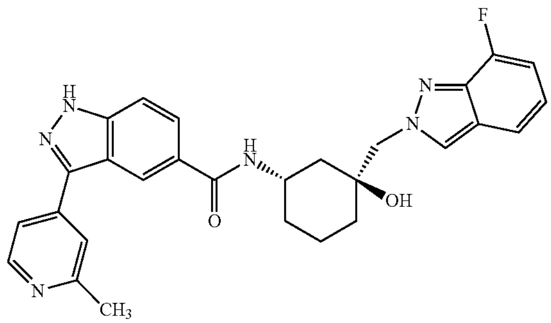 [SMILES: Cc1cc(-c2n[nH]c3ccc(C(=O)N[C@H]4CCC[C@@](O)(Cn5cc6cccc(F)c6n5)C4)cc23)ccn1] | N-[trans-3-[(7-fluoro-2H-indazol-2-yl)methyl]-3-hydroxycyclohexyl]-3-(2-methyl-4-pyridinyl)-1H-indazole-5-carboxamide | 703.7 | 499.2 | 499.1 | 2.57 |
| 103 | 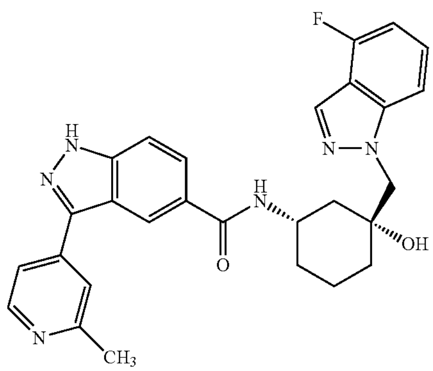 [SMILES: Cc1cc(-c2n[nH]c3ccc(C(=O)N[C@H]4CCC[C@](O)(Cn5ncc6c(F)cccc65)C4)cc23)ccn1] | N-[cis-3-[(4-fluoro-1H-indazol-1-yl)methyl]-3-hydroxycyclohexyl]-3-(2-methyl-4-pyridinyl)-1H-indazole-5-carboxamide | 21.3 | 499.2 | 499.0 | 2.18 |
| 104 | 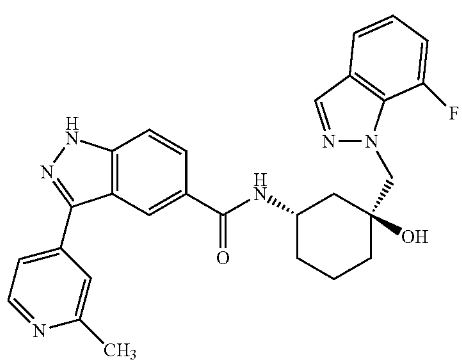 [SMILES: Cc1cc(-c2n[nH]c3ccc(C(=O)N[C@H]4CCC[C@@](O)(Cn5ncc6cccc(F)c65)C4)cc23)ccn1] | N-[trans-3-[(7-fluoro-1H-indazol-1-yl)methyl]-3-hydroxycyclohexyl]-3-(2-methyl-4-pyridinyl)-1H-indazole-5-carboxamide | 74.3 | 499.2 | 499.1 | 2.43 |
| 105 | 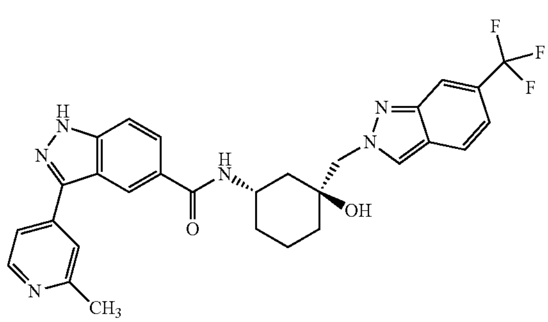 [SMILES: Cc1cc(-c2n[nH]c3ccc(C(=O)N[C@H]4CCC[C@@](O)(Cn5cc6ccc(C(F)(F)F)cc6n5)C4)cc23)ccn1] | N-[trans-3-hydroxy-3-[[6-(trifluoromethyl)-2H-indazol-2-yl]methyl]cyclohexyl]-3-(2-methyl-4-pyridinyl)-1H-indazole-5-carboxamide | 1000.0 | 549.2 | 549.0 | 2.6 |

-continued
| Compd # | Structure | Chemical Names | aERK IC50 nM | M + 1 Cacld. | M + 1 Obs. | Rf min. |
|---|---|---|---|---|---|---|
| 106 | 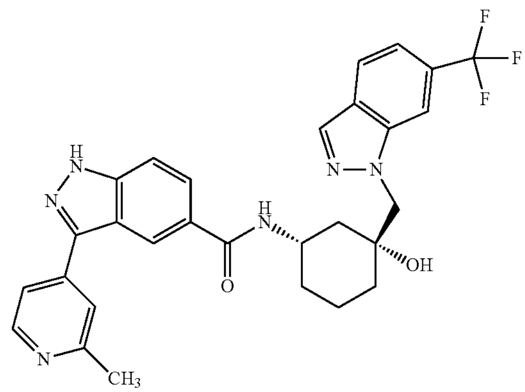 [SMILES: Cc1cc(-c2n[nH]c3ccc(C(=O)N[C@H]4CCC[C@](O)(Cn5ncc6ccc(C(F)(F)F)cc65)C4)cc23)ccn1] | N-[cis-3-hydroxy-3-[[6-(trifluoromethyl)-1H-indazol-1-yl]methyl]cyclohexyl]-3-(2-methyl-4-pyridinyl)-1H-indazole-5-carboxamide | 107.2 | 549.2 | 549.0 | 2.51 |
| 107 | 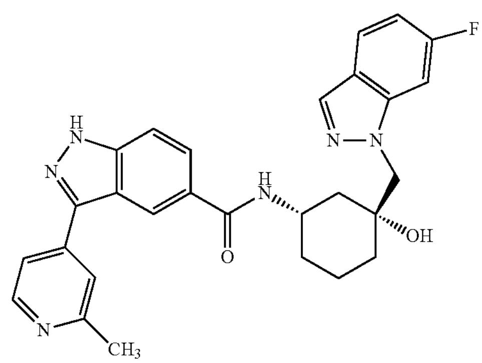 [SMILES: Cc1cc(-c2n[nH]c3ccc(C(=O)N[C@H]4CCC[C@](O)(Cn5ncc6ccc(F)cc65)C4)cc23)ccn1] | N-[cis-3-[(6-fluoro-1H-indazol-1-yl)methyl]-3-hydroxycyclohexyl]-3-(2-methyl-4-pyridinyl)-1H-indazole-5-carboxamide | 361.9 | 499.2 | 499.1 | 2.34 |
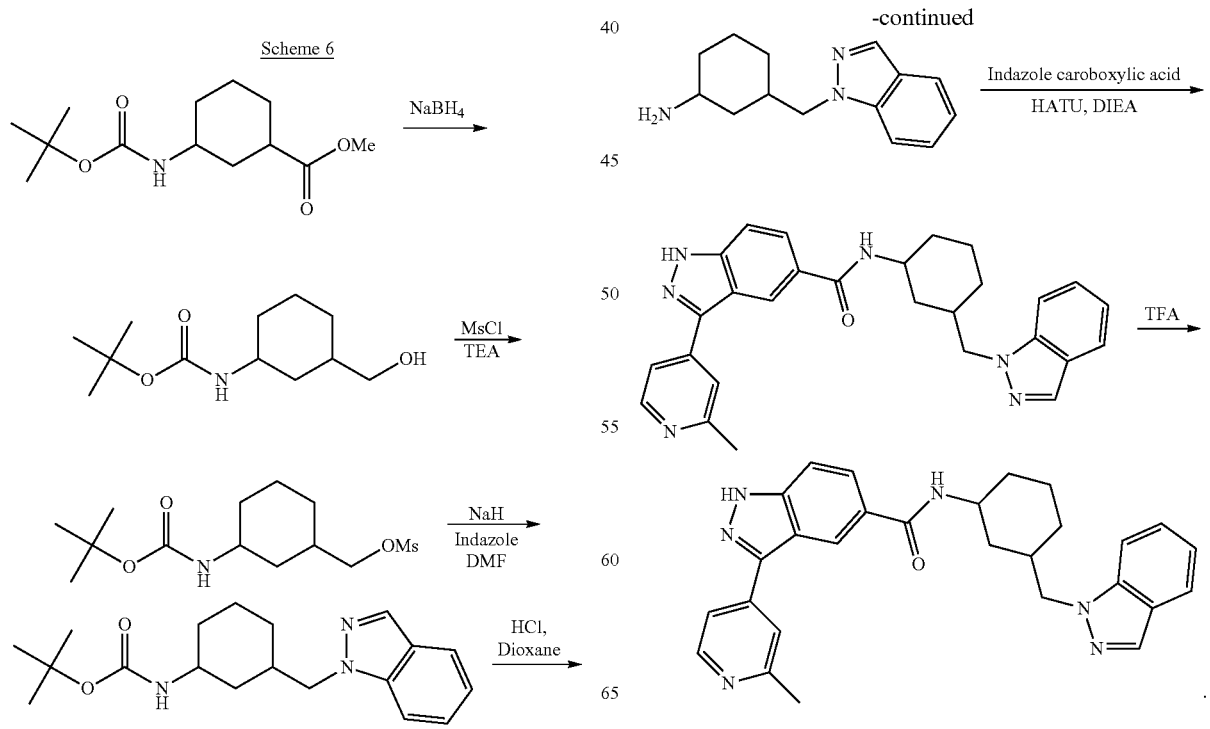
Scheme 6

Preparation of tert-butyl 3-(hydroxymethyl)cyclohexylcarbamate

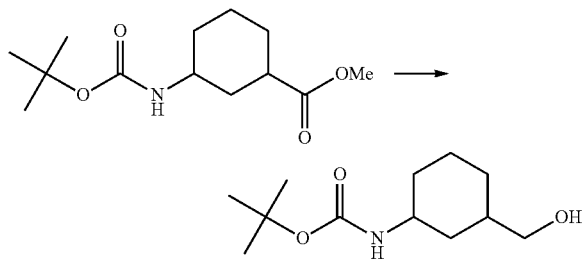

To a solution of methyl 3-(tert-butoxycarbonylamino)cyclohexanecarboxylate (9 mmol) in THF/MeOH/CH₂Cl₂ (36 ml, 10:1:1) was added NaBH₄ (22.5 mmol) and stirred at rt overnight. The reaction was quenched with water and extracted with CH₂Cl₂ (3×10 mL). The extracts were combined and dried using anhydrous sodium sulfate. The product was purified using Biotage.

Preparation of (3-(tert-butoxycarbonylamino)cyclohexyl)methyl methanesulfonate

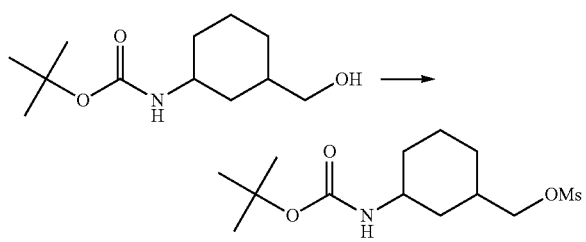

A mixture of tert-butyl 3-(hydroxymethyl)cyclohexylcarbamate (7.9 mmol), methanesulfonyl chloride (23.7 mmol) and triethylamine (119 mmol) in DCM (100 ml) was stirred at rt overnight. The reaction was quenched with water (50 mL) and extracted with ethyl acetate (3×100 mL). The extracts were combined, dried using anhydrous sodium sulfate, filtered, and concentrated in vacuo. The crude product was progressed to the next step without purification.

Preparation of tert-butyl 3-((1H-indazol-1-yl)methyl)cyclohexylcarbamate

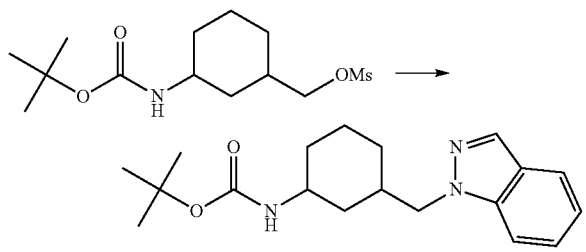

NaH (0.8 mmol) was added to a vial containing indazole (1.6 mmol) in DMF (1 ml). The mixture was stirred at rt for 15 mins, then added 3-(tert-butoxycarbonylamino)-cyclohexyl)methyl methanesulfonate (0.16 mmol). The reaction was stirred at 60° C. overnight. Upon completion, the mixture was quenched by water (3 mL) The mixture was extracted using dichloromethane (3×5 mL). The extracts were combined and dried using anhydrous sodium sulfate. The product was purified using HPLC.

Preparation of 3-((1H-indazol-1-yl)methyl)cyclohexanamine

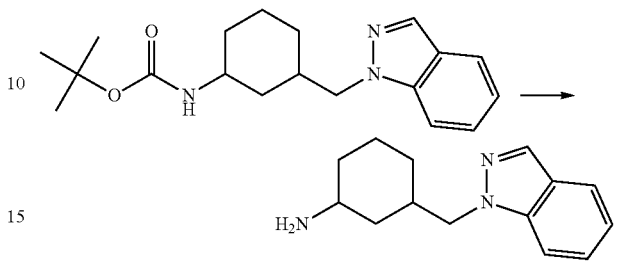

In a flask, hydrochloric acid in dioxane (4M, 2 mL) was added to tert-butyl 34(1H-indazol-1-yl)methyl)cyclohexylcarbamate (50 mg), and the reaction was stirred for 30 minutes. The resulting solution was concentrated in vacuo. The crude product was progressed to the next step without further purification.

Preparation of N-(3-((1H-indazol-1-yl)methyl)cyclohexyl)-3-(2-methylpyridin-4-yl)-1-trityl-1H-indazole-5-carboxamide

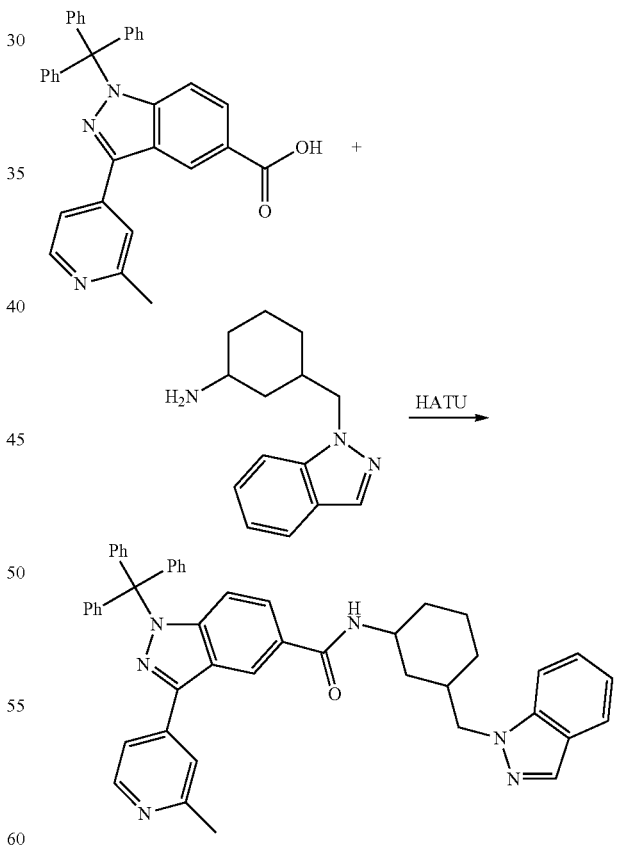

2-(7-Aza-1H-benzotriazole-1-yl)-1,1,3,3-tetramethyluronium hexafluorophosphate (HATU) (0.11 mmol) was added to a suspension of 3-(2-methylpyridin-4-yl)-1-trityl-1H-indazole-5-carboxylic acid (0.1 mmol) in DMF (0.5 mL) and was stirred at room temperature for 15 minutes. A solution of 3-((1H-indazol-1-yl)methyl)cyclohexanamine (0.1 mmol) in

123

DMF (0.5 mL) was added to the reaction and followed by diisopropyl ethyl amine (DIEA) (0.1 mL). The mixture was stirred at room temperature for an additional 30 minutes. The reaction was quenched with water (5 mL) and extracted with ethyl acetate (3×10 mL). The extracts were combined, dried using anhydrous sodium sulfate, filtered, and concentrated in vacuo. The crude product was progressed to the next step without purification.

Preparation of N-(3-((1H-indazol-1-yl)methyl)cyclohexyl)-3-(2-methylpyridin-4-yl)-1H-indazole-5-carboxamide

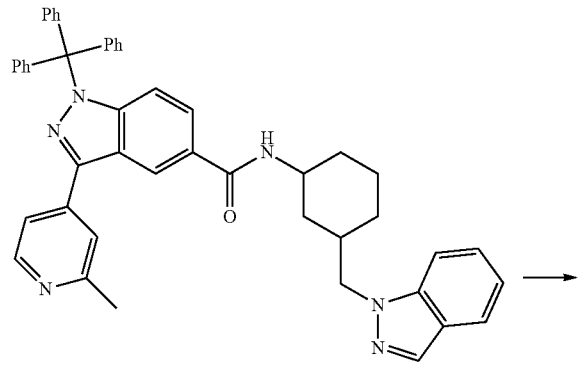

124

-continued

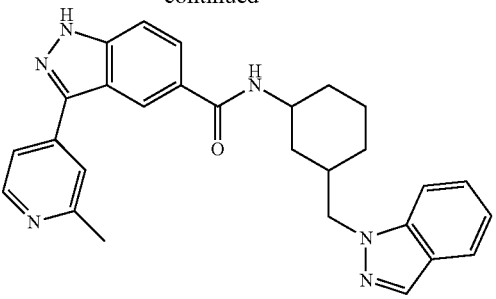

Trifluoroacetic acid (5 mL) was added to N-(3-((1H-indazol-1-yl)methyl)cyclohexyl)-3-(2-methylpyridin-4-yl)-1-trityl-1H-indazole-5-carboxamide (0.1 mmol). The reaction was stirred at room temperature for 30 minutes. Triethylsilane (1 drop) was added to the reaction and stirred for an additional 5 minutes. The crude product purified using prep HPLC.

Following compounds were prepared using similar method:

| Compd # | Structure | Chemical Names | aERK IC50 nM | M + 1 Cacld. | M + 1 Obs. | Rf min. |
|---|---|---|---|---|---|---|
| 108 | 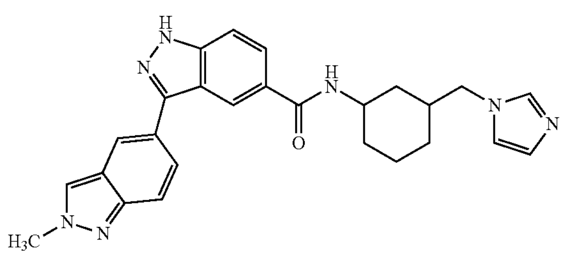 [SMILES: Cn1cc2cc(-c3n[nH]c4ccc(C(=O)NC5CCCC(Cn6ccnc6)C5)cc34)ccc2n1] | N-[3-(1H-imidazol-1-ylmethyl)cyclohexyl]-3-(2-methyl-2H-indazol-5-yl)-1H-indazole-5-carboxamide | 29.3 | 454.2 | 454.2 | 1.87 |
| 109 | 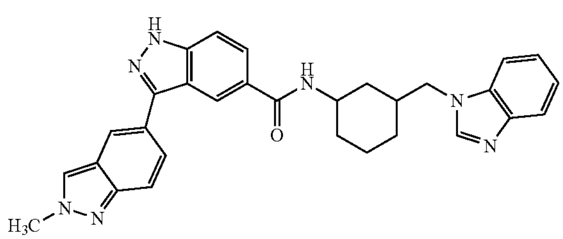 [SMILES: Cn1cc2cc(-c3n[nH]c4ccc(C(=O)NC5CCCC(Cn6cnc7ccccc76)C5)cc34)ccc2n1] | N-[3-(1H-benzimidazol-1-ylmethyl)cyclohexyl]-3-(2-methyl-2H-indazol-5-yl)-1H-indazole-5-carboxamide | 21.1 | 504.2 | 504.2 | 2.15 |
| 110 | 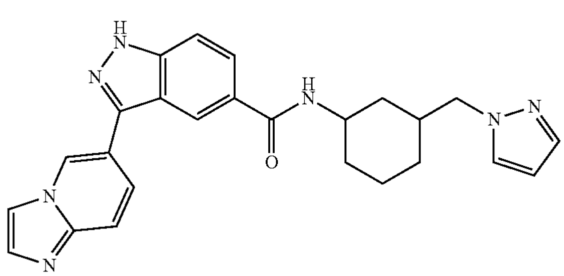 [SMILES: O=C(NC1CCCC(Cn2cccn2)C1)c1ccc2[nH]nc(-c3ccc4nccn4c3)c2c1] | 3-imidazo[1,2-a]pyridin-6-yl-N-[3-(1H-pyrazol-1-ylmethyl)cyclohexyl]-1H-indazole-5-carboxamide | 74.6 | 440.2 | 440.0 | 1.99 |

-continued

| Compd # | Structure | Chemical Names | aERK IC50 nM | M + 1 Calcd. | M + 1 Obs. | Rf min. |
|---|---|---|---|---|---|---|
| 111 | 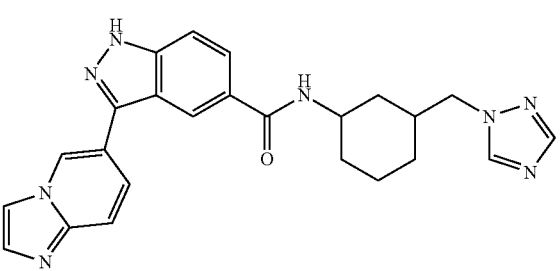 [SMILES: O=C(NC1CCCC(Cn2cncn2)C1)c1ccc2[nH]nc(-c3ccc4nccn4c3)c2c1] | 3-imidazo[1,2-a]pyridin-6-yl-N-[3-(1H-1,2,4-triazol-1-ylmethyl)cyclohexyl]-1H-indazole-5-carboxamide | 77.2 | 441.2 | 441.1 | 1.72 |
| 112 | 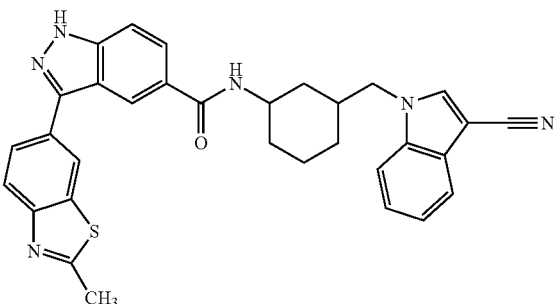 | N-[3-[(3-cyano-1H-indol-1-yl)methyl]cyclohexyl]-3-(2-methyl-6-benzothiazolyl)-1H-indazole-5-carboxamide | 1000.0 | 545.2 | 546.2 | 3.74 |
| 113 | 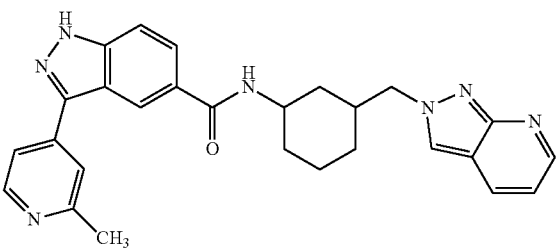 [SMILES: Cc1cc(-c2n[nH]c3ccc(C(=O)NC4CCCC(Cn5cc6cccnc6n5)C4)cc23)ccn1] | 3-(2-methyl-4-pyridinyl)-N-[3-(2H-pyrazolo[3,4-b]pyridin-2-ylmethyl)cyclohexyl]-1H-indazole-5-carboxamide | 163.9 | 466.2 | 466.2 | 1.254 |
| 114 | 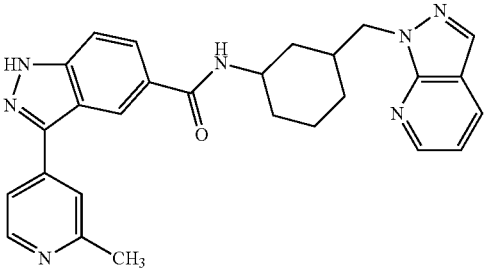 [SMILES: Cc1cc(-c2n[nH]c3ccc(C(=O)NC4CCCC(Cn5ncc6ccncc65)C4)cc23)ccn1] | 3-(2-methyl-4-pyridinyl)-N-[3-(1H-pyrazolo[3,4-b]pyridin-1-ylmethyl)cyclohexyl]-1H-indazole-5-carboxamide | 15.4 | 466.2 | 466.2 | 1.628 |
| 115 | 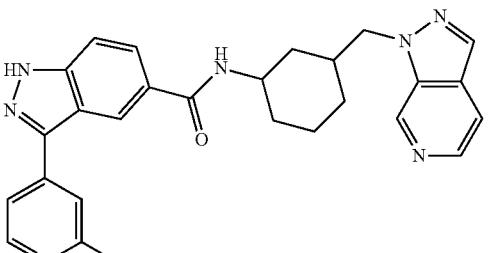 | 3-(2-methyl-4-pyridinyl)-N-[3-(1H-pyrazolo[3,4-c]pyridin-1-ylmethyl)cyclohexyl]-1H-indazole-5-carboxamide | 33.8 | 466.2 | 466.2 | 1.254 |

-continued

| Compd # | Structure | Chemical Names | aERK IC50 nM | M + 1 Cacld. | M + 1 Obs. | Rf min. |
|---|---|---|---|---|---|---|
| 116 | 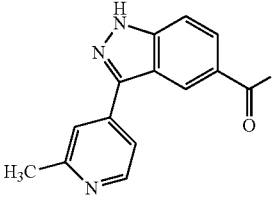 | N-[3-[(2-methyl-1H-imidazo[4,5-c]pyridiN-1-yl)methyl]cyclohexyl]-3-(2-methyl-4-pyridinyl)-1H-indazole-5-carboxamide | 1000.0 | 480.2 | 480.2 | 1.21 |
| 117 | 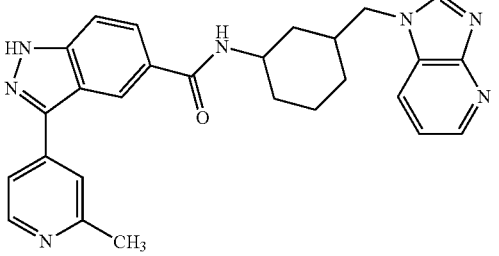 | N-[3-(1H-imidazo[4,5-b]pyridin-1-ylmethyl)cyclohexyl]-3-(2-methyl-4-pyridinyl)-1H-indazole-5-carboxamide | 86.5 | 466.2 | 466.2 | 1.232 |
| 118 | 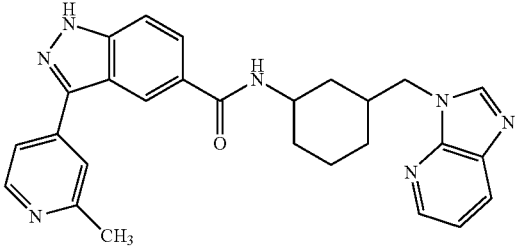 [SMILES: Cc1cc(-c2n[nH]c3ccc(C(=O)NC4CCCC(Cn5cnc6cccnc65)C4)cc23)ccn1] | N-[3-(3H-imidazo[4,5-b]pyridin-3-ylmethyl)cyclohexyl]-3-(2-methyl-4-pyridinyl)-1H-indazole-5-carboxamide | 60.8 | 466.2 | 466.2 | 1.32 |
| 119 | 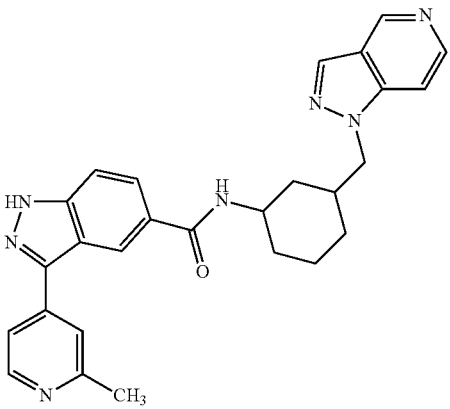 [SMILES: Cc1cc(-c2n[nH]c3ccc(C(=O)NC4CCCC(Cn5ncc6cnccc65)C4)cc23)ccn1] | 3-(2-methyl-4-pyridinyl)-N-[3-(1H-pyrazolo[4,3-c]pyridin-1-ylmethyl)cyclohexyl]-1H-indazole-5-carboxamide | 530.4 | 466.2 | 466.0 | 1.166 |
| 120 | 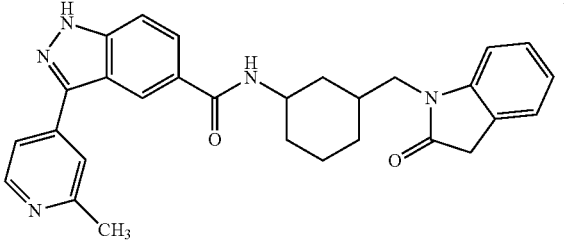 [SMILES: Cc1cc(-c2n[nH]c3ccc(C(=O)NC4CCCC(CN5C(=O)Cc6ccccc65)C4)cc23)ccn1] | N-[3-[(2,3-dihydro-2-oxo-1H-indol-1-yl)methyl]cyclohexyl]-3-(2-methyl-4-pyridinyl)-1H-indazole-5-carboxamide | 17.4 | 480.2 | 480.2 | 5.258 |

| Compd # | Structure | Chemical Names | aERK IC50 nM | M + 1 Cacld. | M + 1 Obs. | Rf min. |
|---|---|---|---|---|---|---|
| 121 | 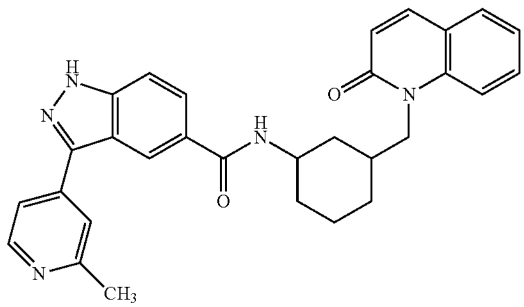 [SMILES: Cc1cc(-c2n[nH]c3ccc(C(=O)NC4CCCC(Cn5c(=O)ccc6ccccc65)C4)cc23)ccn1] | 3-(2-methyl-4-pyridinyl)-N-[3-[(2-oxo-1(2h)-quinolinyl)methyl]cyclohexyl]-1H-indazole-5-carboxamide | 37.2 | 492.2 | 492.0 | 1.694 |
| 122 | 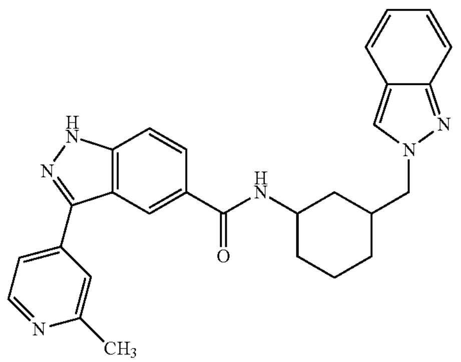 [SMILES: Cc1cc(-c2n[nH]c3ccc(C(=O)NC4CCCC(Cn5cc6ccccc6n5)C4)cc23)ccn1] | N-[3-(2H-indazol-2-ylmethyl)cyclohexyl]-3-(2-methyl-4-pyridinyl)-1H-indazole-5-carboxamide | 14.3 | 465.2 | 465.2 | 5.17 |
| 123 | 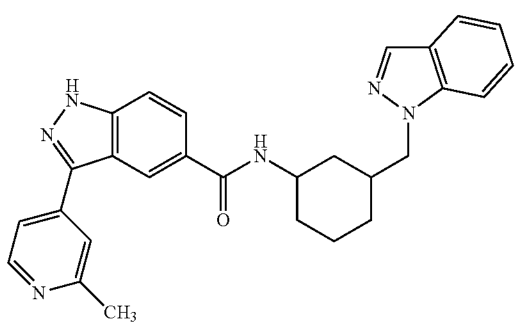 [SMILES: Cc1cc(-c2n[nH]c3ccc(C(=O)NC4CCCC(Cn5ncc6ccccc65)C4)cc23)ccn1] | N-[3-(1H-indazol-1-ylmethyl)cyclohexyl]-3-(2-methyl-4-pyridinyl)-1H-indazole-5-carboxamide | 10.7 | 465.2 | 465.2 | 2.112 |
| 124 | 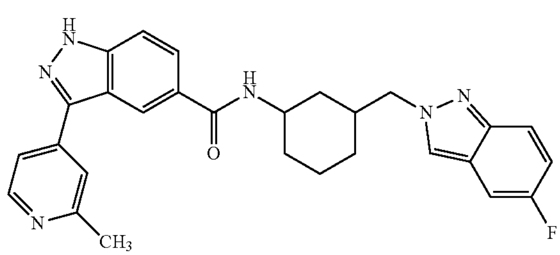 [SMILES: Cc1cc(-c2n[nH]c3ccc(C(=O)NC4CCCC(Cn5cc6cc(F)ccc6n5)C4)cc23)ccn1] | N-[cis/trans-3-[(5-fluoro-2H-indazol-2-yl)methyl]cyclohexyl]-3-(2-methyl-4-pyridinyl)-1H-indazole-5-carboxamide | 263.8 | 483.2 | 483.0 | 2.54 |
| 125 | 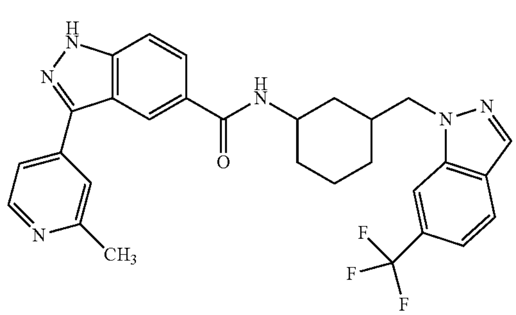 [SMILES: Cc1cc(-c2n[nH]c3ccc(C(=O)NC4CCCC(Cn5ncc6ccc(C(F)(F)F)cc65)C4)cc23)ccn1] | 3-(2-methyl-4-pyridinyl)-N-[cis/trans-3-[[6-(trifluoromethyl)-1H-indazol-1-yl]methyl]cyclohexyl]-1H-indazole-5-carboxamide | 1000.0 | 533.2 | 533.2 | 3 |

-continued
| Compd # | Structure | Chemical Names | aERK IC50 nM | M + 1 Cacld. | M + 1 Obs. | Rf min. |
|---|---|---|---|---|---|---|
| 126 | 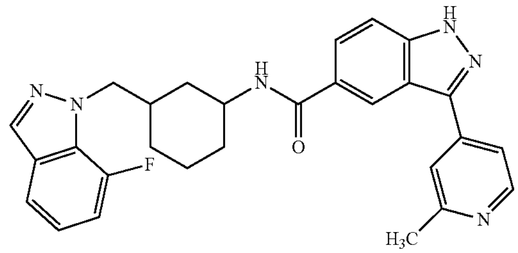 [SMILES: Cc1cc(-c2n[nH]c3ccc(C(=O)NC4CCCC(Cn5ncc6cccc(F)c65)C4)cc23)ccn1] | N-[cis/trans-3-[(7-fluoro-1H-indazol-1-yl)methyl]cyclohexyl]-3-(2-methyl-4-pyridinyl)-1H-indazole-5-carboxamide | 56.6 | 483.2 | 483.0 | 2.41 |
| 127 | 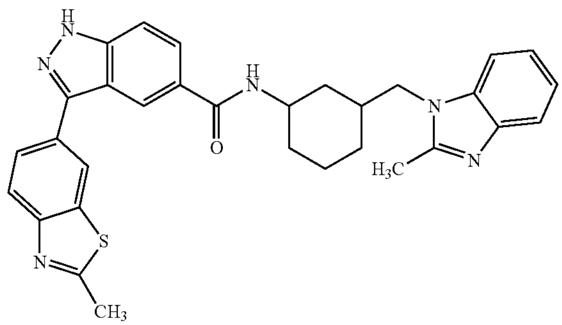 [SMILES: Cc1nc2ccc(-c3n[nH]c4ccc(C(=O)NC5CCCC(Cn6c(C)nc7ccccc76)C5)cc34)cc2s1] | N-[3-[(2-methyl-1H-benzimidazol-1-yl)methyl]cyclohexyl]-3-(2-methyl-6-benzothiazolyl)-1H-indazole-5-carboxamide | 1000.0 | 535.2 | 536.2 | 2.4 |
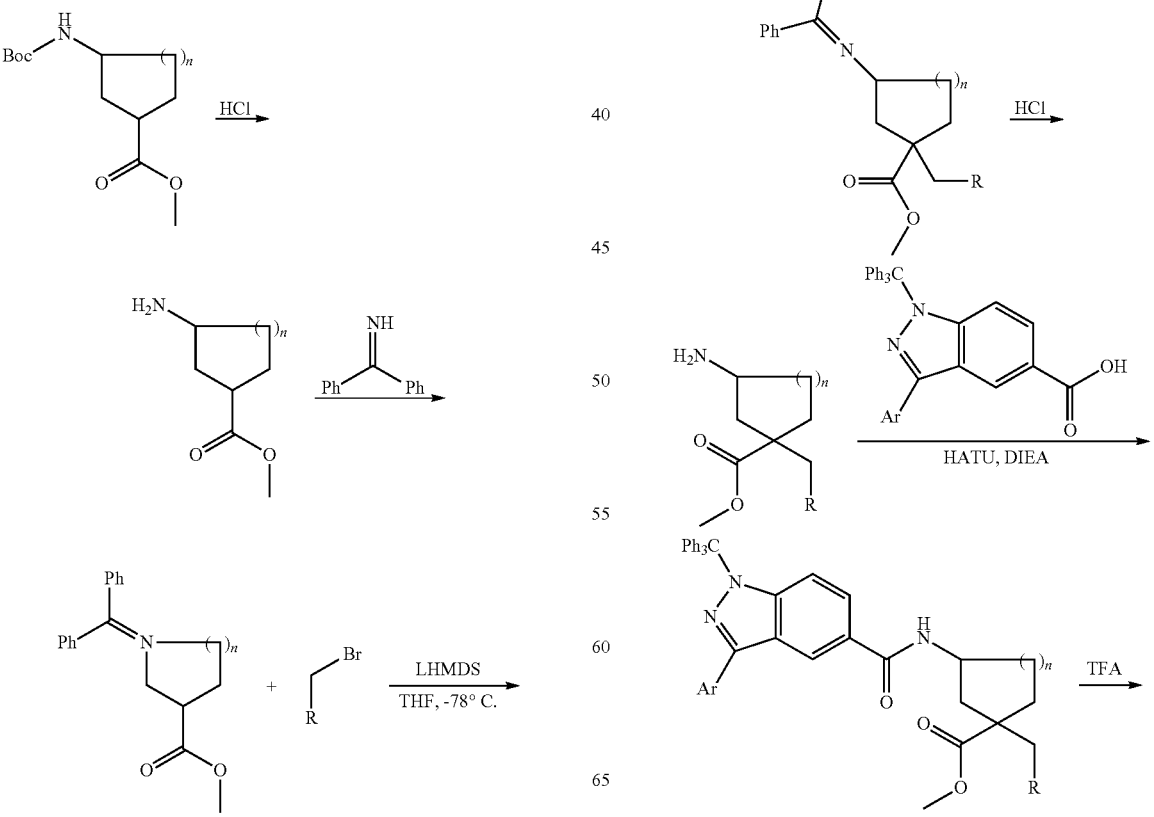
Scheme 7

-continued

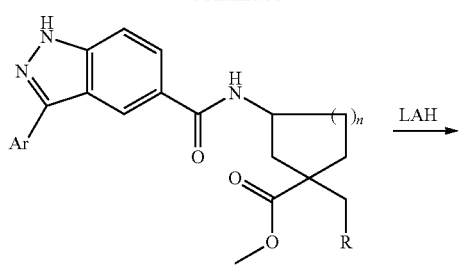

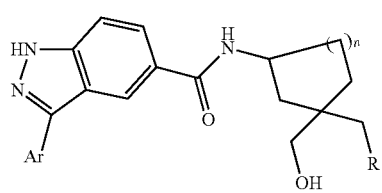

n = 1, or 2

-continued

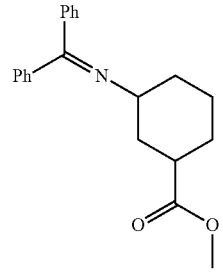

In a flask, methyl 3-aminocyclohexanecarboxylate (3.86 g, 19.94 mmol) was dissolved in dichloromethane (80 mL). Benzophenone imine (3.33 mL, 19.94 mmol) was added to the reaction, and the reaction was stirred at room temperature for 24 hrs. Upon completion, the reaction was concentrated and triturated with diethyl ether. The suspension was filtered. This trituration process was done twice. The remaining filtrate was concentrated and progressed to the next step without further purification.

Preparation of methyl 3-(diphenylmethyleneamino)-1-(4-fluorobenzyl)cyclohexanecarboxylate

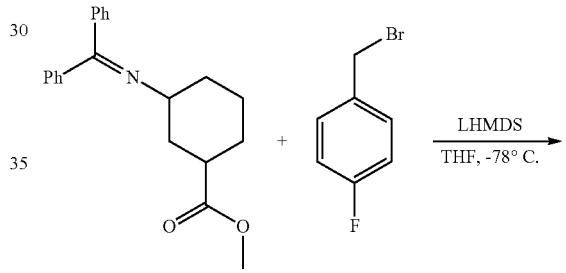

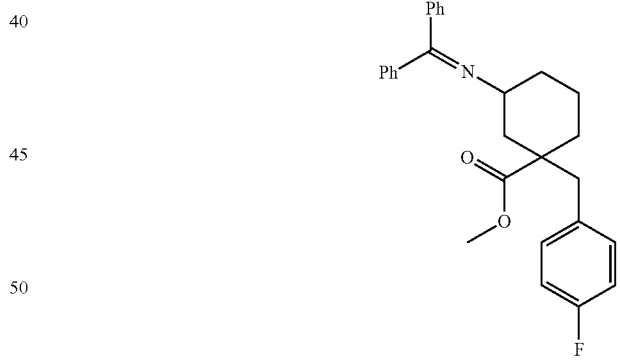

Preparation of methyl 3-aminocyclohexanecarboxylate

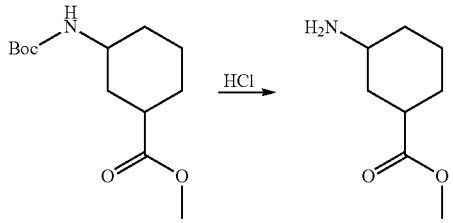 [SMILES: COC(=O)C1CCCC(NC(=O)OC(C)(C)C)C1 ; Cl ; COC(=O)C1CCCC(N)C1]

In a flask, methyl 3-(tert-butoxycarbonylamino)cyclohexanecarboxylate (5.13 g, 19.94 nmol) in 1,4-dioxane (15 ml) was reacted with hydrochloric acid in dioxane (4M) (15 mL). Methanol (2 mL) was added to aid in solubility. The reaction was stirred at room temperature for 1 hour. Upon completion the reaction was concentrated, and the crude (3.86 g) was progressed to the next step without further purification.

Preparation of methyl 3-(diphenylmethyleneamino)cyclohexanecarboxylate

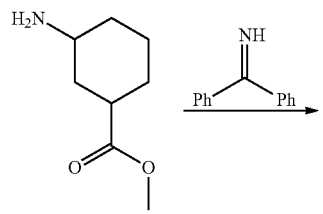

In a flask, lithium bis(trimethylsilyl)amide (LHMDS) (1M) in THF (2.83 mL, 2.83 mmol) was added to tetrahydrofuran (10 mL). The reaction mixture was cooled to −78° C., and then a solution of methyl 3-(diphenylmethyleneamino) cyclohexanecarboxylate (700 mg, 2.18 mmol) and tetrahydrofuran (1 mL) was added drop-wise to the reaction mixture at −78° C. The reaction was stirred at −78° C. for 30 minutes. Afterwards, 4-fluorobenzylbromide (0.402 mL, 3.27 mmol) was added, and the reaction was stirred for an additional 24 hours at 0° C. Upon reaction completion, the reaction was quenched with saturated ammonium chloride solution (50 mL) and extracted three times with ethyl acetate (50 mL). The organic layers were combined, dried with sodium sulfate, and concentrated to yield crude product. The crude product was progressed to the next step without further purification.

Preparation of methyl 3-amino-1-(4-fluorobenzyl)cyclohexanecarboxylate

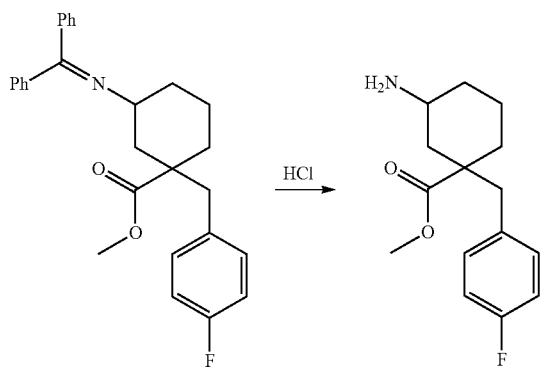 [SMILES: COC(=O)C1(Cc2ccc(F)cc2)CCCC(N=C(c2ccccc2)c2ccccc2)C1 ; Cl ; COC(=O)C1(Cc2ccc(F)cc2)CCCC(N)C1]

In a flask, methyl 3-(diphenylmethyleneamino)-1-(4-fluorobenzyl)cyclohexanecarboxylate (crude, from previous step) was dissolved in tetrahydrofuran (15 mL). Concentrated hydrochloric acid (1.2 mL) was added to the reaction. The reaction was stirred at room temperature for 5 hours. The resulting reaction mixture was concentrated to yield the crude product. The crude product was progressed to the next step without further purification.

Preparation of methyl 1-(4-fluorobenzyl)-3-(3-(2-methylpyridin-4-yl)-1-trityl-1H-indazole-5-carboxamido)cyclohexanecarboxylate

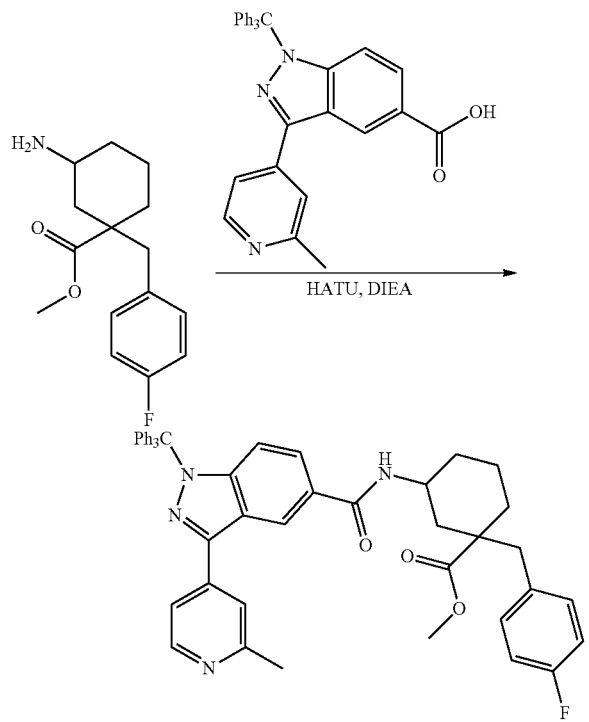

In a flask, 3-(2-methylpyridin-4-yl)-1-trityl-1H-indazole-5-carboxylic acid (567 mg, 1.15 mmol), methyl 3-amino-1-(4-fluorobenzyl)cyclohexanecarboxylate (1.09 mmol), and HATU (622 mg, 1.64 mmol) was dissolved in dimethylformamide (3 mL). The reaction mixture was stirred for 2 minutes at room temperature. Diisopropylethylamine (0.95 mL, 5.45 mmol) was added to the reaction. The reaction was allowed to stir for an additional 1 hr. Upon completion, the reaction was quenched with water (5 mL). The water layer was extracted with ethyl acetate (20 mL) three times. The organic fractions were combined, dried with sodium sulfate, and concentrated to yield the crude product. The crude compound was purified using flash chromatography (0-100% ethyl acetate in hexane gradient) to give the title compound (690 mg).

Preparation of methyl 1-(4-fluorobenzyl)-3-(3-(2-methylpyridin-4-yl)-1H-indazole-5-carboxamido)cyclohexanecarboxylate

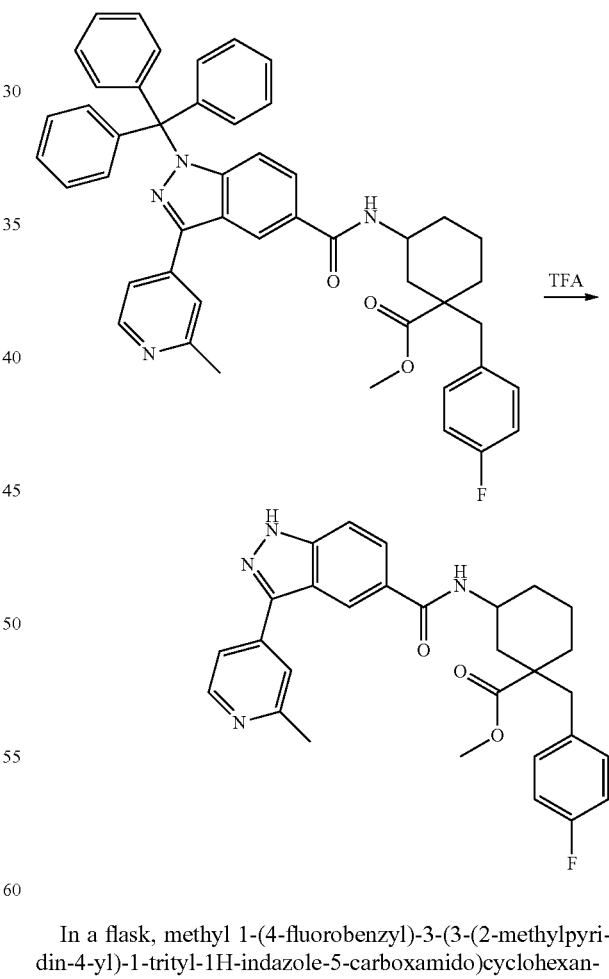

In a flask, methyl 1-(4-fluorobenzyl)-3-(3-(2-methylpyridin-4-yl)-1-trityl-1H-indazole-5-carboxamido)cyclohexanecarboxylate (230 mg, 0.31 mmol) was reacted with trifluoroacetic acid (3 mL) for 1 hour. After reaction completion triethylsilane (0.1 mL) was added, and the reaction was stirred for an additional 15 minutes. The reaction was concentrated and rinsed with diethyl ether. The crude product was progressed to the next step without further purification.

Preparation of N-(3-(4-Fluorobenzyl)-3-(hydroxymethyl)cyclohexyl)-3-(2-methylpyridin-4-yl)-1H-indazole-5-carboxamide centrated and purified using HPLC to give the titled compound. LC-MS: 473.23 [M+H]. LC/MS RT=2.46 min.

Preparation of 1-(4-Fluorobenzyl)-3-(3-(2-methylpyridin-4-yl)-1H-indazole-5-carboxamido)cyclohexanecarboxylic acid

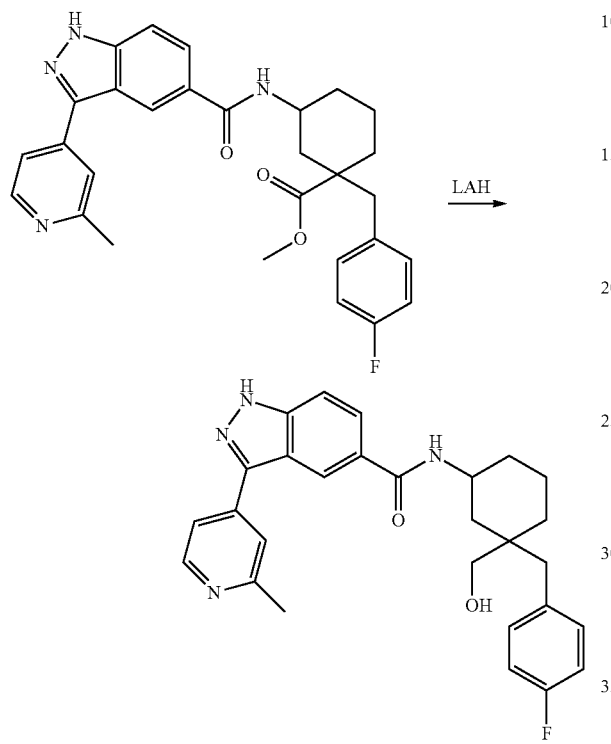
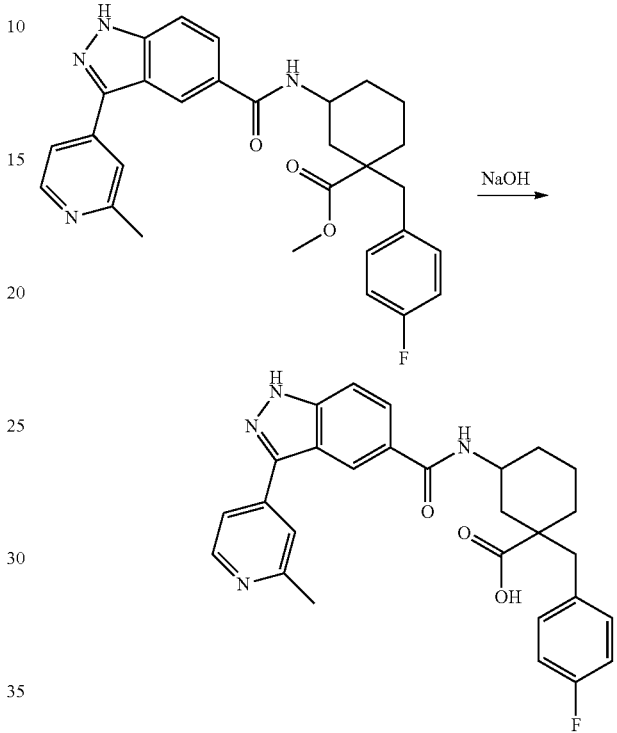

In a flask, methyl 1-(4-fluorobenzyl)-3-(3-(2-methylpyridin-4-yl)-1H-indazole-5-carboxamido)cyclohexanecarboxylate (0.31 mmol) was dissolved in tetrahydrofuran (6 mL). Lithium aluminum hydride in THF (1M) (0.62 ml, 0.62 mmol) was added to the flask. The reaction was stirred for 3 hrs at room temperature. Upon completion, the reaction was quenched with ethyl acetate (5 ml) drop-wise. Water (5 mL) was added to the reaction. The reaction mixture then was extracted 3 times with ethyl acetate (20 mL). The organic layers were combined, were dried with sodium sulfate, con- Sodium hydroxide in water (4 M solution, 1 ml, 4 mmol) was added into a solution of methyl 1-(4-fluorobenzyl)-3-(3-(2-methylpyridin-4-yl)-1H-indazole-5-carboxamido)cyclohexanecarboxylate (0.32 mmol) in methanol (0.5 ml) and THF (2 ml). The reaction solution was stirred at 70° C. for 16 h, and 1.0 N HCl solution was added dropwise to adjust pH to 4. The resulting solution was extracted with EtOAc (10 ml, twice). The combined organic layers were dried over sodium sulfate, filtered, concentrated, and purified using HPLC to give the titled compound. LC-MS: 487.21 [M+H]. LC/MS RT=2.36 min.

| Compd # | Structure | Chemical Names | aERK IC50 nM | M + 1 Cacld. | M + 1 Obs. | Rf min. |
|---|---|---|---|---|---|---|
| 128 | 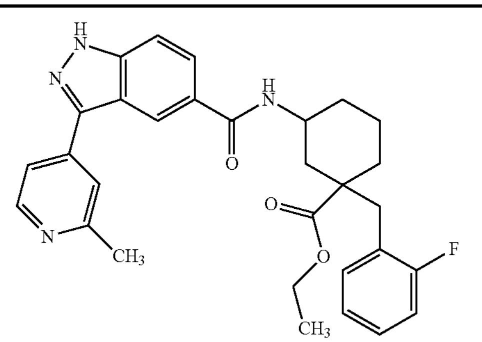 | ethyl cis/trans-1-[(2-fluorophenyl)methyl]-3-[[[3-(2-methyl-4-pyridinyl)-1H-indazol-5-yl]carbonyl]amino]cyclohexanecarboxylate | 1000.0 | 515.2 | 515.2 | 2.81 |

| Compd # | Structure | Chemical Names | aERK IC50 nM | M + 1 Cacld. | M + 1 Obs. | Rf min. |
|---|---|---|---|---|---|---|
| 129 | 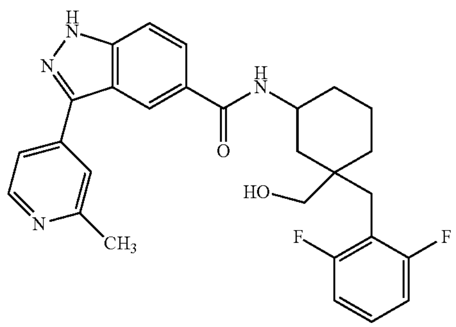 [SMILES: Cc1cc(-c2n[nH]c3ccc(C(=O)NC4CCCC(CO)(Cc5c(F)cccc5F)C4)cc23)ccn1] | N-[3-[(2,6-difluorophenyl)methyl]-3-(hydroxymethyl)cyclohexyl]-3-(2-methyl-4-pyridinyl)-1H-indazole-5-carboxamide | 635.9 | 491.2 | 491.2 | 2.39 |
| 130 | 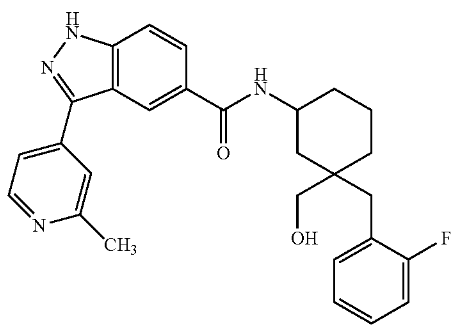 [SMILES: Cc1cc(-c2n[nH]c3ccc(C(=O)NC4CCCC(CO)(Cc5ccccc5F)C4)cc23)ccn1] | N-[cis/trans-3-[(2-fluorophenyl)methyl]-3-(hydroxymethyl)cyclohexyl]-3-(2-methyl-4-pyridinyl)-1H-indazole-5-carboxamide | 1000.0 | 473.2 | 473.2 | 2.42 |
| 131 | 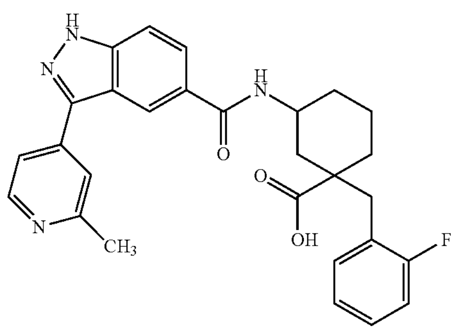 [SMILES: Cc1cc(-c2n[nH]c3ccc(C(=O)NC4CCCC(Cc5ccccc5F)(C(=O)O)C4)cc23)ccn1] | cis/trans-1-[(2-fluorophenyl)methyl]-3-[[[3-(2-methyl-4-pyridinyl)-1H-indazol-5-yl]carbonyl]amino]cyclohexanecarboxylic acid | 1000.0 | 487.2 | 487.2 | 2.36 |
| 132 | 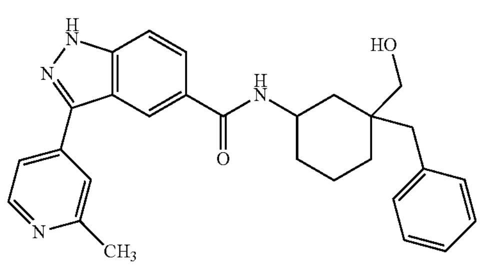 [SMILES: Cc1cc(-c2n[nH]c3ccc(C(=O)NC4CCCC(CO)(Cc5ccccc5)C4)cc23)ccn1] | N-[3-(hydroxymethyl)-3-(phenylmethyl)cyclohexyl]-3-(2-methyl-4-pyridinyl)-1H-indazole-5-carboxamide | 223.0 | 455.2 | 455.1 | 2.43 |
| 133 | 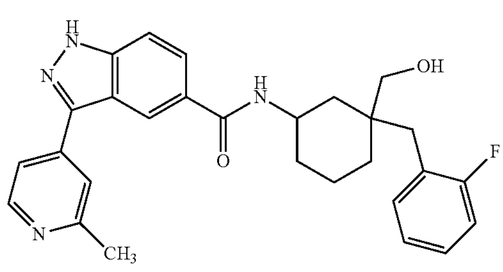 [SMILES: Cc1cc(-c2n[nH]c3ccc(C(=O)NC4CCCC(CO)(Cc5ccccc5F)C4)cc23)ccn1] | N-[3-[(2-fluorophenyl)methyl]-3-(hydroxymethyl)cyclohexyl]-3-(2-methyl-4-pyridinyl)-1H-indazole-5-carboxamide | 108.7 | 473.2 | 473.2 | 2.583 |

-continued

| Compd # | Structure | Chemical Names | aERK IC50 nM | M + 1 Cacld. | M + 1 Obs. | Rf min. |
|---|---|---|---|---|---|---|
| 134 | 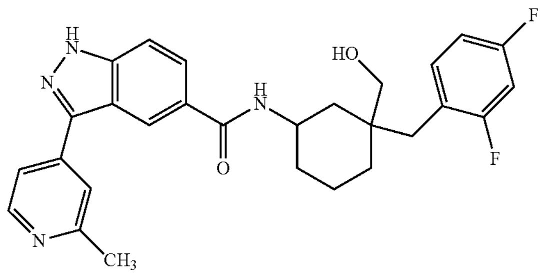 | N-[3-[(2,4-difluorophenyl)methyl]-3-(hydroxymethyl)cyclohexyl]-3-(2-methyl-4-pyridinyl)-1H-indazole-5-carboxamide | 436.5 | 491.2 | 491.2 | 2.5 |
| 135 | 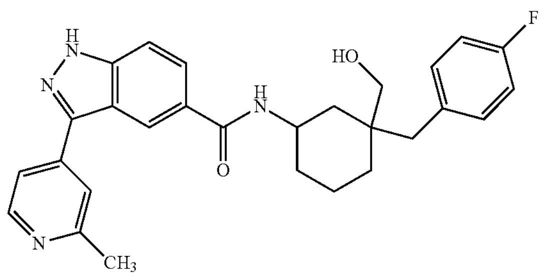 [SMILES: Cc1cc(-c2n[nH]c3ccc(C(=O)NC4CCCC(CO)(Cc5ccc(F)cc5)C4)cc23)ccn1] | N-[3-[(4-fluorophenyl)methyl]-3-(hydroxymethyl)cyclohexyl]-3-(2-methyl-4-pyridinyl)-1H-indazole-5-carboxamide | 357.2 | 473.2 | 473.2 | 2.46 |
| 136 | 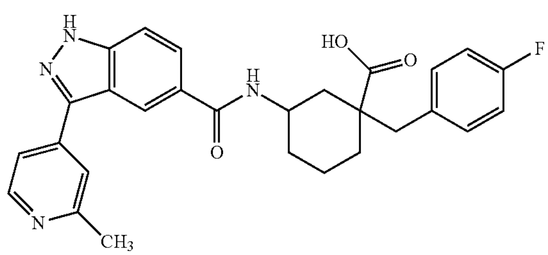 [SMILES: Cc1cc(-c2n[nH]c3ccc(C(=O)NC4CCCC(Cc5ccc(F)cc5)(C(=O)O)C4)cc23)ccn1] | 1-[(4-fluorophenyl)methyl]-3-[[[3-(2-methyl-4-pyridinyl)-1H-indazol-5-yl]carbonyl]amino]cyclohexanecarboxylic acid | 302.0 | 487.2 | 487.2 | 2.36 |
| 137 | 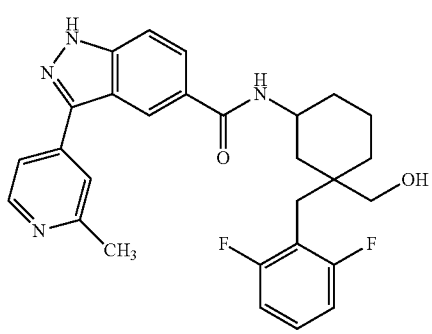 [SMILES: Cc1cc(-c2n[nH]c3ccc(C(=O)NC4CCCC(CO)(Cc5c(F)cccc5F)C4)cc23)ccn1] | N-[3-[(2,6-difluorophenyl)methyl]-3-(hydroxymethyl)cyclohexyl]-3-(2-methyl-4-pyridinyl)-1H-indazole-5-carboxamide | 444.7 | 491.2 | 491.2 | 2.44 |
| 138 | 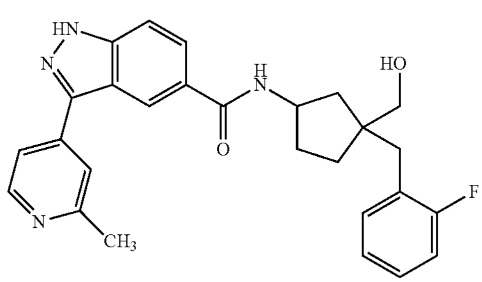 [SMILES: Cc1cc(-c2n[nH]c3ccc(C(=O)NC4CCC(CO)(Cc5ccccc5F)C4)cc23)ccn1] | N-[3-[(2-fluorophenyl)methyl]-3-(hydroxymethyl)cyclopentyl]-3-(2-methyl-4-pyridinyl)-1H-indazole-5-carboxamide | 19.2 | 459.2 | 459.0 | 2.246 |

-continued
| Compd # | Structure | Chemical Names | aERK IC50 nM | M + 1 Cacld. | M + 1 Obs. | Rf min. |
|---|---|---|---|---|---|---|
| 139 | 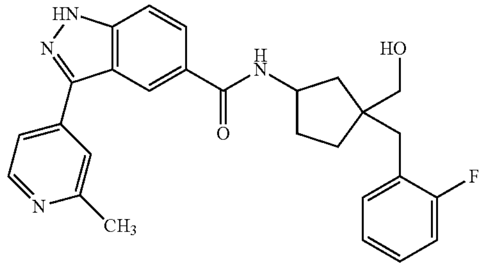 [SMILES: Cc1cc(-c2n[nH]c3ccc(C(=O)NC4CCC(CO)(Cc5ccccc5F)C4)cc23)ccn1] | N-[3-[(2-fluorophenyl)methyl]-3-(hydroxymethyl)cyclopentyl]-3-(2-methyl-4-pyridinyl)-1H-indazole-5-carboxamide | 64.4 | 459.2 | 459.0 | 2.381 |
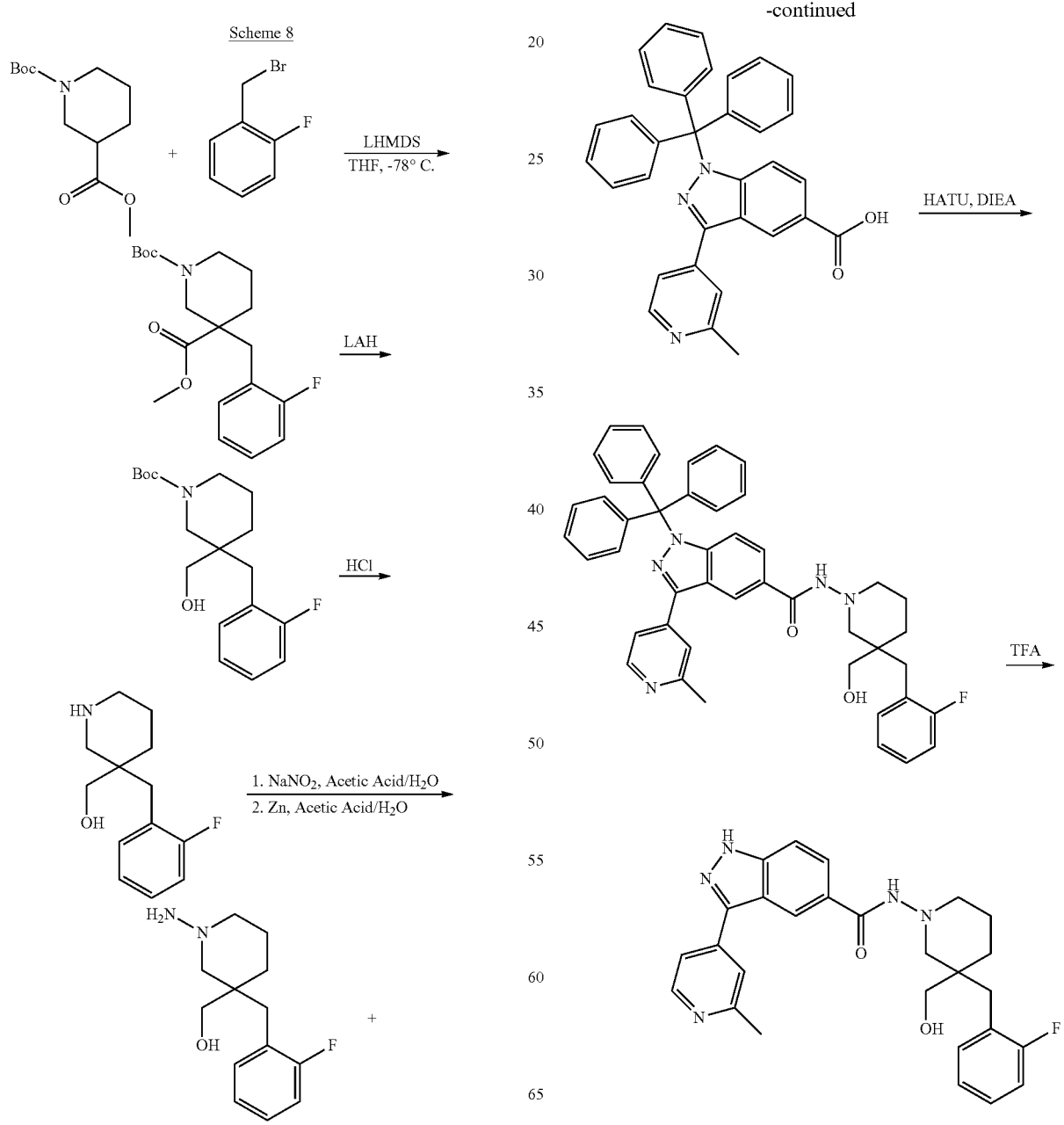
Scheme 8

Preparation of 1-tert-Butyl 3-methyl 3-(2-fluorobenzyl)piperidine-1,3-dicarboxylate

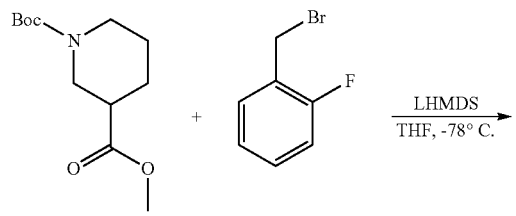

In a flask, lithium bis(trimethylsilyl)amide (LHMDS) (9.24 mL of 1.0 M solution in THF, 9.24 mmol) was added to tetrahydrofuran (20 mL). The reaction mixture was cooled to −78° C., and then a solution of 1-tert-butyl 3-methyl piperidine-1,3-dicarboxylate (1.5 g, 6.17 mmol) in tetrahydrofuran (5 mL) was added drop-wise to the reaction mixture at −78° C. The reaction was stirred at −78° C. for 30 minutes. Afterwards, 2-fluorobenzylbromide (1.12 mL, 9.24 mmol) was added, and the reaction was stirred for an additional 3 hours at 0° C. Upon reaction completion, the reaction was quenched with saturated ammonium chloride solution (50 mL) and extracted three times with ethyl acetate (50 mL). The organic layers were combined, dried with sodium sulfate, and concentrated to yield crude product. The crude product was purified using flash chromatography (0-60% ethyl acetate in hexane) to give the titled compound (1.41 g).

Preparation of tert-Butyl 3-(2-fluorobenzyl)-3-(hydroxymethyl)piperidine-1-carboxylate

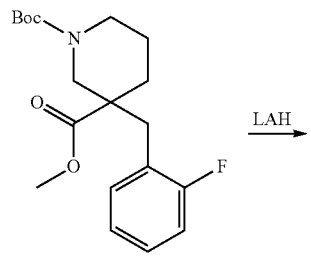

In a flask, 1-tert-butyl 3-methyl 3-(2-fluorobenzyl)piperidine-1,3-dicarboxylate (1.41 g, 4.0 mmol) was dissolved in tetrahydrofuran (20 mL). Lithium aluminum hydride (8.03 mmol) was added to the flask. The reaction was stirred for an hour at room temperature. Upon completion, the reaction was quenched with ethyl acetate (10 ml) drop-wise. Water (30 mL) was added to the reaction. The reaction mixture then was extracted 3 times with ethyl acetate (50 mL). The organic layers were combined, were dried with sodium sulfate, concentrated and purified using flash chromatography (0 60% ethyl acetate in hexane) to give the titled compound (1.29 g).

Preparation of (3-(2-Fluorobenzyl)piperidin-3-yl)methanol

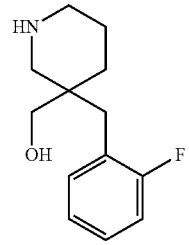

Hydrochloric acid in dioxane (1.5 mL, 4M) was added to a flask containing tert-butyl 3-(2-fluorobenzyl)-3-(hydroxymethyl)piperidine-1-carboxylate (0.43 g, 1.33 mmol). 1,4-dioxane (1.5 mL) was added to the reaction mixture. The reaction was allowed to stir for 4 hours. Upon reaction completion, the reaction was concentrated, and 346 mg of crude product was recovered and progressed to the next step without further purification.

Preparation of (1-Amino-3-(2-fluorobenzyl)piperidin-3-yl)methanol

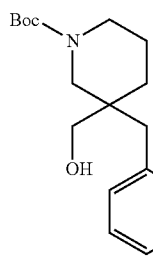 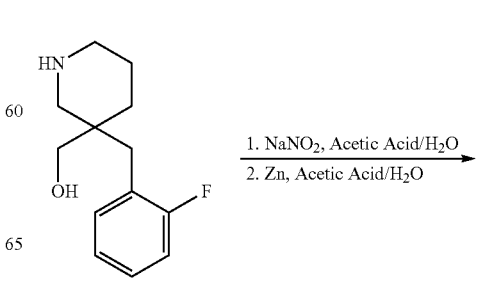

-continued

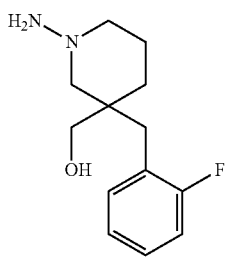

In an argon purged flask, (3-(2-fluorobenzyl)piperidin-3-yl)methanol (346 mg, 1.33 mmol) was dissolved in water (0.8 mL) and acetic acid (2 mL). A solution of sodium nitrite (170 mg, 2.66 mmol) and water (1 mL) was drop wise added to the reaction flask. The reaction was stirred for an hour at room temperature. Water (5 mL) was added to the reaction mixture. The reaction mixture then was extracted 3 times with ethyl acetate (20 mL). The organic layers were combined, dried with sodium sulfate, and concentrated. The oil was dissolved in acetic acid (5 mL). The solution was drop-wise added to a suspension of Zn (347 mg, 5.32 mmol) in acetic acid (1 mL) and water (1 mL) solution. The reaction was stirred for 1.5 hour at room temperature. Upon completion, the reaction was filtered through celite. The Zn and salt was rinsed with 1N HCl in water. The filtrate was concentrated to yield 258 mg of crude hydrogen chloride salt of the amine. The crude product was progressed to the next step without further purification.

Preparation of N-(3-(2-Fluorobenzyl)-3-(hydroxymethyl)piperidin-1-yl)-3-(2-methylpyridin-4-yl)-1-trityl-1H-indazole-5-carboxamide -continued

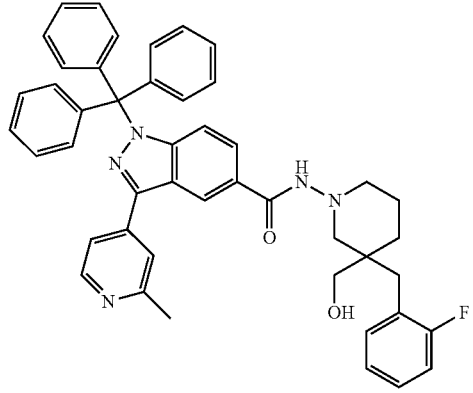

In a flask, 3-(2-methylpyridin-4-yl)-1-trityl-1H-indazole-5-carboxylic acid (605 mg, 1.22 mmol), HATU (572 mg, 1.50 mmol) and (1-amino-3-(2-fluorobenzyl)piperidin-3-yl)methanol (258 mg, 0.94 mmol) was dissolved in dimethylformamide (3 mL). Diisopropylethylamine (0.819 mL, 4.7 mmol) was added to the reaction. The reaction was allowed to stir for an additional 1 h. Upon completion, the reaction was quenched with water (10 mL). The water layer was extracted with ethyl acetate (20 mL) three times. The organic fractions were combined, dried with sodium sulfate, and concentrated to yield the crude product. The crude product was progressed to the next step without further purification.

Preparation of N-(3-(2-Fluorobenzyl)-3-(hydroxyethyl)piperidin-1-yl)-3-(2-methylpyridin-4-yl)-1H-indazole-5-carboxamide

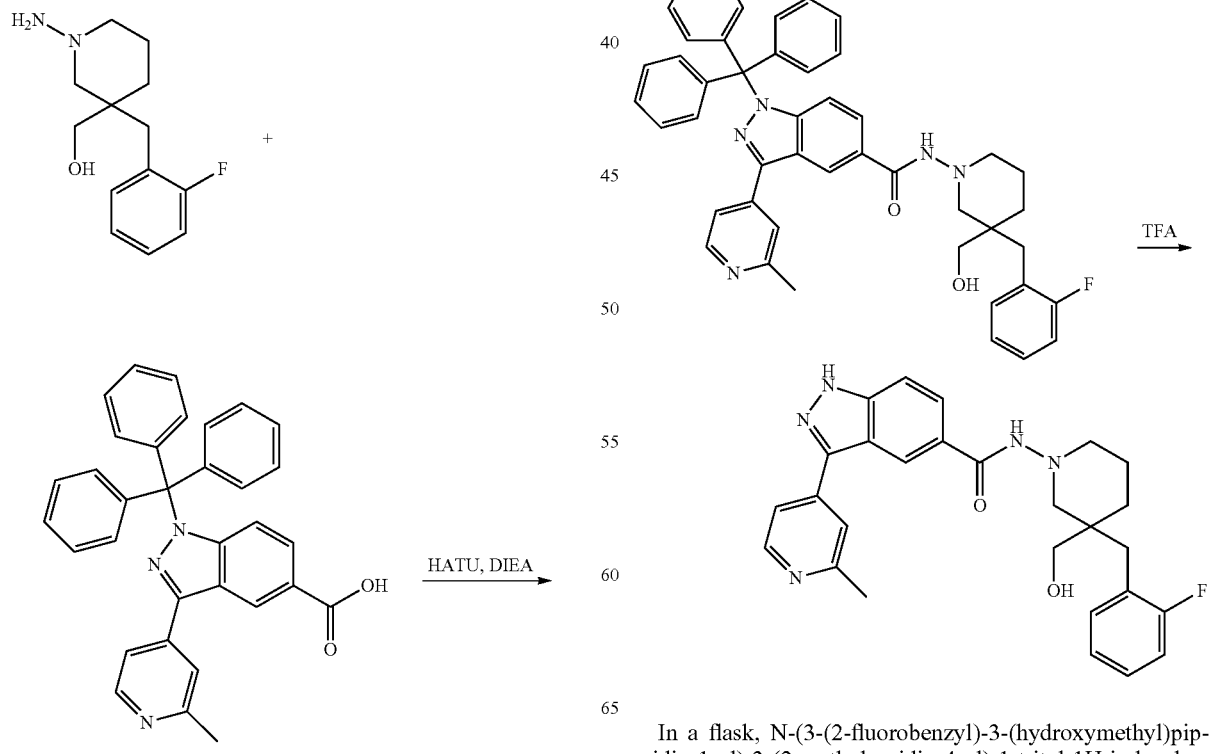

In a flask, N-(3-(2-fluorobenzyl)-3-(hydroxymethyl)piperidin-1-yl)-3-(2-methylpyridin-4-yl)-1-trityl-1H-indazole- 5-carboxamide (crude, from previous step) was reacted with trifluoroacetic acid (3 mL) for 1 hour. After reaction completion triethylsilane (0.1 mL) was added, and the reaction was stirred for an additional 15 minutes. The reaction was concentrated and rinsed with diethyl ether. The resulting remaining precipitate was dried and further purified using HPLC to give the titled compound. LC-MS: 474.22 [M+H]. LC/MS RT=2.18 min.

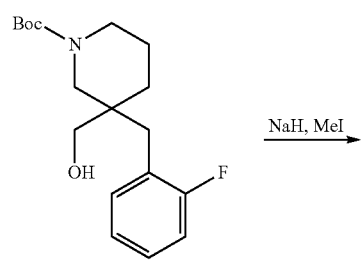

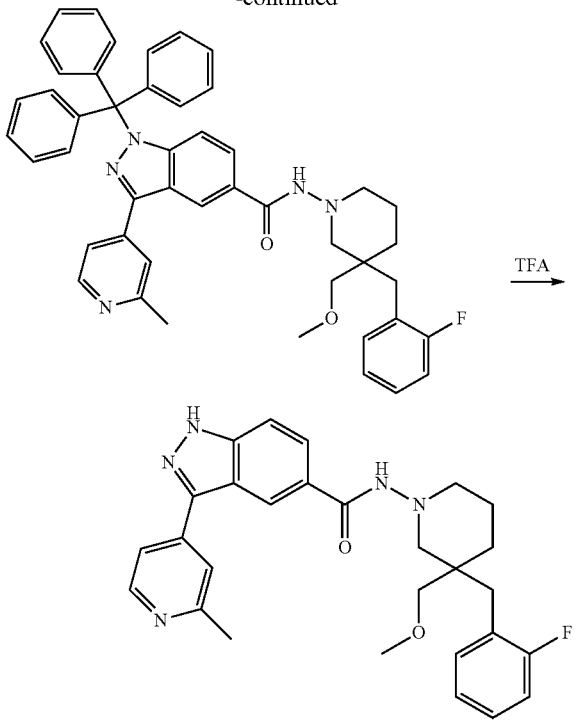

Preparation of tert-Butyl 3-(2-fluorobenzyl)-3-(methoxymethyl)piperidine-1-carboxylate

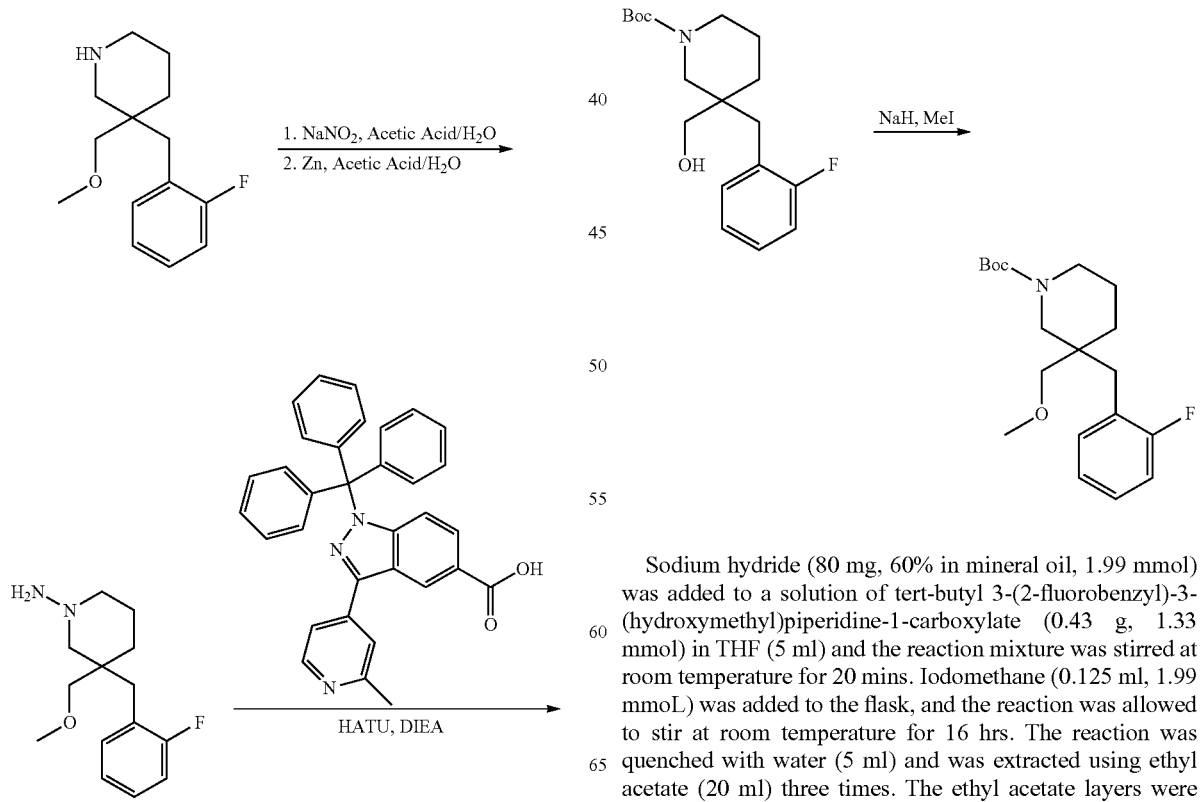

Sodium hydride (80 mg, 60% in mineral oil, 1.99 mmol) was added to a solution of tert-butyl 3-(2-fluorobenzyl)-3-(hydroxymethyl)piperidine-1-carboxylate (0.43 g, 1.33 mmol) in THF (5 ml) and the reaction mixture was stirred at room temperature for 20 mins. Iodomethane (0.125 ml, 1.99 mmoL) was added to the flask, and the reaction was allowed to stir at room temperature for 16 hrs. The reaction was quenched with water (5 ml) and was extracted using ethyl acetate (20 ml) three times. The ethyl acetate layers were combined, dried over sodium sulfate, filtered, and concentrated. The crude mixture was purified using flash chromatography (0-60% ethyl acetate in hexane) to give the titled compound (0.415 g).

Preparation of 3-(2-Fluorobenzyl)-3-(methoxymethyl)piperidine

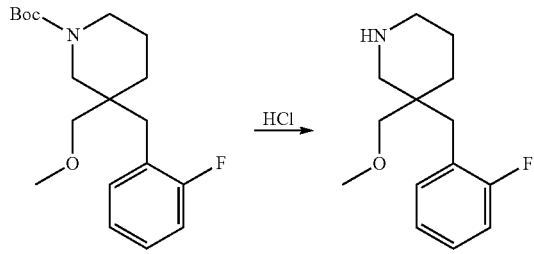 [SMILES: COCC1(Cc2ccccc2F)CCCN(C(=O)OC(C)(C)C)C1 ; Cl ; COCC1(Cc2ccccc2F)CCCNC1]

Hydrochloric acid in dioxane (1.5 mL, 4M) was added to a flask containing tert-butyl 3-(2-fluorobenzyl)-3-(methoxymethyl)piperidine-1-carboxylate (0.415 g, 1.23 mmol). 1,4-dioxane (1.5 mL) was added to the reaction mixture. The reaction was allowed to stir for 4 hours. Upon reaction completion, the reaction was concentrated, and 337 mg of crude product was recovered and progressed to the next step without further purification.

Preparation of 3-(2-Fluorobenzyl)-3-(methoxymethyl)piperidin-1-amine

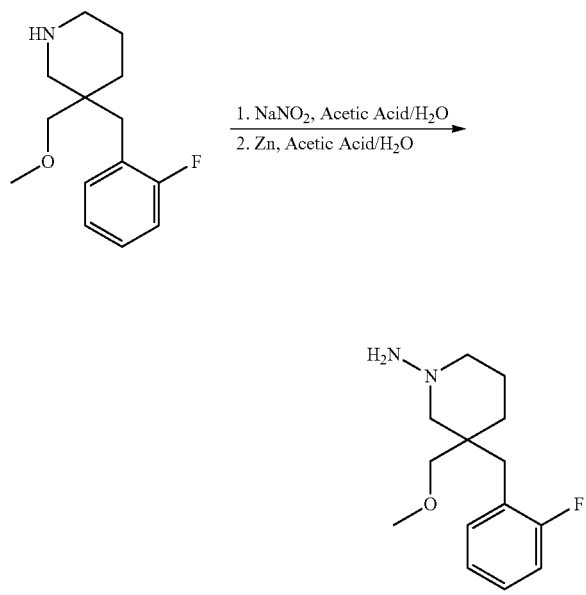

In an argon purged flask, 3-(2-fluorobenzyl)-3-(methoxymethyl)piperidine (337 mg, 1.23 mmol) was dissolved in water (0.8 mL) and acetic acid (2 mL). A solution of sodium nitrite (170 mg, 2.46 mmol) and water (1 mL) was drop wise added to the reaction flask. The reaction was stirred for an hour at room temperature. Water (5 mL) was added to the reaction mixture. The reaction mixture then was extracted 3 times with ethyl acetate (20 mL). The organic layers were combined, dried with sodium sulfate, and concentrated. The oil was dissolved in acetic acid (5 mL). The solution was drop-wise added to a suspension of Zn (321 mg, 4.92 mmol) in acetic acid (1 mL) and water (1 mL) solution. The reaction was stirred for 1.5 hour at room temperature. Upon completion, the reaction was filtered through celite. The Zn and salt was rinsed with 1N HCl in water. The filtrate was concentrated to yield crude hydrogen chloride salt of the amine. The crude product was progressed to the next step without further purification.

Preparation of N-(3-(2-Fluorobenzyl)-3-(methoxymethyl)piperidin-1-yl)-3-(2-methylpyridin-4-yl)-1-trityl-1H-indazole-5-carboxamide

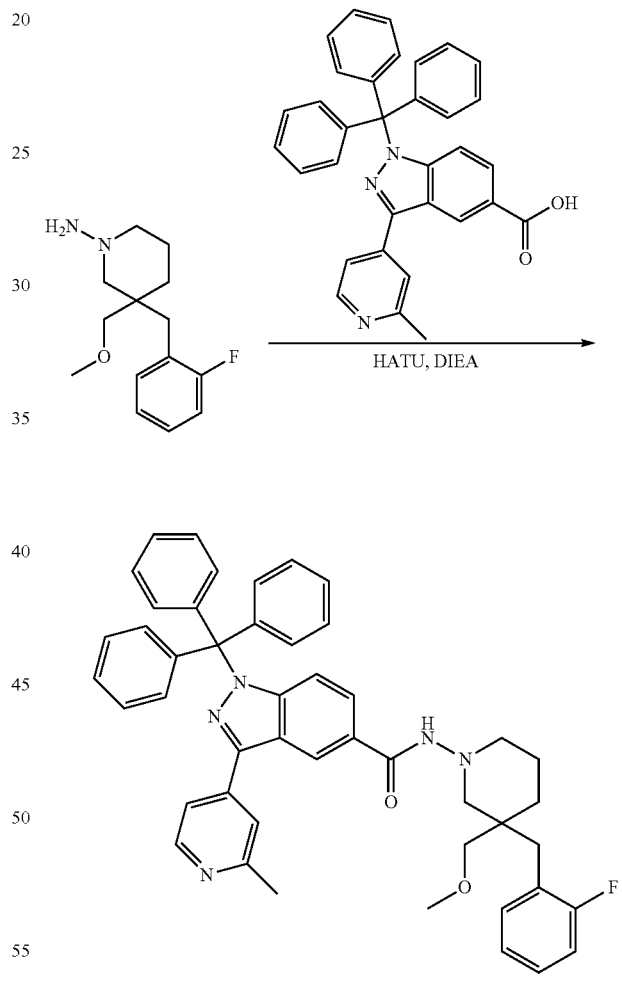

In a flask, 3-(2-methylpyridin-4-yl)-1-trityl-4H-indazole-5-carboxylic acid (271 mg, 0.546 mmol), HATU (256 mg, 0.67 mmol) and 3-(2-fluorobenzyl)-3-(methoxymethyl)piperidin-1-amine (122 mg, 0.42 mmol) was dissolved in dimethylformamide (2 mL). Diisopropylethylamine (0.366 mL, 2.1 mmol) was added to the reaction. The reaction was allowed to stir for an additional 1 h. Upon completion, the reaction was quenched with water (10 mL). The water layer was extracted with ethyl acetate (20 mL) three times. The organic fractions were combined, dried with sodium sulfate, and concentrated to yield the crude product. The crude product was progressed to the next step without further purification.

Preparation of N-(3-(2-Fluorobenzyl)-3-(methoxymethyl)piperidin-1-yl)-3-(2-methylpyridin-4-yl)-1H-indazole-5-carboxamide

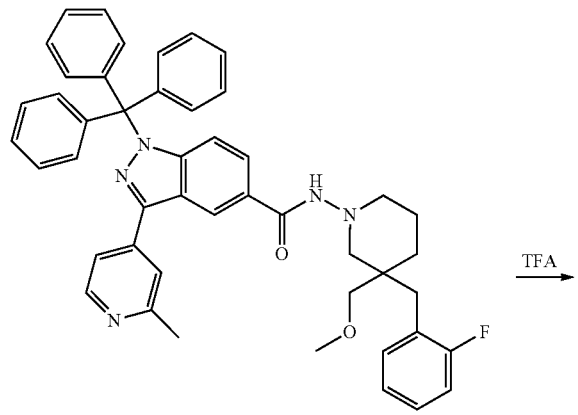

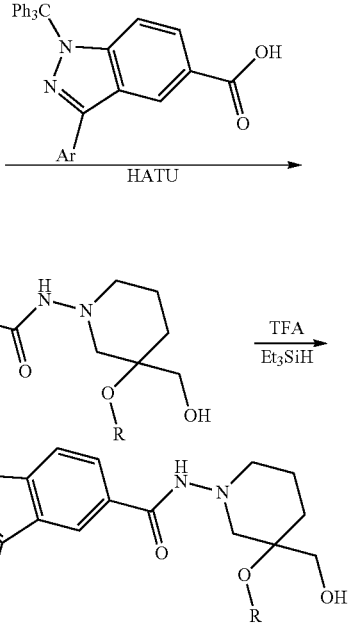

In a flask, N-(3-(2-fluorobenzyl)-3-(methoxymethyl)piperidin-1-yl)-3-(2-methylpyridin-4-yl)-1-trityl-1H-indazole-5-carboxamide (crude, from previous step) was reacted with trifluoroacetic acid (3 mL) for 1 hour. After reaction completion triethylsilane (0.1 mL) was added, and the reaction was stirred for an additional 15 minutes. The reaction was concentrated and rinsed with diethyl ether. The resulting remaining precipitate was dried and further purified using HPLC to give the titled compound. LC-MS: 488.24 [M+H]. LC/MS RT=2.49 min.

Preparation of (3-(2,5-difluorophenoxy)-1-nitrosopiperidin-3-yl)methanol

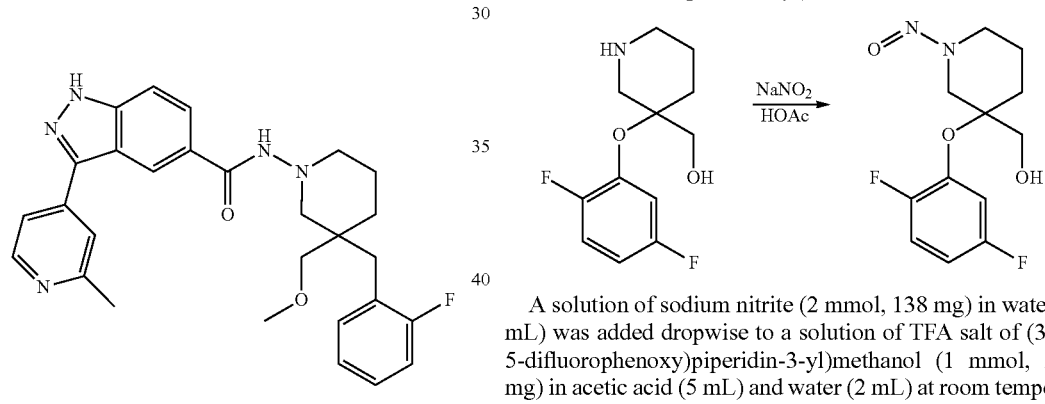

A solution of sodium nitrite (2 mmol, 138 mg) in water (3 mL) was added dropwise to a solution of TFA salt of (3-(2,5-difluorophenoxy)piperidin-3-yl)methanol (1 mmol, 243 mg) in acetic acid (5 mL) and water (2 mL) at room temperature. The reaction mixture was stirred at room temperature for 2 hour, and then heated to 60° C. and stirred for 4 hours. The reaction mixture was cooled to room temperature. Sodium hydroxide aqueous solution was added to adjust the pH of the solution slightly basic. The organics were extracted with EtOAc. The product, (3-(2,5-difluorophenoxy)-1-nitrosopiperidin-3-yl)methanol, was obtained after removal of the solvent.

Preparation of (1-amino-3-(2,5-difluorophenoxy)piperidin-3-yl)methanol

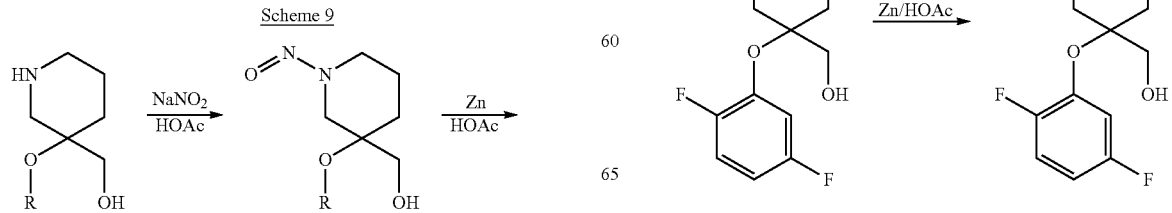

To the suspension of zinc dust (10 mmol, 0.65 g) in a mixture of acetic acid (5 mL) and water (5 mL) was added a solution of (3-(2,5-difluorophenoxy)-1-nitrosopiperidin-3-yl)methanol in acetic acid. The reaction mixture was stirred at room temperature for an hour. The mixture was filtered. The filtrate was basified with sodium hydroxide aqueous solution. The organics were extracted with EtOAc. The product, (1-amino-3-(2,5-difluorophenoxy)piperidin-3-yl)methanol, was obtained after removal of the solvent.

Preparation of N-(3-(2,5-difluorophenoxy)-3-(hydroxymethyl)piperidin-1-yl)-3-(2-methylpyridin-4-yl)-1-trityl-1H-indazole-5-carboxamide

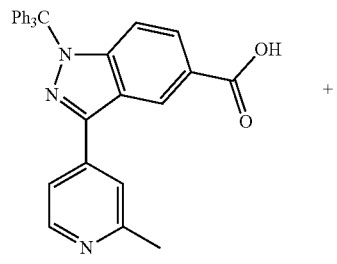

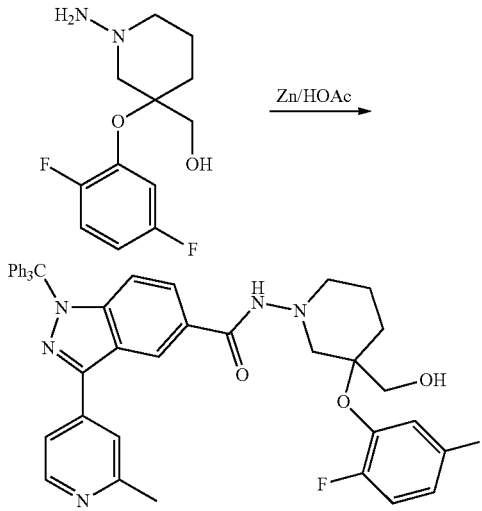

A reaction mixture of 3-(2-methylpyridin-4-yl)-1-trityl-1H-indazole-5-carboxylic acid (0.3 mmol, 150 mg), (1-amino-3-(2,5-difluorophenoxy)piperidin-3-yl)methanol (0.28 mmol, 81 mg), HATU (0.3 mmol, 115 mg) and DIEA in DMA was stirred at room temperature for overnight. The product, N-(3-(2,5-difluorophenoxy)-3-(hydroxymethyl)piperidin-1-yl)-3-(2-methylpyridin-4-yl)-1-trityl-1H-indazole-5-carboxamide, was obtained after rotary evaporation of solvent.

Preparation of N-(3-(2,5-difluorophenoxy)-3-(hydroxymethyl)piperidin-1-yl-3-(2-methylpyridin-4-yl)-1H-indazole-5-carboxamide

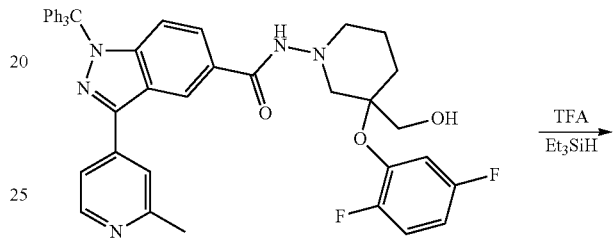

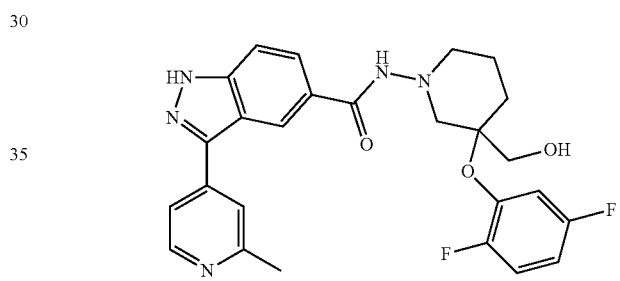

N-(3-(2,5-difluorophenoxy)-3-(hydroxymethyl)piperidin-1-yl)-3-(2-methylpyridin-4-yl)-1-trityl-1H-indazole-5-carboxamide was stirred in neat TFA at room temperature for 10 minutes, and then Et₃SiH (5 equiv.) was added. The reaction mixture was stirred at room temperature for 5 minutes, and then concentrated. The product was obtained by prep-HPLC. Following compounds were prepared using a similar synthetic route:

| Compd # | Structure | Chemical Names | aERK IC50 nM | M + 1 Cacld. | M + 1 Obs. | Rf min. |
|---|---|---|---|---|---|---|
| 140 | 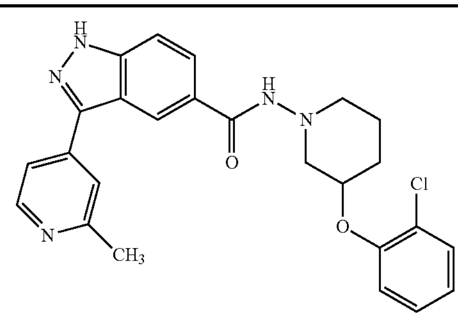 | N-[3-(2-chlorophenoxy)-1-piperidinyl]-3-(2-methyl-4-pyridinyl)-1H-indazole-5-carboxamide | 31.3 | 462.2 | 461.9 | 2.39 |

| Compd # | Structure | Chemical Names | aERK IC50 nM | M + 1 Cacld. | M + 1 Obs. | Rf min. |
|---|---|---|---|---|---|---|
| 141 | 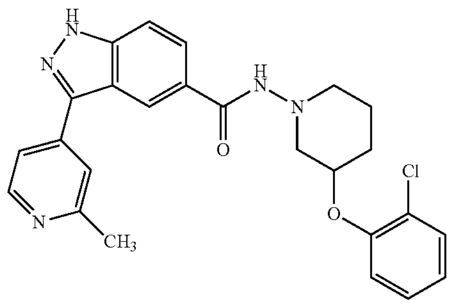 [SMILES: Cc1cc(-c2n[nH]c3ccc(C(=O)NN4CCCC(Oc5ccccc5Cl)C4)cc23)ccn1] | N-[3-(2-chlorophenoxy)-1-piperidinyl]-3-(2-methyl-4-pyridinyl)-1H-indazole-5-carboxamide | 84.4 | 462.2 | 461.9 | 2.38 |
| 142 | 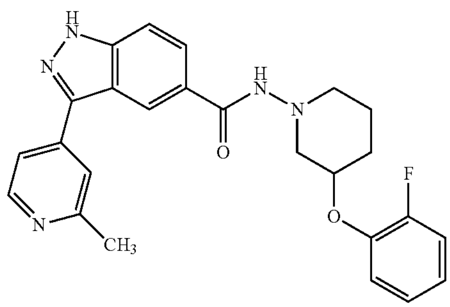 [SMILES: Cc1cc(-c2n[nH]c3ccc(C(=O)NN4CCCC(Oc5ccccc5F)C4)cc23)ccn1] | N-[3-(2-fluorophenoxy)-1-piperidinyl]-3-(2-methyl-4-pyridinyl)-1H-indazole-5-carboxamide | 152.9 | 446.2 | 445.9 | 2.2 |
| 143 | 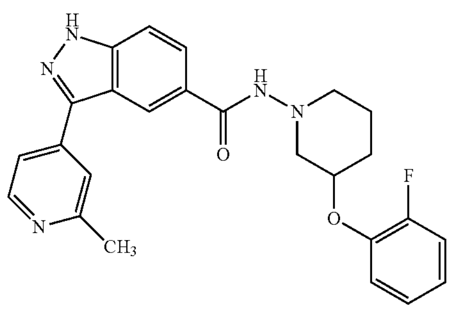 [SMILES: Cc1cc(-c2n[nH]c3ccc(C(=O)NN4CCCC(Oc5ccccc5F)C4)cc23)ccn1] | N-[3-(2-fluorophenoxy)-1-piperidinyl]-3-(2-methyl-4-pyridinyl)-1H-indazole-5-carboxamide | 26.8 | 446.2 | 445.9 | 2.21 |
| 144 | 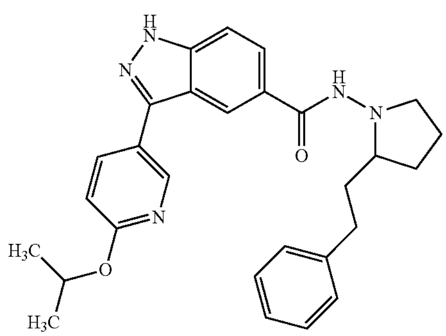 [SMILES: CC(C)Oc1ccc(-c2n[nH]c3ccc(C(=O)NN4CCCC4CCc4ccccc4)cc23)cn1] | 3-[6-(1-methylethoxy)-3-pyridinyl]-N-[2-(2-phenylethyl)-1-pyrrolidinyl]-1H-indazole-5-carboxamide | 496.7 | 470.2 | 470.0 | 3.11 |
| 145 | 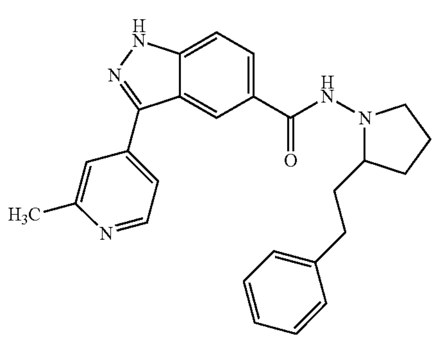 [SMILES: Cc1cc(-c2n[nH]c3ccc(C(=O)NN4CCCC4CCc4ccccc4)cc23)ccn1] | 3-(2-methyl-4-pyridinyl)-N-[2-(2-phenylethyl)-1-pyrrolidinyl]-1H-indazole-5-carboxamide | 28.7 | 426.2 | 426.0 | 2.01 |

-continued

| Compd # | Structure | Chemical Names | aERK IC50 nM | M + 1 Cacld. | M + 1 Obs. | Rf min. |
|---|---|---|---|---|---|---|
| 146 | 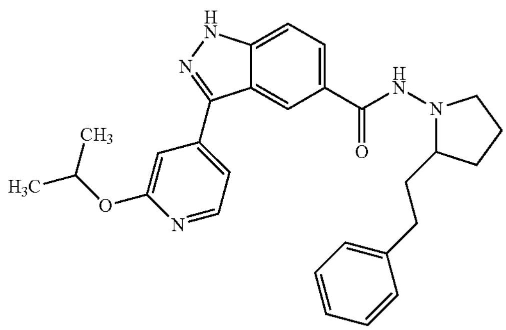 [SMILES: CC(C)Oc1cc(-c2n[nH]c3ccc(C(=O)NN4CCCC4CCc4ccccc4)cc23)ccn1] | 3-[2-(1-methylethoxy)-4-pyridinyl]-N-[2-(2-phenylethyl)-1-pyrrolidinyl]-1H-indazole-5-carboxamide | 1000.0 | 470.2 | 470.0 | 2.91 |
| 147 | 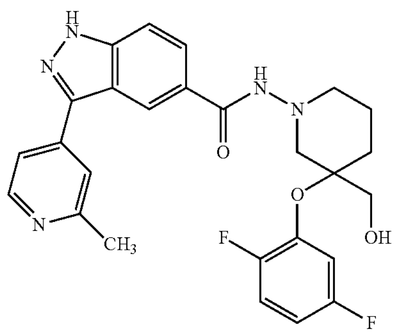 [SMILES: Cc1cc(-c2n[nH]c3ccc(C(=O)NN4CCCC(CO)(Oc5cc(F)ccc5F)C4)cc23)ccn1] | N-[3-(2,5-difluorophenoxy)-3-(hydroxymethyl)-1-piperidinyl]-3-(2-methyl-4-pyridinyl)-1H-indazole-5-carboxamide | 387.9 | 494.2 | 494.0 | 2.14 |
| 148 | 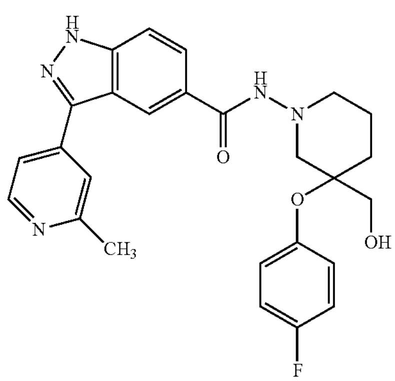 [SMILES: Cc1cc(-c2n[nH]c3ccc(C(=O)NN4CCCC(CO)(Oc5ccc(F)cc5)C4)cc23)ccn1] | N-[3-(4-fluorophenoxy)-3-(hydroxymethyl)-1-piperidinyl]-3-(2-methyl-4-pyridinyl)-1H-indazole-5-carboxamide | 444.8 | 476.2 | 475.9 | 2.01 |
| 149 | 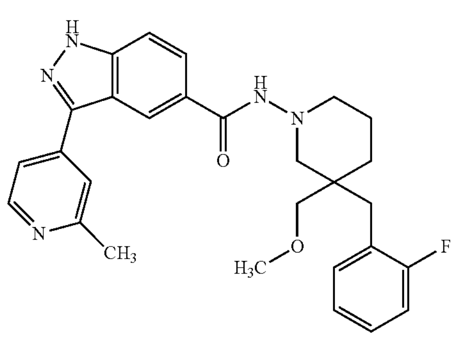 [SMILES: COCC1(Cc2ccccc2F)CCCN(NC(=O)c2ccc3[nH]nc(-c4ccnc(C)c4)c3c2)C1] | N-[3-[(2-fluorophenyl)methyl]-3-(methoxymethyl)-1-piperidinyl]-3-(2-methyl-4-pyridinyl)-1H-indazole-5-carboxamide | 937.2 | 488.2 | 488.2 | 2.48 |

-continued
| Compd # | Structure | Chemical Names | aERK IC50 nM | M + 1 Cacld. | M + 1 Obs. | Rf min. |
|---|---|---|---|---|---|---|
| 150 | 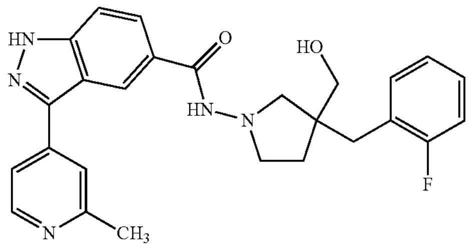 [SMILES: Cc1cc(-c2n[nH]c3ccc(C(=O)NN4CCC(CO)(Cc5ccccc5F)C4)cc23)ccn1] | N-[3-[(2-fluorophenyl)methyl]-3-(hydroxymethyl)-1-pyrrolidinyl]-3-(2-methyl-4-pyridinyl)-1H-indazole-5-carboxamide | 32.2 | 460.2 | 460.0 | 1.901 |
| 151 | 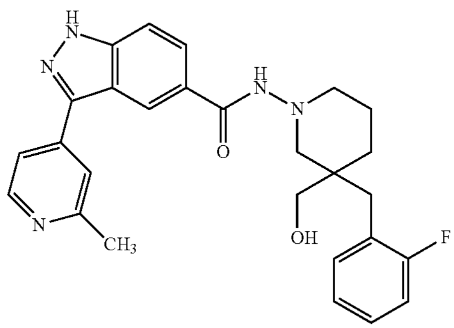 [SMILES: Cc1cc(-c2n[nH]c3ccc(C(=O)NN4CCCC(CO)(Cc5ccccc5F)C4)cc23)ccn1] | N-[3-[(2-fluorophenyl)methyl]-3-(hydroxymethyl)-1-piperidinyl]-3-(2-methyl-4-pyridinyl)-1H-indazole-5-carboxamide | 193.0 | 474.2 | 474.2 | 2.18 |
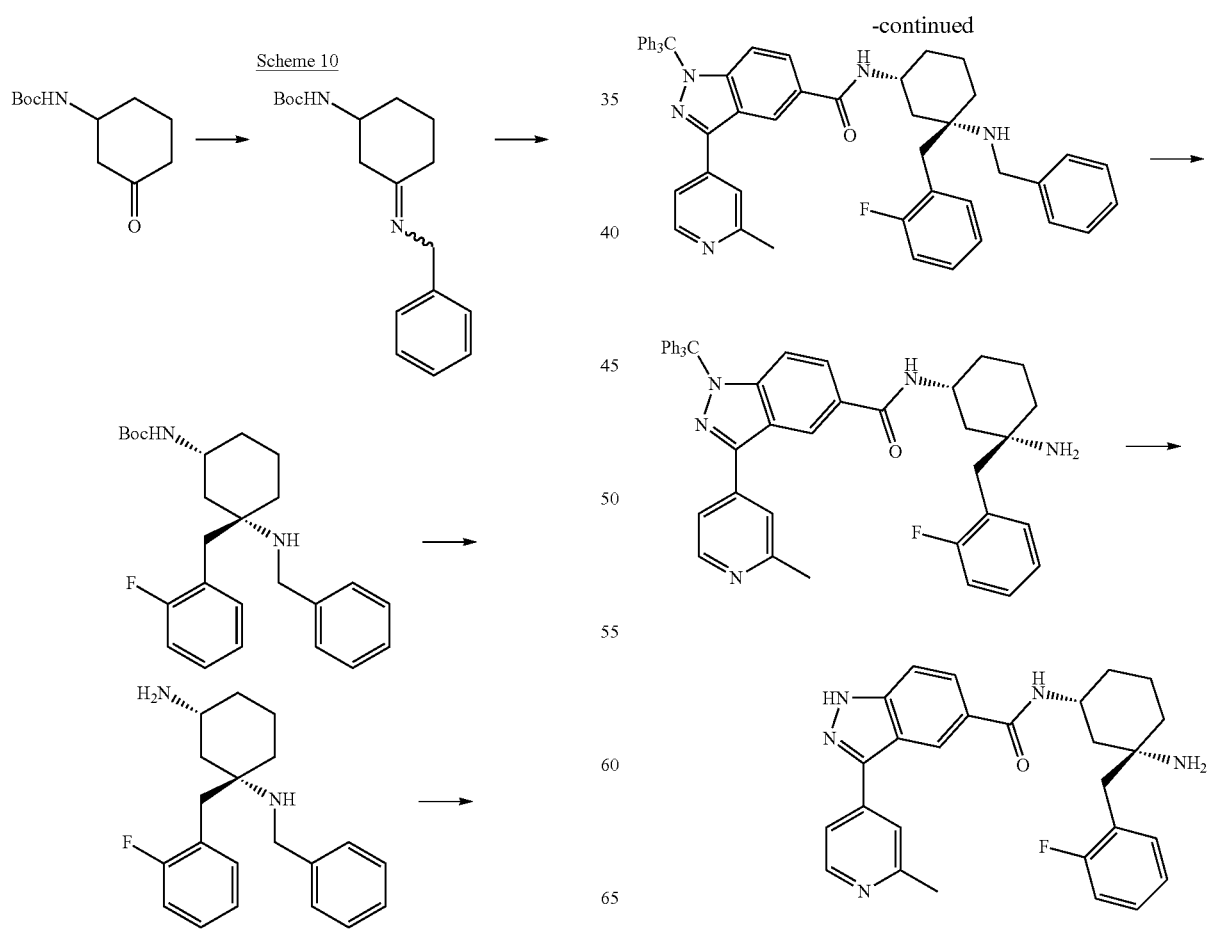
Scheme 10

Preparation of tert-butyl 3-(benzylimino)cyclohexylcarbamate

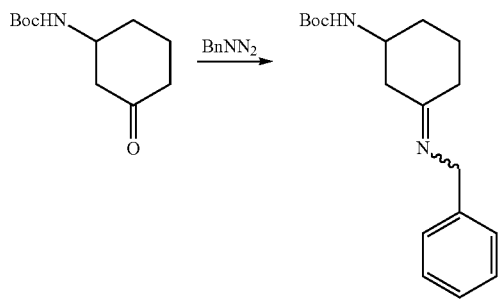 [SMILES: "BnNN2" ; CC(C)(C)OC(=O)NC1CCCC(=O)C1 ; CC(C)(C)OC(=O)NC1CCCC(=NCc2ccccc2)C1]

A reaction mixture of tert-butyl 3-oxocyclohexylcarbamate (4 mmol, 852 mg) and benzylamine (4 mmol, 436 μL) in refluxing toluene (25 mL) in a Dean-Stark apparatus was stirred for overnight. The product, tert-butyl 3-(benzylimino)cyclohexylcarbamate, was obtained after evaporation of solvent.

Preparation of tert-butyl 3-(benzylamino)-3-(2-fluorobenzyl)cyclohexylcarbamate

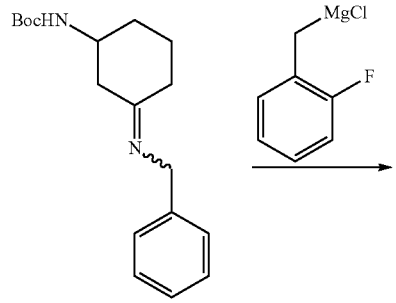

To the solution of tert-butyl 3-(benzylimino)cyclohexylcarbamate (4 mmol) in THF (10 mL) was added a solution of (2-fluorobenzyl)magnesium chloride in ether (9 mmol, 0.25 M, 36 mL) at 0° C. The reaction mixture was allowed to warm to room temperature and stirred for overnight. The reaction mixture was added to the iced water. The organics were extracted using EtOAc from the aqueous mixture. The EtOAc solution was concentrated. The product, tert-butyl 3-(benzylamino)-3-(2-fluorobenzyl)cyclohexylcarbamate, was purified by column chromatography on silica gel.

Preparation of HCl salt of $N^1$-benzyl-1-(2-fluorobenzyl)cyclohexane-1,3-diamine

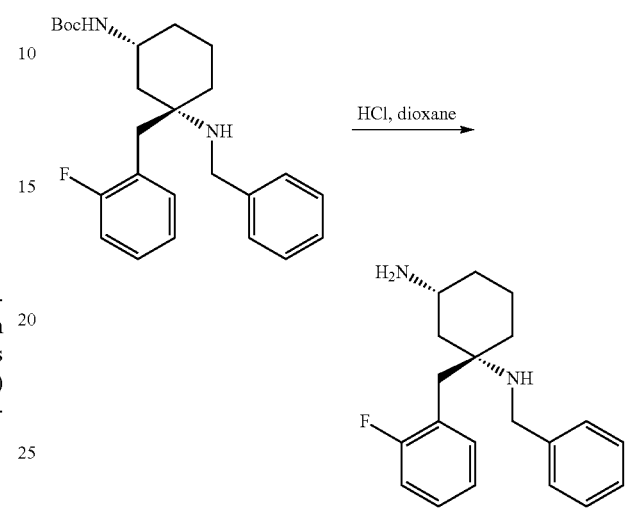

tert-butyl 3-(benzylamino)-3-(2-fluorobenzyl)cyclohexylcarbamate was stirred in a solution of HCl in dioxane (4 M) at room temperature for 5 hours. The product, HCl salt of $N^1$-benzyl-1-(2-fluorobenzyl)cyclohexane-1,3-diamine, was obtained after evaporation of solvent.

Preparation of N-(3-(benzylamino)-3-(2-fluorobenzyl)cyclohexyl)-3-(2-methylpyridin-4-yl)-1-trityl-1H-indazole-5-carboxamide

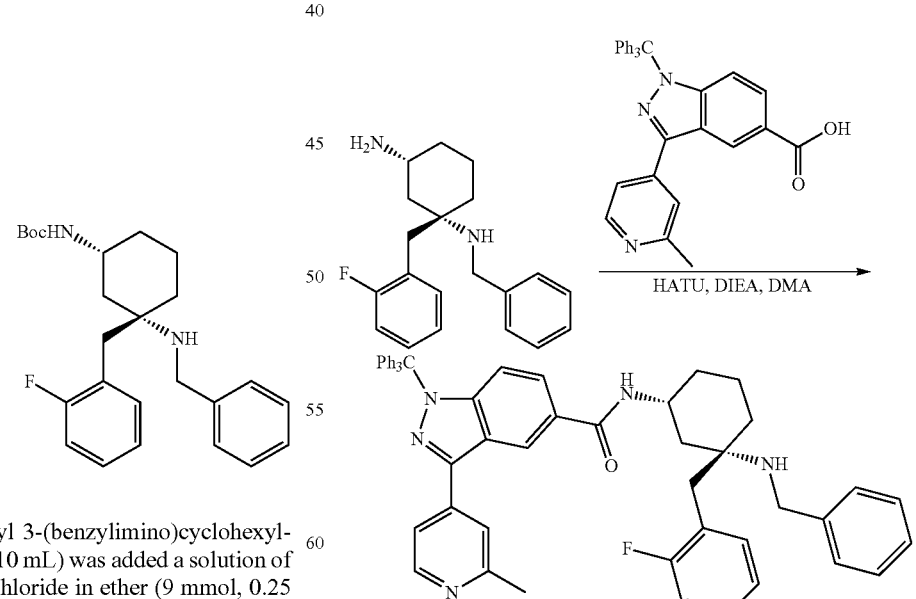

A reaction mixture of 3-(2-methylpyridin-4-yl)-1-trityl-1H-indazole-5-carboxylic acid (0.15 mmol, 75 mg), HCl salt of $N^1$-benzyl-1-(2-fluorobenzyl)cyclohexane-1,3-diamine (0.15 mmol, 52 mg), HATU (0.15 mmol, 57 mg) and DIEA (0.1 mL) in DMA (0.5 mL) was stirred at room temperature for overnight. The product, N-(3-(benzylamino)-3-(2-fluorobenzyl)cyclohexyl)-3-(2-methylpyridin-4-yl)-1-trityl-1H-indazole-5-carboxamide, was purified by column chromatography on silica gel.

Preparation of N-(3-amino-3-(2-fluorobenzyl)cyclohexyl)-3-(2-methylpyridin-4-yl)-1-trityl-1H-indazole-5-carboxamide

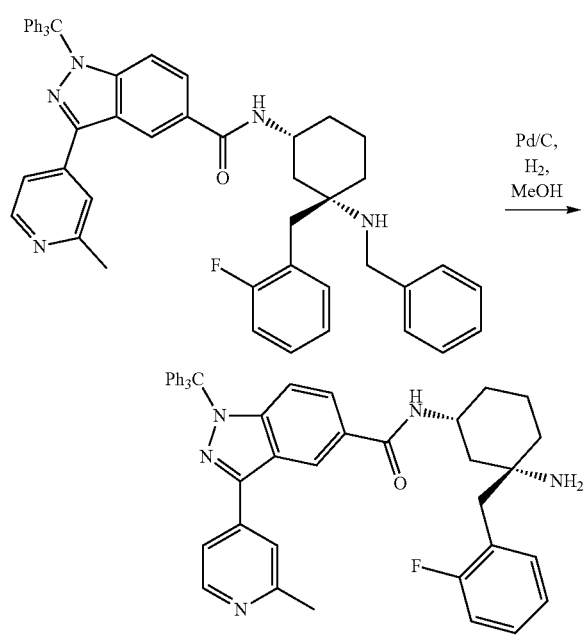

To a solution of N-(3-(benzylamino)-3-(2-fluorobenzyl)cyclohexyl)-3-(2-methylpyridin-4-yl)-1-trityl-1H-indazole-5-carboxamide in MeOH was added palladium on charcoal (10%). The reaction mixture was stirred under an atmosphere of H₂ at room temperature for overnight. The product, N-(3-amino-3-(2-fluorobenzyl)cyclohexyl)-3-(2-methylpyridin-4-yl)-1-trityl-1H-indazole-5-carboxamide, was obtained after evaporation of solvent.

Preparation of N-(3-amino-3-(2-fluorobenzyl)cyclohexyl)-3-(2-methylpyridiN-4-yl)-1H-indazole-5-carboxamide

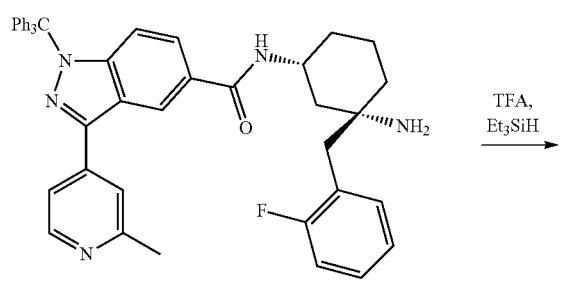

-continued

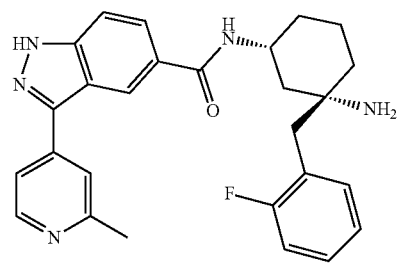

N-(3-amino-3-(2-fluorobenzyl)cyclohexyl)-3-(2-methylpyridin-4-yl)-1-trityl-1H-indazole-5-carboxamide was stirred in neat TFA at room temperature for 10 minutes, and then Et₃SiH (5 equiv.) was added. The reaction mixture was stirred at room temperature for 5 minutes, and then concentrated. The product was obtained and purified by reverse phase HPLC.

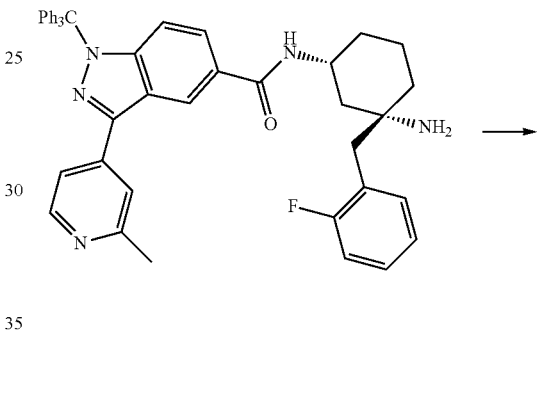

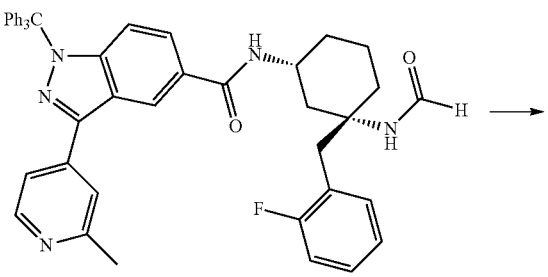

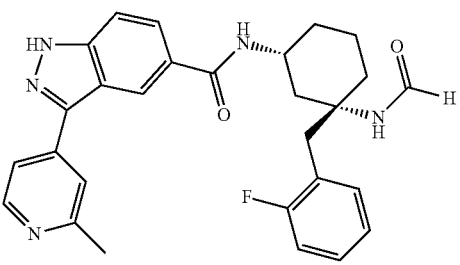

167

Preparation of N-(3-(2-fluorobenzyl)-3-formamidocyclohexyl)-3-(2-methylpyridin-4-yl)-1-trityl-1H-indazole-5-carboxamide

168

Preparation of N-(3-(2-fluorobenzyl)-3-formamidocyclohexyl)-3-(2-methylpyridin-4-yl)-1H-indazole-5-carboxamide

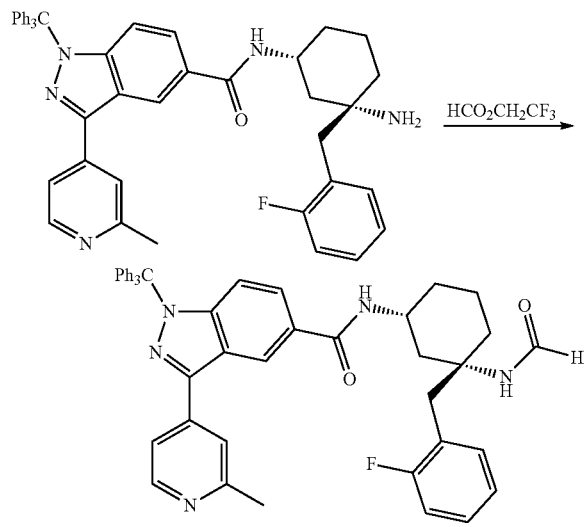
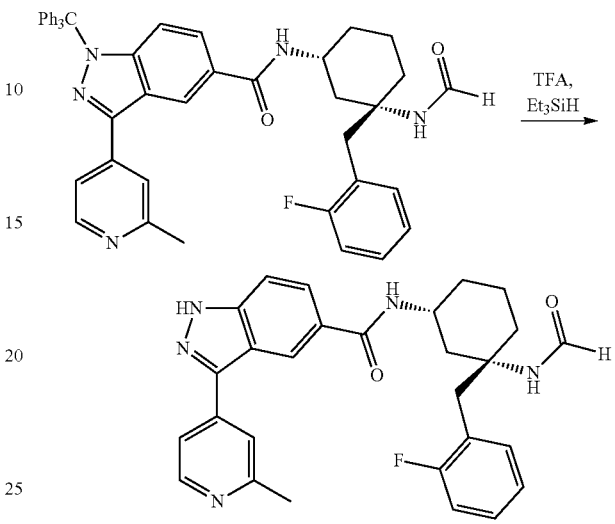

A reaction mixture of N-(3-amino-3-(2-fluorobenzyl)cyclohexyl)-3-(2-methylpyridin-4-yl)-1-trityl-1H-indazole-5-carboxamide (0.01 mmol, 7 mg), 2,2,2-trifluoroethyl formate (0.06 mmol, 6 μL) and DIEA (10 equiv.) in THF was stirred at room temperature for overnight. The product, N-(3-(2-fluorobenzyl)-3-formamidocyclohexyl)-3-(2-methylpyridin-4-yl)-1-trityl-1H-indazole-5-carboxamide, was obtained after evaporation of solvent.

N-(3-(2-fluorobenzyl)-3-formamidocyclohexyl)-3-(2-methylpyridin-4-yl)-1-trityl-1H-indazole-5-carboxamide was stirred in neat TFA at room temperature for 10 minutes, and then Et$_3$SiH (5 equiv.) was added. The reaction mixture was stirred at room temperature for 5 minutes, and then concentrated. The product was obtained and purified by reverse phase HPLC.

| Compd # | Structure | Chemical Names | aERK IC50 nM | M + 1 Cacld. | M + 1 Obs. | Rf min. |
|---|---|---|---|---|---|---|
| 152 | 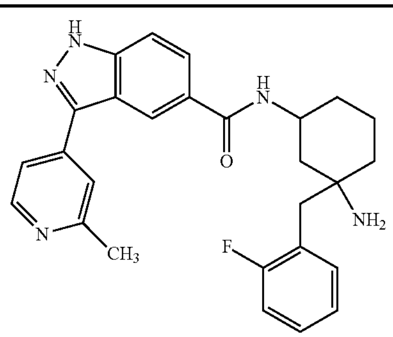 | N-[3-amino-3-[(2-fluorophenyl)methyl]cyclohexyl]-3-(2-methyl-4-pyridinyl)-1H-indazole-5-carboxamide | 514.2 | 458.2 | 458.0 | 1.62 |
| 153 | 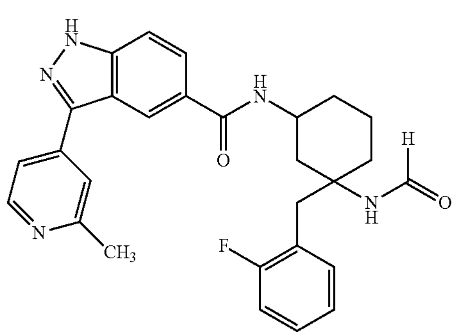 [SMILES: Cc1cc(-c2n[nH]c3ccc(C(=O)NC4CCCC(Cc5ccccc5F)(NC=O)C4)cc23)ccn1] | N-[3-[(2-fluorophenyl)methyl]-3-(formylamino)cyclohexyl]-3-(2-methyl-4-pyridinyl)-1H-indazole-5-carboxamide | 161.5 | 486.2 | 486.0 | 2.16 |

Assays:

TdF Assay for ERK

The SAR (Structure Activity Relationship) for ERK ligands covered by this invention was interrogated using the TdF (Temperature Dependence Fluorescence) assay or best known as thermal shift assay [1]. The TdF assay was mainly conducted in the 96-well based CHROMO-4 real time fluorescence plate reader (BioRad). The Sypro Orange (Sigma-Aldrich), environmentally sensitive fluorescence dye, was used to monitor the protein folding-unfolding transition. Protein-ligand binding was gauged by the change (or shift) in the unfolding transition temperature ($\Delta T_m$) acquired at protein alone with respect to protein in the presence of ligand of interest.

Compound of interest was first prepared in DMSO stock (typical concentration: 10 mM). Sample of 20 µL was then added into the 96-well PCR plate, where it consisted of 3 µM ERK protein and 15, 50 or 100 µM compound (depending on compound's solubility) in buffer (25 mM HEPES, 150 mM NaCl, pH-7.5 and 1 mM DTT) incorporated with Sypro Orange dye (5× final concentration). Final percentage of DMSO resided in the sample was 2%. The sample plate was heated from 30° C. to 90° C. with thermal ramping rate of 1° C./min. The fluorescence signals were acquired with excitation and emission wavelengths centered at 490 and 560 nm respectively. The instrument thermal stability was ±0.2° C. The melting temperatures ($T_m$) for ERK protein under aforementioned conditions occurred at 61.0±0.2° C. and 64.8±0.2° C. respectively.

Theoretical Basis for TdF-Based Ligand Binding Affinity Constant

The derivation of TdF-based ligand binding affinity constant ($K_d$) followed closely those previously formulated by Brandts and Lin [2]. In brief, the binding constant of the ligand at the $T_m$ is expressed as below:

$$K_L(T_m) = \frac{\{\exp\{-(\Delta H_u(T_0)/R)(1/T_m - 1/T_0) + (\Delta Cp_u/R)[\ln(T_m/T_0) + (T_0/T_m) - 1]\} - 1\}}{[L_{Tm}]}$$

where $T_0$ is the midpoint of unfolding for unliganded protein and $T_m$ is the midpoint of unfolding in presence of ligand. $[L_{Tm}]$ is free ligand at $T_m$. The $\Delta H_u$ and $\Delta Cp_u$ are the enthalpy of unfolding and heat capacity change of unfolding for the protein respectively. Following algorithm derived by Winsor and coworker [3], the $T_0$, $\Delta H_u$ and $\Delta Cp_u$ can be determined separately from nonlinear regression fitting the protein alone melting curve:

$$F(T) = \frac{(Y_n + m_n(T)) + (Y_u + m_u(T))\exp\left\{-\left(\frac{\Delta H_u}{RT}\right)\left(1 - \frac{T}{T_0}\right) + \left(\frac{\Delta Cp_u}{RT}\right)\left(T\ln\left(\frac{T}{T_0}\right) + T_0 - T\right)\right\}}{1 + \exp\left\{-\left(\frac{\Delta H_u}{RT}\right)\left(1 - \frac{T}{T_0}\right) + \left(\frac{\Delta Cp_u}{RT}\right)\left(T\ln\left(\frac{T}{T_0}\right) + T_0 - T\right)\right\}}$$

Where F(T) is the observed fluorescence intensity at any temperature T, $Y_n$ and $Y_u$ are the predicted fluorescence intensities for fully folded and unfolded protein, respectively; $m_n$ and $m_u$ are slope correction for changes in $Y_n$ and $Y_u$ with respect to changes in temperature (analogously replace $T_0$ with $T_m$ in the above equation for liganded protein to yield $T_m$).

Finally, the ligand binding affinity constant at any temperature T (i.e. 25° C.) can be thermodynamically connected to the preceding $K_L(T_m)$ via [2,3]

$$K_L(T) = K_L(T_m)\exp\left\{\left(\frac{-\Delta H_L(T)}{R}\right)\left(\frac{1}{T} - \frac{1}{T_m}\right) + \left(\frac{\Delta Cp_L}{R}\right)\left[\ln\frac{T}{T_m} + 1 - \frac{T}{T_m}\right]\right\}$$

where $\Delta H_L(T)$ is the van't Hoff enthalpy of ligand binding at temperature T and $\Delta Cp_L$ is the heat capacity upon ligand binding. For simplicity, the $\Delta Cp_L$ and $\Delta H_L(T)$ were set to zero and −7 kcal/mol respectively. The uncertainty in the calculated ligand binding affinity constant was estimated to be ±50%.

REFERENCES

1. M. W. Pantoliano, E. C. Petrella, T. D. Kwasnoski, V. S. Lobanov, J. Myslik, E. Graf, T. Carver, E. Asel, B. A. Springer, P. Lane, F. R. Salemme, High-density miniaturized thermal shift assays as ageneral strategy for drug discovery, *J. Biomol. Screen* 6 (2001) 429-440
2. J. F. Brandts, L.-N. Lin, Study of strong to ultratight protein interactions using differential scanning calorimetry, *Biochemistry* 29 (1990) 6927-6940
3. Mayhood, T. W., Windsor, W. T., Ligand binding affinity determined by temperature-dependent circular dichroism: Cyclin-dependent kinase 2 inhibitors, *Analytical Biochemistry* 345 (2005) 187-197

Coupled ERK2 (cERK) Assay:

Activity of compounds against inactive ERK2 was tested in a coupled MEK1/ERK2 IMAP assay as follows: Compounds were diluted to 25× final test concentration in 100% DMSO. 14 µl of kinase buffer (10 mM Tris.HCl pH 7.2, 10 mM MgCl2, 0.01% Tween-20, 1 mM DTT) containing 0.4 ng unphosphorylated Mouse ERK2 protein was added to each well of a black 384-well assay plate. 1 µl of 25× compound was added to each well and incubated at room temperature for 30 minutes to allow an opportunity for the compound to bind to the inactive enzyme. DMSO concentration during initial incubation is 6.7%. ERK2 activity was determined to be insensitive to DMSO concentrations up to 20%. ERK2 was then activated and it's kinase activity measured by the addition of 10 µl kinase buffer with the following components (final concentration per reaction): 2 ng active (phosphorylated) human MEK1 protein and 4 µM (total) ERK2 IMAP substrate peptides (3.9 µM unlabeled IPTTPITTTYFFFK-CONH2 and 100 nM IPTTPITTTYFFFK(5-carboxyfluorescein)-CONH2) and 30 µM ATP. DMSO concentration during ERK activation was 4%. After one hour, reactions were terminated by addition of 60 µl IMAP detections beads in binding buffer (Molecular Devices). Binding was allowed to equilibrate for 30 minutes before reading the plate on an LJL Analyst Fluorescence Polarization plate reader. Compound inhibition was calculated relative to DMSO and fully inhibited standards. Active compounds were reconfirmed in an independent assay.

Active ERK2 (aERK) Assay:

Activated ERK2 activity was also determined in the IMAP assay format using the procedure outlined above. 1 µl of 25× compound was added to 14 µl of kinase buffer containing 0.25 ng fully phosphorylated, active Mouse ERK2 protein. Following a 30 minute incubation, the reactions were initiated by addition of 10 µl of kinase buffer containing 1 µM ERK2 IMAP substrate peptide (0.9 µM unlabeled IPTTPITTTY-FFFK-CONH2 and 100 nM IPTTPITTTYFFFK(5-carboxyfluorescein)-CONH2) and 30 µM ATP. Reactions proceeded for 30 minutes before termination by addition of 60 µl IMAP detection beads in binding buffer. Plates were read as above after 30 minute binding equilibration. Active compounds were reconfirmed in an independent assay.

Values for Kd TdF (nM), cERK IC50 (nM) and aERK IC50 (nM) for individual compounds have been set forth above in above Tables. In one embodiment, the compounds of the present invention have aERK 1050 values of from about 0.05 nM to 1 µM; and in a preferred embodiment, less than 100 nM (<100 nM); and in a more preferred embodiment less than 10 nM (<10 nM).

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

Each and every reference publication referred to hereinabove is incorporated herein by reference in its entirety for all purposes.

What is claimed is:
1. The compound selected from the group consisting of:
N-[3-[(2-fluorophenyl)methyl]-3-hydroxycyclohexyl]-3-(2-methyl-4-pyridinyl)-1H-indazole-5-carboxamide;
N-[3-(hydroxymethyl)-3-phenoxycyclohexyl]-3-(2-methyl-4-pyridinyl)-1H-indazole-5-carboxamide;
N-[3-amino-3-[(2-fluorophenyl)methyl]cyclohexyl]-3-(2-methyl-4-pyridinyl)-1H-indazole-5-carboxamide;
N-[3-[(2-fluorophenyl)methyl]-3-hydroxycyclohexyl]-3-(2-methyl-4-pyridinyl)-1H-indazole-5-carboxamide;
N-[3-(2-fluorophenoxy)cyclohexyl]-3-(2-methyl-4-pyridinyl)-1H-indazole-5-carboxamide;
N-[3-(2-fluorophenoxy)cyclohexyl]-3-(2-methyl-4-pyridinyl)-1H-indazole-5-carboxamide;
N-[3-(1H-imidazol-1-ylmethyl)cyclohexyl]-3-(2-methyl-2H-indazol-)-1H-indazole-5-carboxamide;
N-[3-(2-chlorophenoxy)cyclohexyl]-3-(2-methyl-4-pyridinyl)-1H-indazole-5-carboxamide;
N-[3-(2,6-dimethylphenoxy)cyclohexyl]-3-(2-methyl-4-pyridinyl)-1H-indazole-5-carboxamide;
N-[3-(2,6-difluorophenoxy)cyclohexyl]-3-(2-methyl-4-pyridinyl)-1H-indazole-5-carboxamide;
N-[3-(aminocarbonyl)-3-(3-fluorophenoxy)cyclohexyl]-3-(2-methyl-4-pyridinyl)-1H-indazole-5-carboxamide;
N-[cis-3-hydroxy-3-(1H-imidazol-1-ylmethyl)cyclohexyl]-3-(2-methyl-2H-indazol-)-1H-indazole-5-carboxamide;
N-[trans-3-hydroxy-3-(1H-imidazol-1-ylmethyl)cyclohexyl]-3-(2-methyl-2H-indazol-)-1H-indazole-5-carboxamide;
N-[3-[(2-fluorophenyl)methyl]-3-(formylamino)cyclohexyl]-3-(2-methyl-4-pyridinyl)-1H-indazole-5-carboxamide;
N-[3-[(2-fluorophenyl)methyl]-3-methoxycyclohexyl]-3-(2-methyl-4-pyridinyl)-1H-indazole-5-carboxamide;
N-[3-[(2-fluorophenyl)methyl]-3-methoxycyclohexyl]-3-(2-methyl-4-pyridinyl)-1H-indazole-5-carboxamide;
N-[3-(2-fluorophenoxy)cyclohexyl]-3-(2-methyl-4-pyridinyl)-1H-indazole-5-carboxamide;
N-[3-(3-fluorophenoxy)-3-(hydroxymethyl)cyclohexyl]-3-(2-methyl-4-pyridinyl)-1H-indazole-5-carboxamide;
N-[3-(1H-benzimidazol-1-ylmethyl)cyclohexyl]-3-(2-methyl-2H-indazol-)-1H-indazole-5-carboxamide;
N-[trans-3-hydroxy-3-(1H-pyrazol-1-ylmethyl)cyclohexyl]-3-(2-methyl-2H-indazol-)-1H-indazole-5-carboxamide;
N-[cis-3-hydroxy-3-(1H-pyrazol-1-ylmethyl)cyclohexyl]-3-(2-methyl-2H-indazol-)-1H-indazole-5-carboxamide;
N-[trans-3-(1H-benzimidazol-1-ylmethyl)-3-hydroxycyclohexyl]-3-(2-methyl-2H-indazol-)-1H-indazole-5-carboxamide;
N-[cis-3-(1H-benzimidazol-1-ylmethyl)-3-hydroxycyclohexyl]-3-(2-methyl-2H-indazol-5-yl)-1H-indazole-5-carboxamide;
N-[3-(difluorophenylmethyl)-3-hydroxycyclohexyl]-3-(2-methyl-4-pyridinyl)-1H-indazole-5-carboxamide;
N-[3-hydroxy-3-(hydroxyphenylmethyl)cyclohexyl]-3-(2-methyl-4-pyridinyl)-1H-indazole-5-carboxamide;
3-imidazo[1,2-a]pyridin-6-yl-N-[3-(1H-pyrazol-1-ylmethyl)cyclohexyl]-1H-indazole-5-carboxamide;
N-(3-benzoyl-3-hydroxycyclohexyl)-3-(2-methyl-4-pyridinyl)-1H-indazole-5-carboxamide;
N-[3-[(2,6-difluorophenyl)methyl]-3-hydroxycyclohexyl]-3-(2-methyl-4-pyridinyl)-1H-indazole-5-carboxamide;
N-[trans-3-hydroxy-3-(1H-1,2,4-triazol-1-ylmethyl)cyclohexyl]-3-(2-methyl-4-pyridinyl)-1H-indazole-5-carboxamide;
N-[cis-3-hydroxy-3-(1H-1,2,4-triazol-1-ylmethyl)cyclohexyl]-3-(2-methyl-4-pyridinyl)-1H-indazole-5-carboxamide;
3-imidazo[1,2-a]pyridin-6-yl-N-[3-(1H-1,2,4-triazol-1-ylmethyl)cyclohexyl]-1H-indazole-5-carboxamide;
Ethyl-1-[(2-fluorophenyl)methyl]-3-[[[3-(2-methyl-4-pyridinyl)-1H-indazol-5-yl]carbonyl]amino]cyclohexanecarboxylate;
N-[3-[(2-fluorophenyl)methyl]-3-(hydroxymethyl)cyclohexyl]-3-(2-methyl-4-pyridinyl)-1H-indazole-5-carboxamide;
N-[3-(2-chlorophenoxy)cyclohexyl]-3-(2-methyl-4-pyridinyl)-1H-indazole-5-carboxamide;
N-[3 (R)-hydroxy-3-(1H-indazol-1-ylmethyl)-1(R)-cyclohexyl]-3-(2-methyl-4-pyridinyl)-1H-indazole-5-carboxamide;
N-[3 (S)-hydroxy-3-(1H-indazol-1-ylmethyl)-1(R)-cyclohexyl]-3-(2-methyl-4-pyridinyl)-1H-indazole-5-carboxamide;
N-[trans-3-[(2-fluorophenyl)methyl]-3-hydroxycyclohexyl]-3-imidazo[1,2-a]pyridin-6-yl-1H-indazole-5-carboxamide;
3-(6-benzothiazolyl)-N-[3-[(2-fluorophenyl)methyl]-3-hydroxycyclohexyl]-1H-indazole-5-carboxamide;
1-[(2-fluorophenyl)methyl]-3-[[[3-(2-methyl-4-pyridinyl)-1H-indazol-5-yl]carbonyl]amino]cyclohexanecarboxylic acid;
3-(6-benzothiazolyl)-N-[3-[(2-fluorophenyl)methyl]-3-hydroxycyclohexyl]-1H-indazole-5-carboxamide;
N-[3-[(2-methyl-1H-benzimidazol-1-yl)methyl]cyclohexyl]-3-(2-methyl-6-benzothiazolyl)-1H-indazole-5-carboxamide;
N-[3-[(3-cyano-1H-indol-1-yl)methyl]cyclohexyl]-3-(2-methyl-6-benzothiazolyl)-1H-indazole-5-carboxamide;
N-[trans-3-hydroxy-3-[[2-(trifluoromethyl)-1H-benzimidazol-1-yl]methyl]cyclohexyl]-3-(2-methyl-4-pyridinyl)-1H-indazole-5-carboxamide;
N-[cis-3-hydroxy-3-[[2-(trifluoromethyl)-1H-benzimidazol-1-yl]methyl]cyclohexyl]-3-(2-methyl-4-pyridinyl)-1H-indazole-5-carboxamide;
N-[3-(difluorophenylmethyl)-3-hydroxycyclohexyl]-3-(2-methyl-4-pyridinyl)-1H-indazole-5-carboxamide;

N-[trans-3-hydroxy-3-[(2-methyl-1H-benzimidazol-1-yl)methyl]cyclohexyl]-3-(2-methyl-4-pyridinyl)-H-indazole-5-carboxamide;

N-[cis-3-hydroxy-3-[(2-methyl-1H-benzimidazol-1-yl)methyl]cyclohexyl]-3-(2-methyl-4-pyridinyl)-H-indazole-5-carboxamide;

N-[trans-3-hydroxy-3-(1H-imidazo[4,5-b]pyridin-1-ylmethyl)cyclohexyl]-3-(2-methyl-4-pyridinyl)-1H-indazole-5-carboxamide;

N-[trans-3-hydroxy-3-(3H-imidazo[4,5-b]pyridin-3-ylmethyl)cyclohexyl]-3-(2-methyl-4-pyridinyl)-1H-indazole-5-carboxamide;

N-[3-(2-chlorophenoxy)-1-piperidinyl]-3-(2-methyl-4-pyridinyl)-1H-indazole-5-carboxamide;

N-[3-hydroxy-3-(hydroxyphenylmethyl)cyclohexyl]-3-(2-methyl-4-pyridinyl)-1H-indazole-5-carboxamide;

N-[3-hydroxy-3-(hydroxyphenylmethyl)cyclohexyl]-3-(2-methyl-4-pyridinyl)-1H-indazole-5-carboxamide;

N-[3-(hydroxymethyl)-3-(phenylmethyl)cyclohexyl]-3-(2-methyl-4-pyridinyl)-1H-indazole-5-carboxamide;

N-(3-benzoyl-3-hydroxycyclohexyl)-3-(2-methyl-4-pyridinyl)-1H-indazole-5-carboxamide;

N-[trans-3-hydroxy-3-(2H-pyrazolo[3,4-b]pyridin-2-ylmethyl)cyclohexyl]-3-(2-methyl-4-pyridinyl)-1H-indazole-5-carboxamide;

N-[trans-3-hydroxy-3-(1H-pyrazolo[3,4-c]pyridin-1-ylmethyl)cyclohexyl]-3-(2-methyl-4-pyridinyl)-1H-indazole-5-carboxamide;

N-[trans-3-hydroxy-3-(2H-pyrazolo[3,4-c]pyridin-2-ylmethyl)cyclohexyl]-3-(2-methyl-4-pyridinyl)-1H-indazole-5-carboxamide;

N-[trans-3-hydroxy-3-[(2-methyl-1H-imidazo[4,5-c]pyridin-1-yl)methyl]cyclohexyl]-3-(2-methyl-4-pyridinyl)-1H-indazole-5-carboxamide;

N-[3-[(2-fluorophenyl)methyl]-3-(hydroxymethyl)cyclohexyl]-3-(2-methyl-4-pyridinyl)-1H-indazole-5-carboxamide;

N-[3-(2,4-difluorophenoxy)cyclohexyl]-3-(2-methyl-4-pyridinyl)-1H-indazole-5-carboxamide;

N-[3-(4-fluorophenoxy)-3-(hydroxymethyl)-1-piperidinyl]-3-(2-methyl-4-pyridinyl)-1H-indazole-5-carboxamide;

N-[3-[(2,4-di fluorophenyl)methyl]-3-(hydroxymethyl)cyclohexyl]-3-(2-methyl-4-pyridinyl)-1H-indazole-5-carboxamide;

N-[3-[(4-fluorophenyl)methyl]-3-(hydroxymethyl)cyclohexyl]-3-(2-methyl-4-pyridinyl)-1H-indazole-5-carboxamide;

1-[(4-fluorophenyl)methyl]-3-[[[3-(2-methyl-4-pyridinyl)-1H-indazol-5-yl]carbonyl]amino]cyclohexanecarboxylic acid;

N-[3(S)-[(2-fluorophenyl)methyl]-3-hydroxy-1(R)-cyclohexyl]-3-(2-methyl[1,2,4]triazolo[1,5-a]pyridiN-6-yl)-1H-indazole-5-carboxamide;

N-[3(S)-[(2-fluorophenyl)methyl]-3-hydroxy-1(R)-cyclohexyl]-3-(2-methyl-6-benzothiazolyl)-1H-indazole-5-carboxamide;

N-[3(S)-[(2-fluorophenyl)methyl]-3-hydroxy-1(R)-cyclohexyl]-3-imidazo[1,2-a]pyridin-6-yl-1H-indazole-5-carboxamide;

N-[cis-3-hydroxy-3-(2H-pyrazolo[3,4-b]pyridin-2-ylmethyl)cyclohexyl]-3-(2-methyl-4-pyridinyl)-1H-indazole-5-carboxamide;

N-[cis-3-hydroxy-3-(1H-pyrazolo[3,4-b]pyridin-1-ylmethyl)cyclohexyl]-3-(2-methyl-4-pyridinyl)-1H-indazole-5-carboxamide;

N-[cis-3-hydroxy-3-(1H-pyrazolo[3,4-c]pyridin-1-ylmethyl)cyclohexyl]-3-(2-methyl-4-pyridinyl)-1H-indazole-5-carboxamide;

N-[cis-3-hydroxy-3-(1H-imidazo[4,5-b]pyridin-1-ylmethyl)cyclohexyl]-3-(2-methyl-4-pyridinyl)-1H-indazole-5-carboxamide;

N-[cis-3-hydroxy-3-(3H-imidazo[4,5-b]pyridin-3-ylmethyl)cyclohexyl]-3-(2-methyl-4-pyridinyl)-1H-indazole-5-carboxamide;

3-(2-methyl-4-pyridinyl)-N-[3-(2H-pyrazolo[3,4-b]pyridin-2-ylmethyl)cyclohexyl]-1H-indazole-5-carboxamide;

3-(2-methyl-4-pyridinyl)-N-[3-(1H-pyrazolo[3,4-b]pyridin-1-ylmethyl)cyclohexyl]-1H-indazole-5-carboxamide;

3-(2-methyl-4-pyridinyl)-N-[3-(1H-pyrazolo[3,4-c]pyridin-1-ylmethyl)cyclohexyl]-1H-indazole-5-carboxamide;

N-[3-[(2-methyl-1H-imidazo[4,5-c]pyridin-1-yl)methyl]cyclohexyl]-3-(2-methyl-4-pyridinyl)-1H-indazole-5-carboxamide;

N-[3-(1H-imidazo[4,5-b]pyridin-1-ylmethyl)cyclohexyl]-3-(2-methyl-4-pyridinyl)-1H-indazole-5-carboxamide;

N-[3-(3H-imidazo[4,5-b]pyridin-3-ylmethyl)cyclohexyl]-3-(2-methyl-4-pyridinyl)-1H-indazole-5-carboxamide;

N-[3-[(2,6-difluorophenyl)methyl]-3-(hydroxymethyl)cyclohexyl]-3-(2-methyl-4-pyridinyl)-1H-indazole-5-carboxamide;

N-[3(S)-[(2,6-difluorophenyl)methyl]-3-hydroxy-1(R)-cyclohexyl]-3-(2-methyl-6-benzothiazolyl)-1H-indazole-5-carboxamide;

N-[trans-3-hydroxy-3-(1H-pyrazolo[4,3-c]pyridin-1-ylmethyl)cyclohexyl]-3-(2-methyl-4-pyridinyl)-1H-indazole-5-carboxamide;

N-[trans-3-[(2,3-dihydro-2-oxo-1H-indol-1-yl)methyl]-3-hydroxycyclohexyl]-3-(2-methyl-4-pyridinyl)-1H-indazole-5-carboxamide;

N-[trans-3-hydroxy-3-[(2-oxo-1(2h)-quinolinyl)methyl]cyclohexyl]-3-(2-methyl-4-pyridinyl)-1H-indazole-5-carboxamide;

N-[trans-3-hydroxy-3-(2H-indazol-2-ylmethyl)cyclohexyl]-3-(2-methyl-4-pyridinyl)-1H-indazole-5-carboxamide;

N-[cis-3-hydroxy-3-(1H-pyrazolo[4,3-c]pyridin-1-ylmethyl)cyclohexyl]-3-(2-methyl-4-pyridinyl)-1H-indazole-5-carboxamide;

N-[cis-3-[(2,3-dihydro-2-oxo-1H-indol-1-yl)methyl]-3-hydroxycyclohexyl]-3-(2-methyl-4-pyridinyl)-1H-indazole-5-carboxamide;

N-[cis-3-hydroxy-3-[(2-oxo-1(2h)-quinolinyl)methyl]cyclohexyl]-3-(2-methyl-4-pyridinyl)-1H-indazole-5-carboxamide;

N-[cis-3-hydroxy-3-(2H-indazol-2-ylmethyl)cyclohexyl]-3-(2-methyl-4-pyridinyl)-1H-indazole-5-carboxamide;

3-(2-methyl-4-pyridinyl)-N-[3-(1H-pyrazolo[4,3-c]pyridin-1-ylmethyl)cyclohexyl]-1H-indazole-5-carboxamide;

N-[3-[(2,3-dihydro-2-oxo-1H-indol-1-yl)methyl]cyclohexyl]-3-(2-methyl-4-pyridinyl)-1H-indazole-5-carboxamide;

3-(2-methyl-4-pyridinyl)-N-[3-[(2-oxo-1(2H)-quinolinyl)methyl]cyclohexyl]-1H-indazole-5-carboxamide;

N-[3-(2H-indazol-2-ylmethyl)cyclohexyl]-3-(2-methyl-4-pyridinyl)-1H-indazole-5-carboxamide;

N-[3-(1H-indazol-1-ylmethyl)cyclohexyl]-3-(2-methyl-4-pyridinyl)-1H-indazole-5-carboxamide;

N-[3-[(2-fluorophenyl)methyl]-3-(hydroxymethyl)cyclopentyl]-3-(2-methyl-4-pyridinyl)-1H-indazole-5-carboxamide;

N-[3-[(2-fluorophenyl)methyl]-3-(hydroxymethyl)cyclopentyl]-3-(2-methyl-4-pyridinyl)-1H-indazole-5-carboxamide;

N-[trans-3-[(4-fluoro-1H-indazol-)methyl]-3-hydroxycyclohexyl]-3-(2-methyl-4-pyridinyl)-1H-indazole-5-carboxamide;

N-[trans-3-[(6-fluoro-2H-indazol-)methyl]-3-hydroxycyclohexyl]-3-(2-methyl-4-pyridinyl)-1H-indazole-5-carboxamide;

N-[trans-3-[(7-fluoro-2H-indazol-)methyl]-3-hydroxycyclohexyl]-3-(2-methyl-4-pyridinyl)-1H-indazole-5-carboxamide;

N-[cis-3-[(4-fluoro-1H-indazol-)methyl]-3-hydroxycyclohexyl]-3-(2-methyl-4-pyridinyl)-1H-indazole-5-carboxamide;

N-[trans-3-[(7-fluoro-1H-indazol-)methyl]-3-hydroxycyclohexyl]-3-(2-methyl-4-pyridinyl)-1H-indazole-5-carboxamide;

N-[cis-3-hydroxy-3-[[6-(trifluoromethyl)-1H-indazol-1-yl]methyl]cyclohexyl]-3-(2-methyl-4-pyridinyl)-1H-indazole-5-carboxamide;

N-[3-(2-fluorophenoxy)-1-piperidinyl]-3-(2-methyl-4-pyridinyl)-1H-indazole-5-carboxamide;

N-[-3-[(5-fluoro-2H-indazol-)methyl]cyclohexyl]-3-(2-methyl-4-pyridinyl)-1H-indazole-5-carboxamide;

N-[3-[(7-fluoro-1H-indazol-)methyl]cyclohexyl]-3-(2-methyl-4-pyridinyl)-1H-indazole-5-carboxamide;

N-[cis-3-[(6-fluoro-1H-indazol-)methyl]-3-hydroxycyclohexyl]-3-(2-methyl-4-pyridinyl)-1H-indazole-5-carboxamide;

N-[3(S)-[(2-fluorophenyl)methyl]-3-hydroxy-1(R)-cyclohexyl]-3-[2-(1-methylethoxy)-4-pyridinyl]-1H-indazole-5-carboxamide;

N-[3(S)-[(2-fluorophenyl)methyl]-3-hydroxy-1(R)-cyclohexyl]-3-[6-(1-methylethoxy)-3-pyridinyl]-1H-indazole-5-carboxamide;

N-[3 (S)-[(2,6-difluorophenyl)methyl]-3-hydroxy-1(R)-cyclohexyl]-3-[6-(1-methylethoxy)-3-pyridinyl]-1H-indazole-5-carboxamide;

N-[3(S)-[(2,6-difluorophenyl)methyl]-3-hydroxy-1(R)-cyclohexyl]-3-(2-methyl-2H-indazol-)-1H-indazole-5-carboxamide;

3-(6-benzothiazolyl)-N-[3 (S)-[(2,6-difluorophenyl)methyl]-3-hydroxy-1(R)-cyclohexyl]-1H-indazole-5-carboxamide;

N-[3(S)-[(2,6-difluorophenyl)methyl]-3-hydroxy-1(R)-cyclohexyl]-3-(2-methyl[1,2,4]triazolo[1,5-a]pyridin-6-yl)-1H-indazole-5-carboxamide;

N-[3(S)-[(2-fluoro-6-methoxyphenyl)methyl]-3-hydroxy-1(R)-cyclohexyl]-3-(2-methyl-4-pyridinyl)-1H-indazole-5-carboxamide;

N-[3(S)-[(2-fluoro-6-methoxyphenyl)methyl]-3-hydroxy-1(R)-cyclohexyl]-3-imidazo[1,2-a]pyridin-6-yl-1H-indazole-5-carboxamide;

N-[3(S)-[(2-fluoro-6-methoxyphenyl)methyl]-3-hydroxy-1(R)-cyclohexyl]-3-(2-methyl-6-benzothiazolyl)-1H-indazole-5-carboxamide;

N-[3(S)-[(2-fluoro-6-methoxyphenyl)methyl]-3-hydroxy-1(R)-cyclohexyl]-3-[2-(1-methylethoxy)-4-pyridinyl]-1H-indazole-5-carboxamide; and N-[3(S)-[(2-fluoro-6-methoxyphenyl)methyl]-3-hydroxy-1(R)-cyclohexyl]-3-[4-(1-methylethoxy)phenyl]-1H-indazole-5-carboxamide;

or a pharmaceutically acceptable salt thereof.

2. A pharmaceutical composition comprising at least one compound of claim 1, or a pharmaceutically acceptable salt thereof, and a pharmaceutically acceptable carrier.

\* \* \* \* \*